US010590392B2

(12) United States Patent
Kotton et al.

(10) Patent No.: US 10,590,392 B2
(45) Date of Patent: Mar. 17, 2020

(54) GENERATION OF AIRWAY EPITHELIAL ORGANOIDS FROM HUMAN PLURIPOTENT STEM CELLS

(71) Applicant: TRUSTEES OF BOSTON UNIVERSITY, Boston, MA (US)

(72) Inventors: Darrell N. Kotton, Newton, MA (US); Katherine B. McCauley, Brookline, MA (US); Finn Hawkins, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/865,574

(22) Filed: Jan. 9, 2018

(65) Prior Publication Data

US 2018/0208903 A1    Jul. 26, 2018

Related U.S. Application Data

(60) Provisional application No. 62/478,218, filed on Mar. 29, 2017, provisional application No. 62/443,901, filed on Jan. 9, 2017.

(51) Int. Cl.

| | |
|---|---|
| C12N 5/06 | (2006.01) |
| C12N 5/074 | (2010.01) |
| C12N 5/0735 | (2010.01) |
| C07K 14/47 | (2006.01) |
| A61P 11/00 | (2006.01) |
| C12N 15/86 | (2006.01) |
| C12N 5/071 | (2010.01) |
| C12N 15/113 | (2010.01) |

(52) U.S. Cl.
CPC ............ *C12N 5/0696* (2013.01); *A61P 11/00* (2018.01); *C07K 14/4702* (2013.01); *C12N 5/0606* (2013.01); *C12N 5/0689* (2013.01); *C12N 15/86* (2013.01); C12N 15/1138 (2013.01); C12N 2310/14 (2013.01); C12N 2501/415 (2013.01); C12N 2506/45 (2013.01)

(58) Field of Classification Search
None
See application file for complete search history.

(56) References Cited

U.S. PATENT DOCUMENTS

| 9,988,606 B2 * | 6/2018 | Snoeck ................ C12N 5/0688 |
| 2011/0212067 A1 | 9/2011 | Karanu |
| 2015/0276719 A2 | 10/2015 | Beekman |
| 2016/0312190 A1 | 10/2016 | Ghardi et al. |
| 2016/0312191 A1 | 10/2016 | Spence et al. |

FOREIGN PATENT DOCUMENTS

| WO | 1994012649 A2 | 6/1994 |
| WO | 2008098184 A2 | 8/2008 |

OTHER PUBLICATIONS

2013;Oldenborg et al ; 2013 CD47: A Cell Surface Glycoprotein Which Regulates Multiple Functions of Hematopoietic Cells in Health and Disease ISRN Hematology; pp. 1-19.*
2016 Klemann et al., Cut to the chase: a review of CD26/dipeptidyl peptidase-4's (DPP4) entanglement in the immune system Clinical and Experimental Immunology, 185: 1-21.*
Kwan et al, Genome-wide analysis of transcript isoform variation in humans 2008; Nature Genetics pp. 225-231.*
GeneChip Human Gene 2.1 ST Array Strip—Thermo Fisher Scientific ; downloaded Nov. 27, 2018; pp. 1-3.*
Huang et al., 2014; Efficient generation of lung and airway epithelial cells from human pluripotent stem cells 2014; Nature Biotechonolgy pp. 84-91.*
Affymetrix NetAffx Analysis Center pp. 1-2; downloaded Nov. 28, 2018.*
Bellusci et al., "Fibroblast growth factor 10 (FGF10) and branching morphogenesis in the embryonic mouse lung", Development 124(23) 4867-4878 (1997).
Cardoso et al., "FGF-1 and FGF-7 induce distinct patterns of growth and differentiation in embryonic lung epithelium", Dev Dyn 208(3) 398-405 (1997).
Chen et al., "A retinoic acid-dependent network in the foregut controls formation of the mouse lung primordium", J Clin Invest 120(6) 2040-2048 (2010).
Chen et al., "Inhibition of Tgf beta signaling by endogenous retinoic acid is essential for primary lung bud induction", Development 134(16) 2969-2979 (2007).
Cutting et al., "A cluster of cystic fibrosis mutations in the first nucleotide-binding fold of the cystic fibrosis conductance regulator protein", Nature 346(6282) 366-369 (1990).
De Langhe et al., "Dickkopf-1 (DKK1) reveals that fibronectin is a major target of Wnt signaling in branching morphogenesis of the mouse embryonic lung", Dev Biol 277(2) 316-331 (2005).
Dean et al., "Multiple mutations in highly conserved residues are found in mildly affected cystic fibrosis patients", Cell 61(5) 863-870 (1990).
Dekkers et al., "A functional CFTR assay using primary cystic fibrosis intestinal organoids", Nat Med 19(7) 939-945 (2013).
Goss et al., "Wnt2/2b and beta-catenin signaling are necessary and sufficient to specify lung progenitors in the foregut", Dev Cell 17(2) 290-298 (2009).
Harris-Johnson et al., "beta-Catenin promotes respiratory progenitor identity in mouse foregut", Proc Natl Acad Sci USA 106(38) 16287-16292 (2009).
Hashimoto et al., "β-Catenin-SOX2 signaling regulates the fate of developing airway epithelium", J Cell Sci 125(Pt 4) 932-942 (2012).

(Continued)

*Primary Examiner* — Maria G Leavitt
(74) *Attorney, Agent, or Firm* — Nixon Peabody, LLP

(57) ABSTRACT

The technology described herein relates to methods and kits for directed differentation of primordial NKX2-1+ lung progenitors along proximal differentiation pathways into functional airway epithelial cells and airway organoids ("bronchospheres") or along distal lineage pathways using modulation of Wnt signaling. Other aspects relate cell lines, methods, assays and kits comprising airway epithelial cells, and assays for diagnosing a disease that affects swelling of the bronchospheres, and/or for assessing genetic lesions and/or drugs for treating the the disease, where the disease is cystic fibrosis. Other aspects relate to personalized medicine and methods of treatment of cystic fibrosis using the airway epithelial cells.

8 Claims, 66 Drawing Sheets

Specification includes a Sequence Listing.

(56) References Cited

OTHER PUBLICATIONS

Hawkins et al., "Prospective isolation of NKX2-1-expressing human lung progenitors derived from pluripotent stem cells", J Clin Invest 127(6) 2277-2294 (2017).

Hyatt et al., "FGF-10 induces SP-C and Bmp4 and regulates proximal-distal patterning in embryonic tracheal epithelium", Am J Physiol Lung Cell Mol Physiol 287(6) L1116-L1126 (2004).

Kerem et al., "Identification of mutations in regions corresponding to the two putative nucleotide (ATP)-binding folds of the cystic fibrosis gene", Proc Natl Acad Sci USA 87(12) 8447-8451 (1990).

Kerem et al., "Identification of the cystic fibrosis gene: genetic analysis", Science 245(4922) 1073-1080 (1989).

Konishi et al., "Directed Induction of Functional Multi-ciliated Cells in Proximal Airway Epithelial Spheroids from Human Pluripotent Stem Cells", Stem Cell Reports 6(1) 18-25 (2016).

Li et al., "Stabilized beta-catenin in lung epithelial cells changes cell fate and leads to tracheal and bronchial polyposis", Dev Biol 334(1) 97-108 (2009).

Mucenski et al., "beta-Catenin is required for specification of proximal/distal cell fate during lung morphogenesis", J Biol Chem 278(41) 10231-40238 (2003).

Ramasamy et al., "Fgf10 dosage is critical for the amplification of epithelial cell progenitors and for the formation of multiple mesenchymal lineages during lung development", Dev Biol 307(2) 237-247 (2007).

Sekine et al., "Fgf10 is essential for limb and lung formation", Nat Genet 21(1) 138-141 (1999).

Shu et al., "Wnt/beta-catenin signaling acts upstream of N-myc, BMP4, and FGF signaling to regulate proximal-distal patterning in the lung", Dev Biol 283(1) 226-239 (2005).

Volckaert et al., "Localized Fgf10 expression is not required for lung branching morphogenesis but prevents differentiation of epithelial progenitors", Development 140(8) 3731-3742 (2013).

Wang et al., "Development and regeneration of Sox2+ endoderm progenitors are regulated by a Hdac1/2-Bmp4/Rb1 regulatory pathway", Dev Cell 24(4) 345-358 (2013).

Weaver et al., "Bmp signaling regulates proximal-distal differentiation of endoderm in mouse lung development", Development 126(18) 4005-4015 (1999).

Weaver et al., "Bmp4 and Fgf10 play opposing roles during lung bud morphogenesis", Development 127(12) 2695-2704 (2000).

Zemke et al., "beta-Catenin is not necessary for maintenance or repair of the bronchiolar epithelium", Am J Respir Cell Mol Biol 41(5) 535-543 (2009).

Zhou et al., "Arrested lung morphogenesis in transgenic mice bearing an SP-C-TGF-beta 1 chimeric gene", Dev Biol 175(2) 227-238 (1996).

Huang et al., "Efficient generation of lung and airway epithelial cells from human pluripotent stem cells", Nat Biotehcnol 32(1) 84-91 (2014).

Longmire et al., "Efficient derivation of purified lung and thyroid progenitors from embryonic stem cells", Cell Stem Cell 10(4) 398-411 (2012).

* cited by examiner

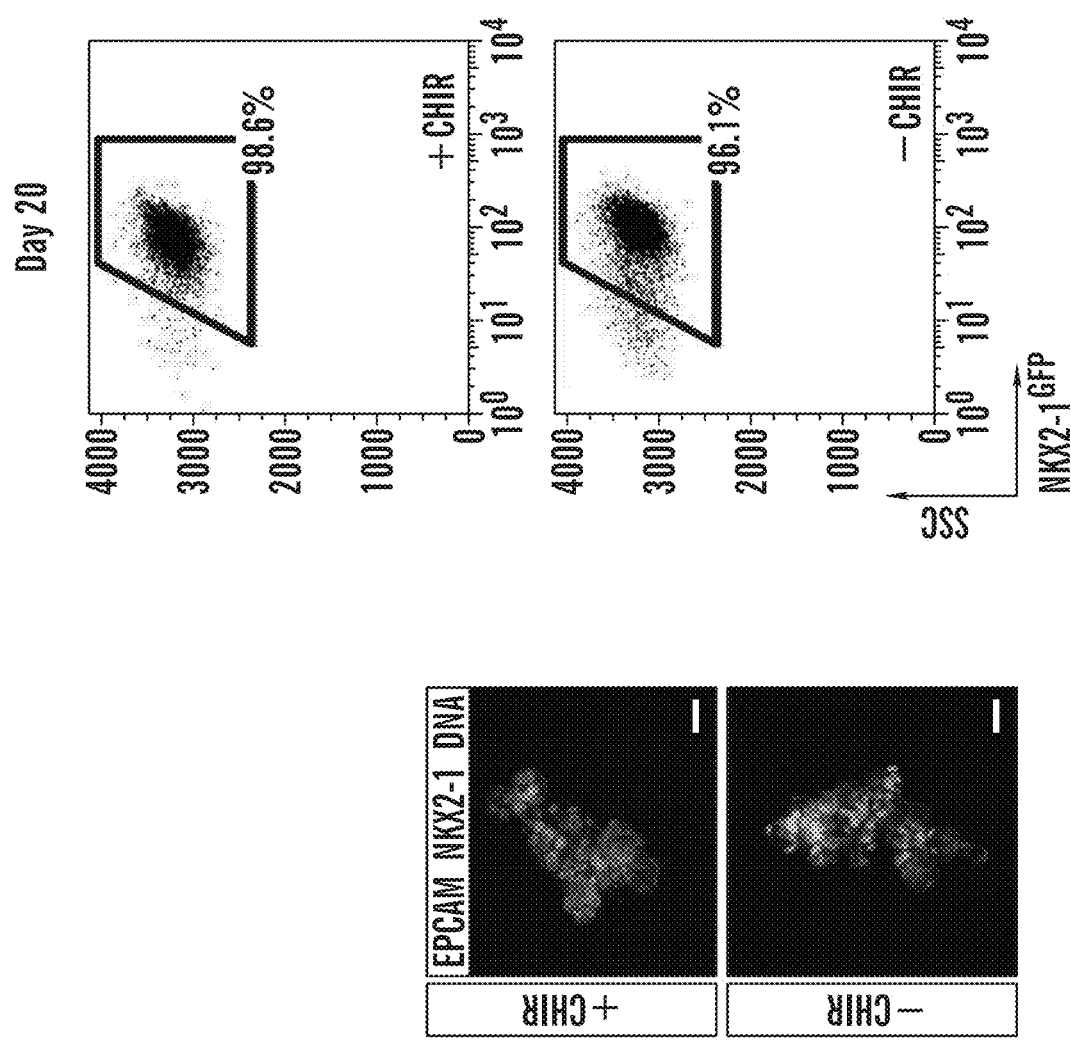

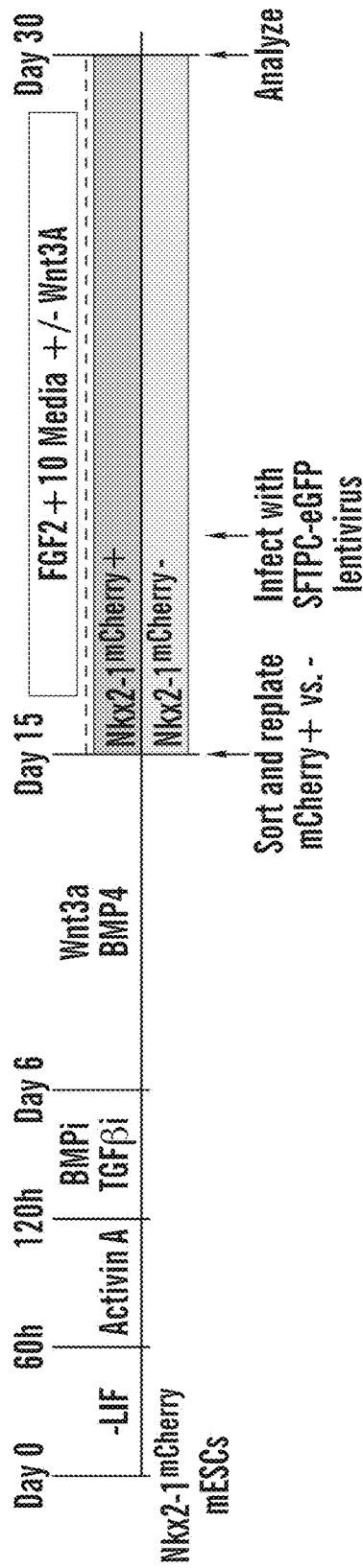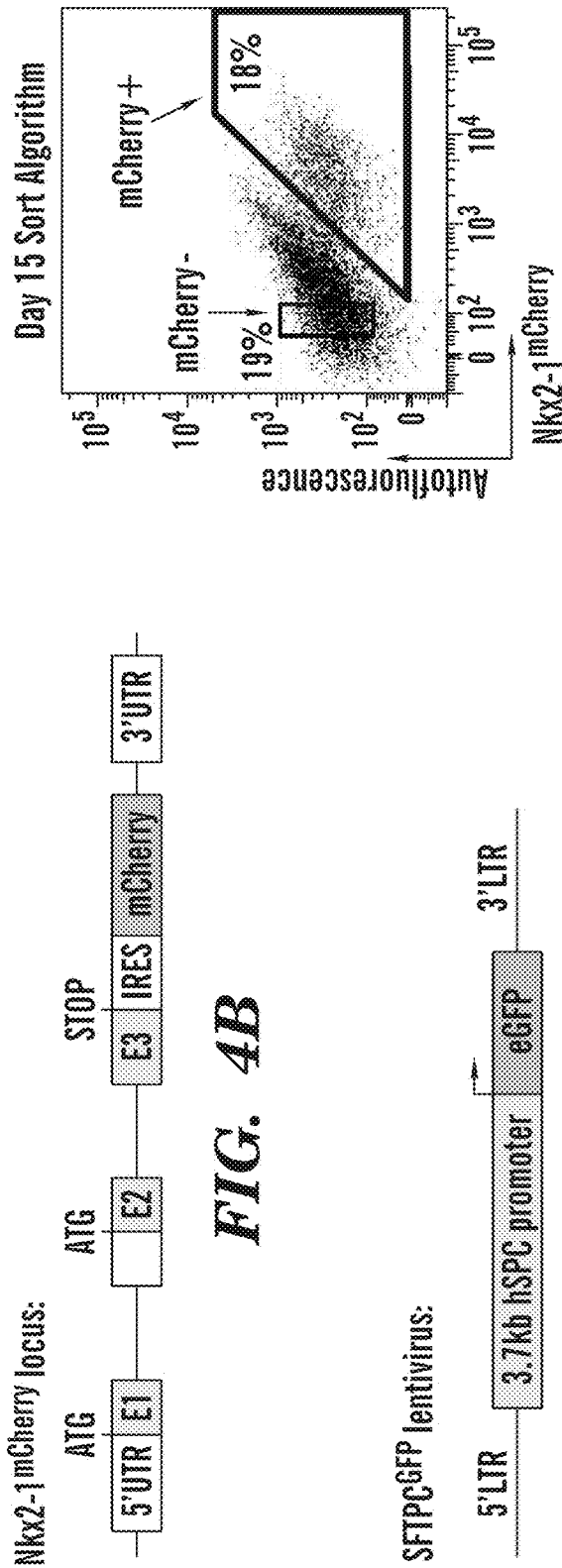
FIG. 4A
FIG. 4B
FIG. 4C
FIG. 4D

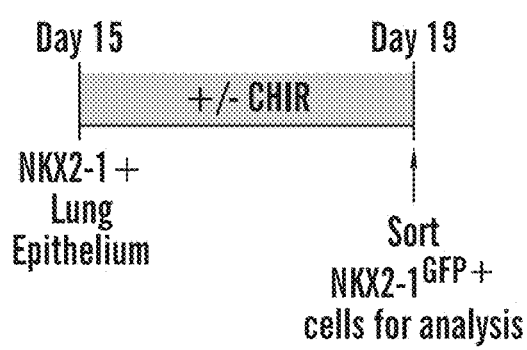
*FIG. 9E*
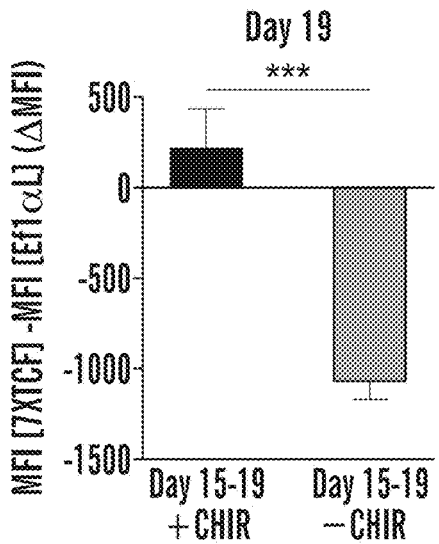
*FIG. 9F*
| CHIR Withdrawal Day 15-19 FC ($2^{-\Delta\Delta Ct}$) | |
|---|---|
| D15 → D19 | |
| → NKD1 | 0.063 |
| WNT8A | 0.2432 |
| DKK4 | 0.2513 |
| GAPDH | 0.2514 |
| → AXIN2 | 0.2536 |
| WNT11 | 0.2542 |
| SFRP4 | 0.4735 |
| WNT16 | 0.4903 |
| FZD3 | 0.4928 |
| HPRT1 | 0.4985 |
| DACT1 | 0.4989 |
| FZD9 | 0.4991 |
| TLE6 | 0.5014 |
| WNT3 | 0.5025 |
| → LEF1 | 0.5084 |
| FRZB | 4.0651 |
| FZD8 | 4.0699 |
| MYC | 4.0739 |
| PITX2 | 4.0923 |
| WNT10B | 4.0948 |
| FZD6 | 4.1088 |
| WNT2 | 4.2619 |
| KREMEN2 | 8.0988 |
| DKK3 | 8.0999 |
| WNT5B | 16.4031 |
| WNT9A | 27.3828 |
| WNT4 | 32.6611 |
| FOXN1 | 33.5584 |
| WNT10A | 64.2712 |
| WNT7A | 544.3912 |
*FIG. 9G* iPSC-derived bronchospheres from normal, CF
and CF corrected iPSC

Establish high-throughput workflow
High-throughput Bronchospheres plates

Using G551D CF iPSC determine the accuracy of
bronchosphere platform to correctly predict drug-
responsiveness Candidate Product:
Cryopreserved patient-specific
bronchospheres

GENERATION OF AIRWAY EPITHELIAL ORGANOIDS FROM HUMAN PLURIPOTENT STEM CELLS

CROSS REFERENCE TO RELATED APPLICATIONS

This application claims under 35 U.S.C. 119(e) claims the benefit of U.S. Provisional Patent Application Ser. No. 62/443,901 filed on Jan. 9, 2017 and U.S. Provisional Patent Application Ser. No. 62/478,218, filed on Mar. 29, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 14, 2018, is named 701586-088653-US_SL.txt and is 27,138 bytes in size.

GOVERNMENT SUPPORT

This invention was made with Government Support under Contract No. HL095993, awarded by the National Institutes of Health. The Government has certain rights in the invention.

FIELD OF THE INVENTION

The technology described herein relates to iPSC-derived airway epithelial cells, and personalized medicine for the treatment of cystic fibrosis and assays comprising iPSC-derived airway epithelial cells.

BACKGROUND OF THE DISCLOSURE

Induced pluripotent stem cells (iPSCs) offer unprecedented opportunities to advance our understanding and treatment of childhood diseases. One such disease is cystic fibrosis (CF). In the U.S., approximately 2,500 infants are born each year with CF and 30,000 children currently live with the disease. Many patients do not live past the age of 40. CF is caused by mutations in the CFTR gene, an anion channel, important in regulating electrolyte and water flow across mucus producing epithelia most notably the lung, pancreas and intestine. CF causing mutations cause abnormally viscous mucus in the airways, infection, inflammation, and lung destruction. Further complicating the situation is the number of cftr mutations, almost 2,000 described to date, and the variable disease severity. Determinants of this heterogeneity include the type of cftr mutation and both genetic and environmental modifiers[5]. The discovery of ivacaftor for treating the subset of cf patients (approx. 7%) with a G551D mutation was a significant advance in the field and represented the first mutation-targeted therapy[6].

For most CF patients, including those with the most common mutation (F508del), effective treatments are not yet available. More potent CFTR correctors are needed. A major question for the community is how an individual's response to cftr modulators can be predicted? Children with CF will benefit the most from early, effective treatment. Some children with less common and less well-characterized mutations might respond to currently approved therapies. Identifying those patients is a priority. Clinical trials in this patient population and with rare mutations are challenging.

Current data suggest that the future of effective CF treatment will be individually tailored combination therapy targeting distinct aspects of CFTR dysfunction[7]. These observations highlight the need for better surrogate preclinical models for drug development but ultimately as part of the routine care of individuals with CF.

A number of cell-based models of CF exist. High-throughput screens (HTS) using Fischer rat thyroid (FRT) cells led to the identification of a number of CFTR modulators. However, this platform is a poor predictor of clinical efficacy in part because thyroid cells are phenotypically different from airway epithelium and this "off the shelf" cell line does not carry the genetic background of patients. As such, although FRT cells are amenable to a HTS approach, these cells are phenotypically different from airway epithelium and the do not represent the genetic background of human patients. Air-liquid interface (ALI) cultures of human bronchial epithelial (HBE) cells[8] more closely resemble the human airway epithelium. However, there are a number of disadvantages to using a HBE CF model: (1) an invasive procedure is required to obtain HBEs, (2) the cell numbers are limiting, (3) HBEs represent only one tissue-type and (4) HBEs are not well suited to genetic engineering (5) Using chamber and patch-clamp assays lack to capacity to measure large numbers of conditions simultaneously.

Intestinal organoid asssays[22] have an established role in CF. The disadvantages to using intestinal organoids are (1) an intestinal or rectal biopsy is required, (2) although the cells can be cultured for long periods, they are not as well less suited to medium to high throughput approaches as iPSCs, and (3) they represent a different tissue (intestine) than the main tissue of interest in CF (lung).

Recent data suggests a promising role for iPSC in the study of CF[9,10]. iPSCs can be routinely and noninvasively generated from any patient, contain that individual's unique genetic background[11]. These cells can be expanded in culture to provide an inexhaustible supply of autologous cells. iPSCs are also suitable for gene-editing approaches[10,12]. Other groups have published modeling CF using iPSCs (9,18).

Directed differentiation of functional lung epithelial cell types from human pluripotent stem cells (PSCs) holds promise for in vitro modeling of complex respiratory diseases and for future cell-based regenerative therapies. Recent studies have demonstrated that a heterogeneous mixture of diverse lung epithelia accompanied by contaminating non-lung lineages can be simultaneously "co-derived" from PSCs differentiated in vitro (Dye et al., 2015; Firth et al., 2014; Gotoh et al., 2014; Green et al., 2011; Huang et al., 2013; Konishi et al., 2016; Longmire et al., 2012; Mou et al., 2012; Wong et al., 2012; Hawkins et al., 2017 and McCauley et al., 2017). However, many pulmonary diseases, such as cystic fibrosis, have their primary effects within distinct regions of the lungs and their constituent cellular subtypes. The heterogeneity of current differentiation outcomes therefore significantly hampers attempts to apply these PSC-based models to recapitulate pulmonary disease and test therapies in vitro. While recent cell sorting methods have enabled the derivation of more homogenous populations of early or primordial lung epithelial progenitor cells from human PSCs (hPSCs), Hawkins et al., 2017), the consistent derivation of well-defined mature functional lineages from these progenitors for effective disease modeling has remained challenging. This is due in part to heterogeneous, stochastic, or chaotic subsequent differentiation of these progenitors in protocols that are often reliant on many weeks or months of cell culture.

One approach to realize the promise of hPSC model systems for studying diseases affecting specific cellular subtypes is to engineer in vitro methods that more closely mimic in vivo developmental cell fate decisions. In contrast to current prolonged in vitro approaches, in vivo lung development is a tightly controlled process, where chaotic heterogeneity is minimized by signaling cascades that act cyclically in a regiospecific manner during narrow stage-dependent windows of time to precisely and rapidly promote appropriate cell fates while suppressing alternate fate options (Perrimon et al., 2012). The patterning of early lung epithelial progenitors in vivo is a classic example of this phenomenon, since soon after lineage specification of primordial lung epithelial progenitors, indicated by emergence of Nkx2-1+ endoderm, their descendants located at advancing distal lung bud tips are iteratively faced with the fate option of either maintaining a distal phenotype or surrendering this fate to assume a proximal airway cell fate (Rawlins et al., 2009). Through these repeated fate decisions, the branching lung airways are patterned post-specification along a proximodistal axis, which is canonically defined by the expression of key transcription factors SOX2 in the proximal developing airway and tracheal epithelium and SOX9 in the budding distal tips(Liu and Hogan, 2002; Que et al., 2009)

Recreating this tightly controlled proximodistal patterning of lung cells during in vitro differentiation of iPSC-derived NKX2-1+ progenitors has been difficult in part due to the plethora of developmental signaling pathways that have been described in mouse models as being important to this process, including Wnt, FGF, BMP, TGFβ, RA, SHUT, and Notch signaling (Bellusci et al., 1997; Cardoso et al., 1997; Chen et al., 2010; 2007; Hashimoto et al., 2012; Hyatt et al., 2004; Mucenski et al., 2003; Sekine et al., 1999; Shu et al., 2005; Y. Wang et al., 2013; Weaver et al., 2000; 1999; Zemke et al., 2009; Zhou et al., 1996). In particular, it has been noted that these pathways exhibit high levels of temporal and regional specificity by which they each promote the migration, differentiation, and maturation of specific cell types at the expense of others.

Perturbations to airway epithelial cell fate are involved in the pathology of many common and incurable pulmonary diseases yet the pathways involved in normal lung cell fate specification remain poorly understood. There is therefore a critical need for studies of the mechanisms by which temporal and spatial control of cell signaling leads to the development of specific lung lineages. The directed differentiation of human lung progenitors from pluripotent stem cells (hPSCs) is a potential source of transient developmental progenitors for these high-resolution studies. Importantly, there remains a critical lack of protocols for deriving airway progenitors from human pluripotent stem cells. Accordingly, there is an urgent need for a rapid, reliable and simple method for producing human airway epithelial cells from iPSC or human iPSCs that does not result in a heterogeneous population of cells.

Additionally, CF is the most common genetic lung disease and second only to sickle cell anemia as a life-shortening, genetic disease, and is caused by mutations in the CFTR gene. There is a pressing need for scalable, human platforms to predict an individual's response to existing CF therapies and to identify novel compounds.

SUMMARY OF THE DISCLOSURE

The technology as described herein relates to methods, compositions and kits for modulating Wnt signaling in NKX2-1 lung epithelial progenitors to direct their differentiation along a proximal or distal differentiation pathway. Some aspects of the technology described herein relates to the derivation of functional airway organoids from human induced pluripotent stem cells (iPSCs), which can be used in models of lung disease and facilitate precision medicine for monogenic airway disorders, such as cystic fibrosis.

However, a limited knowledge of the mechanisms regulating human airway patterning during development has made achieving this goal challenging. Here, the inventors demonstrate the directed differentiation of human iPSCs via an NKX2-1+ progenitor intermediate into functional proximal airway organoids in response to cyclical modulation of the canonical Wnt signaling pathway. The inventors herein have discovered that human NKX2-1+ progenitors have high levels of Wnt activation but respond intrinsically to decreases in Wnt signaling by rapidly patterning into proximal airway lineages at the expense of distal fates. Based on this precise and controlled Wnt signaling during a narrow developmental window of lung competence, the inventors demonstrate the generation of functional cystic fibrosis patient-specific iPSC-derived airway organoids that exhibit quantitative CFTR-dependent forskolin-induced swelling following CFTR gene editing.

Herein, the inventors have developed a method for modulating the cell fate decisions of hPSC-derived primordial lung progenitors in a manner that recapitulates in vivo development, resulting in the synchronized modulation of proximal airway vs. distal alveolar epithelial patterning. The method described herein significantly differs from prior attempts (Konishi et al., 2016) by inducing rapid airway differentiation in response to changes in canonical developmental signaling pathways that act intrinsically on lung progenitors. The inventors demonstrate herein, in human PSC lung developmental model system, that Wnt signaling pathway is an over-arching regulator of proximodistal epithelial patterning. Withdrawal of Wnt activation (or a "low-Mint" media or a Wnt inhibitor) promotes swift emergence of proximal over distal epithelial fates from primordial NKX2-1+ progenitors, whereas maintenance of Wnt signaling promotes distal epithelial fates while suppressing proximal fates. The end result of this approach is the reliable production of "epithelial-only" airway organoids that derive directly from NKX2-1+ precursors and contain diverse airway epithelial cell types, including basal cells, multiciliated cells and secretory cells (e.g., see FIG. 5J).

Stated differently, the inventors have discovered that by modulating the Wnt signaling of primordial NKX2-1+ progenitors, one can generate either (i) airway organoids with "low-Wnt" media (or a Wnt inhibitor), which is highly useful for generating cells for drug screening assays to identify candidate genes for the treatment of CF, or (ii) cells of distal epithelial lineage (i.e., alveolar progenitors) with maintance of Wnt signaling (see e.g., FIG. 5J).

Accordingly, the technology described herein is based on the discovery that by modulating Wnt signaling (i.e., Wnt withdrawal) one can direct lung progenitors derived from human iPSC's specifically into airway progenitors. These airway progenitors can be used in preclinical models of airway disease for analysis, e.g. researching the mechanism of cystic fibrosis, and/or drug discovery for the treatment of CF.

Furthermore, the inventors demonstrate herein that, when generated from cystic fibrosis patient-specific iPSC lines, either before or after gene editing to correct the CFTR genetic lesion responsible for the disease, these organoids allow precise interrogation of mutant vs corrected CFTR function through forskolin-induced epithelial sphere swelling assays. This human developmental model system facilitates disease modeling and drug screening for a variety of genetic diseases affecting the airway epithelium, exemplified by cystic fibrosis.

In particular, the inventors have demonstrated a proof-of-concept application of iPSCs as a pre-clinical model of the airway disease caused by Cystic Fibrosis (CF), which is the most common genetic lung disease and second only to sickle cell anemia as a life-shortening, genetic disease. Herein, the inventors have developed protocols for the derivation of airway organoids (hereafter "iPSC-derived bronchospheres") from iPSCs. The inventors demonstrate that the iPSC-derived bronchospheres swell in response to forskolin, and and have developed a forskolin-induced swelling (FIS) assay, which is more suited to HTS than electrophysiological measurements. Forskolin increased intracellular cAMP and activates CFTR[22]. The swelling of intestinal organoids in response to CFTR activation using forskolin was demonstrated to be CFTR-dependent and correlated with CF disease severity[22]. CFTR-expressing epithelial organoids swell in response to forskolin, and the degree of swelling correlates with the amount of functional CFTR protein present. Herein, the inventors demonstrate that in response to CFTR activation (i.e., forskolin), the iPSC-derived bronchospheres swell in a measurable CFTR-dependent manner and provide a direct read-out of the level of CFTR function in an individual cells. Although individual organoids, i.e., bronchospheres, are analyzed there is high organoid-to-organoid variability, when the amount of swelling is averaged over tens, to hundreds of organoids, the gross change in organoid surface area can be used as a quantitative measure of CFTR function. Accordingly, bronchospheres derived from CF patients and produced according to the methods as disclosed herein, can be used to assess drugs and corrective mutations for functional restoration of CFTR, where a candidate drug or corrective mutation causes the bronchosphere to swell according to wild-type in the presence of forskolin.

Accordingly, the technology described herein provides a methodology and media constituents for differentiating human pluripotent stem cell-derived NKX2-1 lung progenitor cells into airway epithelial cells from. Given a high level of interest in models to study airway diseases, the ability to reproducibly generate clinically relevant airway epithelial cell types from patient-derived cells are important to facilitate clinical applications focused on modeling airway disease, testing novel therapeutic compounds, and potential future regenerative medicine approaches. In particular, the methods, compositions and kits as disclosed herein can be used in assays, e.g., high-throughput assays, e.g., for the discovery of compounds to treat cystic fibrosis.

Additionally, the technology as described herein relates allows for the generation of inexhaustable supplies of airway cell types from patients with clinical airway disease for potential use in disease modeling, drug screening, and cell-based therapy. For example, in some embodiments, the technology as described herein relates allows airway epithelial cells to be generated for use by companies and research groups and clinical applications and/or in cell therapy approaches for producing clinically relevant airway epithelial cells from stem cells.

In some embodiments, the technology as described herein demonstrates the ability to drive purified lung progenitors to airway epithelial cell types based on the manipulation of biological signaling pathways to drive multipotent progenitors to a specific airway cell fate. The inventors have discovered a method by which mature proximal airway epithelial organoids can be derived from human pluripotent stem cells. In some embodiments, these organoids perform in forskolin swelling assays in a CFTR-dependent manner, demonstrating they are an important source of patient-derived airway epithelium for the study of this disease.

Accordingly, the inventors have developed a methodology for generating lung "proximal" airway epithelial cells in the laboratory from human pluripotent stem cells (such as patient specific induced pluripotent stem cells; iPSCs). In some embodiments, a combination of FGF signaling and steroid treatment is used to generate proximal airway cell types from purified lung epithelial cells.

In some embodiments, alternate sorting strategies are envisioned for use, including two- and three-dimensional replating conditions, as well as manipulations to the base media ("cSFDM" or complete serum free differentiation medium), the use of different FGFs or EGFs or omission of the FGF factors entirely, the withdrawal of cyclic AMP and/or IBMX, or changing the steroids used in the media are envisioned.

One aspect of the technology described herein relates to a method for modulating the cononical Wnt pathway in a population of NKX2-1 lung epithelial progenitors to direct their differentiation along a proximal or dorsal epithelial pathway, the method comprising; (i) culturing a population of NKX2-1 lung epithelial progenitors in a low-Wnt media for a sufficient amount of time, wherein the low-Wnt media induces the NKX2-1 lung epithelial progenitors to differentiate along a proximal epithelial pathway into airway epithelial organoids comprising cells selected from any of: NKX2-1+/SOX2+ cells, NKX2-1+/P63+ cells or NKX2-1+/P63+/K5 cells; or (ii) culturing a population of NKX2-1 lung epithelial progenitors in a high Wnt media, or in the presence of a Wnt activator for a sufficient amount of time to allow the NKX2-1 lung epithelial progenitors to differentiate along a distal epithelial pathway into cells selected from any of: NKX2-1+/SOX9+ cells, NKX2-1+/SFTPC+ cells or NKX2-1+/Scgb1a1− cells.

One aspect of the technology described herein relates to a method for producing airway epithelial organoids, comprising culturing a population of NKX2-1 lung epithelial progenitors in a low-Wnt media for at least 4 days, wherein the low-Wnt media induces the NKX2-1 lung epithelial progenitors to differentiate into airway epithelial organoids comprising cells selected from any of: NKX2-1+/SOX2+ cells, NKX2-1+/P63+ cells or NKX2-1+/P63+/K5 cells.

Another aspect of the technology described herein relates to a method of promoting a population of Nxk2.1 lung epithelial progenitor cells to differentiate along a proximal epithelial pathway, comprising culturing the population of NKX2-1 lung epithelial progenitors in a low-Wnt media for a sufficient amount of time to allow the NKX2-1 lung epithelial progenitors to differentiate into cells selected from any of: NKX2-1+/SOX2+ cells, NKX2-1+/P63+ cells or NKX2-1+/P63+/K5 cells.

In some embodiments, the airway epithelial organoids comprise cells that also express at least one of the proximal markers selected from the group consisting of: SCGB3A2+, TP63+, MUC5AC+ and Scgb1a1+, and optionally, the airway epithelial organoids comprise cells that do not express the distal markers selected from the group consisting of: SFTPC, SOX9. In some embodiments, the NKX2-1 lung progenitors are NKX2-1+ve, $CD47^{hi}$ and $CD26^{lo}$ (i.e., express high levels of CD47 and low leves of CD26). In some embodiments, the low-Wnt media comprises FGF2 and FGF10.

In some embodiments of all aspects disclosed herein, the NKX2.1 lung progenitors are differentiated from iPSC or ESCs, e.g., from human iPSC or ESCs, including human iPSC derived from a subject with a pulmonary disease, such as CF. In some embodiments, the NKX2.1 lung progenitors are differentiated from iPSC or human iPSC or human ESCs using a high wnt media, or in the presence of a Wnt activator. In some embodiments, In some embodiments, a low-Wnt media does not contain a Wnt activator (e.g., CHIR or BIO) or comprises a wnt inhibitory agent, e.g., where a wnt inhibitory agent is withdrawal of a Wnt activator, or is an agent which inhibits Wnt or Wnt3, and/or where the wnt inhibitory agent inhibits any one or more of Wls/Evi, Frizzled, Dsh (disheveled), LRP-5, LRP-6, Dally, Dally-like, PAR1, β-catenin, TCF, lef-1 or Frodo. In some embodiments, a wnt inhibitory agent is an RNAi agent which inhibits the RNA transcript of Wls/Evi. In some embodiments, a RNAi agent which inhibits Wls/Evi corresponds to SEQ ID NO:1 (CACAAATC-CTTTCTACAGTAT)) (siWLS-A) or SEQ ID NO:2 (GGGT-TACCGTGATGATATG) (siWLS-B). In some embodiments, the wnt inhibitory agent is selected from the group consisting of: Dickkopf-1 (DKK1), WIF-1, cerberus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins or LRP lacking the intracellular domain. In some embodiments, a wnt inhibitory agent inhibits β-catenin, e.g., where an inhibitor of β-catenin can be selected from, e.g., the group consisting of; protein phosphatase 2A (PP2A), chibby, promtin 52, Nemo/LNK kinase, MHG homobox factors, XSox17, HBP1, APC, Axin, disabled-2 (dab-2) and gruncho (grg). In some embodiments, a wnt inhibitory agent increases the activity and/or expression of GSK-3 and/or GSK3β. In some embodiments, a wnt inhibitory agent is a peptide of GSK3β, and in some embodiments, a wnt inhibitory agent is selected from a group consisting of; a GSK3β peptide, an agent which activates the PKB pathway or wortannin, or a peptide of DKK1.

In some embodiments, the NKX2-1 lung epithelial progenitors are genetically modified NKX2-1 lung epithelial progenitors, for example, genetically modified NKX2-1 lung epithelial progenitors comprises a nucleic acid encoding at least one wnt inhibitory agent operatively linked to a first inducible promoter, or alternatively, the genetically modified NKX2-1 lung epithelial progenitors comprises a nucleic acid encoding multiple copies of a wnt inhibitory agent operatively linked to a first inducible promoter. In some embodiments, the nucleic acid encoding at least one wnt inhibitory agent encodes at least one of the Wnt inhibitory agents selected from the group consisting of: GSK3β, a peptide of GSK3β, protein phosphatase 2A (PP2A), chibby, promtin 52, Nemo/LNK kinase, MHG homobox factors, XSox17, HBP1, APC, Axin, disabled-2 (dab-2) and gruncho (grg), Dickkopf-1 (DKK1), WIF-1, cerberus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins or LRP lacking the intracellular domain. In some embodiments, genetically modified NKX2-1 lung epithelial progenitors comprises a nucleic acid encoding at least one wnt activator operatively linked to a second inducible promoter, and in some embodiments, genetically modified NKX2-1 lung epithelial progenitors comprises a nucleic acid encoding multiple copies of a wnt activator operatively linked to a second inducible promoter.

In some embodiments, a first inducible promoter is not the same as the second inducible promoter, and optionally, the first inducible promoter and second inducible promoter are high efficiency promoters.

In some embodiments, a nucleic acid encoding at least one wnt activator encodes at least one of the Wnt inhibitory agents selected from the group consisting of: β-catenin or a biologically active fragment or homologue thereof, or a stabilized β-catenin homologue with any of the amino acid changes selected from the group consisting of: D32Y; D32G; S33F; S33Y; G34E; S37C; S37F; T41I; S45Y or β-catenin with the deletion of amino acids AA1-173, Frodo, TCF, pitz2, Pretin 52, legless (lgs), pygopus (pygo), hyrax/parafnomin and LKB1/XEEK1. In some embodiments, a NKX2-1 lung epithelial progenitor is differentiated from an iPSC obtained from a human subject with cystic fibrosis, and where the NKX2-1 lung epithelial progenitor is a genetically modified to correct a CTFR genetic lesion responsible for the cystic fibrosis in the subject.

Another aspect of the technology described herein relates to a cell line, e.g., a population of airway epithelial cells produced by the methods disclosed herein, wherein airway epithelial cells are selected from any of: NKX2-1+/SOX2+ cells, NKX2-1+/P63+ cells or NKX2-1+/P63+/K5 cells. In some embodiments, the cell line is in the presence of a low-Wnt media or a Wnt inhibitor, and in some embodiments, a low-Wnt media does not contain a Wnt activator (e.g., BIO or CHIR). In some embodiments, cell line, e.g., a population of airway epithelial cells produced by the methods disclosed herein is cryopreserved and/or present in a cryopreservation media. In some embodiments, the cell line is a genetically modified cell line, e.g., where the cell line has been genetically modified to correct a CFTR genetic lesion responsible for CF in a subject.

Another aspect of the present invention relates to a cell line, e.g., a population of NKX2-1 lung epithelial cells of distal epithelial cell fate, produced by the methods disclosed herein, wherein the NKX2-1 lung epithelial cells of distal epithelial cell fate are selected from selected expressing any of: NKX2-1+/SOX9+ cells, NKX2-1+/SFTPC+ cells or NKX2-1+/Scgb1a1– cells. In some embodiments, a cell line, e.g., a population of NKX2-1 lung epithelial cells of distal epithelial cell fate is in the presence of a high-Wnt media or a Wnt activator. In some embodiments, such a cell line is subsequently cryopreserved and/or present in a cryopreservation media.

Another aspect of the present invention relates to a method of treating cystic fibrosis (CF), comprising: (a) differentiating a population of human iPSC or ESCs into NKX2-1 lung epithelial progenitor cells, (b) culturing the NKX2-1 lung epithelial progenitor cells with a low-wnt media according to the methods as disclosed herein to differentiate into airway epithelial cells expressing any of: NKX2-1+/SOX2+ cells, NKX2-1+/P63+ cells or NKX2-1+/P63+/K5 cells; and (c) administering the airway epithelial cells obtained in step (b) to the subject. In some embodiments, the population of human iPSC are obtained from the subject with cystic fibrosis, and have been genetically modified to correct a CTFR genetic lesion responsible for the cystic fibrosis in the subject prior to being differentiated into NKX2-1 lung epithelial progenitor cells. In some embodiments, the method of treating CF further comprises genetically modifying the airway epithelial cells obtained in step (b) to correct a CTFR genetic lesion responsible for the cystic fibrosis in the subject prior to the step (c). In some embodiments, the airway epithelial cells are transplanted into the lungs of the subject.

Another aspect of the technology described herein relates to use of the airway epithelial cells described herein in a forskolin-induced swelling (FIS) assay, where the assay can be used to select an agent that increases CTFR function. In some embodiments, the assay comprising: (a) contacting a population of airway epithelial cells with forskolin and a candidate agent, wherein the airway epithelial cells are any of: NKX2-1+/SOX2+ cells, NKX2-1+/P63+ cells or NKX2-1+/P63+/K5 cells, (b) measuring the size of each airway epithelial cell at a first timepoint, where the first timepoint is prior to, or shortly after the airway epithelial cells are contacted with the forskolin and candidate agent, (c) culturing the airway epithelial cells for a pre-defined period of time, (d) measuring the size of each airway epithelial cell at a second timepoint, or a plurality of timepoints during the pre-defined period of time, wherein the second timepoint or plurality of timepoints is after the first timepoint, (e) calculating the difference in the size of each airway epithelial cell measured at the second, or plurality of timepoints as compared to the first timepoint, and determining the average change in size of each airway epithelial cell in the population of airway epithelial cells, and (f) selecting the candidate agent as an agent that increases CFTR function where the average size of each airway epithelial cell is increased as compared to the average size of each airway epithelial cell in the absence of the candidate agent, or in the presence of a control candidate agent.

In some embodiments, the assay is a high-throughput screen (HTS) assay. In some embodiments, the population of airway epithelial cells used in the assay are differentiated from human iPSC or ESCs obtained from a subject with CF, or comprise a mutation (i.e, a genetic lesion) in the CFTR gene that is responsible for CF in a subject. In some embodiments, the surface area of each airway epithelial cell is measured at a first timepoint, or second timepoint or a plurality of subsequent timepoints, for example, by imaging the population of airway epithelial cells and using software to calculate the size (e.g., surface area) of each epithelial cell a first timepoint, or second timepoint or plurality of subsequent timepoint. Such imaging can be done with an automated high-definition microscope, and optionally connected to a computer, where software can be used to calculate the change in the size (e.g., surface area) of each cell measured at each timepoint over the pre-defined period of time. In some embodiments, the assay comprises a step of contacting the population of airway epithelial cells with a marker, such as a fluorescent marker prior to measuring the size of the cells. An example of such a marker is calcein green. In some embodiments, the size of each airway epithelial cell is measured at frequent intervals over a pre-defined period of time, selected from any of: between 6-12 hours, between 12-24 hrs, between 24-36 hrs, between 36-48 hours, or more than 48 hours, and optionally, the regular intervals (i.e., plurality of timepoints when the size of each airway epithelial cell is measured) is selected from intervals of any of: 10 minutes, or 15 minutes, or 20 minutes, or 30 minutes, or 60 minutes or 90 minutes, or 120 minutes during the pre-defined time period. In some embodiments, the assay comprises contacting the population of airway epithelial cells with 5-10 µM of forskolin, or more than 10 µM of forskolin.

Another aspect of the technology described herein relates to a method for treating a subject with cystic fibrosis, comprising: (a) differentiating a population of human iPSC obtained from the subject into NKX2-1 lung epithelial progenitor cells by the methods as disclosed herein, (b) culturing the NKX2-1 lung epithelial progenitor cells with a low-wnt media according to the methods as disclosed in claims to 1 to 24, to differentiate into airway epithelial cells expressing any of: NKX2-1+/SOX2+ cells, NKX2-1+/P63+ cells or NKX2-1+/P63+/K5 cells; and collecting the airway epithelial cells; (c) using the airway epithelial cells obtained in step (b) in an forskolin-induced swelling (FIS) assay according to the methods disclosed herein to identify an agent which increase CFTR function; and (d) administering to the subject an agent identified to increase CFTR swelling of the airway epithelial cells obtained from the subject with cystic fibrosis.

BRIEF DESCRIPTION OF THE FIGURES

FIG. 1A is a schematic diagram depicting directed differentiation protocol from hPSCs to NKX2-1+ endodermal lung progenitors. FIG. 1B shows a representative day 15 FACS plot showing typical NKX2-1$^{GFP}$ expression in C17 cells. FIG. 1C shows the experimental approach for testing developmental pathways (BMPi=BMP inhibition using Dorsomorphin, TGFβi=TGFβ inhibition using SB431542. FIG. 1D shows a schematic of murine branching lung depicting key proximodistal patterning markers. FIG. 1E shows RT-qPCR measurement of fold change ($2^{-\Delta\Delta Ct}$) of mRNA expression (compared to day 19 base media) shown for day 0 iPSCs or NKX2-1$^{GFP+}$ sorted cells on day 19 after treatment with indicated growth factors from day 15 to 19. Base media (day 19 control condition without supplements) is defined as fold change=1. Arrows indicate conditions containing CHIR99021. Bars represent mean±S.D. (Base, +CHIR: n=6; others: n=3 biological replicates of independent wells of a differentiation) *p≤0.05, p≤0.01, *p≤0.001, ****p≤0.0001 by unpaired two-tailed Student's t-test between test conditions and base. See also FIG. 7.

FIG. 2A shows gene set enrichment analysis (GSEA) of microarray data indicating the unbiased ranking of Wnt pathway genes differentially expressed comparing iPSC-derived day 6 ("Anterior Foregut Endoderm", or "AFE") cells and day 15 purified NKX2.1$^{GFP+}$ cells. Arrowheads=Wnt target genes anticipated to be most predictive of signaling activity. FIG. 2B shows a schematic of experiment showing manipulation of Wnt signaling from day 15 to 19. FIG. 2C shows RT-qPCR showing fold change in gene expression compared to day 0 ($2^{-\Delta\Delta Ct}$) in day 19 NKX2-1$^{GFP}$ sorted cells after 4 days treatment+/−CHIR or rmWnt3a. Bars represent mean±S.E.M.+CHIR: n=9 biological replicates of independent wells within multiple differentiations, +rmWnt3a: n=3. FIG. 2D shows the fold change of mRNA expression in NKX2-1$^{GFP+}$ cells on day 19 over undifferentiated iPSCs. Unsorted cells were cultured with or without CHIR or rmWnt3a (SOX2, SOX9) from day 15-19 then GFP+ cells were sorted on day 19. Bars represent mean±S.E.M. (Biological replicates for each condition: CHIR treatment SOX2 n=9; SCGB3A2, P63: n=10; SOX9: n=6; MUCSAC, ETVS: n=3. For rmWnt3a, n=3). (c,d) *p≤0.05, p≤0.01, *p≤0.001, ****p≤0.0001 by unpaired, two-tailed Student's t-test. FIG. 2E shows representative immunofluorescence imaging of NKX2-1 (observed in green) and SOX2 or SOX9 (observed in red) protein expression with DNA stain (Hoescht; blue) at day 19 with and without CHIR from day 15-19. Panels are images of the same cells stained for all three markers. Scale bars, 25 µm. FIG. 2F shows the quantification of NKX2-1, SOX2, and SOX9 coexpression by intracellular flow cytometry (SOX2) or by colocalization calculated from staining in FIG. 2E (SOX9). Bars represent mean±S.D., n=3 biological replicates. *p=0.03; ***p=0.0002 by unpaired two-tailed Student's t-test. FIG. 2G shows representative immunofluorescence stains for NKX2-1 (green) and P63 (red) nuclear protein expression with DNA stain (Hoescht; blue) at day 19 with and without CHIR from day 15-19. Left panels and right panel: Scale bars, 50 μm. Second from right panel: Scale bars, 25 μm. FIG. 2H shows the quantification of NKX2-1 and P63 colocalization from staining in FIG. 2G. Bars represent mean±S.D., area from 5 images each of n=3 biological replicates. *p=0.01 by unpaired two-tailed Student's t-test. FIG. 2I shows immunofluorescence images of NKX2-1 (green), P63 (red) and KRT5 (white) at day 19 after culture without CHIR from day 15 to 19. Arrowheads=triple positive cells. Scale bars, 50 μm. See also FIGS. 8-10.

FIGS. 3A-3F shows the inhibition of proximal patterning by Wnt activation is intrinsic to the NKX2-1+ lung epithelium. FIG. 3A shows the experimental design for testing CHIR effects on purified NKX2-1$^{GFP+}$ endodermal lung progenitors. FIG. 3B shows results of live cell fluorescence microscopy on day 20, depicting NKX2-1$^{GFP}$ in iPSC-derived organoids treated with and without CHIR from day 14-20 (6 days post-sort). Scale bars: Left and center panels: 100 μM; Right panel: 25 μM. Dashed boxes represent zoom views. FIG. 3C shows represented whole-mount immunofluorescence images of EPCAM (red) and NKX2-1 (green) expression in day 20 organoids. Scale bars, 25 μm. FIG. 3D shows results of NKX2-1$^{GFP}$ flow cytometry analysis of organoids on day 20. FIG. 3E shows results of quantification of analysis from FIG. 3D. Bars represent mean±S.D., n=3. FIG. 3F shows the fold change of genes in NKX2-1$^{GFP+}$ cells on day 20 over undifferentiated iPSCs by RT-qPCR ($2^{-\Delta\Delta Ct}$). Bars represent mean±S.D., n=3 biological replicates from independently sorted wells of a differentiation. *p≤0.05, p≤0.01, *p≤0.001, ****p≤0.0001 by unpaired, two-tailed Student's t-test.

FIGS. 4A-4F shows that mouse embryonic stem cell (mESC)-derived Nkx2-1$^{mCherry+}$ lung progenitors upregulate Sftpc in response to Wnt3a. FIG. 4A is a schematic depicting directed differentiation of Nkx2-1$^{mCherry+}$ cells from mESCs and transduction of sorted cells with Sfipc$^{GFP}$ reporter lentivirus. FIG. 4B is a schematic of targeted Nkx2-1$^{mCherry}$ locus. FIG. 4C shows a representative flow cytometry plot with gates for day 15 mCherry+ vs – sort. FIG. 4D is a schematic of Sftpc$^{GFP}$ lentivirus. FIG. 4E shows representative images of the induction of the Sftpc$^{GFP}$ reporter in cells from the Nkx2-1$^{mCherry+}$ outgrowth treated with rmWnt3a. FIG. 4F shows the fold change of mRNA expression for Sftpc and Scgb1a1 in outgrowth of Nkx2-1$^{mCherry+}$ vs Nkx2-1$^{mCherry-}$ cells sorted on day 15 and analyzed on day 30 by RT-qPCR ($2^{-\Delta\Delta Ct}$; fold change compared to day 0 mESCs). Bars represent mean±S.D., n=2 biological replicates.

FIG. 5A is a schematic depicting protocol for differentiating organoids from purified NKX2-1$^{GFP+}$ progenitors. FIG. 5B shows representative fluorescence microscopy images for NKX2-1$^{GFP}$ expression in organoids cultured in distalizing (Wnt-high; CFK+DCI vs proximalizing (Wnt-low; 2+10+DCI) conditions until day 27. Scale bars, 50 μm. FIG. 5C shows the quantification of NKX2-1$^{GFP}$ expression in CFK+DCI and 2+10+DCI organoids at day 27 by flow cytometry. Bars represent mean±S.E.M., n=6 biological replicates from independent wells of multiple differentiations. FIG. 5D shows the fold change of mRNA expression in day 27 organoids and adult lung control over undifferentiated iPSCs by RT-qPCR ($2^{-\Delta\Delta Ct}$). Bars represent mean±S.E.M., n=6 biological replicates from independent wells of multiple differentiations. *p≤0.05, p≤0.01, *p≤0.001, ****p≤0.0001 by unpaired, two-tailed Student's t-test. FIG. 5E shows hematoxylin staining of sectioned organoid. FIG. 5F and FIG. 5G are representative whole mount immunofluorescence staining images for indicated markers. Scale bars, 25 μm. FIG. 5H shows the fold change of mRNA expression in 2+10+DCI organoids cultured with DAPT or vehicle alone for 2 weeks (days 31-45). Bars represent mean±S.D., n=3 biological replicates from one differentiation, *p≤0.05 by unpaired, two-tailed Student's t-test. FIG. 5I shows representative z-projection and orthogonal projections of acetylated alpha-tubulin and f-actin staining of 9-day air-liquid interface culture generated from replated outgrowth of proximalized organoids. Upper panel, scale bar, 25 μm; lower panel, scale bar, 10 μm. FIG. 5J is a schematic depicting proposed pathways for the generation of proximal or distal lung lineages. See also FIG. 17 and data not shown.

FIG. 6A shows schematics depicting the generation, gene correction, and differentiation of syngeneic ΔF508/ΔF508 and ΔF508/WT cystic fibrosis patient-derived hPSC lines. FIG. 6B shows representative flow cytometry analysis of intracellular NKX2-1 expression pre- and post-CD47$^{hi}$/CD26− sorting of uncorrected and corrected cystic fibrosis iPSC line RC2 204. Middle plots show typical CD47/CD26 sort gating strategy. FIG. 6C is a schematic describing post-sort outgrowth of differentiated cells. FIG. 6D shows a representative fluorescence microscopy image of live (calcein green stained) organoids from pre- and post-corrected iPSC line RC2 202 at time=0 hours and time=24 hours post-forskolin treatment. Scale bars, 100 μm. FIG. 6E shows time lapse phase contrast microscopy of forskolin treated, gene corrected (ΔF508/WT) organoids from RC2 204. FIG. 6F shows the quantification of normalized swelling area of organoids derived from pre- and post-corrected clones of RC2 202 at time=0, 3, and 25 hours. Calcein green stained area for each well set to 1 at time=0 hours. Bars represent mean±S.D., n=3 biological replicates from independent wells of a differentiation. p=0.0038 by unpaired, two-tailed Student's t-test. See also FIG. 18 and data not shown.

FIG. 7A shows immunofluorescence staining of day 15 cells for NKX2-1 and FOXA2. FIG. 7B shows quantification of differentiation efficiency of C17 by NKX2-1GFP % and of RUES2 by intracellular NKX2-1 flow cytometry. Box and whisker plot; whiskers represent maximum and minimum value (C17: n=28 independent differentiations; RUES2: n=6 independent differentiations). FIG. 7C shows the fold change of mRNA expression in iPSC-derived NKX2-1GFP+cells on Day 15 compared to cells differentiated in neural conditions or to primary adult thyroid tissue. Fold change measured over undifferentiated iPSCs by RT-qPCR (2−ΔΔCt). Bars represent mean±S.D, n=3. *p≤0.001 by unpaired, two-tailed Student's t-test. FIG. 7D shows a flow cytometry plot for EPCAM by FACS array on day 15 differentiated cells. FIG. 7E shows FACS array results for CD24, CD31, CD45, PDGFRα, and CD26 on day 15 differentiated cells compared to NKX2-1GFPexpression. FIG. 7F shows the fold change of mRNA expression in iPSC-derived NKX2-1GFP+cells on Day 19 treated with CHIR and escalating doses of FGF10 (as indicated). Fold change measured over undifferentiated iPSC by RT-qPCR (2−ΔΔCt). Bars represent mean±S.D. (n=3). p=0.0016 by ordinary one-way ANOVA post test for linear trend. For SOX2 condition, p=0.0546. FIG. 7G shows the fold change of mRNA expression in iPSC-derived NKX2-1GFP+cells on Day 19 treated with indicated growth factors to manipulate TGFα signaling from Day 15 to 19. Fold change measured over base condition by RT-qPCR (2−ΔΔCt). Bars represent mean±S.D. (Base, +CHIR: n=6; others: n=3). Arrows indicate conditions containing CHIR99021.

FIG. 8A shows results of kinetic analysis of Log 2 expression of putative Wnt reporter genes from Day 0 to Day 28 of human iPSC differentiation analyzed by Affymetrix microarrays. Error bars represent mean±S.D, n=3 biological replicates. FIG. 8B is a schematic map of EF1α-mCherry and Ef1α-α-cateninΔGSK-SV40-mCherry lentiviral contstructs. FIG. 8C shows the fold change of mRNA expression in Day 19 NKX2-1GFP+ mCherry+cells infected on Day 15 with EF1α-mCherry or Ef1α-α-cateninΔGSK-SV40-mCherry expression and treated with and without CHIR from Day 18 to 22. Fold change measured over undifferentiated iPSCs by RT-qPCR (2−ΔΔCt). Bars represent mean±S.D., n=3. *p<0.05, ***p<0.001 by unpaired, two-tailed Student's t-test. FIG. 8D is a schematic map of 7XTCF-mCherry lentirival reporter containing 7-TCF binding sites and a minimal thymidine kinase (TK MinP) promoter driving mCherry expression. FIG. 8E shows representative images of 7XTCF-mCherry expression in FG293s treated with indicated doses of CHIR99021 for 48 hours.

FIGS. 9A-9G show Wnt signaling manipulation post-lung specification of human iPSCs. (and is Related to FIG. 2). FIG. 9A is a schematic of Wnt signaling manipulation at different stages of the lung differentiation protocol. FIG. 9B shows results of kinetic analysis of NKX2-1GFPexpression quantified by flow cytometry in the presence (blue) and absence (black) of CHIR from Day 6 to 19. Cells analyzed on Days 17 and 19 were cultured without CHIR from Day 6 to 15. FIG. 9C shows the quantification of 7XTCF-mCherry lentiviral reporter expression by flow cytometry from Day 6 to 15 in the presence (red) and absence (black) of CHIR. To control for viral infection efficiency, the percentage of 7XTCF-mCherry positive cells was normalized to the percentage of constitutive eEF1a-mCherry+ cells in a parallel well. (% 7xTCF-mCherry+/% Ef1a-mCherry+). FIG. 9D shows rrepresentative images of 7XTCF-mCherry and Ef1a-mCherry infected cells at day 6 (pre-CHIR treatment) and day 8 (post-CHIR treatment) of differentiation. FIG. 9E is a schematic of experiments manipulating Wnt signaling post-specification. FIG. 9F shows the change in median fluorescence intensity (AMFI) calculated as the difference between the MFI of cells treated with and without CHIR from day 15 to day 19. Cells were infected with the 7XTCF-mCherry reporter and separate controls infected with EF1a-mCherry at the same multiplicity of infection. Bars represent mean±S.D, n=3 biological replicates. MFI was calculated from cells subgated for NKX2.1GFPexpression. FIG. 9G shows the fold change of mRNA expression for 15 most upregulated and 15 most downregulated genes in NKX2.1GFP+ cells at Day 15 compared with Day 19 sorted NKX2.1GFP+ cells cultured without CHIR from Day 15 to 19. Values represent normalized RT-qPCR expression (2−ΔΔCt method) to Day 15 cells.

FIG. 10A shows a representative of flow cytometry analysis of NKX2-1GFPexpression in CHIR and control conditions. FIG. 10B shows the quantification of NKX2-1GFPexpression at Day 15 (n=4) and Day 19 with and without CHIR99021 (n=10). Error bars represent mean±S.E.M. ***p=0.0004 by paired, two-tailed Student's T-test.

FIG. 12A shows a schematic for the efficient in vitro differentiation of human PSCs into lung cells using reproducible induction of NKX2-1. FIG. 12B shows immunostaining results of Day 15 lung differentiation cells for NKX2-1(pink), CD47 (white) and DNA (blue), showing that iPSC-derived lung progenitors at this early stage (Day 15) do not express more differentiated markers of the developing lung ("primordial"). FIG. 12C shows day 15 FACS of lung directed differentiation using NKX2-1GFP line stained for surface markers CD47 and CD26, showing that the $CD47^{hi}$ population is enriched for NKX2-1-GFP+ cells. FIG. 12D shows NKX2-1 mRNA of Day 13 sorted $CD47^{hi}$ and NKX2-1GFP+ NKX2-1GFP− cells. FIG. 12E shows CD47 sort from different efficiency differentiations, where the $CD47^{hi}/CD26^{lo}$ purifies NKX2-1+ cells from lung differentiations with both poor (13%) vs reasonable (56%) efficiencies of NKX2-1 induction.

FIG. 13A shows mRNA levels of key proximal and distal lung markers in lung organoids further matured in either CFK or 2+10 media compared to adult lung biopsy control. FIG. 13B shows immunostaining of "bronchospheres" for NKX2-1 (green), P63 (red), KRT5 (white), EPCAM(red) and SFTPB (red).

FIG. 14A shows representative low magnification images of bronchospheres derived from CFcorrected iPSCs before and after forskolin stimulation. Lower panel shows automated quantitation of surface area. FIG. 14B shows a change in normalized area after forskolin stimulation comparing CF and CF-corrected bronchospheres. FIG. 14C show results of partial drug rescue of CF bronchosperes with VX809 and VX770. FIG. 14D shows swelling of non-lung organoids from CF patients highlights the importance of using robust differentiation protocols. FIG. 14E shows mRNA of CFTR, CDX2 (hindgut) and NKX2-1(lung) in CF and CF corrected organoids that either lung ($CD47^{hi}$) or non-lung)($CD47^{lo}$) confirmed that functional differences in CFTR protein confirmed in FIG. 14B are not due to different CFTR mRNA levels.

FIG. 16A is a schematic of generating bronchospheres from iPSCs and FIG. 16B shows immunostaining of expression of marker F-actin, EPCAM, NKX2-1 and SFTPB.

FIG. 17A-17D shows single channel fluorescence images of organoid immunostains for NKX2-1 with co-staining for: FIG. 17A shows EPCAM immunostaining, FIG. 17B shows SOX2 immunostaining, FIG. 17C shows P63 immunostaining, FIG. 17D shows SPB immunostaining, FIG. 17E shows SCGB3A2 and FIG. 17F shows MUC5AC and DNA (Hoescht). Scale bars, 25 μm. FIG. 17G shows representative z-projection of ALI differentiation stained for acetylated alpha tubulin and F-actin. Left panels, sc=25 μM; right panel, sc=10 μM FIG. 18A shows representative day 15 CD47hi/CD26− sort gate from normal control (BU3) iPSC line. FIG. 18B shows the fold change of mRNA expression in Day 34 2+10+DCI, CFK+DCI organoids derived from BU3 iPSC line, and adult lung control over undifferentiated iPSCs by RT-qPCR. Bars represent mean±S.E.M., n=3. *p≤0.05, p≤0.01, *p≤0.001 by unpaired two-tailed Student's t-test. FIG. 18C show Calcein green and phase images of swelling in proximalized iPSC-derived organoids from a normal donor in response to carrier vehicle (PBS) or 5 μM forskolin from time=0 hours to 20 hours. Arrows indicate organoids with robust, visible swelling. FIG. 18D show quantification of normalized swelling area of Day 38 organoids derived from a normal donor iPSC line treated with PBS or forskolin for 20 hours. Area was calculated from phase contrast images where the total well area of time=0 was set equal to 1 for each condition. Bars represent mean±SD, n=2. FIG. 18E show the quantification of normalized swelling area of Day 22 organoids derived from pre- and post-corrected clones (RC2 204) at time=0 hours (black) and time=24 hours (grey). Area was calculated where the calcein green positive well area of time=0 hours was set equal to 1 for each line tested. Bars represent mean±S.D., n=3. p=0.0131 by unpaired, two-tailed Student's t-test.

FIG. 21A is an image of quantification of the swelling (2D surface area) of Forskolin-induced swelling (CFTR activation) of CF bronchospheres. FIG. 21B is a graph of the swelling of individual cells of F508del (RC202) CF bronchiospheres over a 20 hour time period.

FIG. 22A shows the Forskolin-induced swelling (CFTR activation) of gene-corrected CF bronchospheres. FIG. 22B is a graph of the Forskolin-induced swelling (CFTR activation) of individual cells of F508del (RC202) CF bronchospheres over a 20 hour time period. FIG. 22C is a graph of the Forskolin-induced swelling (CFTR activation) of individual cells of corrected F508del (2-1-20) CF bronchospheres over a 20 hour time period. FIG. 22D is a graph of the comparison of Forskolin-induced swelling (CFTR activation) of individual cells of F508del (RC202) CF bronchospheres vs. the corrected F508del CF bronchospheres over a 20 hour time period, showing that the corrected had an increase in normalized area over the 20 hr time period.

FIG. 25A is a schematic diagram depicting directed differentiation protocol for differentiating hESC or iPSC into NKX2-1+ lung epithelial progenitors via a definitive endoderm intermediate, then an anterior foregut endoderm intermediate using defined medias in a stepwise, stage-specific approach. FIG. 25B shows results of single cell RNA sequencing at day 15 showing NXK2-1+/SOX9+ distal lung bias. FIG. 25C shows results from FACs sorting that 55.5% of the NXK2-1+ population are NXK2-1+/SOX2+. FIG. 25D shows immunostaining for NKX2-1 and SOX2, showing NXK2-1+/SOX2+ cells.

FIG. 26A shows increase in expression of P53 activated genes as cells become 15 day NKX2-1+ lung progenitor cells. FIG. 26B shows increase in expression of hedgehog (SSH) activated genes as cells become 15 day NKX2-1+ lung progenitor cells. FIG. 26C shows increase in expression of Notch activated genes as cells become 15 day NKX2-1+ lung progenitor cells. FIG. 26D shows increase in expression of Wnt/β-catenin activated genes as cells become 15 day NKX2-1+ lung progenitor cells. This demonstrates that in Day 15 NKX2-1+ lung progenitor cells, at least 4 different pathways; P53 signaling, Notch signaling, Hedgehog signaling, and Wnt/β-catenin are active, and it is not certain which pathway in human cells is necessary for differentiation along the proximal pathway to generate airway NXK2-1/SOX2+ epithelial cells.

FIG. 27A is a shematic of assessing the effect of BMP and TGFβ pathways from Day 15 to Day 19. FIG. 27B shows SOX2, SOX9 and SCGB3A2 expression in the presence CHIR (Wnt activation) or absence of CHIR (Wnt withdrawal), in the presence or absence of any of BMP4, FGF10 or FGF2, Dorsomorphin (Dorso; a BMP4 inhibitor), showing that BMP4 signalling contributes to distal patterning by increasing expression of SOX9 and decreasing expression of SOX2, whereas inhibition of BMP4 (using Dorsomprphin) increased SOX2 and SCGB3A2 expression and decreased SOX9 expression and contributed to differentiation along the proximal differentiation pathway to airway epithelial cells. FIG. 27C shows SOX2, SOX9 and SCGB3A2 expression in the presence CHIR (Wnt activation) or absence of CHIR (Wnt withdrawal), also in the presence of TGFβ signaling, showing that TGFβ signaling manipulations had no interpretable effect on marker expression.

DETAILED DESCRIPTION OF THE DISCLOSURE

Figure 1A:
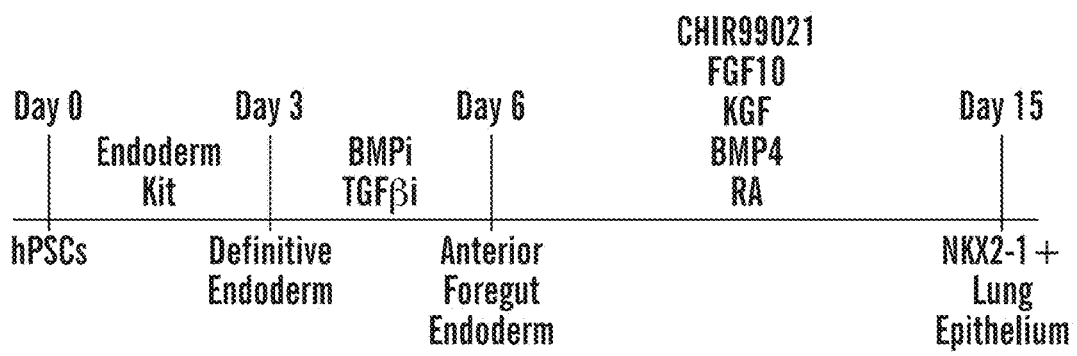
FIGS. 1A-1E show Wnt and BMP4 signaling contribute to proximodistal patterning of hPSC-derived lung progenitors.

The technology as described herein generally relates to methods, compositions and kits for modulating Wnt signaling in human NKX2-1 lung epithelial progenitors in vitro to direct their differentiation along a proximal or distal differentiation pathway. More particularly, one aspect of the present invention is directed to sorting iPSC-derived NKX2-1 lung progenitors based on expressing $CD47^{hi}/CD26^{lo}$ markers, and directed differentiation of these along airway lung lineages using Wnt withdrawal (or a "low-Wnt" media or a Wnt inhibitor) which promotes proximal, over distal, epithelial fates from primordial NKX2-1+ progenitors. These airway organoids, herein referred to "bronchospheres", can be used in drug screening assays, e.g., for the treatment of CF. Accordingly, one aspect of the present invention relates to the use of such bronciospheres in assays and screens to identify candidate drugs for the treatment of CF and/or to study restorative CF mutations.

Accordingly, the technology described herein is based on the inventors discovery of methods for directed differentiation of human iPSCs via an NKX2-1+ progenitor intermediate into functional proximal airway organoids in response to cyclical modulation of the canonical Wnt signaling pathway. In particular, the inventors discovered that human NKX2-1+ progenitors are produced using high levels of Wnt activation, but importantly, rapidly respond to decreases in Wnt signaling (i.e., Wnt withdrawal and/or Wnt inhibition) by differentiating into proximal airway lineages at the expense of distal fates. Stated a different way, the inventors have discovered that at a precise stage in lung development, when the cells exist as a NXK2-1 lung epithelial progenitor intermediate, they respond to bimodal Wnt signaling, where Wnt withdrawal (or Wnt inhibition) results in the cells differentiating along a proximal differentiation pathway to become NXK2-1+/SOX2+ cells airway epithelial cells, whereas sustained Wnt activation results in the cells differentiating along a distal differentiation pathway to become NXK2-1+/SOX9+ cells epithelial cells. Importantly, the inventors have demonstrated that this carefully regulated control of Wnt signaling can be used to differentiate human NXK2-1 lung epithelial progenitor intermediates derived from iPSC or ESCs in vitro, allowing the development of airway epithelial cells for use in research purposes and/or cell-based therapeutic strategies for pulmonary diseases.

Based on this precise and controlled Wnt signaling during a narrow developmental window of lung competence, the inventors demonstrated the generation of functional cystic fibrosis patient-specific iPSC-derived airway organoids that exhibit quantitative CFTR-dependent forskolin-induced swelling following CFTR gene editing. Accordingly, some aspects of the technology described herein relates to the derivation of functional airway organoids from human induced pluripotent stem cells (iPSCs), which can be used in models of lung disease and facilitate precision medicine for monogenic airway disorders, such as cystic fibrosis.

Herein, the inventors demonstrate a human lung developmental model from pluripotent stem cells (PSCs), including iPSC and ESCs. Importantly, the inventors demonstrate that, at a particular timepoint, that is when the human iPSC or ESCs have become NKX2-1+ progenitor intermediates, that Wnt signaling pathway is an over-arching regulator of proximodistal epithelial patterning. Surprisingly, while Wnt activation is required to differentiate the human iPSCs to NKX2-1+ progenitor intermediate cells, at this point the level of Wnt activation and signaling becomes critical to determine if the NKX2-1+ progenitor intermediates differentiate along a distal differentiation pathway or a proximal differentiation pathway. As demonstrated herein, continued Wnt signaling induces the NKX2-1+ progenitor intermediates to differentiate along a distal pathway to become NXK2-1+/SOX9+ cells, and surprisingly, withdrawal of Wnt signaling results in the NKX2-1+ progenitor intermediates to differentiate along a proximal pathway to become NXK2-1+/SOX2+ cells airway epithelial cells. Accordingly, the inventors have discovered a critical bimodal responsiveness of NKX2-1+ progenitor intermediates to Wnt signaling to direct their differentiation either along a distal or proximal differentiation pathway.

Accordingly, the inventors have demonstrated herein a method for directed differentiation of pluripotent stem cells (including, e.g., hiPSCs and hESCs) into functional airway epithelial cells via an NKX2-1+ progenitor intermediate in response to cyclical modulation of developmental signaling pathways. Using genetic mouse models to inform pathway screening during a narrow 4-day window post-lung specification, the inventors demonstrate that tight control of Wnt signaling is important, and that Wnt signaling is a potent and key regulator of proximodistal patterning in human and PSC-derived lung epithelium.

In contrast to the present application, Wnt signaling has been reported only in the development of mice cells occurring in their natural in vivo environment, where such epithelial cells are exposed to the naturally-occurring suite of soluble factors, physiological conditions, including extracellular matrix contacts to assist their development into mature airway cells (see; Bellusci et al., 1997; Cardoso et al., 1997; Chen et al., 2010; 2007; Hashimoto et al., 2012; Hyatt et al., 2004; Mucenski et al., 2003; Sekine et al., 1999; Shu et al., 2005; Y. Wang et al., 2013; Weaver et al., 2000; 1999; Zemke et al., 2009; Zhou et al., 1996). Here, not only are iPSC and ESC-derived NKX2-1 lung progenitors induced to differentiate along proximal differentiation pathways in vitro where they are not exposed to the dynamic and complex signaling pathways that occur in vivo, it is not known if Wnt signaling was could be used in the proximal differentiation of human cells, or human iPSC-derived epithelial cells.

In particular, prior reports have focused only on mouse studies and reported on a requirement for Wnt signaling during the narrow developmental window of lung specification (Goss et al., 2009; Harris-Johnson et al., 2009) followed by alterations in Wnt signaling levels to regulate proximodistal patterning, with Wnt inhibition in mice cells in vivo promoting an increase in proximalization at the expense of distal lineages (Mucenski et al., 2003; Shu et al., 2005; Volckaert et al., 2013). Forced activation of Wnt signaling in mice during mouse lung development in vivo was reported to maintain distal lung progenitor programs while suppressing proximalization(Hashimoto et al., 2012; Li et al., 2009) and block club cell differentiation (Hashimoto et al., 2012). However, oscillations in levels of canonical Wnt signaling has in the developing human airway epithelia has only assessed in vivo (Zhang et al., 2012), where the cells are also in their natural in vivo environment. In contrast to the present invention, Zhang only showed the spatio-temporal expression patterns of Wnt signaling by real time RT-PCR analysis, and did not disclose or demonstrate the precise role Wnt signaling in determining if a lung epithelial progenitor cells progresses along a proximal or distal differentiation pathway. Zhang also do not demonstrate if the Wnt signaling pathway worked independently on proximodistal patterning of lung epithelial progenitors, or if proximal differentiation of epithelial cells was also dependent on other concurrent active pathways, including epithelial-mesenchymal interactions controlled by a number of complex signaling cascades, including bone-morphogenic proteins (BMPs), fibroblast growth factors (FGFs), sonic hedgehog (SHUT) and the wingless-type MMTV integration site family (WNT) which are known to regulate these interactions by the means of autocrine and paracrine processes. Furthermore, and in contrast to the present invention, Zhang do not discuss or disclose the effect Wnt withdrawal for proximal differentiation of lung epithelial progenitor cells, rather Zhang merely disclose that Wnt activation in vivo using CHIR results in airway epithelial cells retarding back from cuboidal to short columnar cells. In contrast to the present invention, Zhang et al., do not demonstrate that precise levels of Wnt signaling (e.g., Wnt withdrawal or inhibition and Wnt activation) are important to control the proximodistal patterning of epithelial cells at a precise developmental stage. That is, Zhang fail to demonstrate or discuss that when the lung epithelial progenitors are at the NKX2-1+ intermediate progenitor stage, absence of Wnt signaling with trigger the cells to differentiate along a proximal differentiation pathway to become airway NKX2-1+/SOX2+ cells, whereas Wnt activation of these NKX2-1+ intermediate progenitor stage cells induces the cells to differentiate along a distal differentiation pathway to become NKX2-1+/SOX9+ cells.

Accordingly, as the process of lung development in vivo is highly complex and relies on the precise coordination of epithelial-mesenchymal interactions, extracellular matrix (ECM) communications, as well as a myriad of multiple intricate pathways of epithelial-mesenchymal interactions controlled by a number of complex signaling cascades, including bone-morphogenic proteins (BMPs), fibroblast growth factors (FGFs), sonic hedgehog (SHUT) and the wingless-type MMTV integration site family (WNT), it is not known if Wnt signaling alone can mediate the proximodistal patterning of epithelial cells in vivo, let alone mediate the proximal differentiation of NKX2-1 lung epithelial progenitors in vitro.

In some aspects relate to a cell line of airway epithelial NKX2-1+/SOX2+ cells differentiated from iPSC-derived, or ESC-derived-NXK2-1+ lung epithelial progenitors (NKX2-1+/CD47$^{hi}$/CD26$^{lo}$ cells). In some embodiments, a population of airway epithelial NKX2-1+ cells can express any one or more of markers selected from SOX2+, SCGB3A2+, TP63+, MUCSAC+ and SCGB1A1. In some embodiments, a population of airway epithelial NKX2-1+ cells comprise one or more of NKX2-1+/SOX2+ cells, NKX2-1+/TP63+ cells, NKX2-1+/TP63+/K5+ cells. In some embodiments, the NKX2-1+ airway epithelial cells do not express at least one or more of the markers of SFTPC, SOX9, or ETV9. In some embodiments, the NKX2-1+ airway epithelial cells as disclosed herein are NKX2-1+/SFTCCPC−/SOX9−/ETV9−. In some embodiments, a population of NKX2-1+ airway epithelial cells are a substantially pure population of NKX2-1+ airway epithelial cells, and comprise less than 15%, or less than 10%, less than 9%, or less than 8%, or less than 7%, or less than 6%, or less than 5%, or less than 4%, or less than 3%, or less than 2%, or less than 1%, of cells that are NKX2-1+/SOX9+ cells, or cells that are NKX2-1+ that also express any one of SFTPC, SOX9 or ETV9.

In some embodiments, the proximal airway NKX2-1+ cells generated using the methods as disclosed herein can differentiate to FOXJ1+/Tubulin+ multiciliated cells in air liquid interface culture or using Notch inhibition. Accordingly, another aspect of the present invention relates to method to differentiate human proximal airway NKX2-1+ cells into multiciliated cells that are positive for the expression of at least markers of FOXJ1+/Tubulin+.

In some embodiments, the low-Wnt media used to direct the differentiation of human iPSC or hESCs-derived NKX2-1 lung epithelial progenitors along a proximal differentiation pathway and into airway epithelial cells comprises FGF2 and/or FGF10. In some embodiments, the low-Wnt media comprises FGF10 at about 10 ng/mL to100 ng/mL. In some embodiments, the low-Wnt media comprises 0 ng/ml FGF10. In some embodiments, the low-Wnt media comprises FGF2. In some embodiments, the low-Wnt media comprises FGF10 at about 0-250 ng/mL. In some embodiments, the low-Wnt media comprises one or more steroids. Exemplary steroids for use include, but are not limited to; dexamethasone, hydrocortisone, cyclic AMP activation. In some embodiments, the low-Wnt media comprises a Rock inhibitor (e.g., Y-27632), for example, at a concentration of about 10 µM, or between about 2-20 µM to promote cell survival post-sorting.

In some embodiments, the airway epithelial cells generated herein by directed differentiation of human iPSC or hESCs-derived NKX2-1 lung epithelial progenitors along a proximal differentiation pathway using either Wnt withdrawal and/or a low-Wnt media can be used for drug screening for patients with genetic lung diseases (e.g. cystic fibrosis, primary ciliary dyskenisia), etc. using in vitro screening assays. In some embodiments, the cells can be used in screening assays to study more complex diseases, such as chronic obstructive pulmonary disease, as well as used in regenerative medicine approaches (e.g. engraftment into lungs or decellularized lung scaffolds) and for cell-based therapies.

Another aspect of the present invention relates to the use of the airway epithelial cells, generated according to the methods as disclosed herein, in an in vitro model of CF. Another aspect of the present invention relates to the use of the airway epithelial cells (i.e., bronchiospheres), generated according to the methods as disclosed herein, in an assay, including a HTS, to identify candidate drugs for the treatment of CF, where the iPSC-derived airway epithelial cells (i.e., bronchiospheres) are differentiated from iPSC obtained from CF patients, and subjected to a forskolin-induced swelling (FIS) assay as described herein, where an agent (e.g., drug) that increases the swelling similar to control bronchospheres (e.g., from healthy subjects) identifies an agent as a candidate CF therapy. In some embodiments, the FIS assay disclosed herein provides a method for personalized CFTR quantification using iPSC-derived airway epithelium derived from individual CF patients in a HTS format. Accordingly, another aspect of the present invention relates to a method for personalized CFTR functional assessment using iPSC-derived bronchospheres from a CF patient, that can be used by academic and/or industry researchers. In some embodiments, the FIS assay as disclosed herein can be used in a precision care of CF patients from infancy to adulthood. Additionally, the FIS assay disclosed herein using iPSC-derived bronchospheres from a CF patient, has the capacity to screen hundreds to thousands of drugs, on a personalized basis, for the treatment of CF.

I. Method for Inhibition of Wnt Signaling.

In some embodiments, methods as disclosed relate to promoting differentiation of human NXK2-1+ lung epithelium progenitors (e.g., NKX2-1+/CD47$^{hi}$/CD26lo) along a proximal differentiation pathway to become airway epithelial cells (e.g., any one of NKX2-1+/SOX2+/SOX9−; or NKX2-1+/P63+/SOX9− or NKX2-1+/P63+/KS+, which can also further express one or more of SCGB3A2+, TB63+, MUCSAC+, SCGB 1A1A+, but does not express SOX9− or TFTPC−) with Wnt withdrawal, or in some embodiments, an inhibitor of Wnt signaling or suppressing the wnt/β-catenin pathway.

In some embodiments, one or more agents are used to inhibit or suppress the wnt pathway, herein termed "wnt inhibitory agents" or "inhibitory agents". In some embodiments wnt inhibitory agents inhibit wnt or homologues thereof, for example wnt3, and in other embodiments, wnt inhibitory agents inhibit components of the wnt/β-canetin-GSK3 pathway, for example but not limited to WLS and DKK1.

Wnt inhibitory agents of the present invention include, but are not limited to, polynucleotides, polypeptides, proteins, peptides, antibodies, small molecules, aptamers, nucleic acids, nucleic acid analogues and other compositions that are capable of selectively inhibiting or suppressing the wnt/β-catenin pathway, or reducing the activity and/or expression of wnt, wnt-dependent genes/proteins and/or β-catenin.

In some embodiments, wnt inhibitory agents useful in the methods of the present invention inhibit and/or suppress the activity of wnt, for example wnt3a. Examples of such wnt inhibitory agents include, but are not limited to, agents that reduce the expression and/or activity of wnt and/or components of the wnt/β-catenin pathway, or induce the expression of repressors and/or suppressors of wnt and/or wnt/β-catenin.

In some embodiments, wnt inhibitor agents directly suppress the expression and/or activity of wnt genes and/or gene products and homologues thereof. Wnt genes include, for example, but are not limited to, Wnt-1, 2A, 2B, 3, 3A, 4, 5A, 5B, 7A, 7B, 8A, 8B, 9A, 9B, 10A, 10B, 11A, and murine Wnt genes, Wnt-1, 2, 3A, 3B, 4, 5A, 5B, 6, 7A, 7B, 8A, 8B, 10B, 11 and 12, the gene or nucleic acid sequences encoding the polypeptides are disclosed in U.S. Pat. Nos. 5,851,984 and 6,159,462, which are incorporated herein by reference in their entirety. In some embodiments, the wnt inhibiting agent comprises an antisense nucleic acid, antisense oligonucleotide, RNAi or other inhibitory molecules directed to one or more or the wnt genes and/or gene products as mentioned above.

In some embodiments, wnt inhibiting agent is a inhibitory nucleic acid, for example an antisense nucleic acid, antisense oligonucleotide (ASO), RNAi, inhibitory or neutralizing antibodies or other inhibitory molecules directed to Wnt3A gene and/or Wnt3A gene product or a modified version, homologue or fragment thereof, for example, but not limited to SEQ ID NO:4 (GenBank accession # NM_009522), SEQ ID NO:5 (GenBank accession # NM_030753); and/or SEQ ID NO:6 (GenBank accession # NM_033131).

In some embodiments, wnt inhibitory agents suppressor are inhibitors and/or inhibitory nucleic acids of essential components of the wnt/β-catenin pathway. Examples include antisense nucleic acids, antisense oligonucleotides (ASO), RNAi, inhibitory or neutralizing antibodies or other inhibitory molecules directed to suppress the Wls/Evi gene or Wls/Evi gene products or homologues thereof. Examples of such a wnt inhibitory agent includes siRNA molecules siWLS-A (SEQ ID NO:1) and siWLS-B (SEQ ID NO:2) as described in the Examples. In alternative embodiments, wnt inhibitory agents can inhibit or be inhibitory nucleic acids to wnt receptors, for example Frizzled receptors and homologues thereof, and alternatively inhibit other essential components of the wnt/β-catenin signaling, including, but not limited to, Dsh (disheveled) LRP-5, LRP-6, Dally (division abnormally delayed), Dally-like, PAR1, β-catenin, TCF, lef-1 and Frodo.

In some embodiments, wnt inhibitory agents can be endogenous suppressors or activate the expression and/or activity of endogenous suppressors of wnt and/or wnt/β-catenin signaling. Such wnt inhibitory agents target endogenous suppressors including, but not limited to, sFRP (secreted frizzled-related proteins), sRFP-1, sFRP-2, collagen 18 (XVIII), endostatin, carboxypeptidase Z, receptor tyrosine kinase, corin, or genetically modified versions, homologues and fragments thereof.

In alternative embodiments, wnt inhibitory agents can be extracellular inhibitors of wnt signaling including, but not limited to, WIF-1, cerberus, Dickkopf-1 (DKK1), Dapper, pertussis toxin, disabled-2 (dab-2), naked cuticle (naked), Frzb-related proteins, FrzA, frzB, sizzled and LRP lacking the intracellular domain and generically modified versions, homologues and fragments thereof. In one embodiment, wnt inhibitory agents that potentiate or enhance sFRP expression are encompassed for use in the present invention, for example expression of Dg1 gene, as discussed in European Patent Application No. EPO 1,733,739, which is incorporated herein by reference in its entirety.

In further aspects, wnt inhibitory agent can inhibit β-catenin, for example, by reducing and/or inhibiting the accumulation of β-catenin in the cytoplasm and/or promoting phosphorylation of β-catenin. In such embodiments, wnt inhibitory agents that inhibit β-catenin include, but are not limited to, protein phosphatase 2 (PP2A), chibby, pontin 52, Nemo/LNK kinase, and HMG homobox factors, for example, XSox17, HBP1, APC, Axin, disabled-2 (dab-2), and grucho (grg).

Alternatively, wnt inhibitory agents useful in the present invention can be agents capable of increasing the activity and/or expression of genes and/or protein that suppress the activity and/or expression of wnt or the wnt/β-catenin pathway including, but not limited to, agents that activate or enhance the activity GSK-3 and/or GSK-3β. For example, wnt inhibitory agents can activate or increase the expression of suppressors of wnt and/or wnt/β-catenin signaling. An example of such an embodiment is activation of GSK-3, for example, wnt inhibitory agents can be agents which dephosphorylate (activate) GSK-3. The GSK-3β polypeptide sequences include, but are not limited to, SEQ ID NO:7 (GenBank accession # NM_002093). In alternative embodiments, the wnt inhibitory agents useful in the present invention that activate GSK3 and/or GSK3β are, for example, agents that trigger PKB-mediated signalling, for example wortannin.

It is encompassed in the present invention that wnt inhibitory agents prevent the wnt/β-catenin signaling in the NKX2-1 lung epithelial progenitor cell that is to be induced to differentiate along a proximal differentiation pathway to a airway epithelial cell as disclosed herein. For example, wnt inhibitor agents can be delivered to the culture media of NKX2-1 lung epithelial progenitor cells, and in some embodiments the wnt inhibitory agent is delivered to the NKX2-1 lung epithelial progenitor cell as a polynucleotide and/or a polypeptide. The polynucleotide can be comprised in a vector, (i.e., a viral vector and/or non-viral vector). For example, viral vectors can include adenoviral vectors, adeno-associated viral (AAV) vectors, retroviral vectors or a lentiviral vector. Alternatively, the wnt inhibitory agent may be delivered to a feeder layer, such that the wnt/β-catenin signaling is inhibited at the level of the feeder layer. In some embodiments, the feeder layer may comprise 'wnt inhibitory agent-producing cells'. In alternative embodiments, wnt inhibitory agents are delivered to the NKX2-1 lung epithelial progenitor cells and/or the feeder layer. In some embodiments, more than one wnt inhibitory agent is delivered to the NKX2-1 lung epithelial progenitor cells and/or feeder layer, and in some embodiments, the wnt inhibitory agents delivered to the NKX2-1 lung epithelial progenitor cells are different from those delivered to the feeder layer. In some embodiments, the expression of a nucleic acid encoding a wnt inhibitory agent is operatively linked to a promoter, and in some embodiments, the promoter is an inducible promoter.

II. Method for the Activation of Wnt Signaling.

Another aspect of the present invention provides methods for promoting the differentiation of human NXK2-1+ lung epithelium progenitors (e.g., NKX2-1+/CD47$^{hi}$/CD26lo) along a distal differentiation pathway to become NKX2-1+/SOX9+ cells) with Wnt activation, or a Wnt activator to induce the activation of of Wnt signaling or the wnt/β-catenin pathway.

In some embodiments, one or more agents are used to activate or enhance the wnt pathway, herein termed "wnt activating agents" or "activating agents" or "Wnt activator". In some embodiments wnt activating agents activate the wnt/β-catenin pathway directly, for example wnt activating agents include wnt or wnt3a or homologues and variants thereof, as well as β-catenin and components of the wnt/β-catenin signaling pathway. In other embodiments, wnt activating agents activate wnt/β-catenin pathway by inhibiting negatively acting components of the wnt/β-canetin-GSK3 pathway. For example, a wnt activating agent can suppress or inhibit the activity and/or expression of wnt/β-catenin endogenous suppressors, for example a wnt activating agent can be an inhibitor of GSK3β.

Wnt activating agents of the present invention include, but are not limited to polynucleotides, polypeptides, proteins, peptides, antibodies, small molecules, aptamers, nucleic acids, nucleic acid analogues and other compositions that are capable of activating or enhancing the wnt/β-catenin pathway, or increasing the activity and/or expression of wnt, wnt-dependent genes/proteins and/or β-catenin. Alternatively, wnt activating agents of the present invention are agents that inhibit the activity and/or expression of genes and/or gene products that suppress the activity and/or expression of wnt or the wnt/β-catenin pathway including, but not limited to, agents that inhibit GSK-3 or GSK-3β, or sFRP, DKK1, WIF-1 etc.

In one embodiment, wnt activating agents activate and/or increase the activity of wnt homologues and/or wnt/β-catenin signaling. In some embodiments, wnt activating agents are a wnt gene and/or wnt gene product, or homologues or genetically modified versions and fragments thereof having wnt signaling activity. Wnt genes and proteins useful as wnt activating agents in the present invention are well known to a person of ordinary skill in the art, and include, for example, human and mouse wnt genes, wnt homologues and fragments and genetically modified versions thereof that have wnt signaling activity. Wnt genes include, but are not limited to human Wnt-1, 2A, 2B, 3, 3A, 4, 5A, 5B, 7A, 7B, 8A, 8B, 9A, 9B, 10A, 10B, 11A, and murine Wnt genes, Wnt-1, 2, 3A, 3B, 4, 5A, 5B, 6, 7A, 7B, 8A, 8B, 10B, 11 and 12. Gene or nucleic acid sequences encoding the polypeptides are disclosed in U.S. Pat. Nos. 5,851,984 and 6,159,462, which are incorporated herein by reference in their entirety. In some embodiments, the wnt activating agent comprises one or more wnt gene and/or gene product as mentioned above. In some embodiments, the wnt activating agent is Wnt3A gene or Wnt3A gene product or a modified version, homologue or fragment thereof, that has wnt signaling activity, including, but not limited to SEQ ID NO:4 (GenBank accession # NM_009522), SEQ ID NO:5(GenBank accession # NM_030753); and/or SEQ ID NO:6 (GenBank accession # NM_033131). Other wnt activating agents that activate wnt/β-catenin signaling can be used, for example compositions listed and discussed in U.S. Pat. Nos. 5,851,984 and 6,159,462 which are incorporated herein by reference in their entirety.

In alternative embodiments, wnt activating agents include but are not limited to disheveled WLS/Evi, (dsh), LRP-5, LRP-6, Dally (division abnormally delayed), Dally-like, PAR1, β-catenin, TCF, lef-1 and Frodo or homologues or genetically modified versions thereof that retain wnt activating activity. In some embodiments, wnt activating agents are inhibitory molecules to endogenous extracellular inhibitors of wnt/β-catenin signalling, for example inhibitors that inhibit their activity and/or expression, for example inhibitory nucleic acid of WIF-1, cerberus, Dickkopf-1 (DKK1), Dapper, pertussis toxin, disabled-2 (dab-2), naked cuticle (naked), Frzb-related proteins, FrzA, frzB, sizzled sFRP (secreted frizzled-related proteins), sRFP-1, sFRP-2, collagen 18 (XVIII), endostatin, carboxypeptidase Z, receptor tyrosine kinase, corin etc.

In further aspects, writ activating agents trigger wnt/β-catenin signaling by activating and/or increasing the activity of β-catenin, for example, that stabilize and/or increase cytosolic accumulation of β-catenin and/or inhibit its phosphorylation. In some embodiments, wnt activating agents are β-catenin gene and/or β-catenin gene product, or homologues, genetically modified version or fragments thereof that retain wnt activating activity. β-catenin gene and gene product are known to persons of ordinary skill in the art, and include but are not limited to SEQ ID NO:8 (which corresponds to SEQ ID NO: 1 in U.S. Pat. No. 6,465,249, which is incorporated in its entirety by reference. In some embodiments, wnt activating agents are stabilized versions of β-catenin, for example versions where serine residues of the GSK-3β phosphorylation consensus motif of β-catenin have been substituted, resulting in inhibition of ubiquitination and stabilization of the protein. Examples of stabilized β-catenins include, but are not limited to those with the amino acid changes D32Y; D32G; S33F; S33Y; G34E; S37C; S37F; T411; S45Y; and deletion of AA 1-173 relative to human β-catenin. A number of publications describe stabilized β-catenin mutations, for example, see Morin et al., 1997; Palacios et al., 1998; Muller et al., 1998; Miyoshi et al., 1998; Zurawel et al., 1998; Voeller et al., 1998; and U.S. Pat. No. 6,465,249, etc., which are incorporated herein in their entirety by reference. In alternative embodiments, other wnt activating agents that activate β-catenin can be used, for example compositions discussed in U.S. Pat. No. 6,465,249, which is incorporated herein in its entirety by reference.

In alternative embodiments, wnt activating agents are any β-catenin binding partners that increase the stability of β-catenin and/or promote β-catenin localization in the nucleus. In alternative embodiments, wnt activating agents include, but are not limited to Frodo, TCF, pitx2, Reptin 52, legless (lgs), pygopus (pygo), hyrax/parafbromin, LKBI/XEEK1 or homologues or modified versions or fragments thereof that retain wnt activating activity. In alternative embodiments, wnt activating agents are inhibitors of negative factors, for example inhibitory nucleic acids and/or peptides that inhibit the activity and/or gene expression of, for example but not limited to APC, Axin, dab-2, grucho, PP2A, chibby, pontin 52, Nemo/LNK kinases etc.

In another embodiment, wnt activating agents useful in the present invention are inhibitors of GSK-3 and/or GSK-3β. Examples of inhibitors of GSK-3 inhibitors include but are not limited to BIO (6-bromoindirubin-3'oxime), acetoxime analogue of BIO, 1-azakenpaullone or analogues or modified versions thereof, as shown in the Examples. In some embodiments, wnt activating agents can be substrate competitive GSK3 peptides, for example the cell permeable substrate competitive GSK3 peptide (SEQ ID NO:3) as discussed in the Examples. Any agent which inhibits GSK3β is potentially useful as a wnt activating agent in the methods described herein, and includes, for example lithium, LiCl, Ro31-8220, as disclosed in International Patent Application No: PCT97/41854, which is incorporated herein in its entirety by reference, and retinoic acid.

In alternative embodiments, other wnt activating agents that inhibit GSK-3 can be used, for example compositions disclosed in U.S. Pat. No. 6,411,053, which is incorporated herein by reference in its entirety. The present invention also encompasses all GSK-3 inhibitors, including those discovered as GSK-3 inhibitors by the methods disclosed in International Patent Application No: PCT97/41854, which is incorporated herein in its entirety by reference.

It is encompassed in the present invention that wnt activating agents activate or enhance Wnt/β-catenin signaling in the NKX2-1 lung epithelial progenitor cells. For example, wnt activating agents can be delivered to the culture media of the NKX2-1 lung epithelial progenitor cells, and in some embodiments the wnt activating agent is delivered to the the NKX2-1 lung epithelial progenitor cells as a polynucleotide and/or a polypeptide. The polynucleotide can be comprised in a vector, (i.e., a viral vector and/or non-viral vector). Examples of the viral vectors include, but are not limited to adenoviral vectors, adeno-associated vectors, retroviral vectors or lentiviral vectors. Alternatively, wnt activating agents may be delivered to a feeder layer, such that the wnt/β-catenin signalling is promoted in the feeder layer. In one embodiment, the feeder layer may comprise 'wnt activating agent-producing cells'. In alternative embodiments, wnt activating agents are delivered to the NKX2-1 lung epithelial progenitor cells and/or the feeder layer. In some embodiments, more than one wnt activating agent is delivered to the NKX2-1 lung epithelial progenitor cells and/or feeder layer, and in some embodiments, the wnt activating agents delivered to the NKX2-1 lung epithelial progenitor cells are different from those delivered to the feeder cell layer. In some embodiments, the wnt activating agent can be encoded in a nucleic acid operatively linked to a promoter, and in some embodiments the promoter is, for example, a tissue-specific promoter, or an inducible promoter, or regulated by SOX9+ expression.

III. Sources of Stem Cells for Generation of Airway Epithelial Cells

In some embodiments, NKX2-1 lung epithelial progenitor cells (i.e., NKX2-1+/CD47$^{hi}$/CD26$^{lo}$) which are differentiated into airway epithelial cells according to the methods disclosed herein, can be derived from human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670, 372, 5,690,926 5,843,780, 6,200,806 and 6,251,671 the disclosures of which are incorporated herein in their entireties by reference.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

Human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used. Stem cells are maintained in culture in a pluripotent state by routine passage until it is desired that they be differentiated into definitive endoderm then ultimately to endocrine precursor cells and/or pancreatic islet hormone-expressing cells.

In some embodiments, NKX2-1 lung epithelial progenitor cells which are differentiated into airway epithelial cells according to the methods disclosed herein, can derived from reprogrammed cells, e.g., induced pluripotent stem cells (iPS cells) derived from differentiated or somatic cells. In such an embodiment, the iPS cells can be derived from, for example, but not limited to, neoplastic cells, tumor cells and cancer cells. Such an embodiment is useful in identifying and/or isolating and/or studying cancerous cells and tumor cells. In some embodiments, the de-differentiated cells are from a subject, and in some embodiments, the de-differentiated stem cells are obtained from a biopsy, e.g., a patient with CF.

In some embodiments, an iPS cell used for generation of NKX2-1 lung epithelial progenitor cells which are differentiated into airway epithelial cells according to the methods disclosed herein, can be produced by any method known in the art can be used, for example virally-induced or chemically induced generation of iPS cells are described in Mauritz et al., Circulation. 2008; 118:507-517, and disclosed in International Application WO2008/088882, EP1970446, US2009/0047263, 052009/0068742, and 2009/0227032, which are incorporated herein in their entirety by reference.

iPS cells can also be generated using other methods commonly known in the art, such as, including but not limited to uses of non-viral methods, polycistronic vectors, mRNA species, miRNA, and proteins, including International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/

0112693, US2010/07542, US2009/0246875, US2009/0203141, US2010/00625343, US2009/0269763, which are incorporated herein in their entirety by reference.

In some embodiments, the NKX2-1 lung epithelial progenitor cells which are differentiated into airway epithelial cells according to the methods disclosed herein are generated from stem cells, preferably adult stem cells, more preferably adult stem cells expressing Lgr5 (Barker et al., Cell Stem Cell 7, 656 2010, WO2010/090513, WO2012/168930 and Sato et al., GASTROENTEROLOGY 2011; 141:1762-1772). In preferred embodiments, the NKX2-1 lung epithelial progenitor cells which are differentiated into airway epithelial cells according to the methods disclosed herein are generated and maintained using the culture media and methods described in WO2010/090513, WO2012/168930 and/or Sato et al., GASTROENTEROLOGY 2011; 141:1762-1772.

In another embodiment, NKX2-1 lung epithelial progenitor cells which are differentiated into airway epithelial cells according to the methods disclosed herein, can be isolated from tissue including solid tissues (the exception to solid tissue is whole blood, including blood, plasma and bone marrow) which were previously unidentified in the literature as sources of stem cells. In some embodiments, the tissue is lung tissue. In other embodiments, the tissue is for example but not limited to, umbilical cord blood, placenta, bone marrow, or chondral villi.

IV. Forskolin-Induced Swelling (FIS) Assay Using Airway Epithleial Cells

Another aspect relates to use and implantation of the human airway epithelial cells as disclosed herein in an animal model to generate human airway lung tissue, and more particularly, the production of an in vivo humanized model of airway diseases. One embodiment relates to the use of the human airway epithelial cells as disclosed herein in an assay, for example to assess drug toxicity and/or identify agents which increase and decrease airway function, or increase CFTR function, for example, increase CFTR function of human airway epithelial cells from a subject with cystic fibrosis. Another embodiment relates to the therapeutic use of human airway epithelial cells, for example, in one embodiment the invention provides methods for the treatment cystic fibrosis in a subject comprising transplanting into subjects human airway epithelial cells, as disclosed herein, and, in some instances, where the human airway epithelial cells are derived from iPSCs from a subject with CF, where the genetic lesion in the CTFR gene is corrected, e.g., using ex vivo gene editing method commonly known in the art.

Another aspect of the technology described herein relates to use of the airway epithelial cells described herein in a forskolin-induced swelling (FIS) assay, where the assay can be used to select an agent that increases CTFR function. In some embodiments, the assay comprising: (a) contacting a population of airway epithelial cells with forskolin and a candidate agent, wherein the airway epithelial cells are any of: NKX2-1+/SOX2+ cells, NKX2-1+/P63+ cells or NKX2-1+/P63+/K5 cells, (b) measuring the size of each airway epithelial cell at a first timepoint, where the first timepoint is prior to, or shortly after the airway epithelial cells are contacted with the forskolin and candidate agent, (c) culturing the airway epithelial cells for a pre-defined period of time, (d) measuring the size of each airway epithelial cell at a second timepoint, or a plurality of timepoints during the pre-defined period of time, wherein the second timepoint or plurality of timepoints is after the first timepoint, (e) calculating the difference in the size of each airway epithelial cell measured at the second, or plurality of timepoints as compared to the first timepoint, and determining the average change in size of each airway epithelial cell in the population of airway epithelial cells, and (f) selecting the candidate agent as an agent that increases CFTR function where the average size of each airway epithelial cell is increased as compared to the average size of each airway epithelial cell in the absence of the candidate agent, or in the presence of a control candidate agent.

In some embodiments, the population of airway epithelial cells used in the assay are in the form of an airway organoid, also referred to as a "bronchosphere" herein. The term "airway organoid" or "bronchosphere" are used interchangeably herein, and refers to an in vitro collection of airway epithelial cells which are any of: NKX2-1+/SOX2+ cells, NKX2-1+/P63+ cells or NKX2-1+/P63+/K5 cells and which resemble their in vivo counterparts and form 3D structures. Thus the assay as disclosed herein is an ex vivo or an in vitro assay.

In some embodiments, the assay relates to a forskolin-induced swelling assay as disclosed in US application 2015/0276719, which is incorporated herein in its entirety by reference, where the cells used in the assay are airway epithelial cells as disclosed herein, which express any of: NKX2-1+/SOX2+ cells, NKX2-1+/P63+ cells or NKX2-1+/P63+/K5 cells. Of note, the 2015/0276719 discloses a variety of different organoids to be used in the FIS assay, however, in contrast to the present application, the '719 application does not teach use of organoids comprising airway epithelial cells which express any of: NKX2-1+/SOX2+ cells, NKX2-1+/P63+ cells or NKX2-1+/P63+/K5 cells.

In some embodiments, the measuring the size of the bronchospheres (e.g., airway epithelial organoids) as disclosed herein, is measuring the swelling of the one or more bronchospheres, and comprises measuring a change in size, such as a change in surface area, diameter and/or volume, and/or wherein the swelling comprises a change in content of the bronchosphere.

Accordingly, the extent of the bronchosphere swelling can be determined by measuring the change in size or the change in content of the one or more bronchospheres in the assay. The "change" may refer to the difference when a normal bronchosphere is compared to a disease bronchosphere and/or when a control bronchosphere is compared to an bronchosphere that has been stimulated by one or more drug or compound. Alternatively, the "change" may refer to the difference in swelling of an bronchosphere before and after stimulation with a drug and/or compound.

Thus in some embodiments, the change in size and/or the change in content is the change in size compared to a healthy control bronchosphere. In some embodiments, the healthy control bronchosphere is similar or substantially identical to the disease bronchosphere, except that it does not have the disease of interest. For example, in a preferred embodiment, the control and disease bronchosphere are derived from related subject, for example, where the control does not have a mutation or genetic lesion in the CFTR gene (can be a healthy control subject or the mutation been corrected by genetic modification), and the disease bronchosphere has a genetic lesion in the CFTR gene, or alternatively, obtained from a subject whom has a symptom of CF. It would be understood by the skilled person that the organoids are preferably the same "age", i.e. the cells have been cultured and/or passaged a similar number of times and/or the starting size is substantially the same.

In an alternative embodiment, the change in size and/or the change in content is the change in size compared to a control bronchosphere that has not been stimulated with the one or more drugs. In a preferred embodiment, the control bronchosphere is similar or substantially identical to the bronchosphere that been stimulated with the one or more drugs, except that it has not been stimulated with the one or more drugs. For example, in a preferred embodiment it is derived from the same tissue type. It would be understood by the skilled person that the organoids are preferably the same "age", i.e. the cells have been cultured and/or passaged a similar number of times and/or the starting size is substantially the same.

In some embodiments, the change in bronchosphere size may occur concurrently with a change in the diameter or volume of the lumen. However, one of the advantages of the assay of the invention is that it allows the bronchosphere size, rather than the lumen size to be used as an indication of healthy versus diseased versus successfully treated bronchosphere. In some embodiments, the assay disclosed herein involves observation of swelling of the bronchosphere themselves, which is advantageous because overall bronchosphere size (e.g. diameter/volume/surface area) is far easier to measure, including for example, use automated quantification methods to determine overall changes in bronchosphere size, which is encompassed for use in the methods disclosed herein.

Accordingly, a change can be assessed by manual or automated measurement of the bronchosphere, as described below.

In some embodiments, measuring comprises quantitatively measuring the change in size of the bronchosphere. By change in size, it is meant that there is a change in the surface area and/or diameter and/or volume of the organoid. In some embodiments, the change in size will be a change of at least 1%, at least 2%, at least 5%, at least 10%, at least 20%, at least 50% or more of the surface area and/or diameter and/or volume of the bronchosphere. In some embodiments, the change in size is a change of at least 2-fold, at least 3-fold, at least 4-fold, at least 5-fold, at least 6-fold at least 7-fold, at least 10-fold, at least 20-fold or more of the surface area and/or diameter and/or volume of the bronchosphere. The change can be an increase in size (enhanced swelling) or a decrease in size (reduced swelling).

In other embodiments, measuring comprises observing the bronchosphere swelling. This may involve, for example, determining the change in content of the bronchosphere. By change in content, it is meant that the content or structure of the bronchosphere changes. In some embodiments, the change in content is characterised by a change in bronchosphere shape (e.g. more ball-like or more folded or less ball-like or less folded); change in cell size and stretching and/or change in internal pressure and/or rigidity. Thus in some embodiments, measuring the change in content or structure comprises observing whether the bronchosphere becomes more or less folded, or for example, determining whether an bronchosphere of interest (a disease bronchosphere or a drug-treated bronchosphere, respectively) is larger or smaller than a control bronchosphere (e.g. a healthy bronchosphere or a non-drug treated bronchosphere, respectively). In some embodiments, if there is reduced swelling, observing the swelling may involve determining whether it becomes more deflated and folded. Change in content and structure can also be quantitatively measured.

In some embodiments, the bronchosphere swelling can be visibly observed such that one or more of the features described above can be seen. It is to be understood that "visibly" does not require visibility using the naked eye, but includes, for example, the use of microscopy, imaging and/or staining techniques.

Various techniques known in the art could be used to determine organoid size or content. In some embodiments, the bronchosphere size or content is determined using live cell imaging, for example using a microscope, such as a confocal microscope. In some embodiments the bronchospheres are stained prior to imaging to improve the contrast of the image. In a further embodiment the bronchospheres are stained with cell-permeable dyes that optionally fluoresce upon metabolic conversion by living cells e.g. Cell Tracker-Orange, Cell Tracker-Green, Calcein-Green (all available commercially from Invitrogen). In one embodiment, the organoids are stained with Calcein-Green, optionally at approximately 10 µM for approximately 60 minutes. Thus in some embodiments the assay of the invention comprises the step of staining the organoids e.g. by incubation with a staining agent.

In some embodiments, the change in size of the bronchosphere can be quantified, for example using imaging software such as "Volocity quantification software". In some embodiments, the total bronchosphere area increase relative to T=0 (time of stimulation) is calculated and optionally averaged from multiples. The area under the curve (AUC) can be calculated, for example using Graphpad Prism, to show the change in area of the bronchosphere.

In some embodiments, the assay is a high-throughput screen (HTS) assay. For example, in some embodiments, organoids are cultured in an array format, for example in multiwell plates, such as 96 well plates or 384 well plates. In some embodiments, computer- or robot-assisted culturing and data collection methods are employed to increase the throughput of the screen.

In some embodiments, the population of airway epithelial cells used in the assay are differentiated from human iPSC or ESCs obtained from a subject with CF, or comprise a mutation (i.e, a genetic lesion) in the CFTR gene that is responsible for CF in a subject. In some embodiments, the airway epithelial cells used in the assay is obtained from a patient biopsy. In some embodiments, the candidate molecule that causes a desired effect on the bronosphere is administered to the patient.

In some embodiments, the surface area of each airway epithelial cell is measured at a first timepoint, or second timepoint or a plurality of subsequent timepoints, for example, by imaging the population of airway epithelial cells and using software to calculate the size (e.g., surface area) of each epithelial cell a first timepoint, or second timepoint or plurality of subsequent timepoint. Such imaging can be done with an automated high-definition microscope, and optionally connected to a computer, where software can be used to calculate the change in the size (e.g., surface area) of each cell measured at each timepoint over the pre-defined period of time. In some embodiments, the assay comprises a step of contacting the population of airway epithelial cells with a marker, such as a fluorescent marker prior to measuring the size of the cells. An example of such a marker is calcein green. In some embodiments, the size of each airway epithelial cell is measured at frequent intervals over a pre-defined period of time, selected from any of: between 6-12 hours, between 12-24 hrs, between 24-36 hrs, between 36-48 hours, or more than 48 hours, and optionally, the regular intervals (i.e., plurality of timepoints when the size of each airway epithelial cell is measured) is selected from intervals of any of: 10 minutes, or 15 minutes, or 20 minutes, or 30 minutes, or 60 minutes or 90 minutes, or 120 minutes during the pre-defined time period.

In some embodiments, the bronchosphere s may undergo rapid swelling, (e.g. in response to stimulation by drugs or compounds) that can be detected within hours, minutes or even seconds. Thus, in some embodiments of the assay, the bronchosphere swelling is measured for a pre-defined period of time, e.g., where the pre-defined period of time can be, e.g., less than 48 hours, less than 36 hours, less than 24 hours, less than 18 hours, less than 12 hours, less than 6 hours, less than 1 hour, less than 45 minutes, less than 30 minutes, less than 15 minutes, less than 10 minutes, less than 9 minutes, less than 8 minutes, less than 7 minutes, less than 6 minutes, less than 5 minutes, less than 4 minutes, less than 3 minutes, less than 2 minutes, less than 1 minute or less than 30 seconds.

In some embodiments, the bronchospheres may undergo slow swelling, (e.g. when determining the difference between a diseased and normal bronchosphere which have not been stimulated by drugs or compounds) that can be detected within weeks or days. Thus, in some embodiments of the assay, the bronchosphere swelling is measured for a pre-defined period of time, e.g., where the pre-defined period of time is less than 4 weeks, less than 3 weeks, less than 2 weeks, less than 1 week, less than 6 days, less than 5 days, less than 4 days or less than 3 days.

Forskolin, which is known to raise intracellular cAMP and thereby activate the cystic fibrosis transmembrane receptor (CFTR) results in enhanced organoid swelling, presumably owing to increased fluid uptake into the organoid lumen. The effect is CFTR-dependent, as demonstrated using CFTR-inhibitors which prevent forskolin-induced swelling. Thus, in some embodiments, the bronchospheres in the assay are stimulated by forskolin, or other CFTR activators, enhance the swollen phenotype seen in normal bronchospheres and also enhance swelling in successfully treated disease bronchospheres. This effect can be used to enhance the "change" in size or content of the bronchosphere measured in the assay of the invention and to achieve rapid bronchosphere responses, which could be useful for rapid diagnosis, drug testing or personalised medicine.

Forskolin is a labdane diterpene, with the chemical formula C22H34O7, that is produced by the Indian Coleus plant. Thus it is a small-molecule inhibitor with a molecular mass of 410.5 g/mol. Its UPAC IC is: (3R,4aR,5S,6S,6aS,10S,10aR,10bS)-6,10,10b-trihydroxy-3,4a,7,7,10a-pentamethyl-1-oxo-3-vinyldodecahydro-1H-benzo[f]chromen-5-yl acetate. Forskolin is commonly used to raise levels of cyclic AMP in the study and research of cell physiology. In some embodiments, the assay comprises contacting the population of airway epithelial cells with 5-10 µM of forskolin, or more than 10 µM of forskolin.

Salbutamol, epinephrine, ritodrine, dopamine and cholera toxin have been shown to have a similar effect to Forskolin on bronchosheres as disclosed herein, therefore, in some embodiments, forskolin can be replaced with any one of Salbutamol, epinephrine, ritodrine, dopamine or cholera toxin, which can cause human bronchosphere to more than double in size in the space of 120 minutes.

In some embodiments, the assay comprises stimulation of the one or more bronchospheres with a compound which is capable of inducing a change in size of the bronchospheres, wherein the compound indirectly activates the CFTR, for example via the cAMP-PKA pathway. In some embodiments, the compound is forskolin, salbutamol, epinephrine, ritodrine, dopamine or cholera toxin.

In some embodiments, the compound is a G-coupled protein receptor (GCPR) that enhances cAMP levels. In some embodiments, the compound is a small-molecule that enhances cAMP levels, for example forskolin. In some embodiments, the compound is a diterpene or diterpenoid, optionally a ladane diterpene and/or a forskolin-like diterpene of diterpenoid as described, for example, in Rijo P et al. (Magn Reson Chem. 2005 July; 43(7):595-8).

All reagents associated with modulation of fluid secretion or absorption by modulating cellular signaling that is generally accepted to regulate CFTR ion channel function. These include modulators of cAMP, cGMP, protein kinase A, protein kinase C, phosphorylation of CFTR and CFTR ATP-ase activity.

In some embodiments, the compound is a cAMP-generating compound, such as an adrenergic receptor stimuli. Examples of adrenergic stimuli include but are not limited to isoproperenol, salbutamol, epinephrine; prostaglandine E2, VIP, and substance P. In some embodiments, the compound is a cGMP generating compound, such as a guanylin or bile acid. In some embodiments, the compound is an inhibitor of phosphodiesterases, for example milrinone, IBMX, sildenafil (Viagra). In some embodiments, the compound is a calcium modulators, for example, ionomycin, acetyl choline or carbachol. In some embodiments, the compound is a modulator of cellular signalling, such as PI3K, Syk or p38. In some embodiments, the compound is a modulator of CFTR folding and trafficking, for example Vertex-809 and Vertex-661, SAHA, miRNA-138. In some embodiments, the compound is an epigenetic modulator, for example, of SAHA or TSA. In some embodiments, the compound is a modulator of CFTR expression, such as miRNA-138, IL-1, TNF-alpha, or p38 regulator. In some embodiments, the compound is a modulator of CFTR degradation, such as a proteasome inhibitor including bortezimib or a modulator of endoplasmic reticulum associated degradation via ubiquitin-dependent pathways. In some embodiments, the compound is a CFTR inhibitor adapted from J R Thiagarajah et al. (Clin Pharmacol Ther, 2012 CFTR Inhibitors for Treating Diarrheal Disease), for example one of the compounds DPC, NPPB, BPD-27, thiazolidine, PPQ-102, disclosed in US application US2015/0276719, or any of the other compounds disclosed in US application US2015/0276719, which is incorporated in its entirety by reference herein.

In some embodiments, forskolin can be substituted with any suitable compound that can be used to stimulate the one or more bronchospheres in the assay as disclosed herein. For example, all reagents associated with modulation of fluid secretion or absorption by modulating cellular signalling may be used to stimulate the one or more bronchospheres in the assay of the invention. Examples of compounds which may be used to stimulate lie one or more bronchospheres in the assay of the invention include modulators of cAMP, cGMP, protein kinase A, protein kinase C, phosphorylation of CFTR and CFTR ATP-ase activity. For example, other compounds which activate the CFTR and thus could replace forskolin in the assay include cholera toxin and salbutamol and mimics and derivatives thereof.

In some embodiments, the assay comprises stimulation of the one or more bronchospheres with a compound which is capable of inducing a change in size of the bronchospheres, wherein the compound is forskolin or a mimic or derivative thereof. In a further embodiment, forskolin-induced swelling (FIS) of the bronchospheres can be reversed upon removal of forskolin by washing. Similarly, swelling of bronchospheres caused by other compounds can be reversed by washing to remove the compound.

A number of non-CFTR ion channels and other proteins are involved in transferring organic and inorganic substances across cellular membranes at the apical and basolateral membranes, and thus affect fluid secretion or uptake. Thus, in some embodiments the compound indirectly activates the CFTR or another ion channel or regulatory protein involved in the regulation of fluid uptake and secretion. In an alternative embodiment, the compound directly activates the CFTR or another ion channel or regulatory protein involved in the regulation of fluid uptake and secretion.

Ion channels other than the CFTR, and other proteins involved in ion channel regulation in cells, are also important for the regulation of fluid and electrolyte homeostasis in cells. For example, all of the ion channels shown in Tables 1 and 2 of US application 2015/0276719, which is disclosed herein, are involved in the regulation of fluid secretion and uptake in cells. In a further example, the CFTR is predicted to help regulate a number of other ion channels including but not limited to: ORCC, ROMKK+, ENaC, and the Cl−/HCO3− exchanger. Modulators of these ion channels and regulatory proteins, such as the activators and inhibitors listed in Tables 1 and 2 of US application 2015/0276719, (which is disclosed herein) are encompassed for use in the assays disclosed herein in place of forskolin, to enhance or reduce the swelling of bronchospheres. Thus, in some embodiments of the invention, forskolin is replaced in the assay with a compound which is capable of inducing a change in size of the bronchosphere as disclosed herein, either directly or indirectly activates or inhibits any one or more of the ion channels in Tables 1 or 2 of US application 2015/0276719, which is disclosed herein, and/or any one or more of NHE3 ion exchanger, DRA, SGLT1, short-chain fatty acid transporters, ORCC, ROMKK+, ENaC, or the Cl−/HCO3− exchanger.

Accordingly, in some embodiments, the assay disclosed herein, comprises contacting a bronchosphere as disclosed herein with a compound that is capable of inducing a change in size of the bronchosphere, where the compound can be selected from one or more of the activators or inhibitors listed in Tables 1 or 2 of US application 2015/0276719, which is disclosed herein in its entirety by reference.

Accordingly, as described herein, the bronchospheres (i.e., airway organoids comprising a population of airway epithelial cells which are any of: NKX2-1+/SOX2+ cells, NKX2-1+/P63+ cells or NKX2-1+/P63+/K5 cells) can be used in an assay for screening a compound library to identify compounds that affect the fluid uptake and/or secretion, wherein the assay comprises: stimulation of one or more bronchospheres with the compound library; imaging swelling of said one or more bronchospheres; and identifying a compound which is capable of inducing swelling of the bronchospheres.

It is to be understood that any of the compounds listed in this section may be equally applicable as examples of drugs for drug screening and personalised medicine. Conversely, any of the examples of drugs provided in the drug screening and personalised medicine section may be equally applicable as examples of compounds for inducing organoid swelling. One difference that may exist between appropriate compounds for stimulating organoid swelling in the assay versus the drugs that might be tested in the assay is that the compounds typically act upstream of the ion channels and/or proteins that regulate fluid secretion and uptake into a cell and thereby enhance (or reduce) organoid swelling. By contrast, the drugs typically act on and/or downstream of dysfunctional ion channels and/or proteins to correct normal fluid secretion and uptake.

In some embodiments, the bronchospheres (i.e., airway organoids comprising a population of airway epithelial cells which are any of: NKX2-1+/SOX2+ cells, NKX2-1+/P63+ cells or NKX2-1+/P63+/K5 cells) can be used in an in vitro assay as disclosed herein, for diagnosing a disease or affliction that affects fluid uptake or secretion (of bronchospheres and/or airway epithelial cells which are any of: NKX2-1+/SOX2+ cells, NKX2-1+/P63+ cells or NKX2-1+/P63+/K5 cells) or for studying the effectiveness of one or more drugs for treating the disease or affliction, for example, wherein the disease is cystic fibrosis or cholera.

Thus, in one embodiment the invention provides an assay according to the invention wherein the swelling of the one or more bronchospheres is a measure of the effect of CFTR mutation and/or drug treatment. Other diseases or afflictions, in addition to cystic fibrosis and cholera, that are relevant for use with the assay of the invention include, but are not limited to: bacterially induced diarrhea (e.g. enterohemorrhagic *E. coli* or caused by cholera toxins or other bacterial toxins); rotavirus infection; adrenoleukodystrophy; asthma, Tangier disease; multi-drug resistance (many cancers, as well as some antibiotic resistant bacteria); obstetric cholestasis, COPD, smoking, sinusitis, pancreatic insufficiency, pancreatitis, infertility, malnutrition, inflammatory diseases, renal disease including polycystic kidney disease, allergic disease, osteoporosis, diabetics, hypertension, hypotension, pathogen-induced diarrhea (cholera, *E. coli*), 'drying out', liver cirrhosis, malfunction of liver, tumorigenesis. Smoking can reduce CFTR function and thus smoker's cough or other side-effects of smoking are other afflictions that are relevant for use with the assay of the invention.

In some embodiment, the bronchospheres in the assay as disclosed herein have a genetic defect or genetic lesion in the CFTR gene, e.g., as disclosed herein, e.g, CFTR-ΔF508 (also known as CFTR-delF508) CTFR-G551D, CFTR-G542X, CFTR-L927P, CFTR-E60X, CFTR-4015delATTT, CFTR-A455E. In some embodiments, the bronchospheres in the assay as disclosed herein can have a genetic defect or genetic lesion in the CFTR gene as disclosed in Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451), or any of the >1000 disease causing mutations in the CF gene identified and disclosed on the database site at: world-wide-web: genet.sickkids.on.ca/cftr/. In some embodiments, the bronchospheres in the assay as disclosed herein have been genetically modified to correct one or more of these CFTR mutations.

In some embodiments, the bronchospheres (i.e., airway organoids comprising a population of airway epithelial cells which are any of: NKX2-1+/SOX2+ cells, NKX2-1+/P63+ cells or NKX2-1+/P63+/K5 cells) can be used in an in vivo assay, where a population of human airway epithelial cells as described herein are implanted into an animal subject, the animal can be use as an in vivo humanized model of airway diseases. For example, an animal model which comprises a population of human airway epithelial cells as described herein, can be used to screen for agents which affect any one, or a combination of viability, functionality, of the airways in the lung.

Accordingly, one embodiment relates to the use of an in vivo humanized model of lung disease as an assay, for example to assess drug toxicity on human lung tissue in vivo (e.g. to identify agents which increase apoptosis, decrease viability, modulate (e.g. increase or decrease by a statistically significantly amount) the function of lung tissue). In some embodiments, the drugs and/or compounds can be existing drugs or compounds, and in other embodiments, the drugs or compounds can be new or modified drugs and compounds.

In some embodiments, the assay as disclosed herein comprising bronchospheres is a drug screen, where the bronchospheres are derived from one individual patient. In some embodiments, the bronchospheres in the drug screen, for example in the array, are derived from different patients. In other embodiments, the drug screen, for example the array, comprises bronchospheres derived from one or more diseased patients in addition to bronchospheres derived from one or more healthy controls.

Libraries of molecules can be used to identify a molecule that affects the organoids. In some embodiments, libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) natural compound libraries (Specs, TimTec) or small molecule libraries. Furthermore, genetic libraries can be used that induce or repress the expression of one of more genes in the progeny of the stem cells. These genetic libraries comprise cDNA libraries, antisense libraries, and siRNA or other non-coding RNA libraries. The bronchospheres can be exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death.

In some embodiments, the bronchospheres as disclosed herein can be used in the assay to test libraries of chemicals, antibodies, natural product (plant extracts), etc for suitability for use as drugs, cosmetics and/or preventative medicines. For instance, in some embodiments, a cell biopsy from a patient of interest, such as intestinal cells from a cystic fibrosis patient, can be cultured using culture media and methods of the invention and then treated with a drug or a screening library. It is then possible to determine which drugs effectively restore function to the faulty ion channel or other regulatory protein. This allows specific patient responsiveness to a particular drug to be tested thus allowing treatment to be tailored to a specific patient. Thus, this allows a personalized medicine approach, which is described in more detail below.

The added advantage of using bronchospheres for identifying drugs in this way is that it is also possible to screen normal bronchospheres (i.e., airway epithelial cells derived from iPSC obtained from healthy tissue) to check which drugs and compounds have minimal effect on healthy tissue. This allows screening for drugs with minimal off-target activity or unwanted side-effects.

In some embodiments, the assay is for testing the effect of novel drugs on functional restoration of mutant ion channels or other proteins involved in regulating fluid uptake or secretion. In some embodiments, functional restoration comprises restoration of translation, transcription, of gene loci or biological interactors, for treatment of diseases and afflictions associated with fluid uptake or secretion.

Figure 14A:
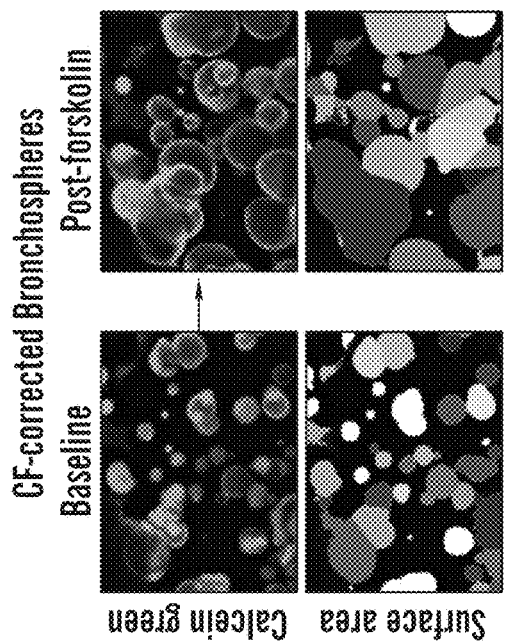
FIGS. 14A-14E show that iPSC-derived broncospheres can be used to measure CFTR function.
Figure 14B:
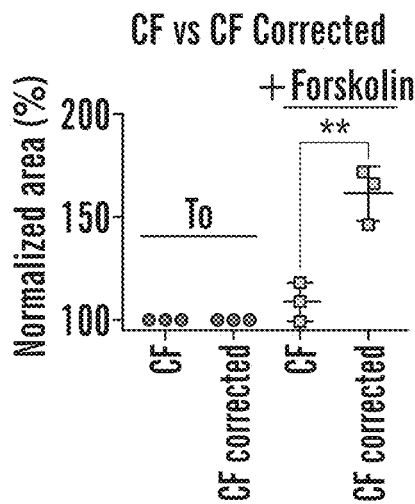
Figure 14C:
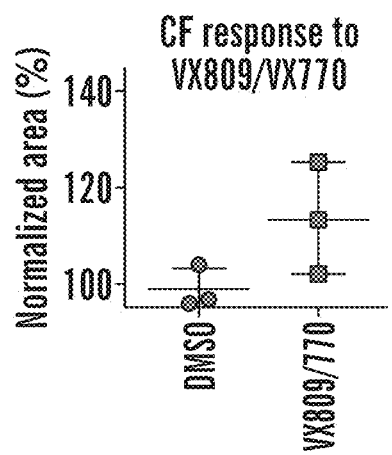

For example, the inventors demonstrated forskolin-induced swelling in CF bronchosheres upon addition of drugs that are known to correct CFTR function in vitro (e.g., VX809/770 in FIG. 14C). Thus, in some embodiments, the assay of the invention can be used to measure the effect of existing or novel treatments for CFTR.

In some embodiments, the invention provides a method or assay using the bronchospheres to test effect of novel drugs to treat CFTR deficiency through CFTR function correction.

The inventors demonstrated forskolin-induced swelling in CF bronchosheres correction of CF mutations (e.g., see FIG. 14B and **).

Therefore, in some embodiments, the assay disclosed herein can be used for testing the effect of novel drugs on functional restoration of mutant CFTR protein, or functional restoration of CFTR translation, transcription, CFTR gene loci or biological interactors of CFTR, for example for treatment of cystic fibrosis or microbial toxins, such as cholera. In some embodiments the drugs are potentiators or correctors.

Functional restoration of CFTR comprises functional restoration of mutant CFTR protein, functional restoration of CFTR translation (e.g. premature stop codons), transcription (e.g. splicing defects), or functional restoration of the CFTR gene (e.g. gene therapy) or the CFTR interactome (some mutations impact protein-protein interactions required for CFTR function).

In some embodiments, the assay for drug screening is for identifying drugs that target mutation-specific defects in ion channels or other proteins involved in regulating fluid uptake or secretion, for example mutation-specific defects of the CFTR protein itself. For example, in some embodiments, the assay for drug screening is for identifying drugs that induce i) premature stop codon readthrough, ii) correction of plasma membrane trafficking of CFTR (correctors), and/or iii) enhance CFTR gating (potentiators). In some embodiments, the assay for drug screening is for identifying combinations of correctors and potentiators, for example for treatment of the CFTR-delF508 dominant patient-group.

In some embodiments, the assay for drug screening comprises stimulation of the one or more organoids with a drug known to treat the disease or affliction of interest, or being tested for its efficacy in treating the disease or affliction of interest, wherein enhancement or reduction of bronchosphere swelling is indicative of an effective drug for treatment of said disease or affliction.

In some embodiments, the drug being tested is selected from a synthetic small molecule, protein, peptide, antibody (or derivative thereof), aptamer and nucleic acid (such as an antisense compound).

In a further embodiment, the assay for drug screening additionally comprises stimulation of the one or more bronchospheres with a compound, such as forskolin, which is capable of enhancing swelling of the bronchospheres. In some embodiments, the assay for drug screening comprises stimulation of one or more organoids with a compound which is capable of inducing swelling of the bronchospheres; stimulation of the one or more organoids with a drug known to affect CFTR function or with a drug being tested for its efficacy in affecting CFTR function; and imaging the swelling of the one or more bronchospheres, and optionally comparing the swelling of the bronchosphere to the swelling of an bronchosphere which has been stimulated with the compound but has not been stimulated with the drug; wherein swelling of the one or more bronchospheres in response to stimulation by the drug indicates that the drug is effective for treatment of functional restoration of mutant CFTR.

In some embodiments, the assay further comprises the step of selecting the effective drug and optionally using said drug for treatment. The invention also provides the use of one or more bronchospheres for drug screening, wherein the drug screening comprises using an assay according to the invention.

Use of the Assay in Personalised Medicine

In some embodiments, the invention provides an assay wherein the bronchospheres are patient derived and comprises stimulation of the one or more bronchospheres with one or more drugs, for example for use in personalised medicine, e.g., use in personalised medicine, for example to test individual patient response to drugs for the disease or affliction of interest.

In some embodiments, the assay comprising patient-derived bronchospheres can be used for testing individual patient response to drugs such as correctors or potentiators or other drugs used to treat CF, for example any of the drugs shown in Table 3 or Table 4 in US application 2015/0276719, which is incorporated herein in its entirety by reference, or CFTR correctors such as VRT-325, VX809, VX770, C8 (http://cftrfolding.org) and corr-4a, or disclosed at e.g., world-wide web at: "cftrfolding.org".

Accordingly, the present invention relates to an in vitro assay to predict in vivo drug-responsiveness of individual patients. An ideal therapeutic model for CF would be to screen effectiveness of available CFTR-restoring drugs directly after CF diagnosis to optimize treatment at the personal level before disease onset. Personalized medicine approaches may also facilitate the development and approval of drugs to which only subgroups of patients respond, and limit the economic risks associated with drug research. Furthermore, the assay of the invention can be used for approval of drugs in patients that are genotypically mismatched with drugs that have been validated for a specific CFTR-genotype. Interim phase II results of a current trial published on websites of the North American Cystic Fibrosis Foundation (www.cff.org) and Vertex (www.vrtx.com) indicate that drug-responses to VX-809 and VX770, or VX-770 monotreatment14, in CFTR F508del subjects are highly variable between patients. Accordingly, in some embodiments, the assay comprising patient-derived bronospheres as disclosed herein can be used for the assessment of the responsiveness to a particular treatment option, wherein the assessment comprises use of an assay according to the invention and wherein bronchosphere swelling is indicative of successful treatment.

Another aspect of the invention relates use of the population of human airway epithelial cells as described herein to screen for agents, for example molecules and genes involved in biological events. In such an embodiment, the biological event is an event that affects the function of the airway epithelial cells.

In another embodiment, a population of human airway epithelial cells as described herein can be used to assess the effect of genetic variation (e.g. ethnicity, human mutations or gene variants or polymorphism) on lung function. For example, the effect of different environmental factors, such as, for example, pollen, pollution, high fat diet, lack of exercise, can be assessed in human lung tissue as described herein, generated from populations of human airway epithelial cells as described herein from different genetic and socio-economic backgrounds. In an alternative embodiment, the effect (e.g. efficacy and/or safety profile) of different therapeutic agents and lung drugs, including asthma related drugs, can be assessed in vivo in an animal model of lung disease comprising a population of human airway epithelial cells as described herein from different genetic backgrounds. Accordingly, in some embodiments, a population of human airway epithelial cells as described herein which are a variant human airway epithelial, for example but not limited to a genetic variant and/or a genetically modified a airway epithelial cells.

In another embodiment, a population of human airway epithelial cells as described herein can be used in an assay for studying the differentiation pathways of airway epithelial cells into multiple downstream lineages, for example but not limited to, secretory cells (e.g., SCGB3A2+, SCGB1A1+, SPB+ cells), multicilliated cells (e.g., FOXJ1+ cells) or basal cells (e.g., P63+, KRT5+ cells) (see e.g., FIG. 5J) human endothelial cell lineages. In some embodiments, the human primordial ISL1+ progenitors can be genetically engineered to comprise markers operatively linked to promoters that are expressed in one or more of the lineages being studied.

In alternative embodiments, the human NKX2-1 lung progenitors used to generate a population of human airway epithelial cells as described herein can comprise a mutation and/or polymorphism that relates to the disease phenotype, and in other embodiments, a population of human airway epithelial cells as described herein been genetically engineered to carry a mutation and/or polymorphism.

Any suitable animal can be used for implanting a population of human airway epithelial cells as described herein, for example, rodents (such as mice, rats), monkeys, pigs and the like. In some embodiments, the subject animal is a transgenic or knockout animal, e.g., a transgenic mice or knock out mice. In some embodiments, the subject animal is a humanized mouse, such as the SCID mouse.

In some embodiments, a population of human airway epithelial cells as described herein is useful as an in vivo assays and screening method to detect agents for the effect of the agent assessed by monitoring output parameters, such as expression of markers, cell viability, differentiation characteristics, multipotenticy capacity and the like.

In some embodiments, the in vivo humanized model of lung disease can be produced by implanting a population of human airway epithelial cells as described herein into an immunodeficient animal (such as nude mice, such as SCID mice, or animals rendered immunodeficient chemically or by irradiation).

In some embodiments, a population of human airway epithelial cells as described herein administered to the subject can express a detectable label (such as green fluorescent protein, or beta-galactosidase); that have been prelabeled (for example, with BrdU or [3H]thymidine), or by subsequent detection of a constitutive cell marker (for example, using human-specific antibody). The presence and phenotype of the administered human airway epithelial cells as described herein can be assessed by immunohistochemistry or ELISA using human-specific antibody, or by RT-PCR analysis using primers and hybridization conditions that cause amplification to be specific for human polynucleotides, according to published sequence data.

The effect of an agent administered to an in vivo humanized model of lung disease can be assessed by the degree of CFTR function or lung function that ensues from inflicting injury or having a mutation in the CFTR gene to the human lung tissue.

A population of human airway epithelial cells for use in an assay as described herein may be freshly isolated, cultured, or frozen and thawed, or genetically engineered as described above, or the like. A population of human airway epithelial cells as described herein may be environmentally induced variants of clonal cultures: e.g. split into independent cultures and grown under distinct conditions, for example with or without virus; in the presence or absence of other cytokines or combinations thereof. Alternatively, a population of human airway epithelial cells as described herein may be variants with a desired pathological characteristic. For example, the desired pathological characteristic includes a mutation and/or polymorphism which contribute to disease pathology, e.g., cystic fibrosis or other airway disease.

In such an embodiment, a population of human airway epithelial cells as described herein can be used to screen for agents which alleviate the pathology. In alternative embodiments, a population of human airway epithelial cells as described herein can be assessed by the degree of CFTR functional recuperation, e.g., to screen for agents in which some airway epithelial cells comprising a particular CFTR mutation and/or polymorphism respond differently compared with airway epithelial cells without the mutation and/or polymorphism, therefore the methods can be used for example, to assess an effect of a particular drug and/or agent on human airway epithelial cells from a defined subpopulation of people and/or cells, therefore acting as a high-throughput screen for personalized medicine and/or pharmogenetics. The manner in which a population of human airway epithelial cells as described herein respond to an agent, particularly a pharmacologic agent, including the timing of responses, is an important reflection of the physiologic state of the human airway epithelial cells.

In some embodiments, an agent administered in an assay comprising a population of human airway epithelial cells as disclosed herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

In some embodiment, at least one agent is administered to a population of human airway epithelial cells as described herein by any suitable means known to one of ordinary skill in the art. In some embodiments, administration occurs more than once, for example at multiple different time points. In some embodiments, the administration of an agent to a population of human airway epithelial cells as described herein is continuous, for example via means of an infusion pump or cather or the like, or via a slow-release formulation of the agent.

In some embodiments, where the population of human airway epithelial cells as described herein is implanted into an animal lung model, i.e., an in vivo assay, an agent can be administered via any or a combination of the following administration methods; systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

The term "agent" refers to any chemical, entity or moiety, including without limitation synthetic and naturally-occurring non-proteinaceous entities. In certain embodiments the compound of interest is a small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

In some embodiments, a population of human airway epithelial cells as described herein for use in an in vitro or in vivo assay can be genetically modified to express markers, e.g. bioluminescence markers, such as luciferase and the like and other bioluminescent markers commonly known in the art for real-time imaging of the function, and/or growth of a population of human airway epithelial cells as described herein in vivo in real time. The is advantageous as it allows the continuous and/or time-point analysis of the effect of an agent on the population of human airway epithelial cells in the same animal over a period of time, as well as allows one to compare the effect of multiple different agents (administered to the subject at different timepoints) in the same in vivo subject without sacrificing the in vivo animal model.

[While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

A plurality of assays as disclosed herein may be run in parallel (e.g. different subjects used to derive the populations of human airway epithelial cells) with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, a population of human airway epithelial cells as described herein used in the screen can be manipulated to express desired gene products. Gene therapy can be used to either modify a cell to replace a gene product or add or knockdown a gene product. In some embodiments the genetic engineering is done to facilitate regeneration of tissue, to treat disease, or to improve survival of the cells following implantation into a subject.

A skilled artisan could envision a multitude of genes which would convey beneficial properties to a population of human airway epithelial cells as described herein to be used in implantation (discussed in more detail below). The added gene may ultimately remain in the recipient human airway epithelial cells and all its progeny, or may only remain transiently, depending on the embodiment. For example, genes encoding corrected CTTR genes could be transfected into human NKX2-1 lung primordial progenitor then go to form human a population of human airway epithelial cells as described herein as disclosed herein. The desired gene can be transfected into a population of human airway epithelial cells using a variety of techniques. Preferably, the gene is transfected into a population of human airway epithelial cells using an expression vector. Suitable expression vectors include plasmid vectors (such as those available from Stratagene, Madison Wis.), viral vectors (such as replication defective retroviral vectors, herpes virus, adenovirus, adenovirus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used to generate "knockout" or modified ES cells, which can be applied to human or marine ES cells (U.S. Pat. Nos. 5,616,491; 5,614,396, which are incorporated herein in their entirety by reference). These techniques take advantage of the ability of embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the present invention can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

V. Methods of Using Human Airway Epithelial Cells in the Treatment of Cystic Fibrosis Another embodiment relates to the therapeutic use of human airway epithelial cells, for example, in one embodiment the invention provides methods for the treatment cystic fibrosis in a subject comprising transplanting into subjects human airway epithelial cells, as disclosed herein, and, in some instances, where the human airway epithelial cells are derived from iPSCs from a subject with CF, where the genetic lesion in the CTFR gene is corrected, e.g., using ex vivo gene editing method commonly known in the art.

Another aspect of the present invention relates to a method for treating a subject with cystic fibrosis, comprising: (a) differentiating a population of human iPSC obtained from the subject into NKX2-1 lung epithelial progenitor cells, (b) culturing the NKX2-1 lung epithelial progenitor cells with a low-wnt media according to the methods as disclosed in claims to 1 to 24, to differentiate into airway epithelial cells expressing any of: NKX2-1+/SOX2+ cells, NKX2-1+/P63+ cells or NKX2-1+/P63+/K5 cells; and collecting the airway epithelial cells; (c) using the airway epithelial cells obtained in step (b) in an forskolin-induced swelling (FIS) assay as disclosed herein to identify an agent which increase CFTR function; and administering to the subject an agent identified to increase CFTR swelling of the airway epithelial cells obtained from the subject with cystic fibrosis.

In some embodiments, a population of airway epithelial cells as disclosed herein, can be implanted into a subject as a substantially pure a population of airway epithelial cells, and in some embodiments, a population of airway epithelial cells is implanted in conjunction with an additional cell population. In some embodiments, a population of airway epithelial cells is a population of airway epithelial cells is a heterogenous population of cells comprising cells selected from any of: NKX2-1+/SOX2+ cells, NKX2-1+/P63+ cells, and NKX2-1+/P63+/K5+ cells differentiated from the human NKX2-1+ lung progenitors cells as disclosed herein, for example, where the population of airyway epithelial cells comprises at least about 0.2% or at least about 0.3%, or at least about 0.4%, or at least about 0.5%, or at least about 0.6%, or at least about 0.7%, or at least about 0.8%, or at least about 0.9%, or at least about 1.0%, or at least about 1.2%, or at least about 1.4%, or at least about 1.5%, or at least about 2.0%, or at least about 3.0%, or at least about 4.0%, or at least about 5.0%, or at least about 6.0%, or at least about 7.0%, or at least about 8.0%, or at least about 9.0%, or at least about 10%, or at least about 20-30%, or about 30-40%, or about 40-50%, or about 50-60%, or about 60-70%, or about 70-80%, or about 80-90%, or about 90-95%, or about 96%, or about 97%, or about 98%, or about 99% of the cells are any of: NKX2-1+/SOX2+ cells, NKX2-1+/P63+ cells, and NKX2-1+/P63+/K5+ cells.

In some embodiments, a substantially pure population of airway epithelial cells is a population of airway epithelial cells is a heterogenous population of cells comprising cells selected from any of: NKX2-1+/SOX2+ cells, NKX2-1+/P63+ cells, and NKX2-1+/P63+/K5+ cells, and where the population of airway epithelial cells comprise no more than 1%, or no more than about 2%, or about 3%, or about 4%, or about 5%, or about 6%, or about 7%, or about 8%, or about 9%, or about 10%, or about 11%, or about 12%, or about 13%, or about 14%, or about 15%, or no more than about 15-20%, or about 20-30%, or about 30-40%, or about 40-50%, or about 50-60% or no more than about 60-70% of cells that are of a distal epithelial lung progenitor phenotype (i.e. alveolar progenitors), e.g., cells that are any of: NKX2-1+/SOX9+ cells, NKX2-1+/SFTPC+ or and NKX2-1+/Scgb1a1-cells, or cells that express SOX9 or TFTPC.

In some embodiments, a population of airway epithelial cells as disclosed herein, can be implanted concurrently with the additional cell population, e.g. as a mixture, or substantially immediately before or after implantation of the additional cell population (e.g. concurrent administration) to generate the human airway lung tissue as disclosed herein. In alternative embodiments, there can be temporal separation of administration of a population of airway epithelial cells as disclosed herein and the additional population of cells, such as, for example, a subject can be implanted with a population of ISL1+ progenitors, in some embodiments at multiple timepoints, prior to, or after the implantation of the additional cell population. In some embodiments, the separation of administration of the different cell populations is at least about 1 hr, or at least about 2 hrs, or at least about 6 hrs, or at least about 12 hrs, or at least about 24 hrs, or a least about 48 hrs, a least about 3 days, or at least about 4 days, or at least about 7 days, or at least about 2 weeks, or a least about 21 days, or at least about a month or more in duration.

The additional cells to be implanted in combination with a population of airway epithelial cells as disclosed herein can be from any origin and any species. Preferably, in some embodiments, the cells are human cells. In some embodiments, where a population of airway epithelial cells as disclosed herein is mixed with a population of other cells, such as e.g., cells of a distal epithelial cell phenotype as disclosed herein, any ratio of the cells which are airway epithelial cells to cells which belong to another cell population can be used, for example, 1:1, 2:1, 3:1, 4:1, 5:1, 6:1, 7:1, 8:1, 9:1, 10:1, 15:1, 20:1, 50:1, 100:1, 200:1, 300:1, 500:1 and 1000:1 ratios, or 1:1000, 1:500, 1:300, 1:200, 1:100, 1:50. 1:20, 1; 15, 1:10, 1:5, 1:4, 1; 3 and 1:2 where the ratios relates to the number of a population of airway epithelial cells to the number of cells of another cell population (e.g., distal lung epithelial cells).

In some embodiments, the number or amount of airway epithelial cells as disclosed herein implanted into a subject can be determined by one of ordinary skill in the art, and depends on part on the site of implantation and the species of subject which is the recipient of the implanted cells. For example, a pig or monkey or human subject can have a greater number of a population of airway epithelial cells as disclosed herein implanted than a rodent subject, such as a mouse. Similarly, the site of impanation can determine the number of airway epithelial cells implanted, for example more airway epithelial cells can be implanted into a peritoneal cavity or subcutaneous space as compared to a kidney capsule. By way of example only, one can implant at least about 2,000 cells, for example about 500-1000, or about 1000-2000, or about 2000-5000 cells into the kidney capsule of a mouse.

In some embodiments, the number of human airway epithelial cells as disclosed herein implanted is the total amount of cells which is less than (e.g. about 5% or about 0% less) the total amount of cells where the cells begin to compete for nutrients and thus decrease in viability after implantation. In some embodiments, the amount or number of human airway epithelial cells as disclosed herein implanted is the amount in which at least about 50% or at least about 60% or at least about 70% or at least about 80% or at least about 90% or at least about 95% or at least about 98% or at least about 99% or more of the originally implanted human airway epithelial cells as disclosed herein are viable after about 2 weeks of implantation, or a after about 3 weeks or a month after implantation into a subject.

In some embodiments, a population of human airway epithelial cells as disclosed herein do not proliferate or self-renew once implanted into a subject.

In some embodiments, a population of human airway epithelial cells as disclosed herein can be genetically modified prior to implantation into a subject. In some embodiments, a population of human airway epithelial cells as disclosed herein can be genetically modified to correct a genetic defect or genetic lesion in the CFTR gene, e.g., as disclosed herein, e.g, CFTR-ΔF508 (also known as CFTR-delF508) CTFR-G551D, CFTR-G542X, CFTR-L927P, CFTR-E60X, CFTR-4015delATTT, CFTR-A455E, or modified to prolong the survival of the human airway epithelial cells after inplantation, for example, by inhibiting apoptosis, promoting survival pathways, and minimizing immune rejection of the cells.

Accordingly, a population of human airway epithelial cells as disclosed herein can be modified to correct any one or more of CFTR disease causing mutations as disclosed in Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451), or any of the >1000 disease causing mutations in the CF gene identified and disclosed on the database site at: world-wide-web: genet.sickkids.on.ca/cftr.

In some embodiments, a population of human airway epithelial cells as disclosed herein can be modified to express growth factors or agents useful in the treatment of cystic fibrosis. In some embodiments, the expression of the transgenes can be regulated by tissue-specific promoters and/or inducible promoters as commonly known by methods of one of ordinary skill in the art.

VI. Kits

Another aspect of the present disclosure relates to kits or pharmaceutical packages comprising at least a low-wnt media. In some embodiments, the kit comprises human NKX2-1+ lung progenitor cells (e.g., lung epithelium progenitors (e.g., NKX2-1+/CD47hi/CD26lo), that can be used as a control cells, or to differentiate along a proximal pathway to airway epithelial cells or along a distal pathway, as disclosed herein. In some embodiments, the kit can comprise other cell types as controls, e.g, airway epithelial cells (e.g., any one of NKX2-1+/SOX2+/SOX9–; or NKX2-1+/P63+/SOX9– or NKX2-1+/P63+/K5+, which can also further express one or more of SCGB3A2+, TB63+, MUC-SAC+, SCGB 1A1A+, but does not express SOX9– or TFTPC–) differentiated from lung epithelium progenitors (e.g., NKX2-1+/CD47$^{hi}$/CD26$^{lo}$) for use as control cells (e.g., as a positive control cell type), and/or the kit can optionally comprise distal NKX2-1+/SOX9+ cells (as control, e.g., negative control cells).

In some embodiments, the kit can comprise one or more of: FGF2, FGF10, EGF, 3-Isobutyl-1-methylxanthine (IBMX), BIO, CHIR, KGF, BMP4, rhBMP4, retinoic acid, or a Wnt inhibitor as disclosed herein, and the like The kit can comprise any one or more of: cSFDM (complete serum free differentiation media), alone, or optionally containing 10 ng/mL FGF10, dexamethasone, 8-Bromoadenosine 3',5'-cyclic monophosphate sodium salt, 3-Isobutyl-1-methylxanthine (IBMX) (Sigma), In some embodiments, the kit can comprise CFK media (media containing +CHIR/FGF10/KGF). In some embodiments, the kit can comprise DCI media (media containing: examethasone, cyclic AMP, IBMX, and ITS supplement). In some embodiments, for a control, the kit can comprise cSFDM (complete serum free differentiation medium) containing 3 µM CHIR99021, 10 ng/mL recombinant human FGF10 (rhFGF10), 10 ng/mL recombinant human KGF (rhKGF), 10 ng/mL recombinant human BMP4 (rhBMP4), and 50 nM retinoid acid (Sigma) to induce a lung epithelial progenitor fate.

VII. Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

By an "increase" in the expression or activity of a gene or protein is meant a positive change in protein or polypeptide or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

As used herein, the term "gene" includes a segment of DNA that contains all the information for the regulated biosynthesis of an RNA product, including promoters, exons, introns, and other untranslated regions that control expression. Those in the art will readily recognize that nucleic acid molecules can be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference can be made to either strand and still comprise the same polymorphic site and an oligonucleotide can be designed to hybridize to either strand. Throughout this specification, in identifying a polymorphic site, reference is made to the sense strand, only for the purpose of convenience. As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyedenosine, deoxycytidine, deoxyguanosine, and deoxythymidine. For purposes of clarity, when referring herein to a nucleotide of a nucleic acid, which can be DNA or RNA, the terms "adenosine", "cytosine", "guanosine", and thymidine" are used. It is understood that if the nucleic acid is RNA, a nucleotide having a uracil base is uridine. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that can be formed into a polynucleotide that retains the ability to hybridize in a sequence specific manner to a target polynucleotide. As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "variant", "variance", "mutation" or "polymorphism" are used interchangeably herein and as used herein with respect to nucleic acid sequence refers to a difference in nucleic acid sequence in the population. Polymorphisms are sometimes referred to as "single nucleotide polymorphism" or "SNP" can be synonymous or non-synonymous. Synonymous polymorphisms when present in the coding region typically do not result in an amino acid change. Non-synonymous polymorphism when present in the coding region alter one or more codons resulting in an amino acid replacement in the amino acid chain. Such mutations and polymorphisms can be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members can have an altered sequence (e.g., the variant or, mutant "allele"). In the simplest case, only one mutated variant of the sequence can exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished "+" or "−". Using these symbols, homozygous individuals are +/+, or −/− or two of the same symbol, for example A/A, G/G, T/T and C/C. Heterozygous individuals are +/− or two different symbols, for example A/G, A/T. A/C, G/T etc. The occurrence of alternative mutations can give rise to tri-allelic and tetra-allelic polymorphisms, etc. An allele can be referred to by the nucleotide(s) that comprise the mutation. In some instances a "silent mutation" is a synonymous codon change, or silent SNP is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide.

The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom.

The term "endogenously expressed" or "endogenous expression" refers to the expression of a gene product at normal levels and under normal regulation for that cell type.

The term "entity" refers to any structural molecule or combination of molecules.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising;

chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct of indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The terms "patient", "subject" and "individual" are used interchangeably herein, and refer to an animal, particularly a human, to whom treatment including prophylaxic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "tissue" refers to a group or layer of similarly specialized cells which together perform certain special functions. The term "tissue-specific" refers to a source or defining characteristic of cells from a specific tissue.

As used herein, the term "donor" refers to a subject to which a organ, tissue or cell to be transplanted is harvested from.

As used herein, the term "recipient" refers to a subject which will receive a transplanted organ, tissue or cell.

The term "allograft" refers to a transplanted cell, tissue, or organ derived from a different animal of the same species.

The term "effective amount" includes within its meaning a sufficient amount of a pharmacological composition to provide the desired effect. For example, an effective amount using the methods as disclosed herein would be considered as the amount sufficient to reduce a symptom of a a pulmonary disease, e.g., cystic fibrosis by at least 10%. Further, an effective amount as used herein would also include an amount sufficient to prevent or delay the development of a symptom experienced by a subject with a pulmonary disease, e.g. CF, or alter the course of a symptom disease (for example but not limited to, slow the progression or development of at least one symptom experienced by a subject with a pulmonary disease, e.g., CF), or reverse at least one symptom experienced by a subject with a pulmonary disease, e.g. CF.

As used herein, the term "treating" includes administering a population of airway epithelial cells or bronchospheres as disclosed herein to a subject to reduce at least one symptom experienced by a subject with a pulmonary disease, e.g, CF. In some embodiments, a reduction in at least one symptom at least one symptom experienced by a subject in need treatment for CF would also be considered as affective treatments by the methods as disclosed herein.

The term "polynucleotide" as used herein, refers to single- or double-stranded polymer of deoxyribonucleotide, ribonucleotide bases or known analogies of natural nucleotides, or mixtures thereof. The term includes reference to the specified sequence as well as to the sequence complementary thereto, unless otherwise indicated.

The term "polypeptide" means a polymer made up of amino acids linked together by peptide bonds. The terms "polypeptide" and "protein" are used interchangeably herein, although for the purposes for the present disclosure, a polypeptide may constitute a portion or the full length protein.

The term "expression" as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

The term "endogenously expressed" or "endogenous expression" as used herein, refers to the expression of a gene product at normal levels and under normal regulation for that cell type.

In the context of this specification, the term "activity" as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term "standard deviation" is a measure of the dispersion of a set of data from its mean. The more spread apart the data, the higher the deviation. Standard deviation is calculated as the square root of variance and can be calculated by one of ordinary skill in the art.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. The appropriate cell culture media, for a particular cell type, is known to those skilled in the art.

The term "drug screening" as used herein refers to the use of the bronchospheres as disclosed herein in the laboratory to identify drugs with a specific function. In some embodiments, the present disclosure provides drug screening methods of to identify compounds or drugs which increase the function of the CFTR gene in the bronchospheres. In alternative embodiments, the present disclosure provides drug screening on the bronchospheres to identify compounds or drugs useful as therapies for diseases or illnesses (e.g. human diseases or illnesses), e.g., for the treatment of cystic fibrosis.

The term "contacting" or "contact" as used herein as in connection with contacting a population of airway epithelial cells or bronchospheres as disclosed herein, can be in vitro, for example, in conditioned media or exogenously added agent or growth factor.

As used herein, the terms "administering," and "introducing" are used interchangeably, and refer to the placement of a population of airway epithelial cells, or bronchospheres as disclosed herein into a subject by a method or route which results in at least partial localization of the population of airway epithelial cells, or bronchospheres at a desired site, such as, e.g. the lung or airways. A population of airway epithelial cells, and/or bronchospheres as of the present disclosure can be administered by any appropriate route which results in an effective treatment in the subject.

The term "transplantation" as used herein refers to introduction of new cells (e.g. a population of airway epithelial cells as disclosed herein), tissues (such as, e.g., a bronchospheres as disclosed herein produced from the airway epithelial cells), or organs into a host (i.e. transplant recipient or transplant subject).

The term "genetically modified" cell, e.g. a genetically modified population of airway epithelial cells or bronchospheres as disclosed herein as used herein refers to a population of airway epithelial cells or bronchospheres as disclosed herein into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (e.g., sequences naturally found in the cells) but in a non-naturally occurring arrangement (e.g., a coding region linked to a promoter from a different gene), or altered versions of native sequences, etc., e.g., a correction of a genetic lesion or mutation in the CFTR gene that causes CF. The process of transferring the nucleic into the cell is referred to as "transducing a cell" and can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "transduction" as used herein refers to the use of viral particles to introduce new genetic material into a cell.

The term "transfection" as used herein refers the use of chemical methods, most often lipid containing vesicles, to introduce new genetic material into a cell.

The term "transformation" as used herein refers to when a cell becomes functionally abnormal in the process of malignancy, often obtaining a new capacity to multiply indefinitely or under new circumstances.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of a population of airway epithelial cells, or bronchospheres or their progeny and/or compound and/or other material other than directly into the pulmonary system, e.g., lungs or airways, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising; nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within the cell.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. As will be evident to one of skill in the art, the term "selectable marker" as used herein can refer to a gene or to an expression product of the gene, e.g., an encoded protein.

A "reporter gene" as used herein encompasses any gene that is genetically introduced into a cell that adds to the phenotype of the stem cell. Reporter genes as disclosed in this invention are intended to encompass fluorescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, e.g., "selective conditions". To ensure an effective selection, a population of cells can be maintained under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not airway epithelial cells as disclosed herein, that are any of: NKX2-1+/SOX2+ cells, NKX2-1+/P63+ cells or NKX2-1+/P63+/K5 cells.

As used herein the term "comprising" or "comprises" is used in reference to compositions, methods, and respective component(s) thereof, that are essential to the disclosure, yet open to the inclusion of unspecified elements, whether essential or not. Accordingly, compositions or methods "comprising" one or more recited elements may include other elements not specifically recited. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Thus, the use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%. The present disclosure is further explained in detail by the following, including the Examples, but the scope of the disclosure should not be limited thereto.

Although any known methods, devices, and materials may be used in the practice or testing of the invention, the methods, devices, and materials in this regard are disclosed herein.

In some embodiments, the present application may be defined in any of the following paragraphs:

1. A method for modulating the cononical Wnt pathway in a population of NKX2-1 lung epithelial progenitors to direct their differentiation along a proximal or dorsal epithelial pathway, the method comprising;
   a. culturing a population of NKX2-1 lung epithelial progenitors in a low-Wnt media for a sufficient amount of time, wherein the low-Wnt media induces the NKX2-1 lung epithelial progenitors to differentiate along a proximal epithelial pathway into airway epithelial organoids comprising cells selected from any of: NKX2-1+/SOX2+ cells, NKX2-1+/P63+ cells or NKX2-1+/P63+/K5 cells; or
   b. culturing a population of NKX2-1 lung epithelial progenitors in a high Wnt media, or in the presence of a Wnt activator for a sufficient amount of time to allow the NKX2-1 lung epithelial progenitors to differentiate along a distal epithelial pathway into cells selected from any of: NKX2-1+/SOX9+ cells, NKX2-1+/SFTPC+ cells or NKX2-1+/Scgb1a1− cells.
2. The method of paragraph 1, wherein the airway epithelial organoids comprise cells that also express at least one of the proximal markers selected from the group consisting of: SCGB3A2+, TP63+, MUCSAC+ and Scgb1a1+.
3. The method of paragraph 1, wherein the airway epithelial organoids comprise cells that do not express the distal markers selected from the group consisting of: SFTPC, SOX9.
4. The method of paragraph 1, wherein the Nxk2.1 lung progenitors are NKX2-1+ve, $CD47^{hi}$ and $CD26^{lo}$.

5. The method of any of paragraphs 1 to 4, wherein the low-Wnt media comprises FGF2 and FGF10.
6. The method of paragraph 1, wherein the Nxk2.1 lung progenitors are differentiated from iPSC or ESCs.
7. The method of paragraph 1, wherein the Nxk2.1 lung progenitors are differentiated from human iPSC or ESCs.
8. The method of paragraph 6 or 7, wherein the Nxk2.1 lung progenitors are differentiated from iPSC or human iPSC or human ESCs using a high wnt media, or in the presence of a Wnt activator.
9. The method of paragraph 7, wherein the human iPSC are derived from a subject with a pulmonary disease.
10. The method of paragraph 9, wherein the subject has cystic fibrosis.
11. The method of any of paragraphs 1 to 10, wherein the low-Wnt media does not contain a Wnt activator (e.g., CHIR or BIO) or comprises a wnt inhibitory agent.
12. The method of paragraph 11, wherein the wnt inhibitory agent is withdrawal of a Wnt activator, or is an agent which inhibits Wnt or Wnt3.
13. The method of paragraph 11, wherein the wnt inhibitory agent inhibits any one or more of Wls/Evi, Frizzled, Dsh (disheveled), LRP-5, LRP-6, Dally, Dally-like, PAR1, β-catenin, TCF, lef-1 or Frodo.
14. The method of paragraph 13, wherein the wnt inhibitory agent is an RNAi agent which inhibits the RNA transcript of Wls/Evi.
15. The method of paragraph 14, wherein the RNAi agent corresponds to SEQ ID NO:1 (CACAAATCCTTTCTA-CAGTAT)) (siWLS-A) or SEQ ID NO:2 (GGGTTAC-CGTGATGATATG) (siWLS-B).
16. The method of paragraph 11, wherein the wnt inhibitory agent is selected from the group consisting of: Dickkopf-1 (DKK1), WIF-1, cerberus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins or LRP lacking the intracellular domain.
17. The method of paragraph 11, wherein the wnt inhibitory agent inhibits β-catenin.
18. The method of paragraph 17, wherein the inhibitor of β-catenin is selected from the group consisting of; protein phosphatase 2A (PP2A), chibby, promtin 52, Nemo/LNK kinase, MHG homobox factors, XSox17, HBP1, APC, Axin, disabled-2 (dab-2) and gruncho (grg).
19. The method of paragraph 11, wherein the wnt inhibitory agent increases the activity and/or expression of GSK-3 and/or GSK3β.
20. The method of paragraph 11, wherein the wnt inhibitory agent is a peptide of GSK3β.
21. The method of paragraph 11, wherein the wnt inhibitory agent is selected from a group consisting of; a GSK3β peptide, an agent which activates the PKB pathway or wortannin.
22. The method of paragraph 11, wherein the wnt inhibitory agent is a peptide of DKK1.
23. The method of paragraph 1, wherein the NKX2-1 lung epithelial progenitors are genetically modified NKX2-1 lung epithelial progenitors.
24. The method of paragraph 23, wherein the genetically modified NKX2-1 lung epithelial progenitors comprises a nucleic acid encoding at least one wnt inhibitory agent operatively linked to a first inducible promoter.
25. The method of paragraph 24, wherein the genetically modified NKX2-1 lung epithelial progenitors comprises a nucleic acid encoding multiple copies of a wnt inhibitory agent operatively linked to a first inducible promoter.
26. The method of paragraph 23 or 24, wherein the nucleic acid encoding at least one wnt inhibitory agent encodes at least one of the Wnt inhibitory agents selected from the group consisting of: GSK3β, a peptide of GSK3β, protein phosphatase 2A (PP2A), chibby, promtin 52, Nemo/LNK kinase, MHG homobox factors, XSox17, HBP1, APC, Axin, disabled-2 (dab-2) and gruncho (grg), Dickkopf-1 (DKK1), WIF-1, cerberus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins or LRP lacking the intracellular domain
27. The method of paragraph 23, wherein the genetically modified NKX2-1 lung epithelial progenitors comprises a nucleic acid encoding at least one wnt activator operatively linked to a second inducible promoter.
28. The method of paragraph 27, wherein the genetically modified NKX2-1 lung epithelial progenitors comprises a nucleic acid encoding multiple copies of a wnt activator operatively linked to a second inducible promoter.
29. The method of paragraph 24 to 28, wherein the first inducible promoter is not the same as the second inducible promoter.
30. The method of paragraph 24 to 29, wherein the first inducible promoter and second inducible promoter are high efficiency promoters.
31. The method of paragraph 27 to 29, wherein the nucleic acid encoding at least one wnt activator encodes at least one of the Wnt inhibitory agents selected from the group consisting of: β-catenin or a biologically active fragment or homologue thereof, or a stabilized β-catenin homologue with any of the amino acid changes selected from the group consisting of: D32Y; D32G; S33F; S33Y; G34E; S37C; S37F; T41I; S45Y or β-catenin with the deletion of amino acids AA1-173, Frodo, TCF, pitz2, Pretin 52, legless (lgs), pygopus (pygo), hyrax/paraf-nomin and LKB1/XEEK1.
32. The method of paragraph 23, wherein the NKX2-1 lung epithelial progenitor is differentiated from an iPSC obtained from a human subject with cystic fibrosis, and where the NKX2-1 lung epithelial progenitor is a genetically modified to correct a CTFR genetic lesion responsible for the cystic fibrosis in the subject.
33. A method for producing airway epithelial organoids, comprising culturing a population of NKX2-1 lung epithelial progenitors in a low-Wnt media for at least 4 days, wherein the low-Wnt media induces the NKX2-1 lung epithelial progenitors to differentiate into airway epithelial organoids comprising cells selected from any of: NKX2-1+/SOX2+ cells, NKX2-1+/P63+ cells or NKX2-1+/P63+/K5 cells.
34. A method of promoting a population of Nxk2.1 lung epithelial progenitor cells to differentiate along a proximal epithelial pathway, comprising culturing the population of NKX2-1 lung epithelial progenitors in a low-Wnt media for a sufficient amount of time to allow the NKX2-1 lung epithelial progenitors to differentiate into cells selected from any of: NKX2-1+/SOX2+ cells, NKX2-1+/P63+ cells or NKX2-1+/P63+/K5 cells.
35. The method of paragraph 33 or 24, wherein the airway epithelial organoids comprise cells that also express at least one of the proximal markers selected from the group consisting of: SCGB3A2+, TP63+, MUCSAC+ and Scgb1a1+.

36. The method of paragraph 33 or 24, wherein the airway epithelial organoids comprise cells that do not express the distal markers selected from the group consisting of: SFTPC, SOX9.
37. The method of any of paragraphs 33 to 36, wherein the low-Wnt media comprises FGF2 and FGF10.
38. The method of paragraph 33, wherein the Nxk2.1 lung progenitor are differentiated from iPSC or ESCs.
39. The method of paragraph 33, wherein the Nxk2.1 lung progenitor are differentiated from human iPSC or human ESCs.
40. The method of paragraph 33, wherein the Nxk2.1 lung progenitor are NKX2-1+ve, $CD47^{hi}$ and $CD26^{lo}$.
41. The method of paragraph 38, wherein the human iPSC are derived from a subject with a pulmonary disease.
42. The method of paragraph 41, wherein the subject has cystic fibrosis.
43. The method of any of paragraphs 33 to 42, wherein the low-Wnt media does not comprise a Wnt activator (e.g., CHIR or BIO) or comprises a wnt inhibitory agent.
44. The method of paragraph 43, wherein the wnt inhibitory agent inhibits Wnt or Wnt3 or is withdrawal of a Wnt activator.
45. The method of paragraph 43, wherein the wnt inhibitory agent inhibits any one or more of Wls/Evi, Frizzled, Dsh (disheveled), LRP-5, LRP-6, Dally, Dally-like, PAR1, β-catenin, TCF, lef-1 or Frodo.
46. The method of paragraph 43, wherein the wnt inhibitory agent is an RNAi agent which inhibits the RNA transcript of Wls/Evi.
47. The method of paragraph 46, wherein the RNAi agent corresponds to SEQ ID NO:1 (siWLS-A) or SEQ ID NO:2 (siWLS-B).
48. The method of paragraph 43, wherein the wnt inhibitory agent is selected from the group consisting of: Dickkopf-1 (DKK1), WIF-1, cerberus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins or LRP lacking the intracellular domain.
49. The method of paragraph 43, wherein the wnt inhibitory agent inhibits β-catenin.
50. The method of paragraph 49, wherein the inhibitor of β-catenin is selected from the group consisting of; protein phosphatase 2A (PP2A), chibby, promtin 52, Nemo/LNK kinase, MHG homobox factors, XSox17, HBP1, APC, Axin, disabled-2 (dab-2) and gruncho (grg).
51. The method of paragraph 43, wherein the wnt inhibitory agent increases the activity and/or expression of GSK-3 and/or GSK3β.
52. The method of paragraph 43, wherein the wnt inhibitory agent is a peptide of GSK3β.
53. The method of paragraph 43, wherein the wnt inhibitory agent is selected from a group consisting of; a GSK3l3 peptide, an agent which activates the PKB pathway or wortannin.
54. The method of paragraph 43, wherein the wnt inhibitory agent is a peptide of DKK1.
55. The method of paragraph 33, wherein the NKX2-1 lung epithelial progenitor is a genetically modified NKX2-1 lung epithelial progenitor.
56. The method of paragraph 55, wherein the NKX2-1 lung epithelial progenitor is differentiated from an iPSC obtained from a subject with cystic fibrosis, and where the NKX2-1 lung epithelial progenitor is a genetically modified to correct a CTFR genetic lesion responsible for the cystic fibrosis in the subject.
57. A method of promoting a population of Nxk2.1 lung epithelial progenitor cells to differentiate along a distal epithelial fate, comprising culturing the population of NKX2-1 lung epithelial progenitors in a high Wnt media, or in the presence of a Wnt activator for a sufficient amount of time to allow the NKX2-1 lung epithelial progenitors to differentiate into cells selected from any of: NKX2-1+/SOX9+ cells, NKX2-1+/SFTPC+ cells or NKX2-1+/Scgb1a1− cells.
58. The method of paragraph 57, wherein the wnt activator inhibits the expression and/or activity of GSK3.
59. The method of paragraph 58, wherein the GSK3 is GSK3β.
60. The method of paragraph 57, wherein the wnt activator is 6-bromoindirubin-3'-oxime (BIO), or CHIR99021 (CHIR), or an analogue thereof.
61. The method of paragraph 60, wherein the BIO analogue is an acetoxime analogue of BIO or 1-Azakenpaulline or a functional analogue thereof.
62. The method of paragraph 57, wherein the wnt activator is a peptide inhibitor of GSK3β comprising SEQ ID NO:3 or a functional fragment thereof.
63. The method of paragraph 57, wherein the wnt activator is lithium, LiCl, retinoic acid, Ro31-8220 or analogues thereof.
64. The method of paragraph 57, wherein the wnt activator increases the expression and/or activity of wnt and/or wnt3a or homologues thereof.
65. The method of paragraph 57, wherein the wnt activator is, or increases the expression and/or biological activity of the group consisting of; Wls/Evi, Frizzled, Dsh (disheveled), LRP-5, LRP-6, Dally, Dally-like, PAR1, β-catenin, TCF, lef-1 or Frodo.
66. The method of paragraph 57, wherein the wnt activator inhibits the expression and/or biological activity of the group consisting of; Dickkopf-1 (DKK1), WIF-1, cerbertus, secreted frizzled-related proteins (sFRP), sFRP-1, sFRP-2, collagen 18 (collagen XVIII), endostatin, carboxypeptidase Z, receptor tyrosine kinase, corin, Dg1, Dapper, pertussis toxin, naked, Frz-related proteins, LRP lacking the intracellular domain, APC, Axin, dab-2, gruncho, PP2A, chibby, pontin 52 and Nemo/LNK kinases.
67. The method of paragraph 57, wherein the wnt activator is β-catenin or a biologically active fragment or homologue thereof, or a stabilized β-catenin homologue.
68. The method of paragraph 67, wherein a stabilized β-catenin homologue is β-catenin with any of the amino acid changes selected from the group consisting of: D32Y; D32G; S33F; S33Y; G34E; S37C; S37F; T41I; S45Y and β-catenin with the deletion of amino acids AA1-173.
69. The method of paragraph 57, wherein the wnt activator activates and/or stabilizes the expression β-catenin.
70. The method of paragraph 57, wherein the wnt activator agent is selected from a group of; Frodo, TCF, pitz2, Pretin 52, legless (lgs), pygopus (pygo), hyrax/parafnomin and LKB1/XEEK1.
71. A cell line produced by the methods of any of paragraphs 1 to 56.
72. The cell line of paragraph 71, in the presence of a low-Wnt media or a Wnt inhibitor.
73. The cell line of paragraph 71, in the presence of a low-Wnt media that does not contain a Wnt activator (e.g., BIO or CHIR).
74. The cell line of paragraph 71, wherein the clonal cell line is cryopreserved.
75. The cell line of paragraph 71, wherein the clonal cell line is present in a cryopreservation media.

76. A cell line produced by the methods of any of paragraphs 1 to 32, or 57 to 70.

77. The cell line of paragraph 75, in the presence of a high-Wnt media or a Wnt activator.

78. The cell line of paragraph 75, wherein the cells are subsequently cryopreserved.

79. The cell line of paragraph 75, wherein the clonal cell line is present in a cryopreservation media.

80. A method of treating cystic fibrosis, comprising:
  a. differentiating a population of human iPSC or ESCs into NKX2-1 lung epithelial progenitor cells,
  b. culturing the NKX2-1 lung epithelial progenitor cells with a low-wnt media according to the methods as disclosed in paragraphs to 1 to 24, to differentiate into airway epithelial cells expressing any of: NKX2-1+/SOX2+ cells, NKX2-1+/P63+ cells or NKX2-1+/P63+/K5 cells;
  c. administering the airway epithelial cells obtained in step (b) to the subject.

81. The method of paragraph 80, wherein the population of human iPSC are obtained from the subject with cystic fibrosis, and have been genetically modified to correct a CTFR genetic lesion responsible for the cystic fibrosis in the subject prior to being differentiated into NKX2-1 lung epithelial progenitor cells.

82. The method of paragraph 80, further comprising a step of genetically modifying the airway epithelial cells obtained in step (b) to correct a CTFR genetic lesion responsible for the cystic fibrosis in the subject prior to the step (c).

83. The method of paragraph 80, wherein the airway epithelial cells are transplanted into the lungs of the subject.

84. An assay to select an agent that increases CTFR function, the assay comprising:
  a. contacting a population of airway epithelial cells with forskolin and a candidate agent, wherein the airway epithelial cells are any of: NKX2-1+/SOX2+ cells, NKX2-1+/P63+ cells or NKX2-1+/P63+/K5 cells,
  b. measuring the size of each airway epithelial cell at a first timepoint, where the first timepoint is prior to, or shortly after the airway epithelial cells are contacted with the forskolin and candidate agent,
  c. culturing the airway epithelial cells for a pre-defined period of time,
  d. measuring the size of each airway epithelial cell at a second timepoint, or a plurality of timepoints during the pre-defined period of time, wherein the second timepoint or plurality of timepoints is after the first timepoint,
  e. calculating the difference in the size of each airway epithelial cell measured at the second, or plurality of timepoints as compared to the first timepoint, and determining the average change in size of each airway epithelial cell in the population of airway epithelial cells,
  f. selecting the candidate agent as an agent that increases CFTR function where the average size of each airway epithelial cell is increased as compared to the average size of each airway epithelial cell in the absence of the candidate agent, or in the presence of a control candidate agent.

85. The assay of paragraph 84, wherein the assay is a high-throughput screen (HTS) assay.

86. The assay of paragraph 84, wherein the population of airway epithelial cells are differentiated from human iPSC or ESCs obtained from a subject with CF, or comprising a mutation in the CFTR gene.

87. The assay of any of paragraphs 84 to 86, measuring the size of each airway epithelial cell at a first timepoint, or second timepoint or a plurality of subsequent timepoints comprises measuring the surface area of each airway epithelial cell.

88. The assay of any of paragraphs 84 to 87, wherein the measuring the size of each airway epithelial cell at a first timepoint, or second timepoint or a plurality of subsequent timepoints, comprises imaging the population of airway epithelial cells and using software to calculate the size of each epithelial cell a first timepoint, or second timepoint or plurality of subsequent timepoint.

89. The assay of any of paragraphs 84 to 89, wherein imaging the cells comprises imaging the cells with an automated high-definition microscope.

90. The assay of of any of paragraphs 84 to 89, further comprising contacting the population of airway epithelial cells with a flurescent marker prior to measuring the size of the cells.

91. The assay of paragraph 90, wherein the fluorescent marker is calcein green.

92. The assay of any of paragraphs 84 to 91, wherein the pre-defined period of time is selected from any of: between 6-12 hours, between 12-24 hrs, between 24-36 hrs, between 36-48 hours, or more than 48 hours.

93. The assay of any of paragraphs 84 to 92, wherein the plurality of timepoints comprises measuring the size of each cell at intervals of any of: 10 minutes, or 15 minutes, or 20 minutes, or 30 minutes, or 60 minutes or 90 minutes, or 120 minutes during the pre-defined time period.

94. The assay of any of paragraphs 84 to 93, wherein the population of airway epithelial cells are contacted with 5-10 µM of forskolin.

95. The assay of any of paragraphs 84-94, wherein the population of airway epithelial cells are produced according to the methods according to any of paragraphs 33-56.

96. A method for treating a subject with cystic fibrosis, comprising:
  a. differentiating a population of human iPSC obtained from the subject into NKX2-1 lung epithelial progenitor cells,
  b. culturing the NKX2-1 lung epithelial progenitor cells with a low-wnt media according to the methods as disclosed in paragraphs to 1 to 24, to differentiate into airway epithelial cells expressing any of: NKX2-1+/SOX2+ cells, NKX2-1+/P63+ cells or NKX2-1+/P63+/K5 cells; and collecting the airway epithelial cells;
  c. using the airway epithelial cells obtained in step (b) in an forskolin-induced swelling (FIS) assay according to any of paragraphs 84-95 to identify an agent which increase CFTR function; and
  d. administering to the subject an agent identified to increase CFTR swelling of the airway epithelial cells obtained from the subject with cystic fibrosis.

97. Use of the cell line of any of paragraphs 71 to 79 in an assay.

98. The use of paragraph 97, wherein the assay is a drug screening assay.

99. The use of paragraph 97 or 98, wherein the assay is a high-throughput assay.

100. Use of the cell line of any of paragraphs 71 to 75 in a method to treat a subject with a pulmonary airway disease.

101. The use of paragraph 100, wherein the cell line is derived from an iPSC cell obtained from a subject who has cystic fibrosis and wherein the cell line has been modified to correct a CFTR mutation.

102. The use of paragraph 100, wherein the pulmonary airway disease is cystic fibrosis.

It is understood that the foregoing detailed description and the following examples are illustrative only and are not to be taken as limitations upon the scope of the disclosure. Various changes and modifications to the disclosed embodiments, which will be apparent to those of skill in the art, may be made without departing from the spirit and scope of the present disclosure. Further, all patents, patent applications, and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the disclosure. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The disclosure can be understood more fully by reference to the following detailed description and illustrative examples, that are intended to exemplify non-limiting embodiments of the disclosure.

EXAMPLES

The examples presented herein relate to methods and compositions to drive purified lung progenitors to airway epithelial cell types based on the manipulation of coninocial Wnt signaling pathways to drive multipotent progenitors to a specific airway cell fate. The technology describes a method by which mature proximal airway epithelial organoids can be derived from human pluripotent stem cells (such as patient specific induced pluripotent stem cells; iPSCs). Throughout this application, various publications are referenced. The disclosures of all of the publications and those references cited within those publications in their entireties are hereby incorporated by reference into this application in order to more fully describe the state of the art to which this disclosure pertains. The following examples are not intended to limit the scope of the claims to the disclosure, but are rather intended to be exemplary of certain embodiments. Any variations in the exemplified methods that occur to the skilled artisan are intended to fall within the scope of the present disclosure.

Materials and Methods—STAR Methods

Human ESC/iPSC Reporter Line Generation and Maintenance

The NKX2-1$^{GFP}$ iPSC lines ("BU3" and "C17") was derived from a cystic fibrosis patient carrying a published compound heterozygeous CFTR genotype (Crane et al., 2015) and was targeted with an NKX2-1$^{GFP}$ fluorescent reporter using TALENs technology as described previously (Hawkings et al., 2017. Prospective isolation of NKX2-1+/CD47+ human lung progenitors derived from pluripotent stem cells. J. Clin. Invest.). Two CFTR mutant iPSC lines of genotype ΔF508/ΔF508 (clones RC2 202 and RC2 204; generated from two individual donors with cystic fibrosis) (Somers et al., 2010) and their gene-edited subclones, engineered to each carry one corrected CFTR allele, were obtained from the iPSC Core of the CReM of Boston University and Boston Medical Center (Crane et al., 2015). The RUES2 human embryonic stem cell line was a generous gift from Dr. Ali H. Brivanlou of The Rockefeller University. All human PSC lines were maintained in feeder-free culture conditions in 6-well tissue culture dishes (Corning, Corning, N.Y.) on growth factor reduced Matrigel (Corning) in mTeSR1 medium (Stem Cell Technologies, Vancouver, Canada) by passaging with ReLeSR (Stem Cell Technologies) and Gentle Cell Dissociation Reagent (Stem Cell Technologies). All human ESC/iPSC lines used were characterized for pluripotency and were found to be karyotypically normal. Further details of iPSC derivation, characterization, and culture are available at world-wide web at: "bu.edu/dbin/stemcells/protocols.php."

Mouse ESC Reporter Line Maintenance

Nkx2-1mCherry mESCs (Bilodeau et al., 2014) were maintained on inactivated mouse embryonic fibroblasts in DMEM supplemented with 15% FBS, L-glut, LIF, and BME (Kurmann et al., 2015; Longmire et al., 2012). Undifferentiated cells were passaged routinely by single cell dissociation using trypsin, enzyme inactivation, and centrifugation at 300×g for 5 minutes at 4° C. and replated onto previously prepared feeder layers on gelatin-coated plastic.

Directed Differentiation of hPSCs to Lung Epithelial Progenitors

NKX2-1+ lung progenitors were generated from hPSCs first by inducing definitive endoderm with STEMdiff Definitive Endoderm Kit (Stem Cell Technologies) for 72 hours (day 0-72 hours; this differs from the numbering convention used by the manufacturer's protocol, which describes this period as day 1-day 4). Endoderm-stage cells were dissociated and passaged in small clumps to growth factor reduced Matrigel-coated (Corning) tissue culture plates (Corning) in base media of IMDM (ThermoFisher, Waltham, Mass.) and Ham's F12 (ThermoFisher) with B27 Supplement with retinoic acid (Invitrogen, Waltham, Mass.), N2 Supplement (Invitrogen), 0.1% bovine serum albumin Fraction V (Invitrogen), monothioglycerol (Sigma, St. Louis, Mo.), Glutamax (ThermoFisher), ascorbic acid (Sigma), and primocin (complete serum free differentiation medium, cSFDM (Kurmann et al., 2015; Longmire et al., 2012)) containing 10 µM SB431542 (Tocris, Bristol, United Kingdom) and 2 µM Dorsomorphin (Stemgent, Lexington, Mass.) for 72 hours (72 hours-144 hours) to pattern cells towards anterior foregut endoderm. Cells were then cultured for 9-11 additional days (typically, 144 hours-day 15) in cSFDM containing 3 µM CHIR99021 (Tocris), 10 ng/mL recombinant human FGF10 (rhFGF10, R&D Systems, Minneapolis, Minn.), 10 ng/mL recombinant human KGF (rhKGF, R&D Systems), 10 ng/mL recombinant human BMP4 (rhBMP4, R&D Systems), and 50 nM retinoid acid (RA, Sigma) or with CHIR, BMP4, and RA alone (for organoid immunostaining), to induce a lung epithelial progenitor fate. Doses of growth factors were determined based on previously published directed differentiation protocols (Huang et al., 2013; Kurmann et al., 2015; Longmire et al., 2012). Lung epithelial specification was evaluated at day 15 of differentiation by flow cytometry for NKX2.1GFP expression, expression of surrogate cell surface markers $CD47^{hi}/CD26^-$, or nuclear NKX2-1 protein content. Surface marker expression was evaluated at this stage of differentiation using a human cell surface marker screening panel (BD Biosciences, San Jose, Calif.). This protocol is based on previously described approaches (Hawkins et al., 2017; Huang et al., 2013; Longmire et al., 2012).

Neuroectodermal NKX2-1GFP+ cells were generated using STEMDdiff Neural Induction Medium (Stem Cell Technologies) according to the manufacturer's protocol with additional puromorphamine (Stemgent, 2 uM) supplementation from Day 6 to Day 12-15. NKX2-1GFP+ cells were purified by cell sorting at Day 12-15 (Hawkins et al., 2017).

Purification of NKX2-1+ Lung Progenitors by Cell Sorting

Figure 17A:
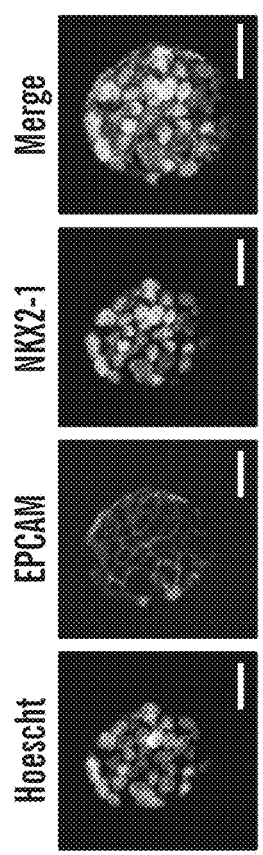
FIGS. 17A-17G shows the characterization of hPSC-derived proximal organoids (and is related to FIG. 5).
Figure 17B:
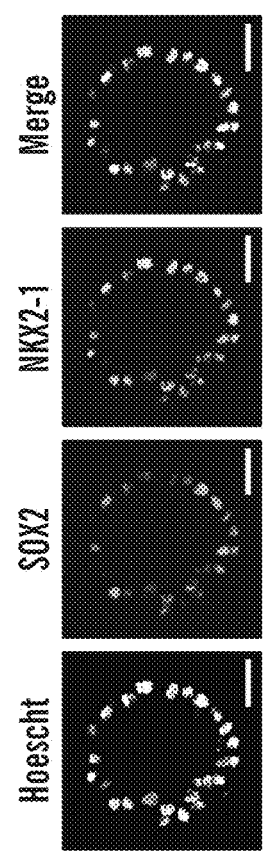
Figure 18A:
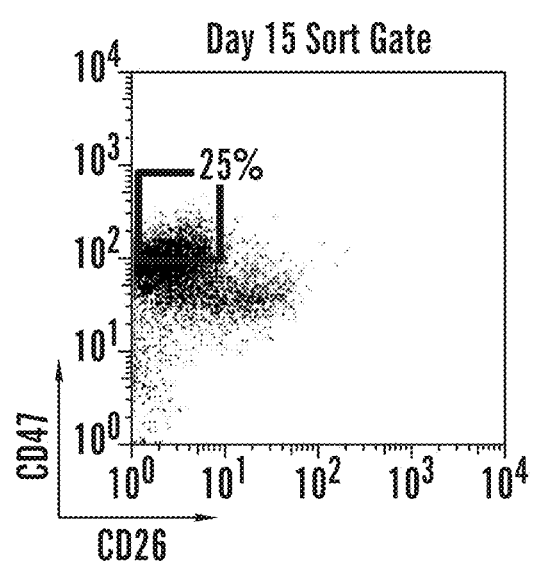
FIG. 18A-18E show forskolin swelling of hPSC-derived proximal airway organoids (and is related to FIG. 6).
Figure 18B:
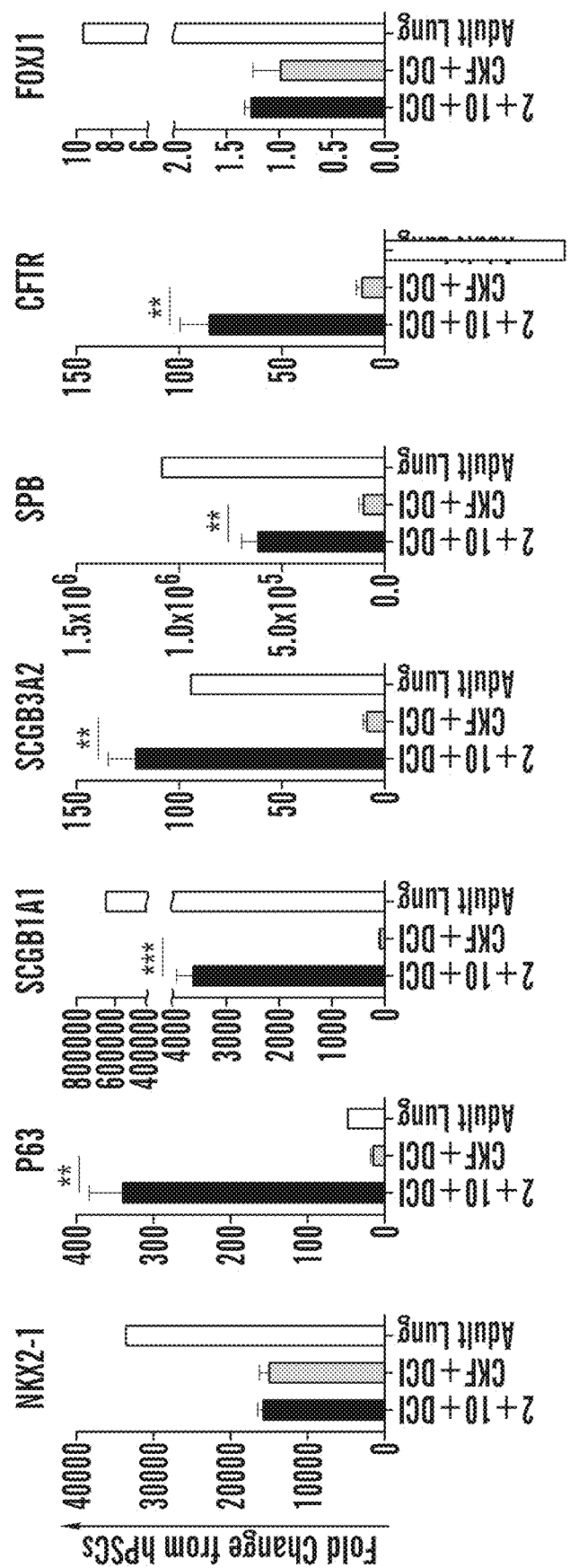

Cells grown in two-dimensional culture were harvested by incubation with 0.05% Trypsin-EDTA for 10-20 minutes at 37° C. Cells cultured in three-dimensional growth factor reduced Matrigel were harvested by incubation with 2 mg/mL dispase (ThermoFisher) for 30-60 minutes at 37° C. then subsequent incubation with 0.05% trypsin at 37° C. until a single cell suspension was achieved. Cells were washed with media containing 10% fetal bovine serum (FBS, ThermoFisher.) Harvested cells were spun at 300 RCF for 5 minutes at 4° C. and resuspended in buffer containing Hank's Balanced Salt Solution (ThermoFisher), 2% FBS and 10 µM Y-27632 (Tocris) and stained with propidium iodide (ThermoFisher) or calcein blue AM (ThermoFisher) for dead cell exclusion during flow cytometry. Live cells were sorted on a high speed cell sorter (MoFlo Legacy, Beckman Coulter, Pasadena, Calif.) at the Boston University Medical Center Flow Cytometry Core Facility based on NKX2-1GFP expression or by staining for CD47 (Biolegend) and CD26 (Biolegend) and gating for $CD47^{hi}/CD26^-$. Although nearly 100% of all differentiated cells are CD47+ at day 15 of directed differentiation, isolating cells in the region of the CD47 cloud brighter than the CD26+ population ($CD47^{hi}$, representative gate depicted in FIG. 17A) results in significant enrichment of the NKX2-1+ lung progenitor population (FIG. 18B, FIG. 17A) (Hawkins et al., 2017).

Gene Set Enrichment Analysis

Gene set enrichment analysis was performed using MSigDB v5.1 hallmark gene sets (http://software.broadinstitute.org/gsea/index.jsp) (Mootha et al., 2003; Subramanian et al., 2005) on our previously described microarray database (Hawkins et al., 2017; all raw data files can be downloaded from the gene expression ombinus, GEO #: GSE83310). Significant pathways were considered those with Benjamini-Hochberg false discovery rate-adjusted p value (FDR)<0.1.

Generation of Lentiviral Reporters for Wnt signaling

VSV-G pseudotyped lentiviral plasmids for β-catenin overexpression (EF1alpha-betacatenin(deltaGSK)-SV40-mCherry, Addgene Plasmid #23412) (Fuerer and Nusse, 2010) and the canonical Wnt reporter 7xTcf-mCherry (Addgene Plasmid #24315) (Berge et al., 2008) were used. Lentiviral particles were packaged in 293T cells using a five-plasmid system as previously described(Wilson et al., 2010). Briefly, 293T cells were transfected using Trans-IT Transfection Reagent (Mirus Bio, Madison, Wis.) with plasmids for a lentiviral backbone (e.g. 7XTCF-mCherry) and lentiviral packaging proteins tat, rev, gag/pol and vsv-g. Supernatants were collected after 48 hours and concentrated by centrifugation at 16.5K RPM for 90 minutes. To calculate titers of packaged viruses, FG293 cells were transduced with concentrated virus in 10% FBS with polybrene (5 □g/mL) and transduction efficiency was quantified after 72 hours by flow cytometry. For the 7XTCF-mCherry virus, cells were treated for 48 hours of 3 µM CHIR99021 prior to titering by flow cytometry. For each experiment, parallel wells were infected with the same MOI of a pHAGE EF1a-mCherry virus as a control for infection efficiency and nonspecific effects of lentiviral infection.

Reverse Tanscriptase Quantitative Real Time Polymerase Chain Reaction (RT-qPCR)

Measurement of mRNA expression by reverse transcriptase quantitative real time PCR (RT-qPCR) was performed as previously described(Longmire et al., 2012). Briefly, RNA was extracted from cells using a QIAzol Lysis Reagent (Qiagen, Venlo, Netherlands) and 150 ng of RNA was transcribed to cDNA using reverse transcription reagents (Applied Biosystems). Real time PCR (qPCR) was performed using TaqMan Fast Universal PCR Master Mix (ThermoFisher) and TaqMan (Applied Biosystems) reagents. The cDNA was diluted 1:3 and 2 µL of cDNA was added to each 25 µL (for Applied Biosystems StepOne 96-well System) or 12.5 µL (for Applied Biosystems QuantStudio7 384-well system) qPCR reaction. Each sample was run in technical triplicates and cycle (Ct) values were averaged between triplicates for analysis. Relative gene expression, normalized to 18S control, was calculated as fold change in 18S-normalized gene expression, compared to baseline, using the $2^{(-\Delta\Delta CT)}$ method. Baseline, defined as fold change=1, was set to undifferentiated iPSC levels, or if undetected, a cycle number of 40 was assigned to allow fold change calculations. Adult lung control RNA was extracted from a normal lung biopsy sample. Primers were all TaqMan probes purchased from Applied Biosystems. Specifics of primers used are detailed in Table 1.

TABLE 1

TaqMan Gene Expression Assay Information (Life Technologies).

| Human Gene | TaqMan Probe Number (Applied Biosystems) |
|---|---|
| AXIN2 | Hs00610344_m1 |
| CDX2 | Hs01078080_m1 |
| CFTR | Hs00357011_m1 |
| ETV5 | Hs00927557_m1 |
| FOXJ1 | Hs00230964_m1 |
| LEF1 | Hs01547250_m1 |
| MUC5AC | Hs00873651_mH |
| MUC5B | Hs00861595_m1 |
| NKD1 | Hs00263894_m1 |
| NKX2-1 | Hs00968940_m1 |
| P63 | Hs00978340_m1 |
| SCGB1A1 | Hs00171092_m1 |
| SCGB3A2 | Hs00369678_m1 |
| SOX2 | Hs01053049_s1 |
| SOX9 | Hs01001343_g1 |
| SFTPB | Hs01090667_m1 |
| SFTPC | Hs00161628_m1 |
| Mouse Gene | |
| Sftpc | Mm00488144_m1 |
| Scgb1a1 | Mm01230908_m1 |

Intracellular Flow Cytometry for NKX2-1 and SOX.

Cells were harvested for intracellular flow cytometry and fixed for 10-20 minutes at 37° C. in fresh 1.6% paraformeldehyde. Cells were permeabilized with Cell Permeabilization Buffer (eBioscience, San Diego, Calif.) containing 4% normal donkey serum (Sigma) in PBS and stained with primary antibody for NKX2-1 (Abcam # ab76013, rabbit EP1584Y, 1:100) or a conjugated antibody for SOX2 (BD #561506, PerCP-Cy5.5 conjugated, mouse O30-678, 1:100). Anti-NKX2-1 antibody was detected by secondary antibody stainings with either Cy3, Alexa Fluor 488, or Alexa Fluor 647 fluorophore-conjugated secondary antibodies (AffiniPure Donkey Anti-Rabbit IgG (H+L); 1:500; Jackson ImmunoResearch, West Grove, Pa.). Stained cells were analyzed on a FacsCalibur instrument (BD Biosciences, San Jose, Calif.) and data was analyzed with FlowJo software (Ashland, Oreg.).

Immunofluorescence Microscopy of Cultured Cells

Cells for immunofluorescence microscopy were cultured on glass coverslips (ThermoFisher). Cultured cells were fixed with fresh 4% paraformeldehyde and stained as described previously(Kurmann et al., 2015). Briefly, cells were permeabilized with 0.3% Triton-X (Sigma) for 10 minutes at room temperature then blocked with 4% normal donkey serum (Sigma) for 30 minutes at room temperature. Cells were incubated with primary antibodies (detailed in Key Resources Table 3) overnight at 4° C., washed, and incubated with secondary antibodies for 30-60 minutes at room temperature. All secondary antibodies were conjugated to Alexa Fluor 488, Cy3, or Alexa Fluor 647 (Jackson Immunoresearch, 1:500). After antibody staining, nuclei were stained with Hoescht dye (ThermoFisher, 1:500). Coverslips with cells were mounted on glass slides using Prolong Diamond Anti-Fade Mounting Reagent (Thermo-Fisher) and imaged on a Nikon (Tokyo, Japan) deconvolution microscope.

Three-dimensional organoids were harvested by incubating for 1 hour with dispase and fixed with fresh 4% paraformaldehyde. Whole organoids were stained as described for cultured cells, with slightly longer permeabilization, blocking wash, and antibody incubation steps. For whole mount imaging, organoids were mounted on cavity slides and visualized with a Zeiss (Jena, Germany) confocal microscope.

Quantification of nuclear colocalization was performed using Nikon NIS Elements software using the Object Count function. 3-5 areas from each slide were analyzed for each replicate. The total image area where NKX2-1 and SOX2 or P63 overlapped was divided by the area containing only the NKX2-1 stain.

Directed Differentiation of mESCs to Nkx2-1+ Lung Epithelium

Nkx2-1$^{mCherry}$ mESCs(Bilodeau et al., 2014) were differentiated to lung epithelium as described previously (Longmire et al., 2012). Briefly, LIF was withdrawn for 60 hours to induce embryoid body (EB) formation. EBs were then treated with 100 ng/mL activin A (R&D Systems) for 60 hours. Anterior foregut endoderm was generated by dual BMP4 and TGFβ inhibition by SB431542 (10 μM) and rmNoggin (100 ng/mL, R&D Systems) for 24 hours. Lung specification was induced using rmWnt3a (100 ng/mL) and rmBMP4 (10 ng/mL). Cells were sorted on day 14 for Nkx2-1$^{mCherry}$ expression and replated for 2D culture outgrowth containing rhFGF2 (250 ng/mL) and rhFGF10 (100 ng/mL) as previously published(Kurmann et al., 2015) and rmWnt3a (100 ng/mL), as per experimental conditions. On day 16, cells were infected overnight with a SftpcGFP lentivirus (Longmire et al., 2012) containing a 3.7 kb fragment of the human SPC promoter cloned into the promoter of the pHAGE CMV-GFP-w lentiviral plasmid in the place of the CMV promoter (Wilson et al., 2010) in 5 ug/mL polybrene for quantification on day 30 of SftpcGFP+ cell induction.

Post-Specification Patterning of Lung Epithelial Progenitors

Day 14-16 cells from the lung progenitor directed differentiation protocol were harvested with 0.05% Trypsin-EDTA (Invitrogen) and replated in clumps in either Matrigel-coated tissue culture dishes in two-dimensional culture or in three-dimensional Matrigel drops. Matrigel drops were formed by resuspending cell clumps directly in undiluted Matrigel matrix, pipetting 50-100 μL into each well, and allowing the Matrigel/cell mixture to gel for 30 minutes at 37° C. Cell drops were then covered completely with growth medium.

Alternately, purified lung epithelial cells were plated in three-dimensional Matrigel droplets immediately post-sorting. In cell lines not targeted with the NKX2-1$^{GFP}$ reporter, differentiated cells were enriched for lung epithelial progenitors by staining for the cell surface markers CD47 (Biolegend, San Diego, Calif., #323110, PerCP-Cy5.5 conjugated, mouse CC2C6, 1:200) and CD26 (Biolegend #302705, PE conjugated, mouse BA5b, 1:200), as described previously (Hawkings et al., 2017. Prospective isolation of NKX2-1+/CD47+ human lung progenitors derived from pluripotent stem cells. J. Clin. Invest).

Post-specification culture conditions were determined by the addition of growth factors to cSFDM. For patterning experiments, growth factors were added to a base media containing 10 ng/mL rhFGF10 ("Base") and additional factors detailed in the results text. For concentrations of growth factors required for each experiment, see Table 2. Cells were additionally cultured with 10 μM Y-27632 (Tocris) for 24 hours after replating. Doses of growth factors were determined based on previously published directed differentiation protocols (Huang et al., 2013; Kurmann et al., 2015; Longmire et al., 2012) as well as dose-response experiments using 7XTCF lentiviral reporters for CHIR99021 (Figure S2d-e). Cells were additionally cultured with 10 µM Y-27632 (Tocris) for 24 hours after replating.

TABLE 2

Growth Factor Concentrations

| Growth Factor | Stock Concentration | Final Concentration |
| --- | --- | --- |
| CHIR99021 | 3 mM | 3 µl |
| rhBMP4 | 10 mg/mL | 10 µg/mL |
| Dorsomorphin | 2 mM | 2 µM |
| FGF2 | 250 mg/mL | 250 µg/mL |
| FGF10$^{high}$ | 100 mg/mL | 100 µg/mL |
| rhTGFb | 10 mg/mL | 10 µg/mL |
| SB431542 | 10 mM | 10 µM |
| DAPT | 10 mM | 2 µM |

The final protocol for generating rapidly proximalized NKX2-1+ lung epithelium was replating unsorted or sorted cells for 4 days of culture post-specification in cSFDM containing 10 ng/mL FGF10. Sorted cells were cultured with additional factors: 50 nM dexamethasone (Sigma), 0.1 mM 8-Bromoadenosine 3',5'-cyclic monophosphate sodium salt (Sigma) and 0.1 mM 3-Isobutyl-1-methylxanthine (IBMX) (Sigma) (DCI), and Y-27632. Cells were analyzed for expression of proximal markers 4 days post-replating in FGF10 media.

For organoid experiments, cells were cultured in "CFK media" containing 3 µM CHIR99021, 10 ng/mL rhFGF10, and 10 ng/mL rhKGF or "2+10 media" containing 250 ng/mL recombinant human FGF2 (rhFGF2, R&D Systems) and 100 ng/mL rhFGF10. We further supplemented these medias with DCI and Y-27632.

Therefore, in the final protocol for the generation of proximalized organoids, single sorted NKX2-1+ cells were replated as 50,000-100,000 cells per well cultured in cSFDM with FGF2 (250 ng/mL), FGF10 (100 ng/mL), DCI, and Y-27632 for at least one week post-sort prior to analysis. Proximalized organoids were maintained for up to 6 weeks after sorting, with media changed every other day. Ciliation was induced in proximalized organoids by Notch inhibition using DAPT (2 µM) in organoids after outgrowth least 2 weeks post-sort. Generation of motile cilia was observed by 2 weeks post-DAPT treatment.

Images of cultured organoids, including videos, were taken on a Keyence (Osaka, Japan) BZ-X700 fluorescence microscope. Z-stack images were processed using full focus image analysis using Keyence software.

For formation of ALI cultures, proximalized cells were trypsinized and replated in two-dimensional culture on TransWell inserts (Corning) at a confluency of 100,000 cells/cm$^2$. Expansion was performed in PneumaCult ALI media (Stem Cell Technologies) containing dexamethasone to replace hydrocortisone with additional SMAD inhibition by Dorsomorphin (2 µM) and SB431542 (10 µM)(Mou et al., 2016) until confluent. After expansion of cells to confluence, media was removed from the top chamber and cells were differentiated in PneumaCult ALI media with dexamethasone but without SMAD inhibition. Motile ciliated cells were observed by one week post-induction of ALI differentiation. ALI cultures were characterized by immunofluorescent staining for acetylated alpha tubulin, Hoescht, and F-actin (primary antibody information are detailed in Table 3) and z-stack images were taken on a confocal microscope (Zeiss). Orthogonal and maximum intensity Z-projections were generated using ImageJ.

TABLE 3

Primary Antibody Information.

| Antigen | Host | Clone | Company | Cat. # | Dilution |
| --- | --- | --- | --- | --- | --- |
| NKX2.1 | Rabbit | EP1584Y | Abcam | ab76013 | 1:100 |
| SOX2 | Mouse | O30-678 | BD Biosciences | 561469 | 1:100 |
| P63 | Mouse | 4A4 | BioCare Medical | 163 | 1:200 |
| P63 | Rabbit | Polyclonal | Santa Cruz | sc-8344 | 1:500 |
| KRT5 | Chicken | Polyclonal | BioLegend | 905901 | 1:500 |
| EPCAM | Mouse | AUA1 | Abcam | ab20160 | 1:250 |
| Pro-SPB | Rabbit | Polyclonal | Seven Hills | WRAB-55522 | 1:1000 |
| Acetylated alpha-tubulin | Rabbit | D20G3 | Cell Signaling Technologies | 5335 | 1:1000 |

Forskolin-Induced Swelling of Organoids

Swelling was induced in organoids at Day 22-35 of differentiation. Organoids grown in in three-dimensional Matrigel culture in the absence of cyclic AMP and IBMX were passaged to new droplets in 3 µL Matrigel at least one day prior to swelling. For swelling analysis, organoids were incubated in media containing 5-10 µM forskolin (Sigma) and 10 µM calcein green (ThermoFisher) for 4-24 h at 37° C. and 5% CO2. Whole well images were taken using a Keyence BZ-X700 fluorescence microscope at time of forskolin addition and 24 hours later and stitched using Keyence software. Videos were created by imaging every 15 minutes for 24 hours. Quantification of swelling area was performed from replicate wells images on the calcein green channel using ImageJ. Total well surface area covered by organoids was calculated based on thresholded images and the total well area of circular organoids (circularity=0.5-1) were measured. If necessary, organoid edges were smoothed using a Gaussian blur filter prior to thresholding and watershedding. The well area at time=0 was set to 1. Images were again analyzed at 3 and 24 hours post-forskolin addition and the ratio of the post-swelling area to the original area was calculated. Statistics were calculated from separate wells of organoids, with each value comprising 20-50 individual organoids.

Statistical Methods

Statistical methods relevant to each figure are outlined in the figure legend. Briefly, unless indicated otherwise in the figure legend, unpaired, two-tailed Student's t-tests were used to compare quantitative analyses comprising two groups of n=3 or more samples, where each replicate ("n") represents either entirely separate differentiations from the pluripotent stem cell stage or replicates differentiated simultaneously and sorted into separate wells. Further specifics about the replicates used in each experiment are available in the figure legends. In these cases, a Gaussian distribution and equal variance between samples was assumed as the experiments represent a large number of random samples of the measured variable. As we anticipated that biologically relevant differences between conditions would have a large effect size and due to the large technical burden of directed differentiation experiments, we set our sample size threshold to at least 3 replicates to ensure our samples were large enough to perform t-tests to compare the populations and observe predicted differences. The p-value threshold to determine significance was set at p=0.05. Data for quantitative experiments is typically represented as the mean with error bars representing the standard deviation or standard error of the mean, depending on the experimental approach. These details are available in the figure legends. For analysis of dose escalation experiments, an ordinary one-way ANOVA with post test for linear trend to test the linear trend in the mean value at the indicated doses from left to right.

The microarray database of the timecourse of differentiating NKX2-1+ lung epithelium used to generate the heat map in FIG. 2 was described in Hawkins et al., 2017 and has been deposited in GEO Database, GEO #: GSE83310.

Example 1

Figure 1B:
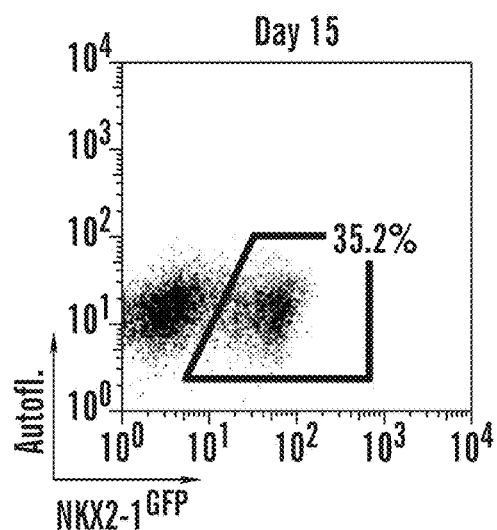
Figure 7A:
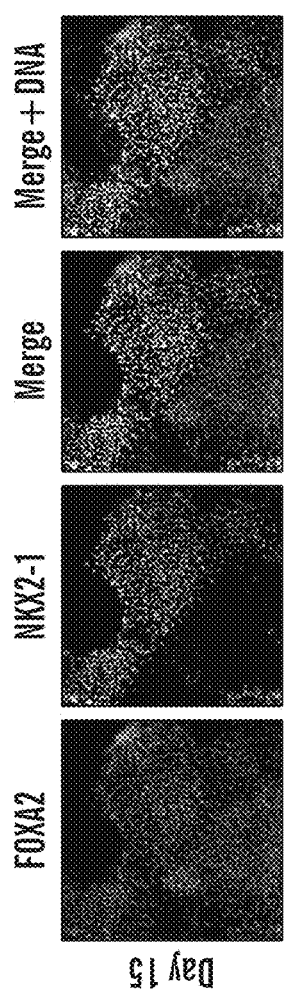
FIGS. 7A-7G show directed differentiation of lung epithelial progenitors (and is related to FIG. 1).
Figure 7B:
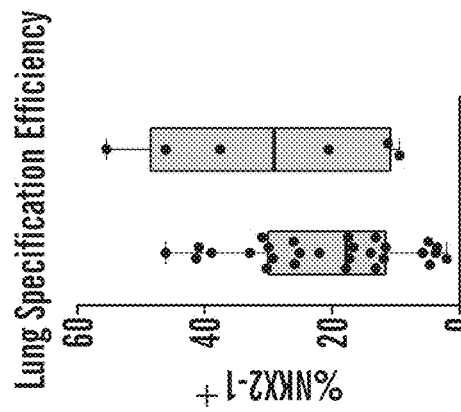
Figure 7C:
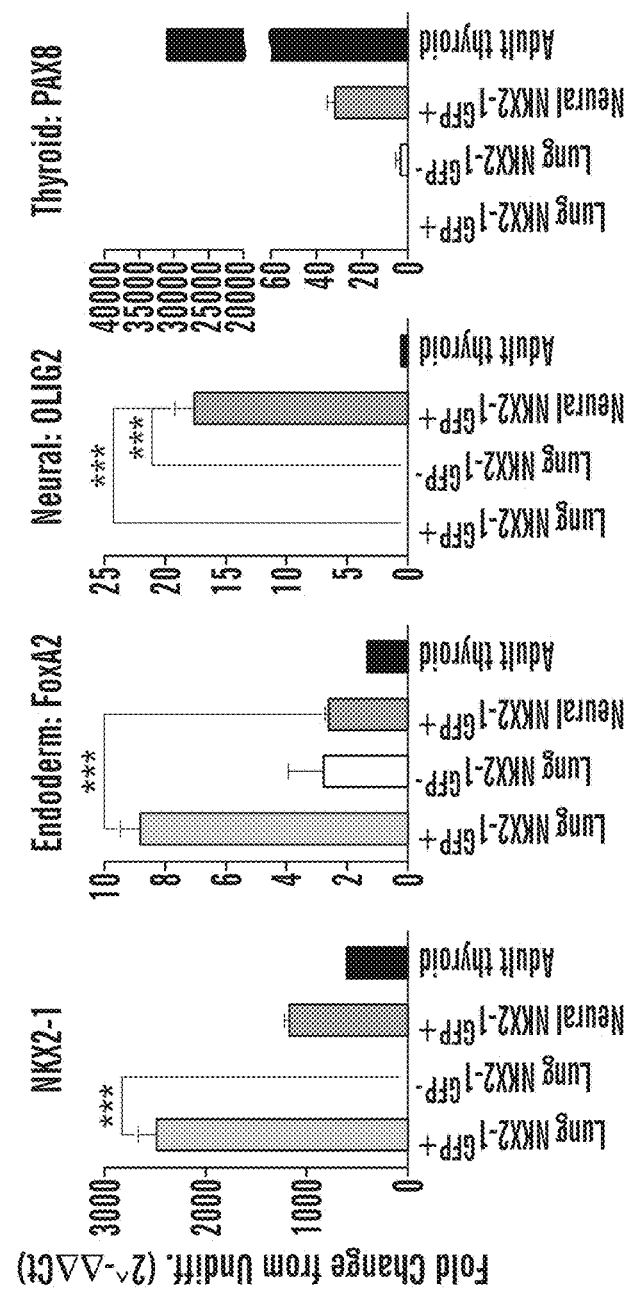
Figure 7D:
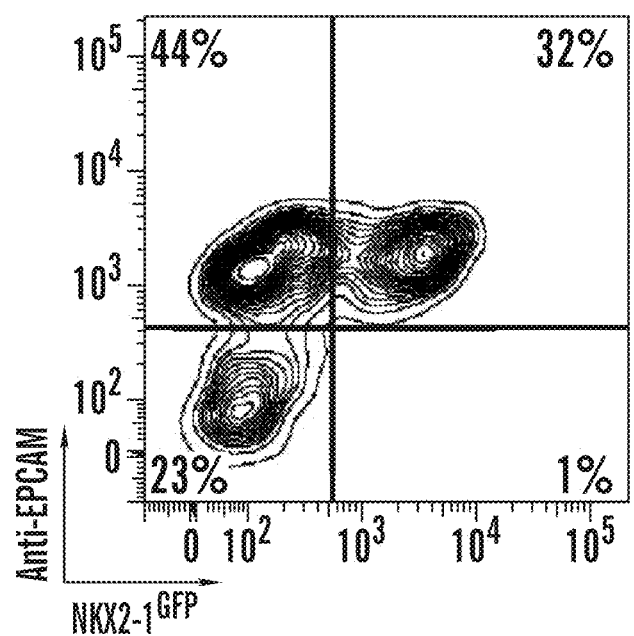
Figure 7E:
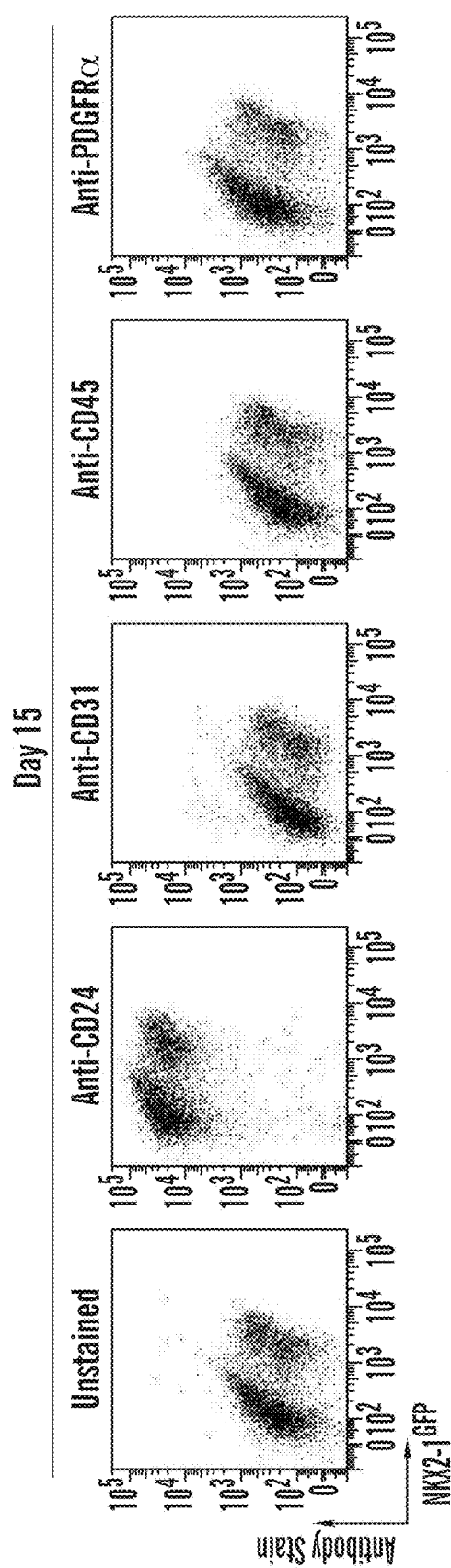
Figure 12A:
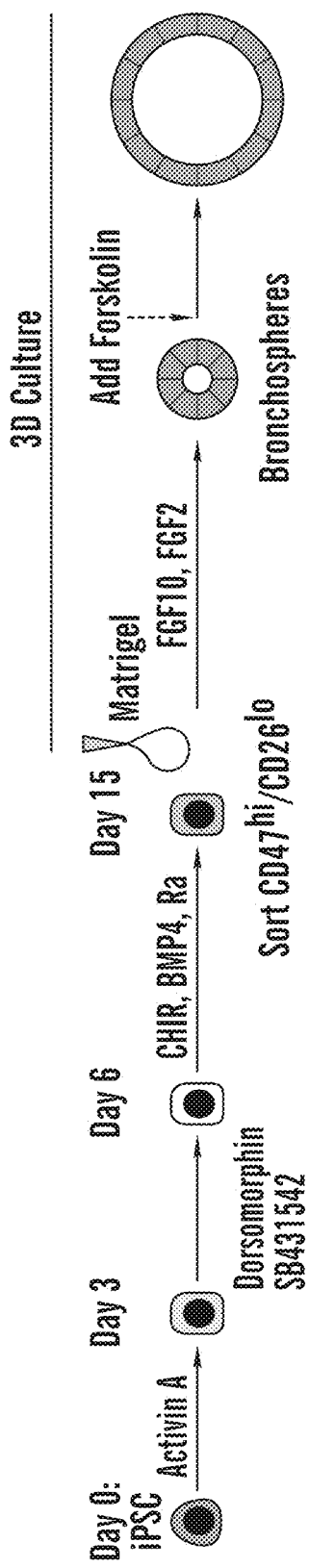
FIG. 12A-12E shows in vitro directed differentiation of human PSCs into lung-linage committed cells.
Figure 12B:
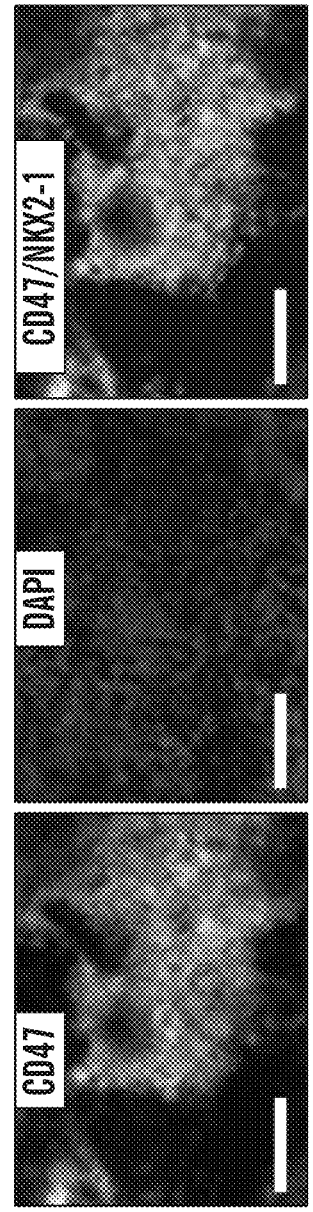
Figure 12C:
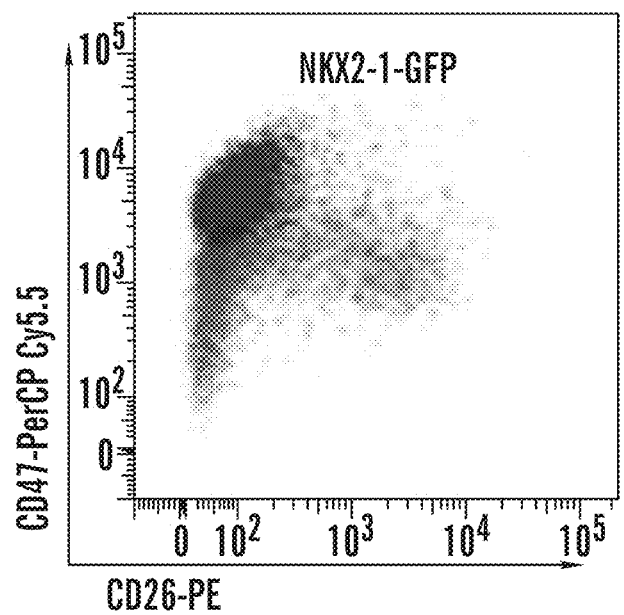
Figure 12D:
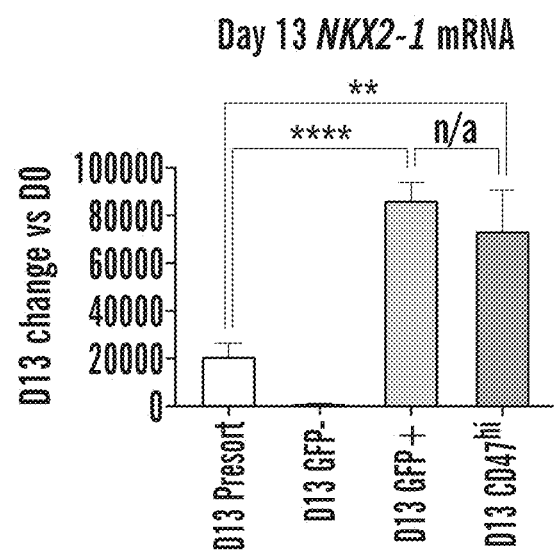

Screening Developmental Signaling Pathways Reveals Contribution from Wnt and BMP Signaling to Proximodistal Patterning of hPSC-Derived Lung Epithelium To screen for potential mechanisms regulating human lung epithelial patterning after lung lineage specification, the inventors sought to employ an in vitro lung development model system that uses sequential medias in a stepwise, stage-specific approach to recapitulate the lineage specification of relatively undifferentiated (primordial) FOXA2+ NKX2-1+ endodermal lung progenitors via anterior foregut endoderm from mouse or human pluripotent stem cells (PSCs) (FIG. 1A, FIG. 12A, 16A) (Huang et al., 2013; 2015; Longmire et al., 2012). Using this approach, the inventors derived NKX2-1+lung epithelial progenitors at varying efficiencies from several hPSC lines, including RUES2 (untargeted) and an iPSC line (hereafter C17) carrying a green fluorescent protein (GFP) reporter targeted to NKX2-1, the first gene locus activated in developing endoderm at the time of lung lineage specification (hereafter NKX2-1$^{GFP}$) (FIG. 1B, FIG. 7B). Using these lines, the inventors discovered that differentiated lung progenitors were enriched for NKX2-1 and FOXA2 expression (FIG. 7C) and did not express appreciable markers of other NKX2-1+ lineages (thyroid, PAX8; neural, OLIG2) in comparison to neuroectodermal and thyroid controls (FIG. 7C). Nearly 100% of NKX2-1GFP+ cells were EPCAM+ (FIG. 7D), and did not express markers of other non-endodermal lineages including PDGFRα, CD31, and CD45 (FIG. 7E). Although these NKX2-1$^{GFP+}$ progenitors are initially undifferentiated or primordial at the time of their emergence in culture (days 9-15; Hawkins et al., 2017), further time in culture in media supplemented with CHIR99021, FGF10 and KGF results in their differentiation into a heterogeneous population of cells expressing markers consistent with multiple lung lineages characteristic of both proximal airway and distal alveolar epithelia, including SOX2, SOX9, TP63, SFTPB, CFTR, SFTPC, FOXJ1, and SCGB3A2 (Hawkins et al., 2017).

Figure 1C:
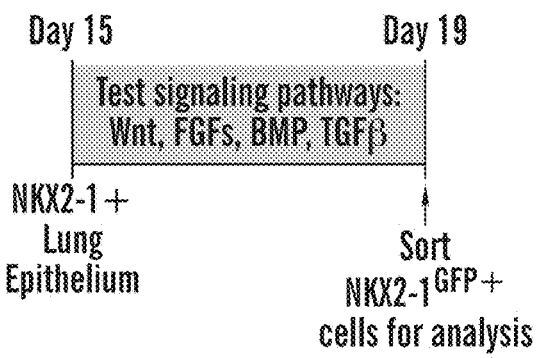
Figure 1D:
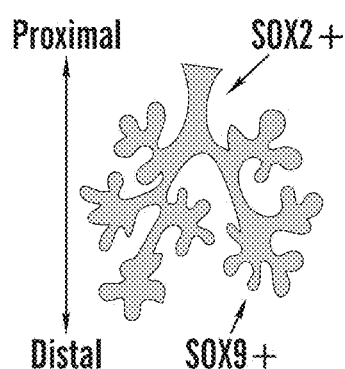

To test whether the inventors could efficiently induce a proximal vs distal program in iPSC-derived lung progenitors, the inventors modulated key developmental pathways beginning on day 15 of differentiation in our model system (FIG. 1C-1E), and monitored changes in SOX2 and SOX9 expression that are due to coordinated proximal vs distal patterning changes in purified NKX2-1$^{GFP+}$ cells within 4 days of treatment. At day 15, post-lung specification, the inventors cultured cells in a base media of "low dose" (10 ng/mL) FGF10 to promote proliferation without strongly inducing patterning(Volckaert et al., 2013). From this base media, the inventors stimulated the following pathways: Wnt signaling via the potent GSK3β inhibitor CHIR99021, hereafter CHIR; FGF signaling using FGF2 or high dose (100 ng/mL) FGF10; BMP signaling using BMP4; and TGFβ signaling using TGFβ

Figure 1E:
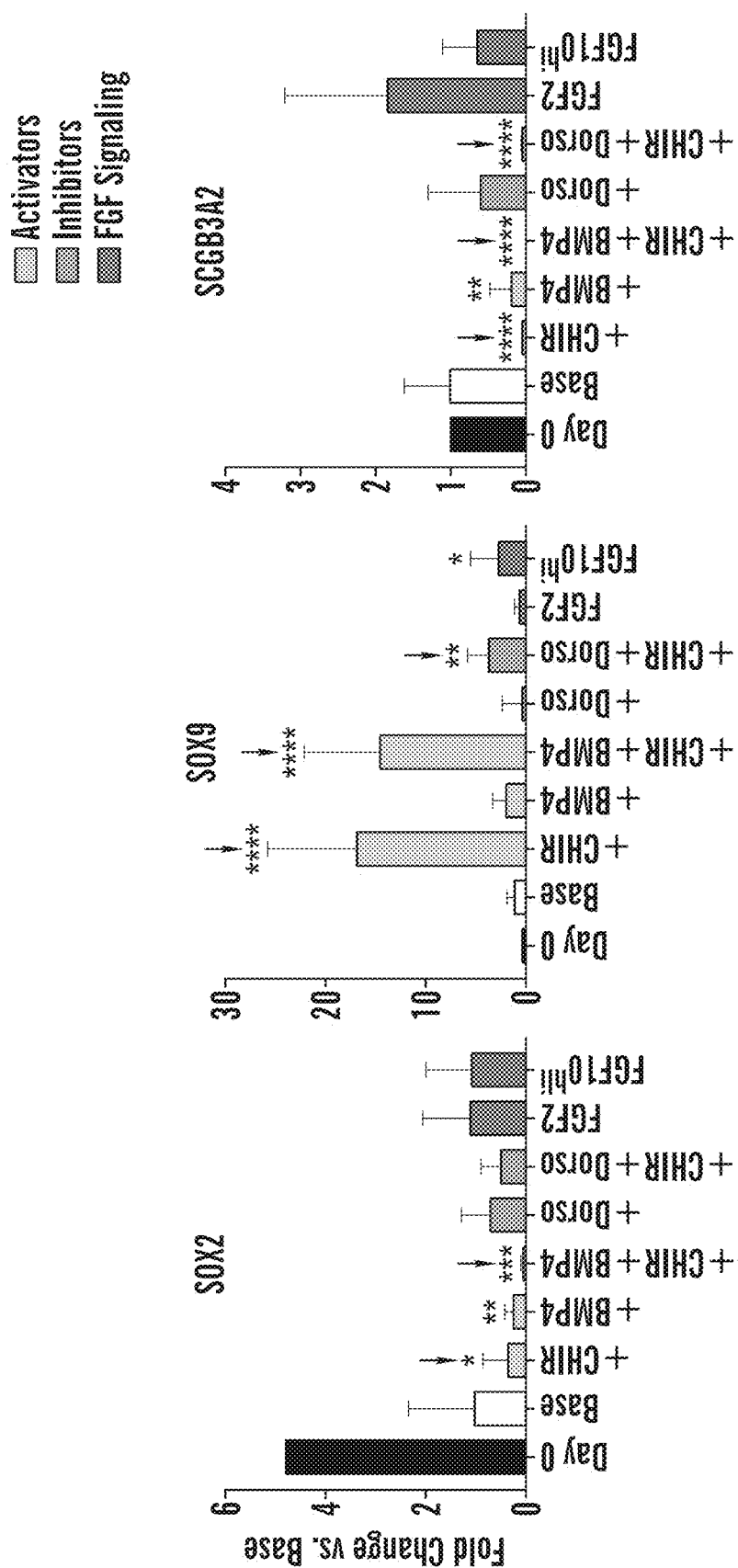
Figure 7F:
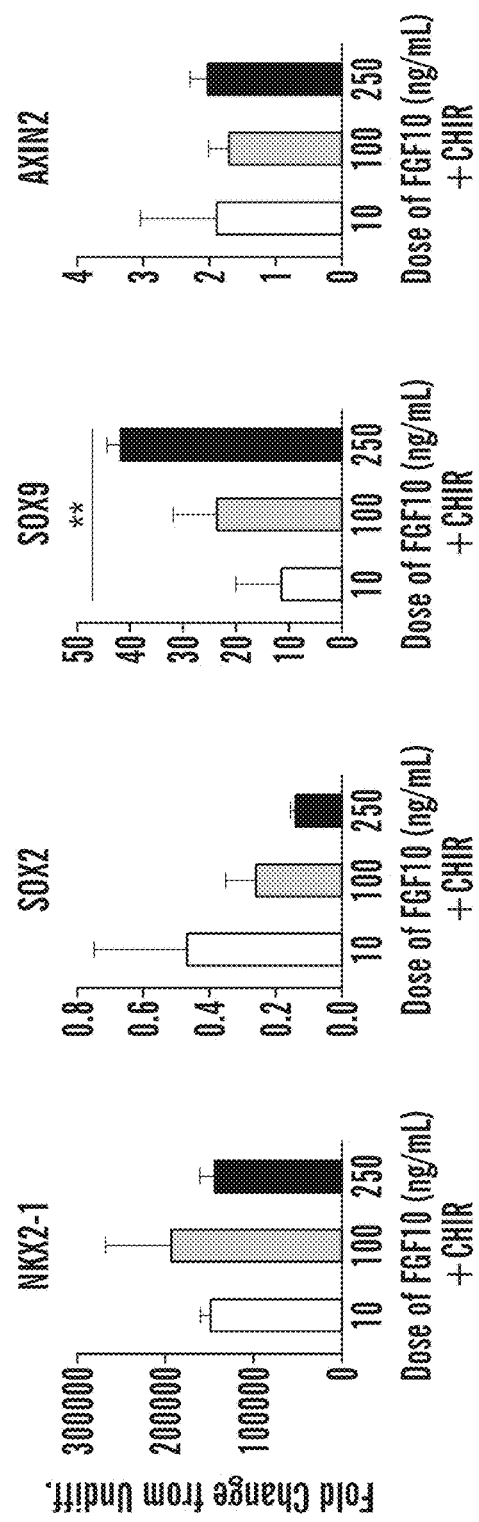
Figure 7G:
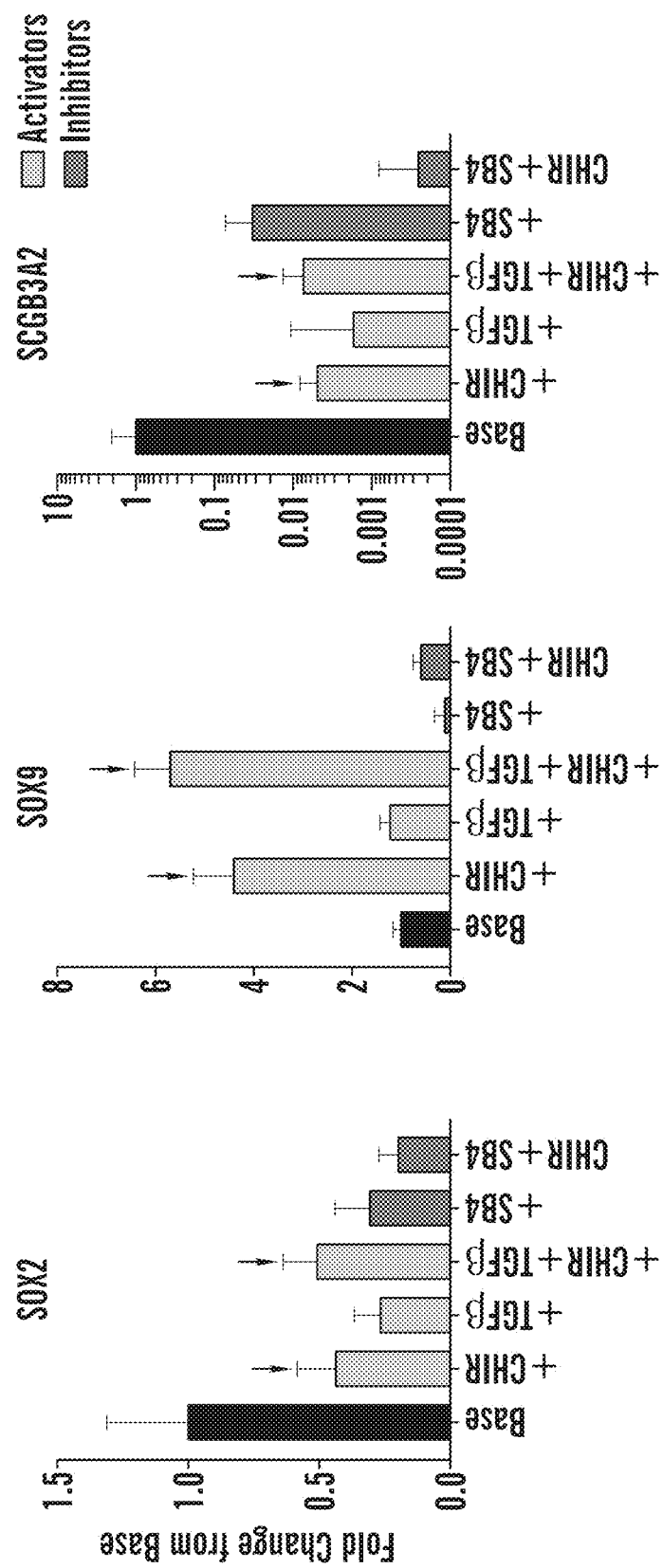

The inventors found that conditions containing CHIR resulted in significantly decreased SOX2 and increased SOX9 expression in sorted NKX2-1$^{GFP+}$ cells, suggesting abrogated proximal and increased distal patterning within 4 days (day 19; FIG. 1E). Suppression of proximal cell fate by CHIR was further supported by decreased expression of the highly-specific proximal lung epithelial marker, SCGB3A2. BMP signaling activation also suppressed SOX2 and SCGB3A2 expression while permitting SOX9 expression, although to a lesser extent than Wnt activation. Inhibition of BMP signaling with the SMAD1/5/8 inhibitor, Dorsomorphin, significantly blocked CHIR induced distal patterning (CHIR vs CHIR+Dorso p=1×10$^{-6}$). Addition of the Wnt inhibitor, XAV939, had no effect in conditions without CHIR (data not shown), demonstrating low basal Wnt signaling High dose FGF10 resulted in smaller but statistically significant increased SOX9 expression (FIG. 1E). Concordantly, treatment with escalating doses of FGF10 together with CHIR resulted in additionally increased distal (SOX9) and decreased proximal (SOX2) patterning (FIG. 7F). In contrast, the inventors determined that TGFβ signaling had no significant effect on patterning markers (FIG. 7G).

Taken together, this initial signaling pathway screen demonstrated that hPSC-derived lung epithelium responds within 4 days to signaling cues and that Wnt activation via CHIR potentially maintains distal over proximal epithelial patterning early post-lung specification. These patterning changes in human cells are consistent with prior mouse genetic studies suggesting modulation of Wnt activity impacts lung proximodistal patterning during development (De Langhe et al., 2005; Hashimoto et al., 2012; Mucenski et al., 2003; Ramasamy et al., 2007; Shu et al., 2005; Volckaert et al., 2013; Zemke et al., 2009).

Wnt Signaling is Required in a Stage-Dependent Manner for Normal Lung Epithelial Specification Having identified Wnt signaling as a putative patterning pathway, the inventors assessed the stage-dependent role of this pathway in hPSC lung differentiation. By comparing iPSC-derived anterior foregut endoderm to purified NKX2-1$^{GFP}$+ progenitors at day 15 of differentiation through unbiased gene set enrichment analysis (GSEA) of their global transcriptomes, the inventors identified 19/50 gene sets statistically upregulated in day 15 NKX2-1+ progenitors (FDR<0.1), including Wnt/β-catenin signaling (Table 4).

TABLE 4

Gene set enrichment analysis showing significantly upregulated pathways from Day 6 anterior foregut endoderm to Day 15 NKX2.1GFP+ cells. Related to FIG. 2.

| Name | Size | Normalized Enrichment Score | FDR Q-Value |
|---|---|---|---|
| Hallmark_Tnfa_Signaling_Via_Nfkb | 198 | −1.8240850 | 0.006348000 |
| Hallmark_Hypoxia | 200 | −1.7880290 | 0.0037740 |
| Hallmark_Angiogenesis | 36 | −1.7711890 | 0.003736000 |
| Hallmark_Estrogen_Response_Early | 199 | −1.7205740 | 0.006668000 |

TABLE 4-continued

Gene set enrichment analysis showing significantly upregulated pathways from Day 6 anterior foregut endoderm to Day 15 NKX2.1GFP+ cells. Related to FIG. 2.

| Name | Size | Normalized Enrichment Score | FDR Q-Value |
| --- | --- | --- | --- |
| Hallmark_Uv_Response_Dn | 144 | −1.5744670 | 0.030400000 |
| Hallmark_Bile_Acid_Metabolism | 111 | −1.5310850 | 0.042757000 |
| Hallmark_Peroxisome | 102 | −1.5136110 | 0.042758000 |
| Hallmark_Cholesterol_Homeostasis | 72 | −1.5047460 | 0.040901000 |
| Hallmark_Apoptosis | 160 | −1.4711340 | 0.050714000 |
| Hallmark_Coagulation | 135 | −1.4658420 | 0.04762100 |
| Hallmark_Wnt_Beta_Catenin_Signaling | 42 | −1.4453040 | 0.051529000 |
| Hallmark_P53_Pathway | 196 | −1.4307700 | 0.05486400 |
| Hallmark_Il2_Stat5_Signaling | 197 | −1.3720960 | 0.09475000 |
| Hallmark_Notch_Signaling | 32 | −1.367708 | 0.09090900 |
| Hallmark_Interferon_Gamma_Response | 198 | −1.3676510 | 0.08493100 |
| Hallmark_Androgen_Response | 100 | −1.3614840 | 0.083668000 |
| Hallmark_Hedgehog_Signaling | 36 | −1.3410130 | 0.09431400 |
| Hallmark_Estrogen_Response_Late | 196 | −1.3259910 | 0.09967200 |
| Hallmark_Interferon_Alpha_Response | 97 | −1.3192650 | 0.099256000 |
| Hallmark_Epithelial_Mesenchymal_Transition | 197 | −1.2952380 | 0.11539900 |
| Hallmark_Il6_Jak_Stat3_Signaling | 87 | −1.2755990 | 0.12782500 |
| Hallmark_Apical_Junction | 199 | −1.255455 | 0.14274200 |
| Hallmark_Kras_Signaling_Up | 198 | −1.2520570 | 0.14007000 |
| Hallmark_Complement | 198 | −1.2445410 | 0.14189900 |
| Hallmark_Inflammatory_Response | 199 | −1.224236 | 0.16050700 |
| Hallmark_Fatty_Acid_Metabolism | 155 | −1.1272990 | 0.3016230 |
| Hallmark_Xenobiotic_Metabolism | 198 | −1.0933240 | 0.3609340 |
| Hallmark_Uv_Response_Up | 158 | −1.0775980 | 0.38219800 |
| Hallmark_Tgf_Beta_Signaling | 52 | −1.0613540 | 0.40488400 |
| Hallmark_Apical_Surface | 44 | −0.99059900 | 0.56656800 |
| Hallmark_Glycolysis | 198 | −0.97763200 | 0.58223700 |
| Hallmark_Allograft_Rejection | 196 | −0.9665040 | 0.5927930 |
| Hallmark_Pancreas_Beta_Cells | 40 | −0.94818300 | 0.6248670 |
| Hallmark_Unfolded_Protein_Response | 111 | −0.89226100 | 0.74870700 |
| Hallmark_Mtorc1_Signaling | 198 | −0.82918400 | 0.86852600 |
| Hallmark_Heme_Metabolism | 198 | −0.7689400 | 0.9319400 |

Figure 2A:
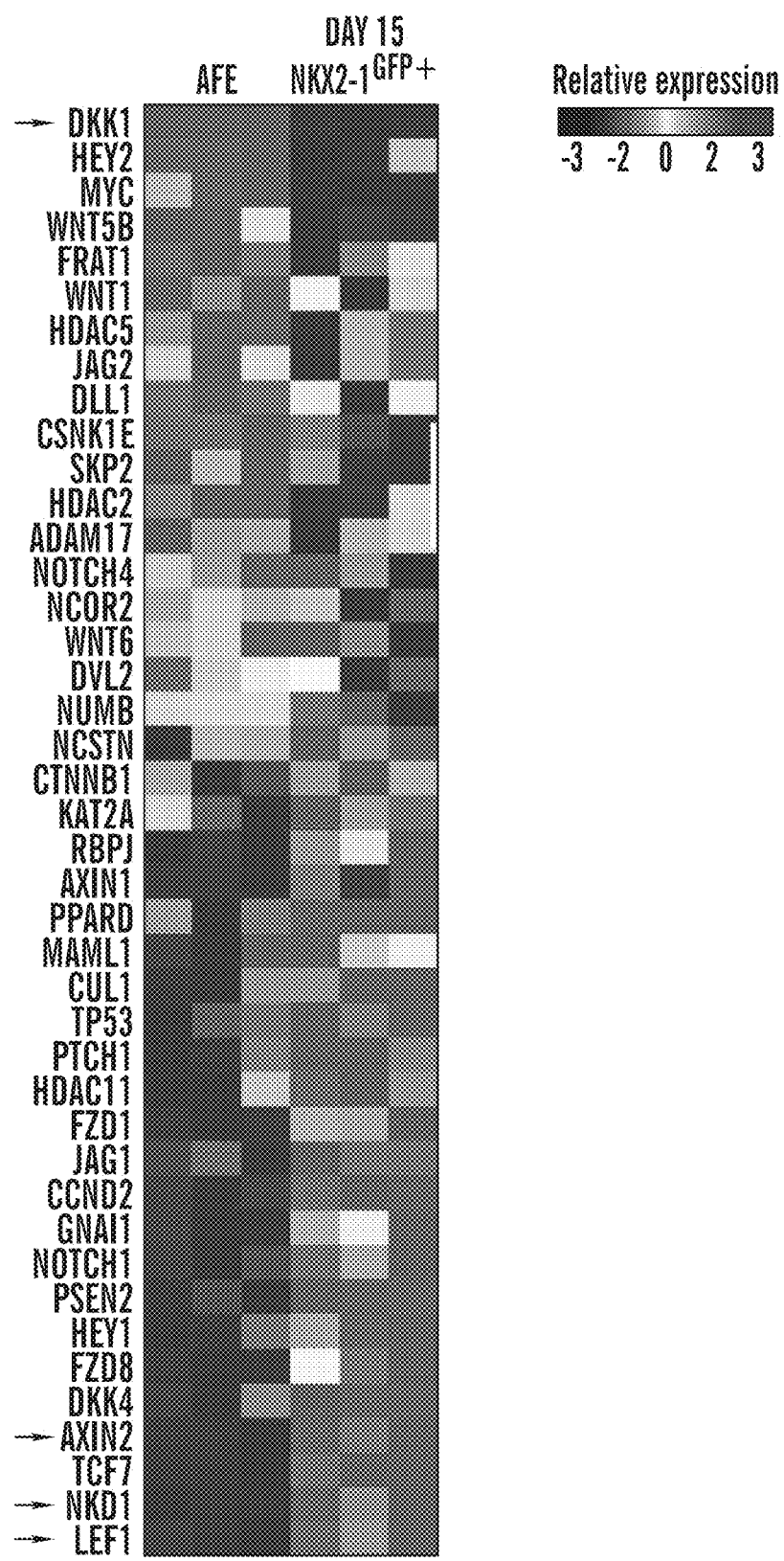
FIGS. 2A-2I shows that withdrawal of Wnt signaling activity post-lung specification leads to increased proximal patterning.
Figure 8A:
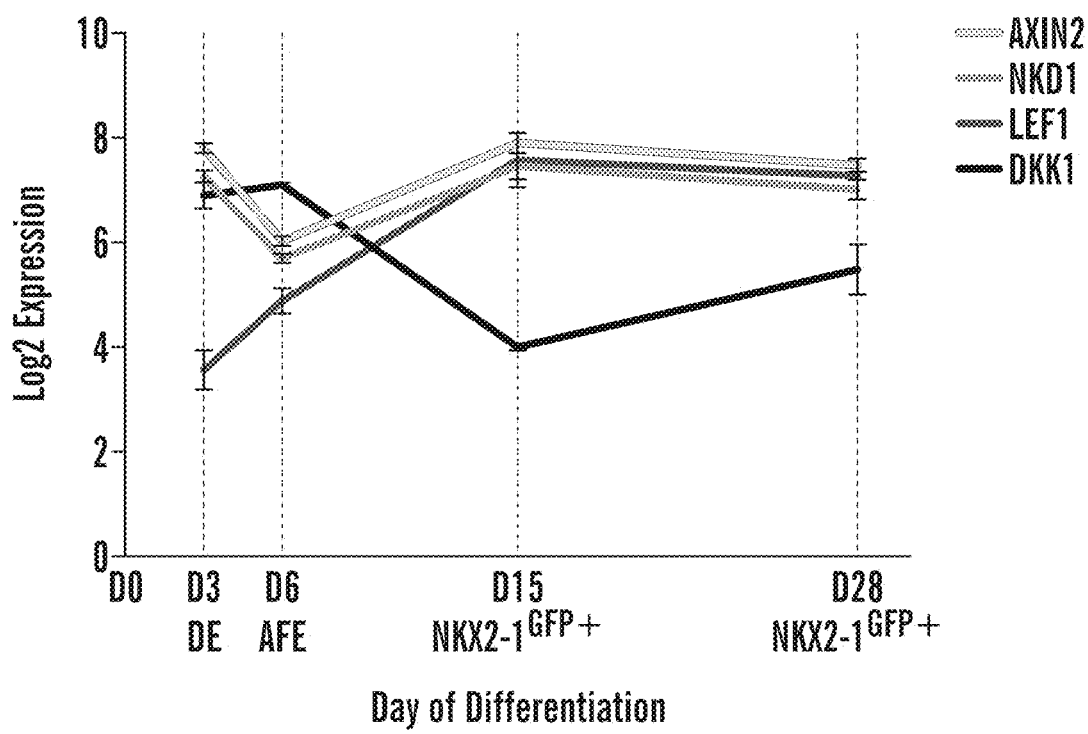
FIGS. 8A-8E show that Wnt signaling is activated in response to culture with CHIR during directed differentiation (and is related to FIG. 2).
Figure 8B:
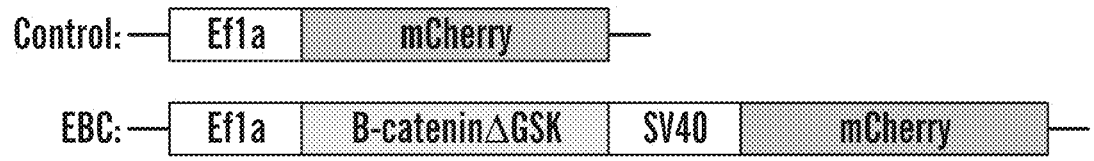
Figure 8C:
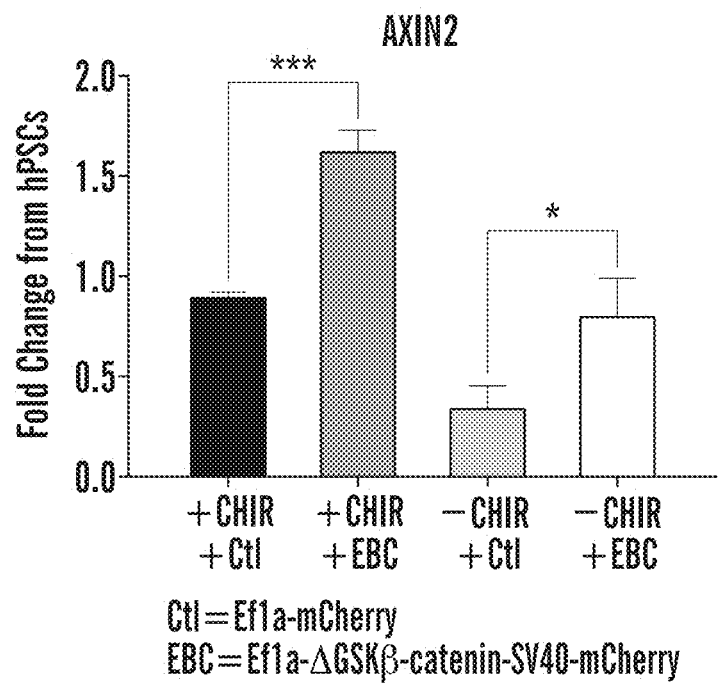
Figure 8D:
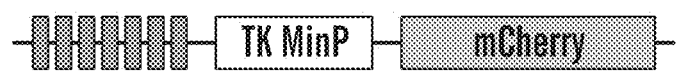
Figure 8E:
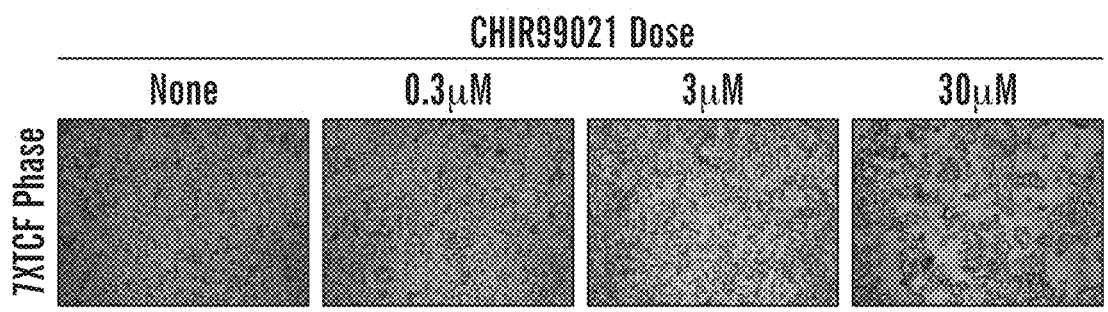
Figure 9A:
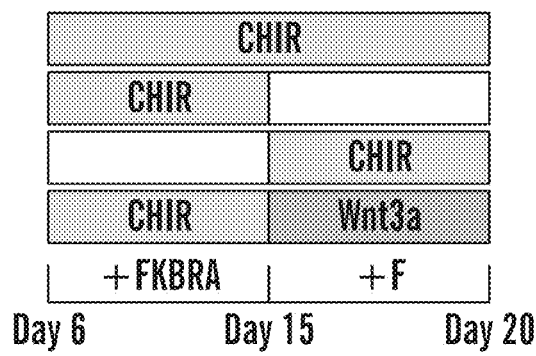
Figure 9B:
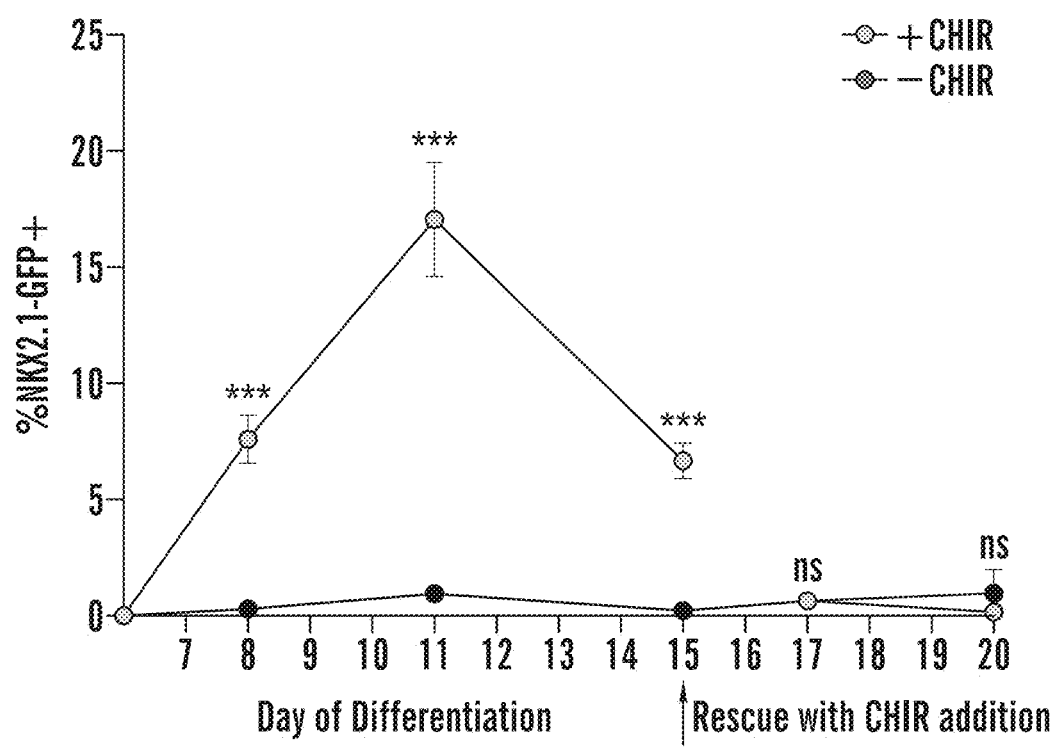
Figure 9C:
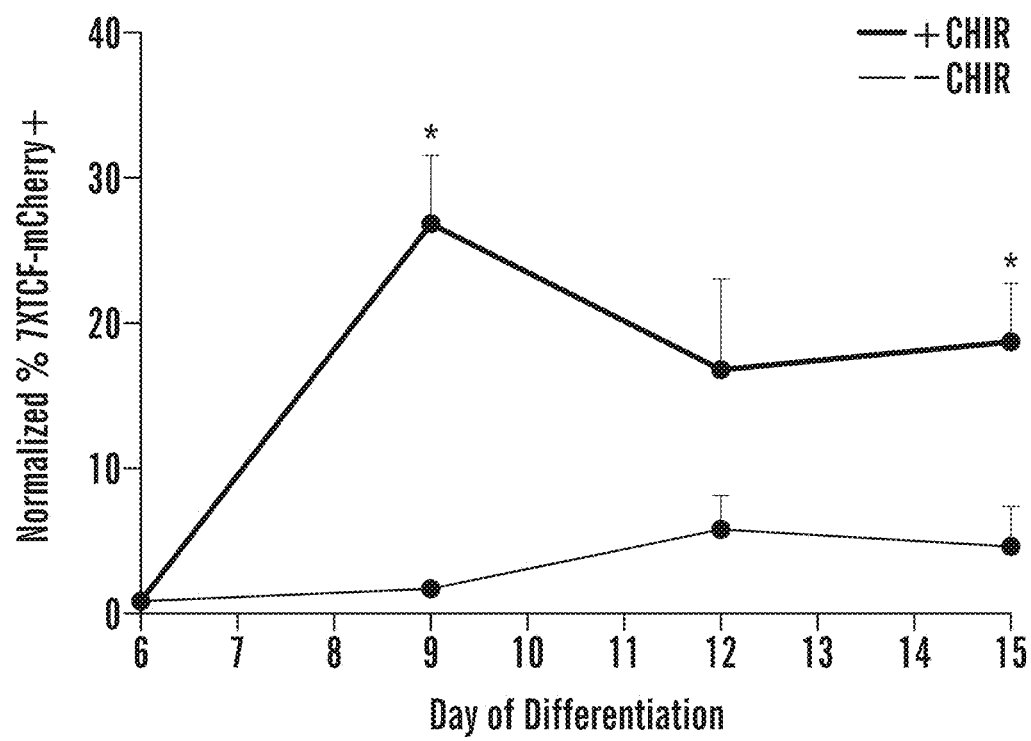

Upregulation of the canonical target Wnt genes, AXIN2, NKD1, and LEF1 and downregulation of the Wnt inhibitor DKK1 were particularly predictive of Wnt activity as cells progress developmentally from anterior foregut to NKX2-1+ lung epithelial progenitors in this in vitro human model system (FIG. 2A). These changes were maintained until day 28 in NKX2-1+ cells cultured in media containing CHIR. (FIG. 8A). The faithfulness of AXIN2 as a canonical Wnt response reporter in this human system was further supported by separate experiments where lentiviral overexpression of phosphorylation-incompetent murine beta-catenin (Fuerer and Nusse, 2010) in NKX2-1+ progenitors resulted in upregulation of AXIN2 even in the absence of CHIR (FIG. 9B-9C). Furthermore, lentiviral TCF reporters in FG293 cells confirmed that the dose of CHIR used at this stage and later differentiation (3 μM) was appropriate to induce Wnt activation without significant cytotoxicity (FIG. 8D-8E).

Figure 9D:
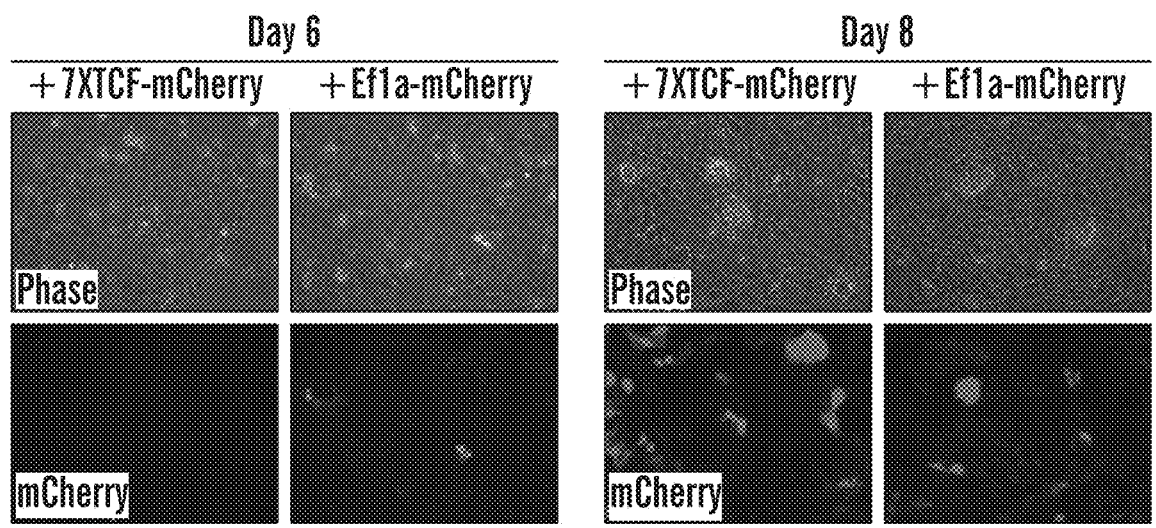

Next, the inventors compared the stage-dependent effects of withdrawal of Wnt signaling pre- vs post-lung specification in the disclosed directed differentiation model using both CHIR and recombinant Wnt3a (Figure S3A). Cells differentiated from anterior foregut endoderm in the presence of CHIR expressed significantly higher levels of NKX2-1$^{GFP}$ as early as 48 h after the initiation of specification in comparison to cells cultured without this compound, and this difference was maintained until at least day 15. NKX2-1$^{GFP}$ expression could not be rescued in cells differentiated without CHIR to day 15 by later addition of this molecule demonstrating that this effect was restricted to a narrow developmental stage (FIG. 9B). Activation of canonical Wnt signaling in response to CHIR at these time points was further verified using lentiviral TCF-driven reporters, and conditions without CHIR again exhibited minimal, if any, basal Wnt activity (FIG. 9C-9D). Together, these results demonstrate that canonical Wnt activity is required for in vitro specification of human lung epithelial progenitors, and that this effect is limited to a narrow window of developmental competence.

Example 2

Figure 2B:
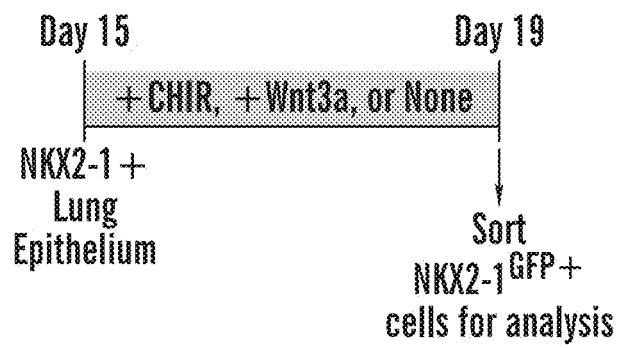
Figure 2C:
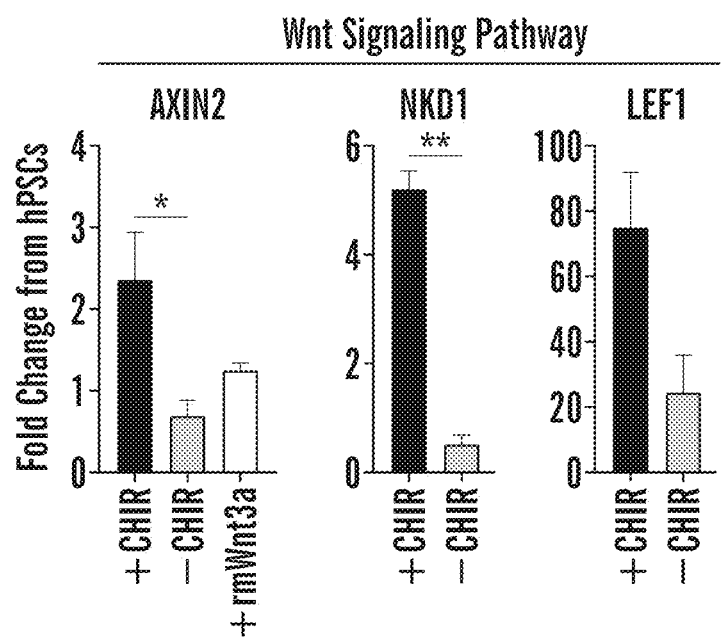

CHIR Withdrawal Post Lung Epithelial Specification Results in the Generation of Diverse Proximal Lung Lineages, Including NKX2-1+P63+ Basal-Like Cells Next, the inventors assessed the effect of sustained vs. withdrawn Wnt signaling on the differentiation repertoire of hPSC-derived NKX2-1+ lung progenitors after lung lineage specification. The inventors treated cells post-specification with CHIR, recombinant mouse Wnt3a (Kishida et al., 1999), or neither in a base media of 10 ng/mL FGF10 from day 15 to day 19 (FIG. 2B, FIG. 9E). To ensure this treatment correlated with expected decreases in canonical Wnt signaling activity, the inventors confirmed reduced lentiviral TCF-driven reporter expression by day 19 (FIG. 9F) as well as reduced expression of the Wnt signaling responsive genes LEF1, NKD1, and AXIN2 (FIG. 2C). In addition, an unbiased comparison between NKX2-1GFP+ cells at day 15 and at day 19 after culture without CHIR using a Wnt pathway-specific qRT-PCR array confirmed this finding (FIG. 9G).

Figure 2D:
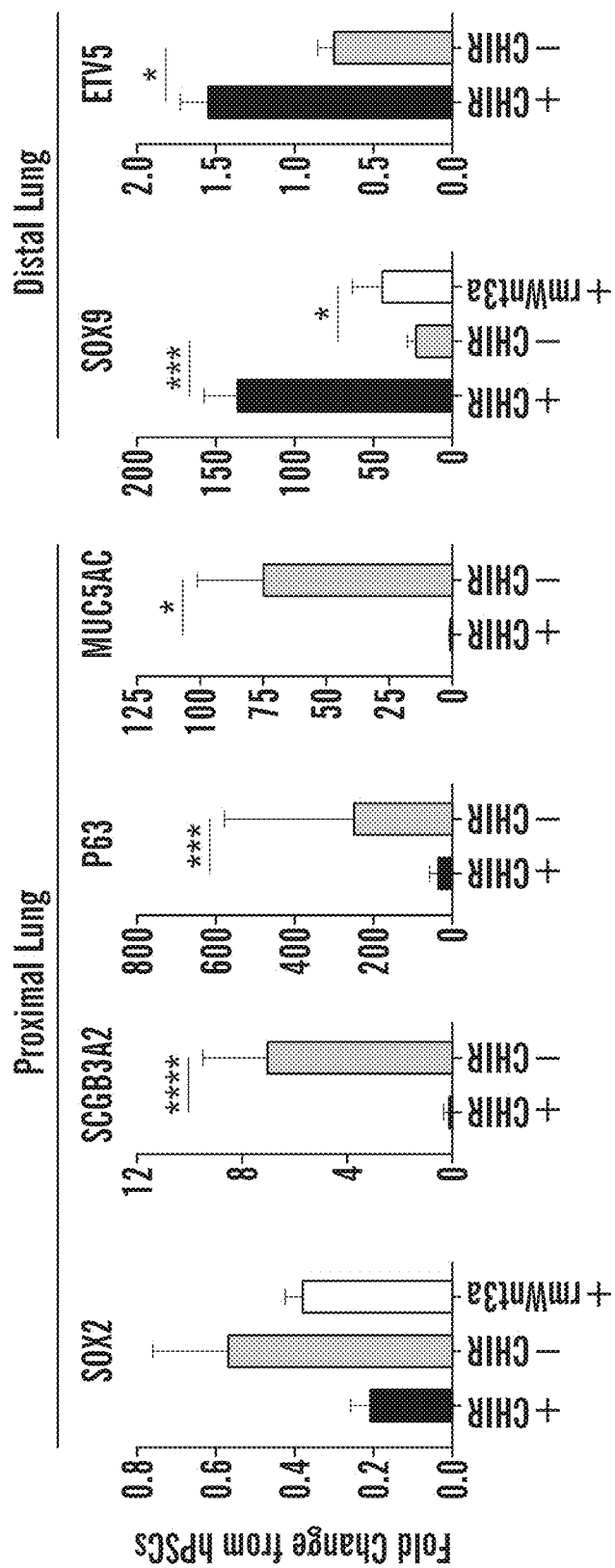
Figure 2E:
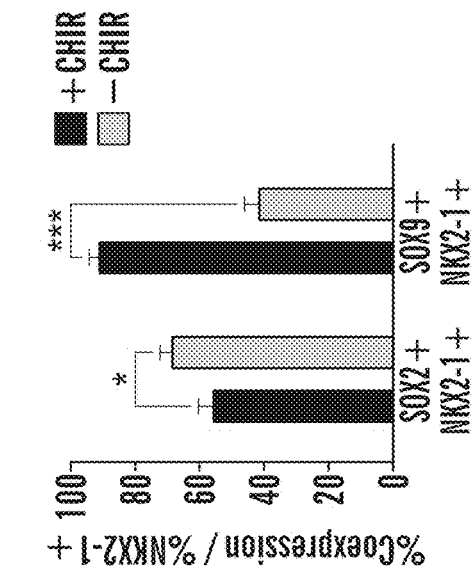
Figure 2F:
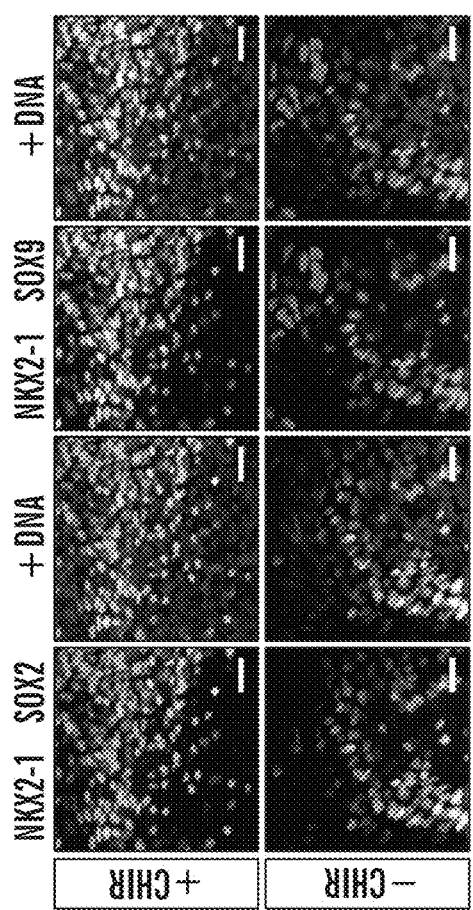
Figure 2G:
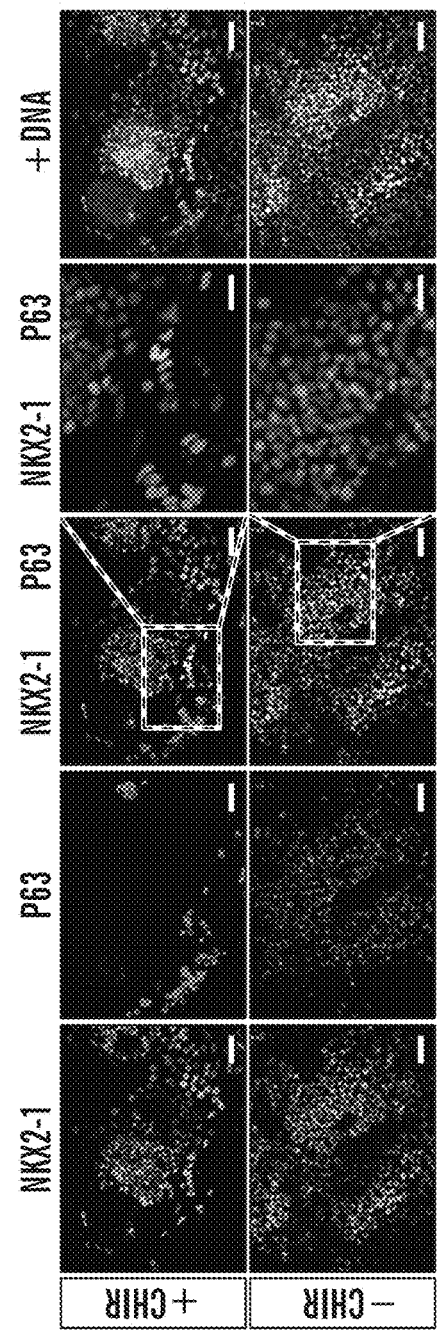
Figure 2H:
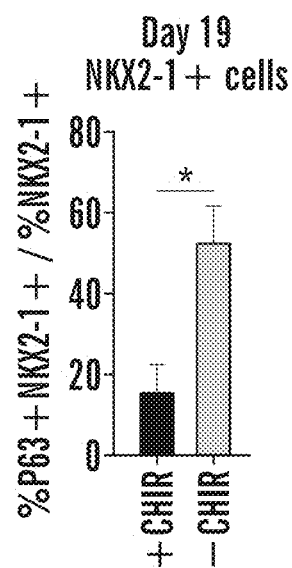
Figure 2I:
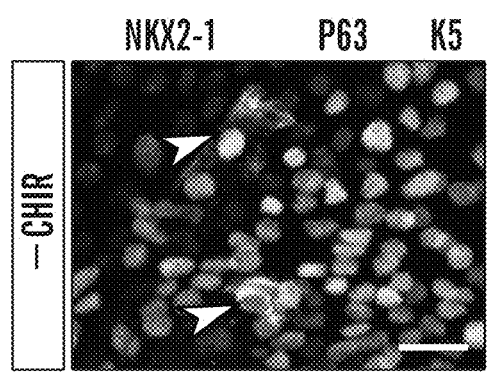

Within 4 days, withdrawal of CHIR resulted in significant changes in gene expression and emergence of a proximal airway phenotype concordant with loss of distal cell fate in NKX2-1$^{GFP+}$ cells. Specifically, proximal airway markers SCGB3A2, TP63, and MUC5AC were all upregulated and distal markers SOX9 and ETV5 (Liu et al., 2003) were downregulated in response to CHIR withdrawal (FIG. 2D). Proximal airway patterning of individual NKX2-1+ cells in response to CHIR withdrawal was validated at the protein level by both immunofluorescence microscopy and flow cytometry. Triple immunostaining for NKX2-1, SOX2, and SOX9 nuclear proteins demonstrated that >90% of NKX2-1+ cells were SOX9+ in the presence of sustained CHIR, whereas 4 days after the withdrawal of CHIR, <40% of NKX2-1+ cells maintained detectable SOX9 staining (FIG. 2E-2F). Although NKX2-1+ cells in both conditions contained >50% SOX2+ cells, CHIR withdrawal resulted in a significantly higher percentage of cells coexpressing NKX2-1 and SOX2 and a concordant absence of SOX9 in the majority of these NKX2-1+/SOX2+ cells (FIG. 2E-2F, and data not shown). This result further revealed a number of cells in both outgrowth conditions simultaneously expressing NKX2-1, SOX2, and SOX9 (data not shown).

Furthermore, CHIR withdrawal resulted in increased frequencies of cells co-expressing NKX2-1 and P63 (FIG. 2G-2H) and a subset of cells co-expressing NKX2-1, P63, and K5, a triad unique to airway basal cells (FIG. 2I)(Ikeda et al., 1995; Rock et al., 2009). Cells treated with rhWnt3a during this same window showed a milder distal patterning response relative to CHIR treatment (FIG. 2C-2D) with only partial activation of canonical Wnt activity detected as measured by AXIN2 expression, concordant with the previously reported low-level response of human cells to in vitro treatment with recombinant Wnt (Fuerer and Nusse, 2010).

Example 3

CHIR Acts Intrinsically on the Epithelium to Pattern Early Lung Progenitors

Figure 3A:
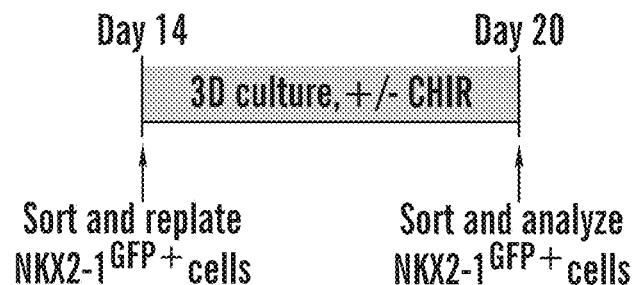
Figure 3B:
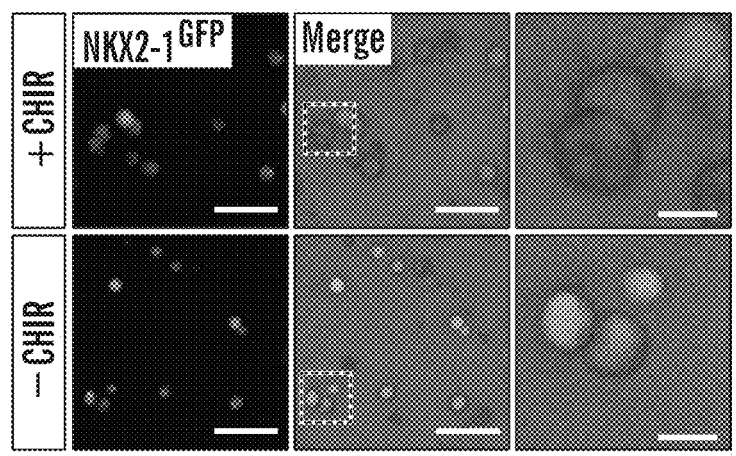
Figure 3F:
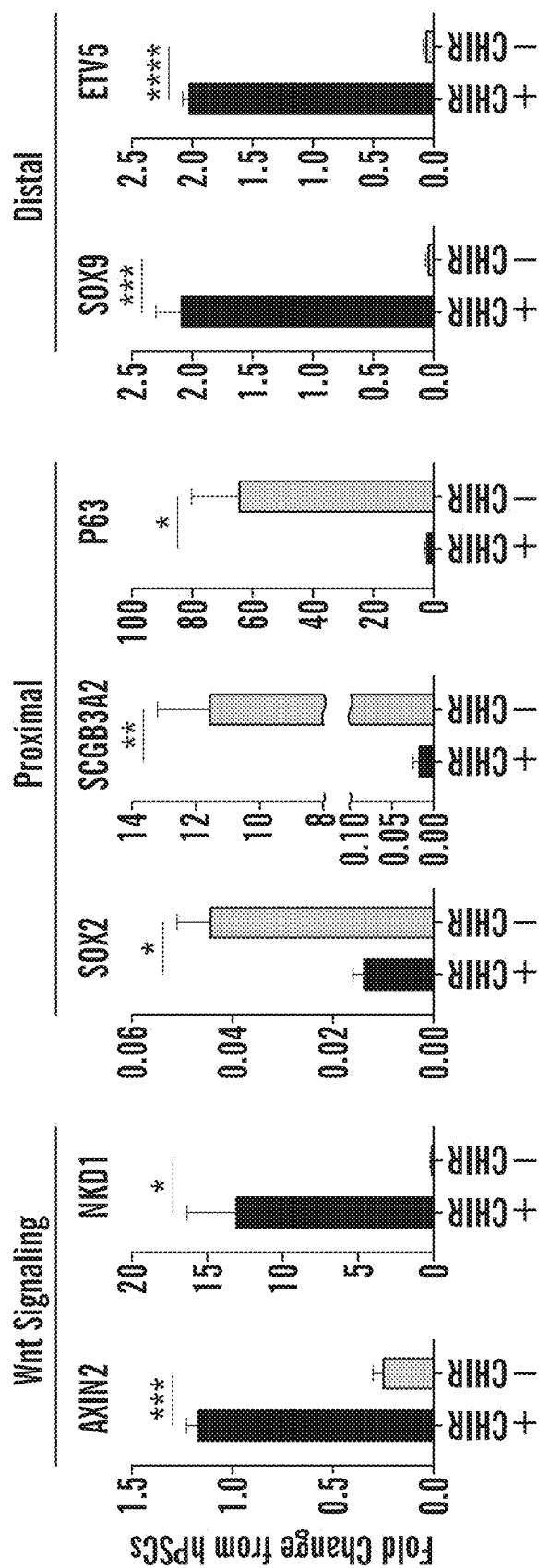
Figures 10A, 10B:
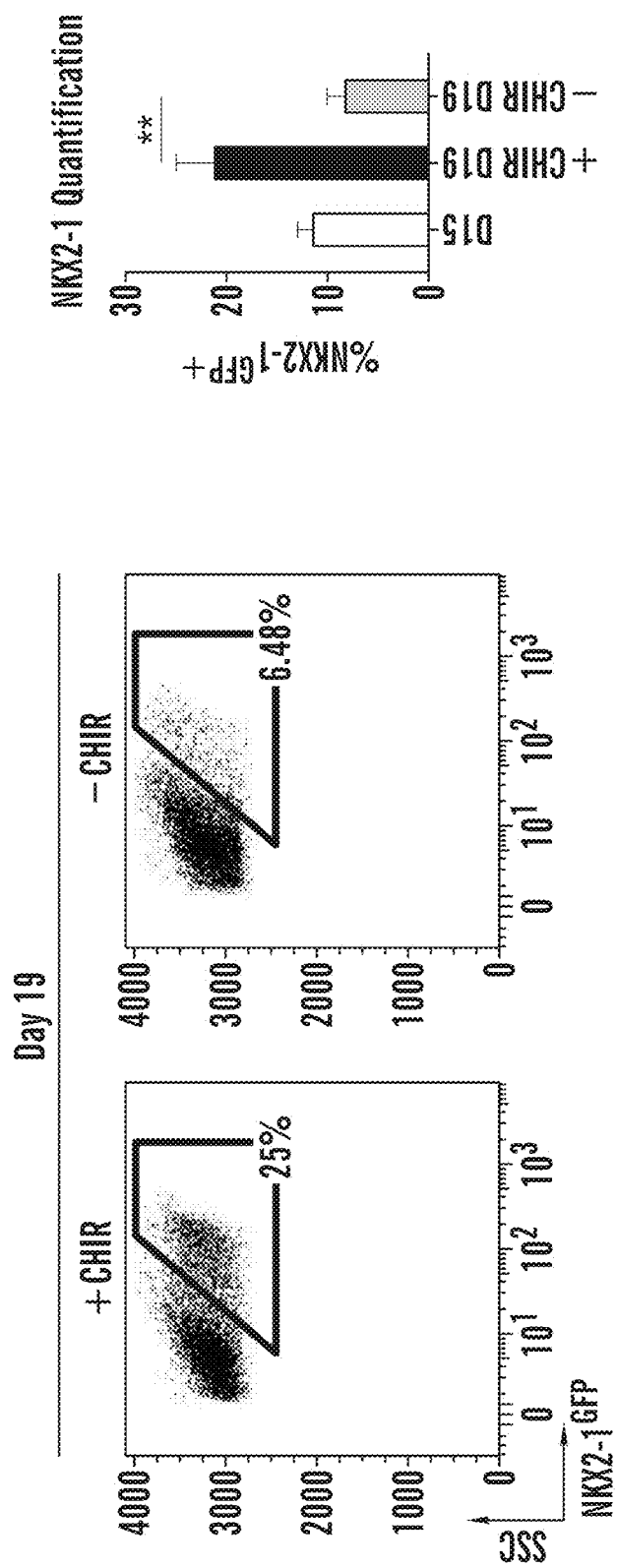
FIGS. 10A-10B show that lung progenitors differentially express patterning markers in response to CHIR treatment. (Related to FIG. 2).
Figure 11:
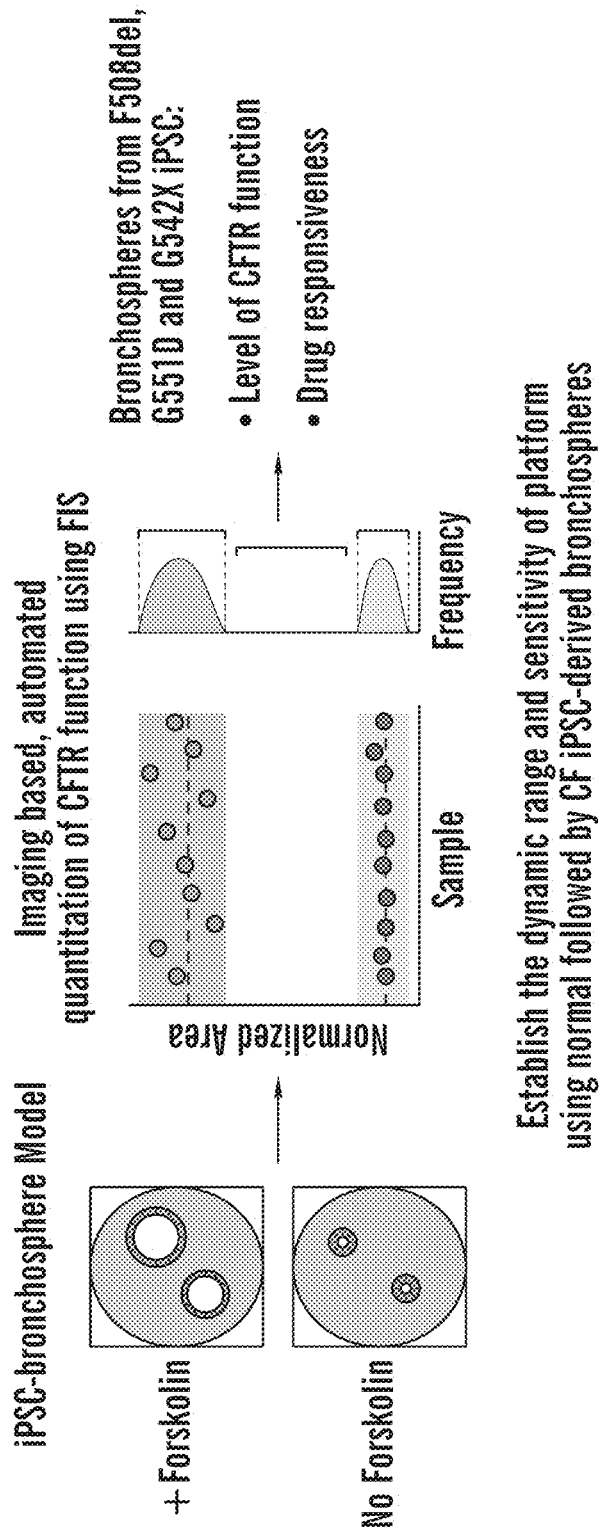
FIG. 11 shows a schematic diagram outlining a high-throughput screening platform for personalized assessment of CFTR function using iPSC-derived bronchospheres.

Withdrawal of CHIR from day 15 to 19 resulted in a significantly decreased percentage of NKX2-1$^{GFP+}$ outgrowth cells by day 19 (FIG. 10A-10B), raising the question of whether contaminating non-lung lineages were outcompeting lung lineages in the absence of sustained Wnt, and potentially contributing to secondary patterning effects in the NKX2-1+ population. The inventors next assessed whether the effect of CHIR manipulation on proximodistal lung patterning was intrinsic to lung epithelial cells rather than due to secondary or bystander effects. FACS was used to purify NKX2-1+$^{GFP+}$ epithelial lung progenitors at day 14 and replated them in three-dimensional (3D) culture with or without CHIR (FIG. 3A) added to a base media ("DCI") that has been previously reported to support epithelial gene expression in sorted NKX2-1$^{GFP+}$ PSC-derived cells (Kurmann et al., 2015; Longmire et al., 2012). By day 20, the sorted cells formed small spheres coexpressing NKX2-1 and EPCAM (FIG. 3B-3C). >90% of all outgrowth cells in either culture conditioned maintained NKX2-1$^{GFP}$ (+CHIR: 98.2±0.5%−CHIR: 93.4±2.3%) (FIG. 3D-3E) and cells in each condition formed organoids with no measured statistical difference in efficiency. Analysis of re-sorted NKX2-1$^{GFP}$+ cells at day 20 demonstrated withdrawal of Chir resulted in upregulation of proximal lung genes SOX2, SCGB3A2, and TP63, and downregulation of distal lung genes SOX9 and ETV5 (FIG. 3F). Thus, the inventors have demonstrated that Wnt signaling levels regulate proximodistal patterning of NKX2-1+ lung progenitors via intrinsic actions on the epithelium.

Figure 4E:
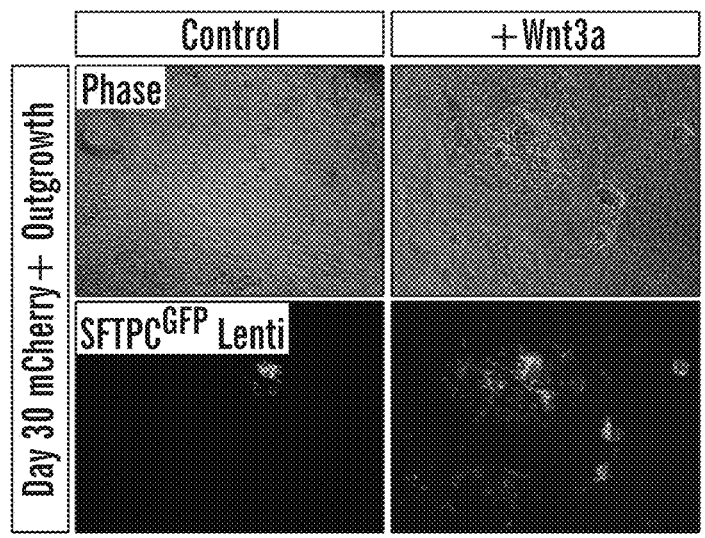
Figure 4F:
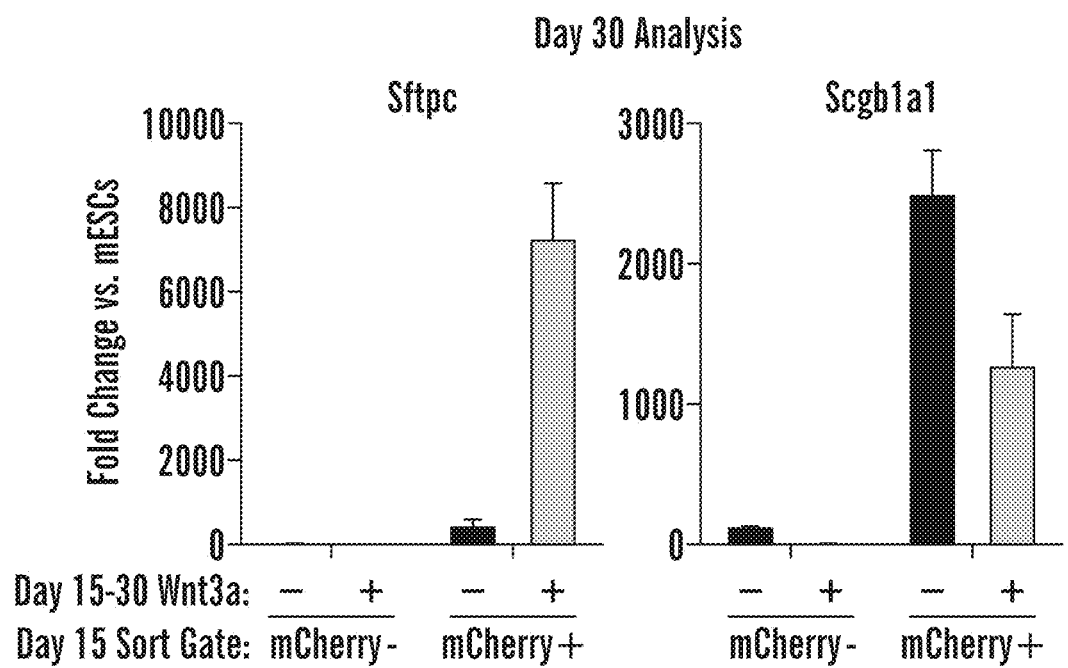

Recombinant Wnt3a Promotes Sftpc Expression and Inhibits Proximalization in Nkx2-1+ Mouse ESC-Derived Lung Progenitors Next, the inventors assessed whether the patterning response to canonical Wnt signaling is conserved in other mammalian PSC model systems known to respond directly to Wnt ligands. As we have previously described the use of Wnt3a to drive lung differentiation in murine PSCs (Kurmann et al., 2015; Longmire et al., 2012), (FIG. 4A), the inventors differentiated a mouse embryonic stem cell (mESC) line that contains an mCherry reporter targeted to the Nkx2-1 locus (Bilodeau et al., 2014; Kurmann et al., 2015) (FIG. 4B). Following lung lineage specification into Nkx2-1+ primordial progenitors, on day 14 the inventors replated sorted Nkx2-1$^{mCherry-}$ vs Nkx2-1$^{mCherry-}$ cells (FIG. 4C) for further differentiation in sustained vs withdrawn Wnt3a protein. By transducing these cells with a reporter lentivirus engineered to carry a human SFTPC promoter driving GFP expression (Longmire et al., 2012), the inventors screened for the emergence of lung cells expressing this canonical distal epithelial differentiation marker (FIG. 4D). By day 18, the emergence of many clusters of Sftpc$^{GFP+}$ cells deriving from mCherry+ sorted progenitors cultured in the presence of Wnt3a was discovered, but few, if any, detectable clusters in the absence of Wnt3a (FIG. 4E). As accurately predicted by the Sftpc$^{GFP}$ reporter, Sftpc mRNA was expressed at high levels in the presence of Wnt3a and proximal lung marker Scgb1a1 expression was suppressed in these conditions. In contrast, in the absence of Wnt3a, Scgb1a1 expression was upregulated and Sftpc expression was almost entirely lost (FIG. 4F), findings consistent with our human PSC model. Importantly, no detectable GFP signal and no Sftpc or Scgb1a1 mRNA expression was observed arising from outgrowth of the sorted mCherry negative population in any condition (FIG. 4F). These results provide further evidence that canonical Wnt activation promotes the differentiation of distal lung epithelium from PSC-derived Nkx2-1+ lung progenitors while suppressing the proximal lung program and that this effect is conserved across species.

Example 4

Figure 5A:
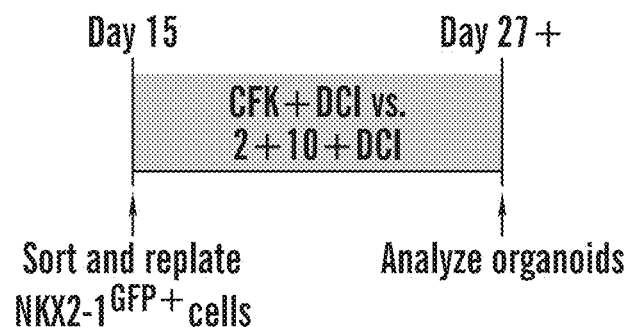
FIGS. 5A-5J show the generation of iPSC-derived airway organoids via purified NKX2-1+ lung progenitors.

Derivation of Proximal Airway Organoids from Purified PSC-Derived Lung Epithelial Cells Having demonstrated that Wnt manipulation acts intrinsically on NKX2-1+ lung epithelium to induce rapid changes in proximodistal patterning, the inventors developed a "low-Wnt" protocol for the reproducible and efficient generation and maturation of functional proximal airway organoids from patient-specific lines for the purposes of disease modeling and the testing of gene therapies. The inventors extended previous research on 2D mESC differentiations (FIG. 4) to extend to human cells, to assess if containing FGF2 and a low level of FGF10 ("2+10 media") could ligate FGF receptors to drive proliferation of sorted human NKX2-1$^{GFP+}$ lung progenitors while allowing proximal patterning, consistent with previous reports of use of 2+10 media in mouse cells (Longmire et al., 2012). Therefore, the inventors assessed whether in 3D conditions with 2+10 media without CHIR or Wnt3a would result in proliferation and differentiation of proximalized human lung epithelial spheres in comparison to previously published high-Wnt media containing CHIR as well as FGF10, and KGF ("CFK media") (Huang et al., 2013) (detailed in Hawkins et al., 2017) (FIG. 5A).

Figure 5B:
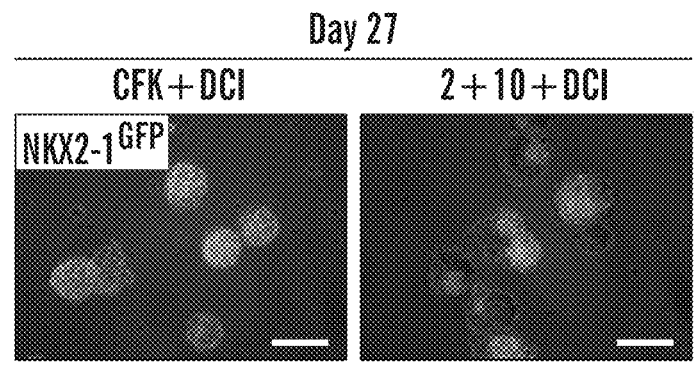
Figure 5C:
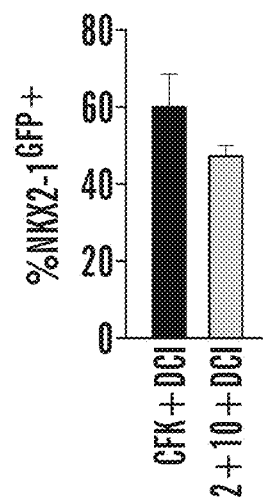
Figure 5D:
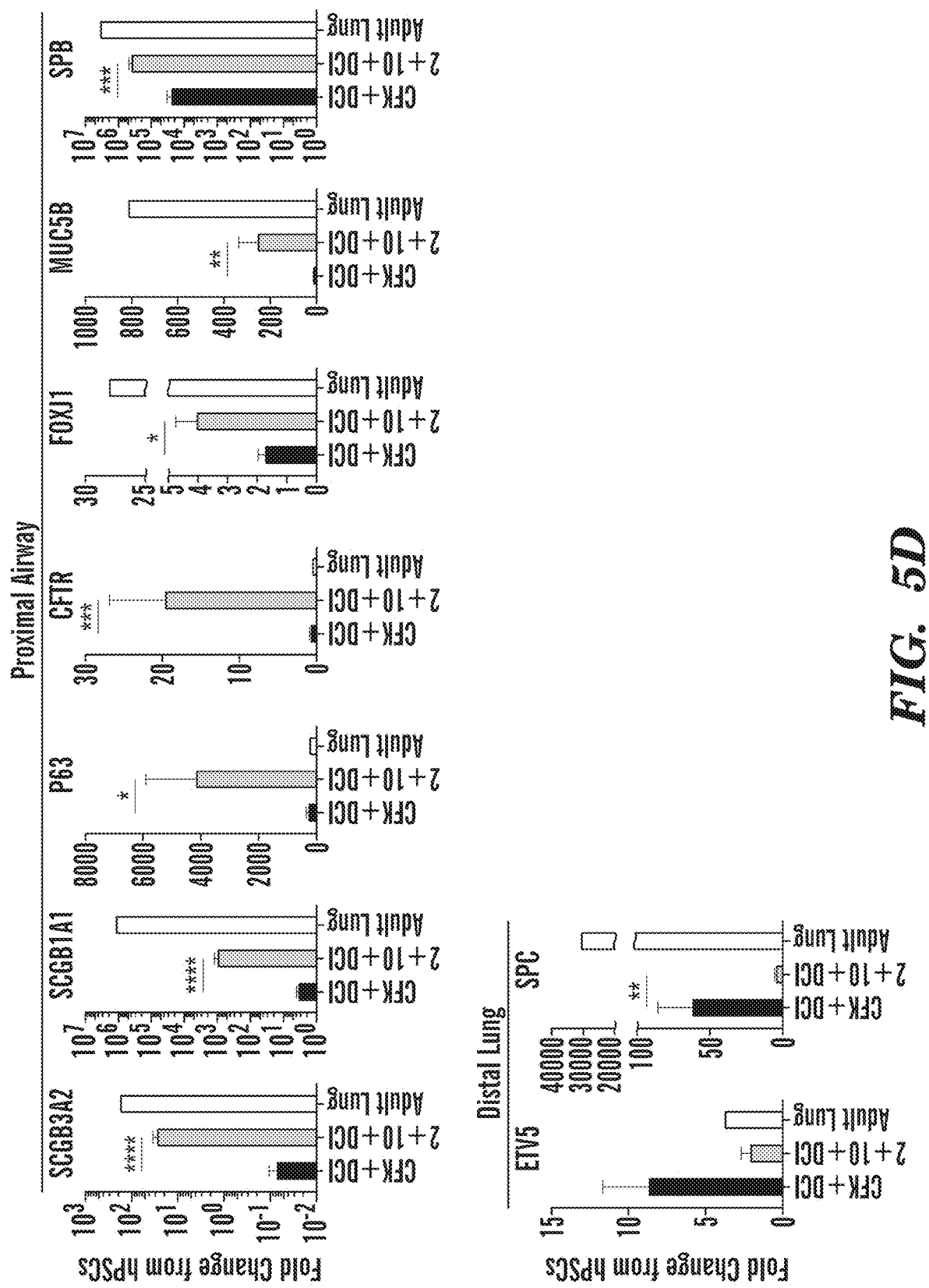
Figure 5E:
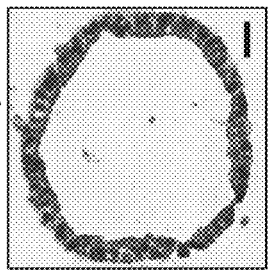

To ensure that organoids originated from an NKX2-1+ progenitor population, sorted NKX2-1GFP+cells were replated and cultured in both "high Wnt" and "low Wnt" conditions in 3D. Cells in both conditions initially proliferated and formed epithelial spheres that maintained variable levels of NKX2-1 expression (FIG. 5B-5C). However, the spheres formed in low-Wnt media expressed significantly higher levels of proximal airway genes than cells in high-Wnt media, including TP63, SCGB3A2, SCGB1A1, MUC5B, CFTR, FOXJ1, and SFTPB (FIG. 5D). Although SFTPB has been previously referred to as a marker specific to type II pneumocytes, it is also highly expressed in the developing human airway epithelium (e.g., an alveolar marker) (Phelps and Floros, 1988; Venkatesh et al., 1995). In contrast, cells cultured in high-Wnt media again expressed lower levels of proximal lung markers and higher levels of distal lung markers ETV5 and SFTPC (FIG. 5D). Expression of additional distal alveolar epithelial markers, ABCA3 and LPCAT1, was also detected in cells cultured in high-Wnt media (data not shown.)

Figure 5F:
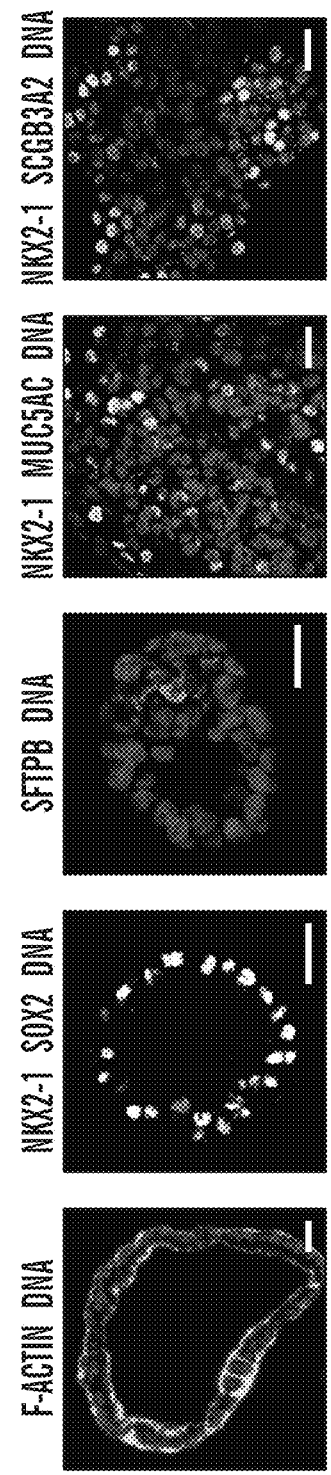
Figure 5H:
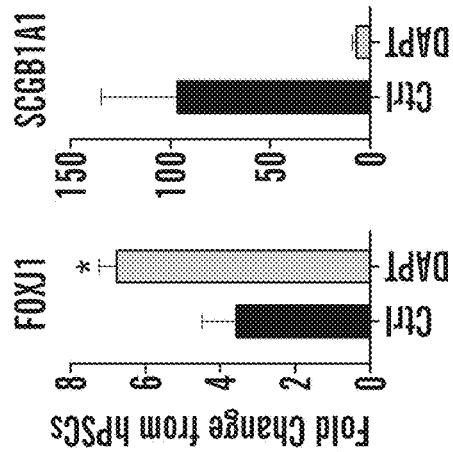
Figure 5G:
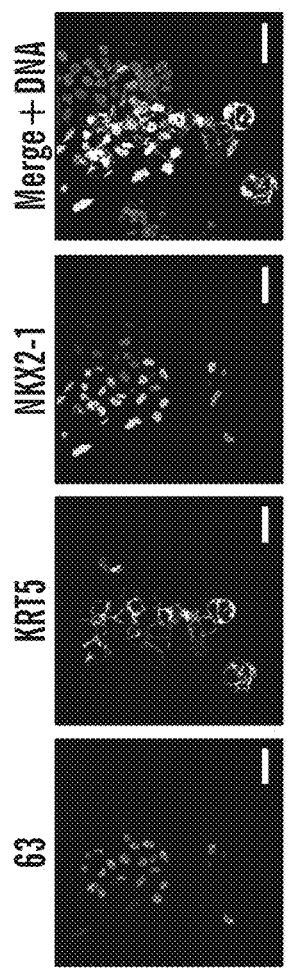
Figure 5I:
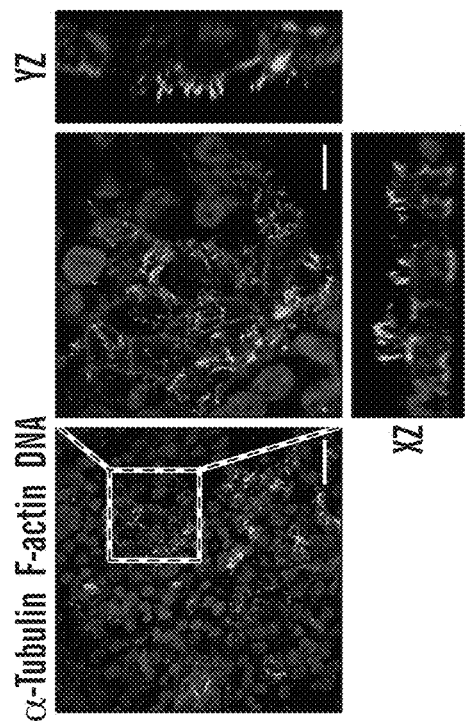
Figure 17C:
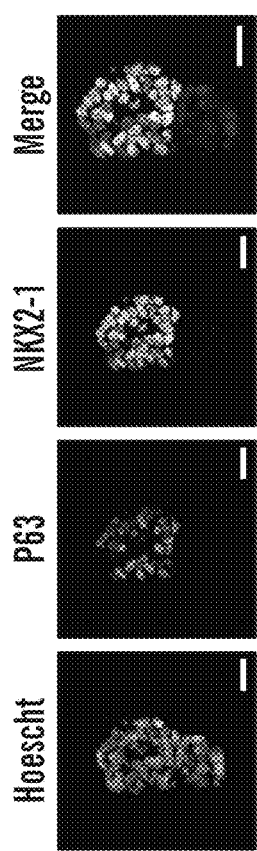
Figure 17D:
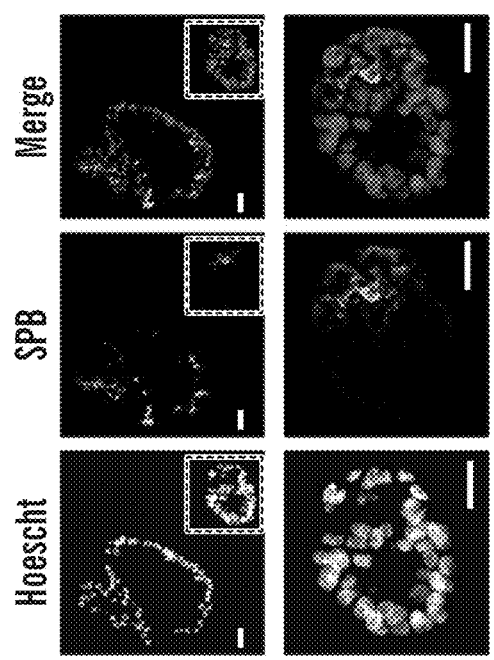
Figure 17E:
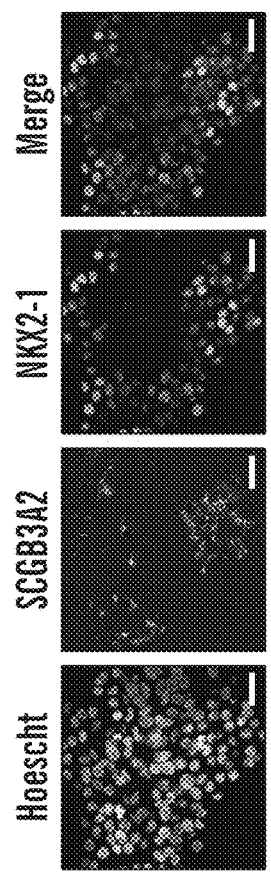
Figure 17F:
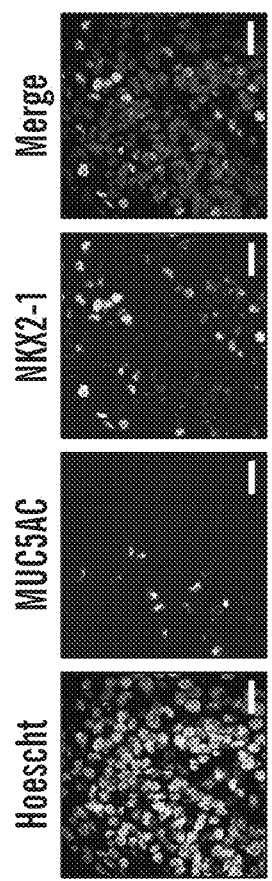
Figure 17G:
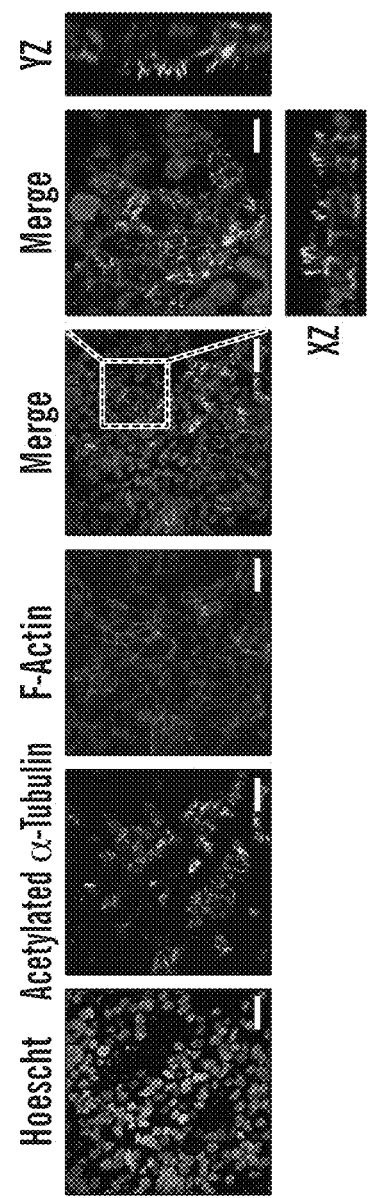
Figure 19:
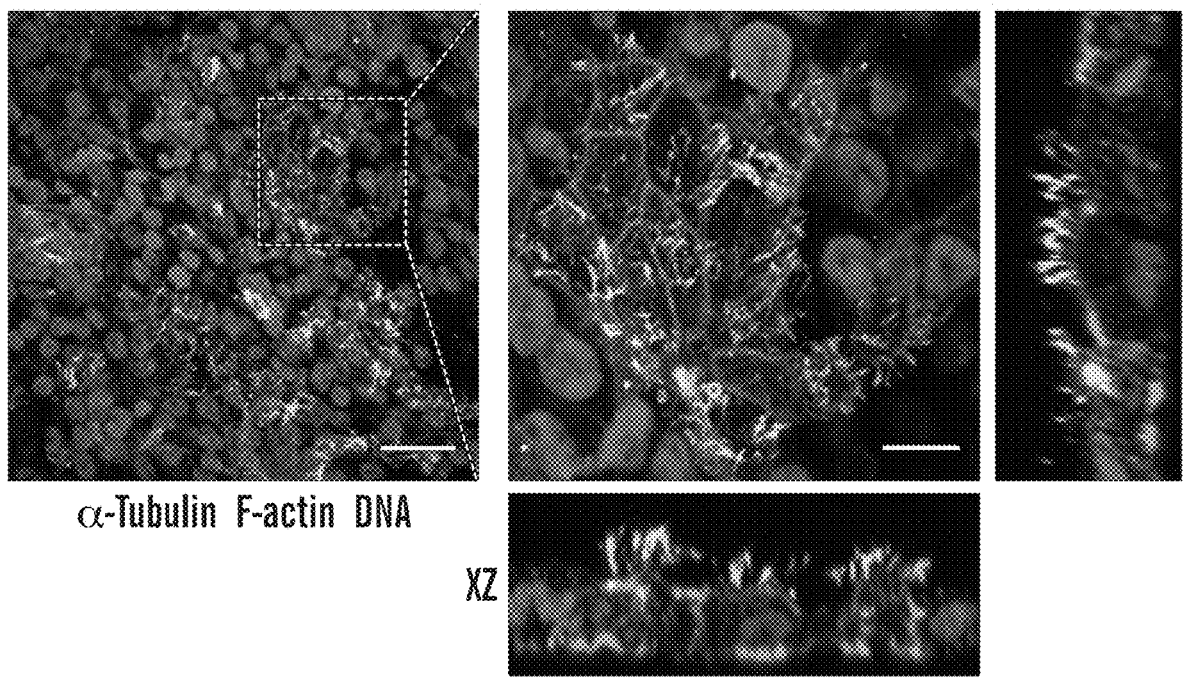
FIG. 19 shows a representative z-projection of ALI differentiation immunostained for acetylated alpha tubulin (observed in green), and F-actin (observed in red).
Figure 20:
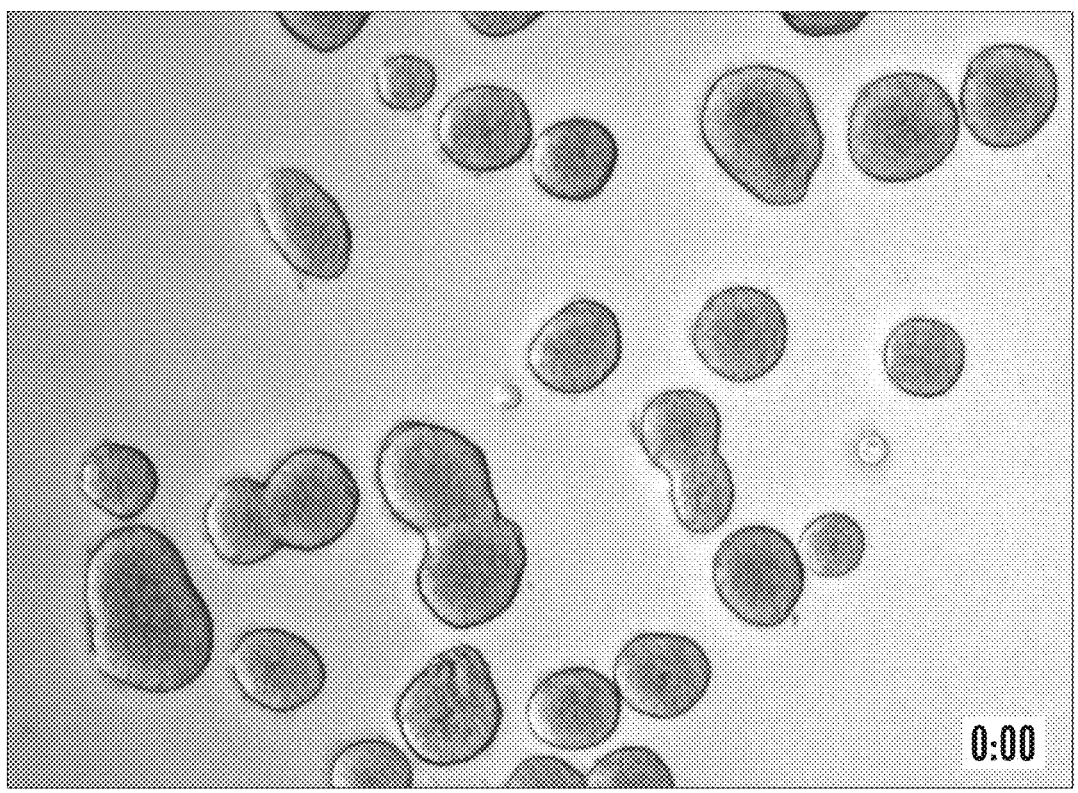
FIG. 20 shows a representative bright phase image of the Forskolin-induced swelling (CFTR activation) of CF bronchospheres.
Figure 21A:
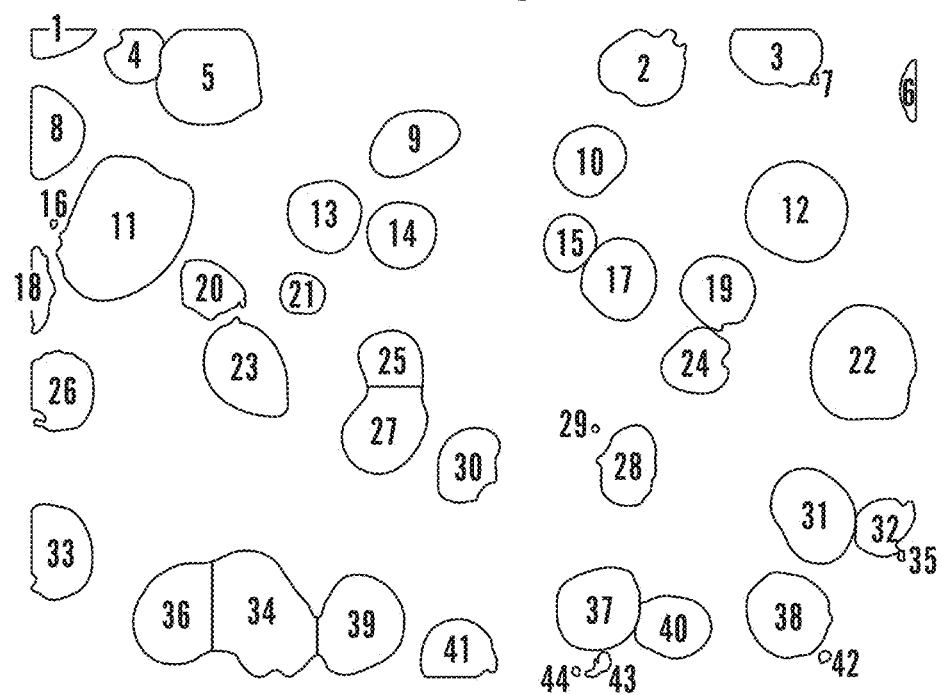
FIG. 21A-21B shows quantification of Forskolin-induced swelling (CFTR activation) of CF bronchospheres.
Figure 21B:
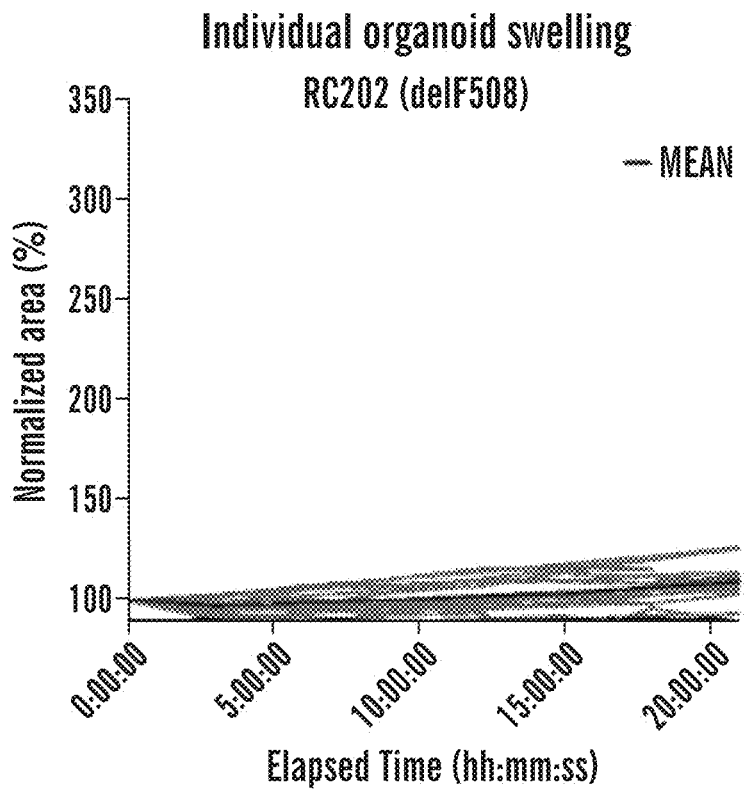

Airway-like epithelial identity of the low-Wnt outgrowth was supported by immunostaining revealing luminal organoids where all cells maintained EPCAM expression and subsets expressed markers of secretory (SPB+/NKX2-1+) and basal (NKX2-1+/P63+/KRT5+) lung lineages (FIG. 5F-5G, FIG. 17A-17C). These spheres were initially primarily secretory in nature and exhibited low levels of FOXJ1 expression with no observed formation of multiciliated structures. However multiciliated epithelial cells with upregulated FOXJ1, downregulated SCGB1A1, and beating motile cilia could be generated from these proximalized epithelial spheres either in continued 3D culture in the presence of Notch inhibition with DAPT (Tsao et al., 2009) (FIG. 5H, and data not shown) or after transfer into 2D conditions in air liquid interface culture (FIG. 5I, FIG. 19, FIG. 17G and data not shown).

Figure 5J:
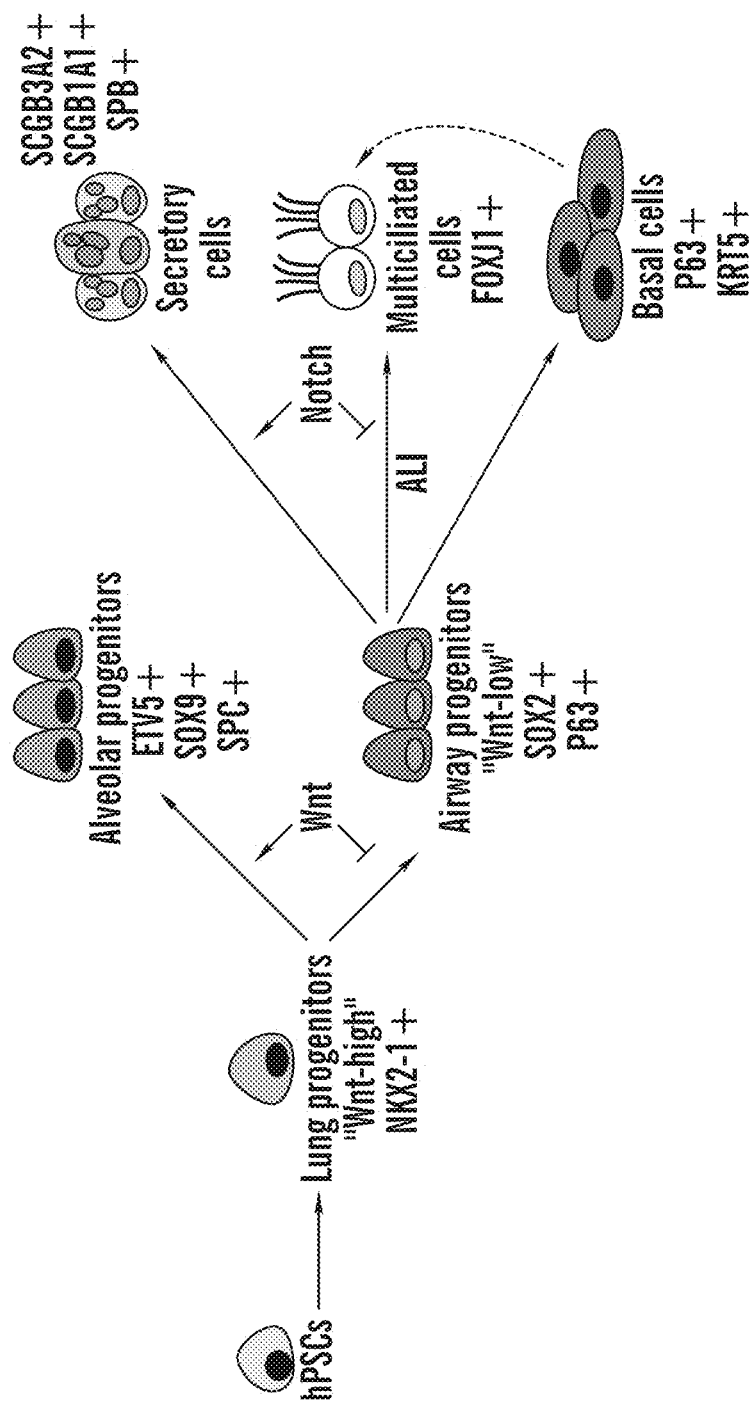

Taken together, the inventors have demonstrated that proximalized airway spheres generated in low-Wnt conditions resemble airway epithelium and provide a mechanistic roadmap by which hPSC-derived NKX2-1+ lung progenitors can be differentiated to diverse lineages of distinct clinical interest (FIG. 5J). In particular, identification of Wnt signaling as a key regulator of proximodistal patterning is a critical step for the rapid and reproducible generation from hPSC lines of proximal lung epithelial NKX2-1+/SOX2+ progenitors and their downstream basal, secretory, or multiciliated progeny.

Example 5

CFTR-Dependent Forskolin Swelling of Proximalized Organoids

To test whether the organoids differentiated herein using the the proximalized lung protocol contained functional epithelia of potential clinical benefit for cystic fibrosis disease modeling, the inventors next performed in vitro quantitative assessment of epithelial CFTR function using patient-specific iPSC-derived airway organoids. It has been previously reported in non-lung systems that the activation of adenylyl cyclase by forskolin induces CFTR-dependent organoid swelling, providing a robust and quantifiable in vitro functional readout of this ion channel (Dekkers et al., 2013). To initially test whether the airway organoids swell in response to forskolin treatment, the inventors differentiated iPSCs derived from either a healthy individual (BU3) or 2 individuals with cystic fibrosis due to homozygous ΔF508 CFTR mutations (RC2 202 and RC2 204). To purify NKX2-1+ primordial lung progenitors without requiring NKX2-1$^{GFP}$ knock-in reporters, cell surface markers CD47 and CD26 were used to isolate CD47$^{hi}$CD26$^{lo}$ cells highly enriched in NKX2-1+ progenitors by day 15 from all 3 lines (Hawkins et al., 2017 and FIG. 18A). Importantly, sorted progenitors from all lines replated from day 15 to 22-35 showed a similar proximalized patterning response to withdrawal of CHIR and expansion in 2+10 media as the C17 NKX2-1$^{GFP}$ targeted line (FIG. 18B and data not shown), demonstrating that this protocol reproducibly generates airway organoids from lung progenitors derived from different hPSC lines purified using cell surface marker sorting.

Figure 18C:
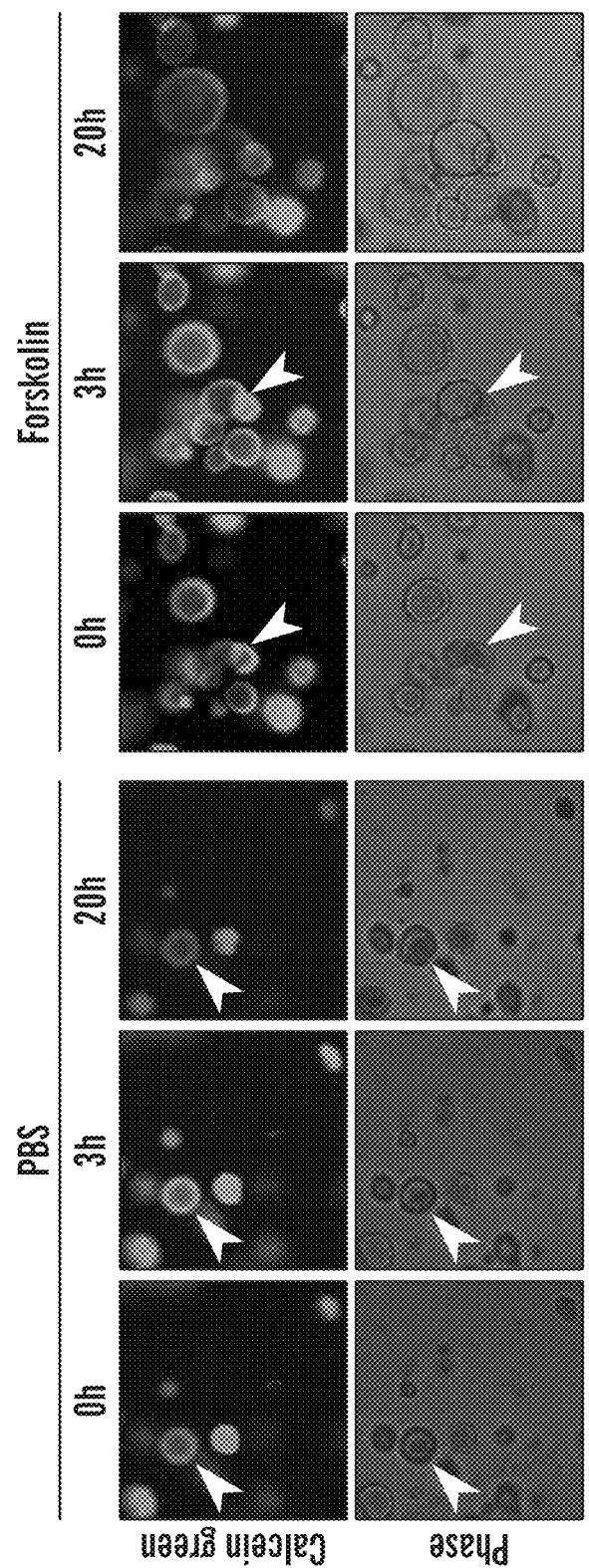
Figures 18D, 18E:
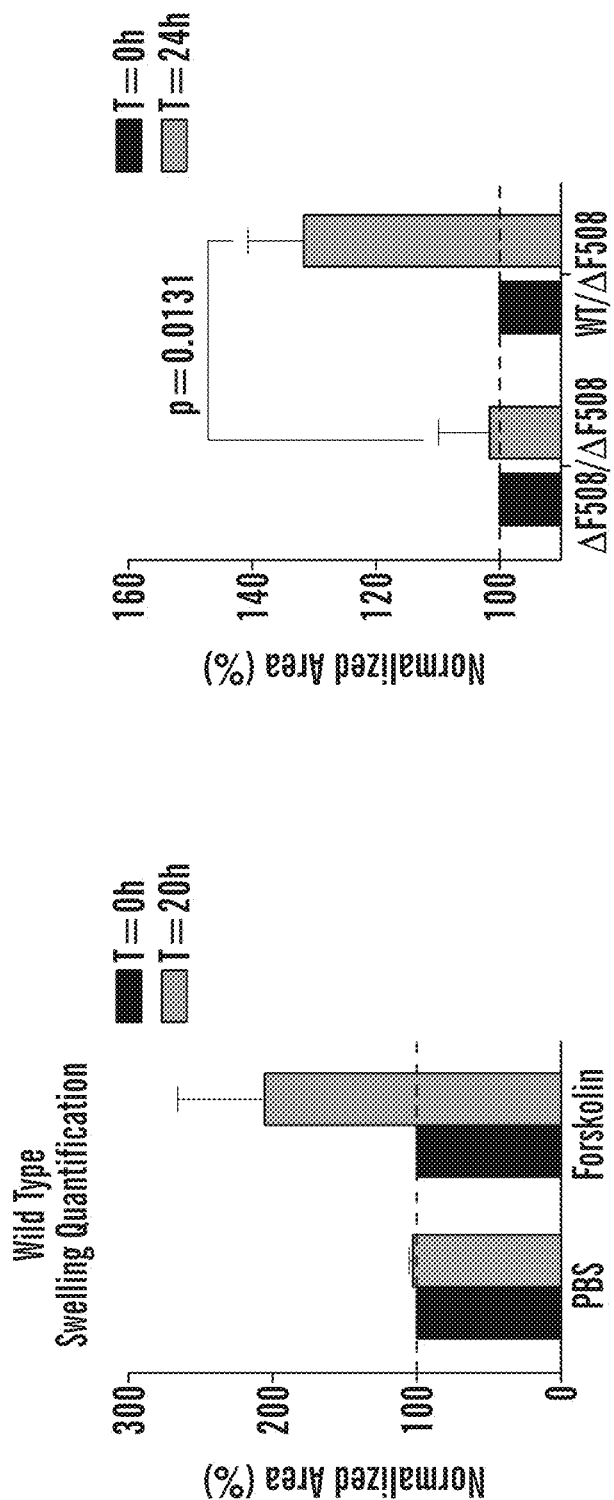

By time lapse microscopy after exposure to forskolin, the inventors detected significant organoid swelling in the BU3 line within 3 hours and swelling continued for at least 20 hours. In contrast little, if any, swelling was observed in either cystic fibrosis line (RC2 202 or RC2 204) after exposure to forskolin or in BU3 organoids stimulated with carrier vehicle alone (PBS only: 1.02+/−0.03, FIG. 18C-18D).

Figure 6A:
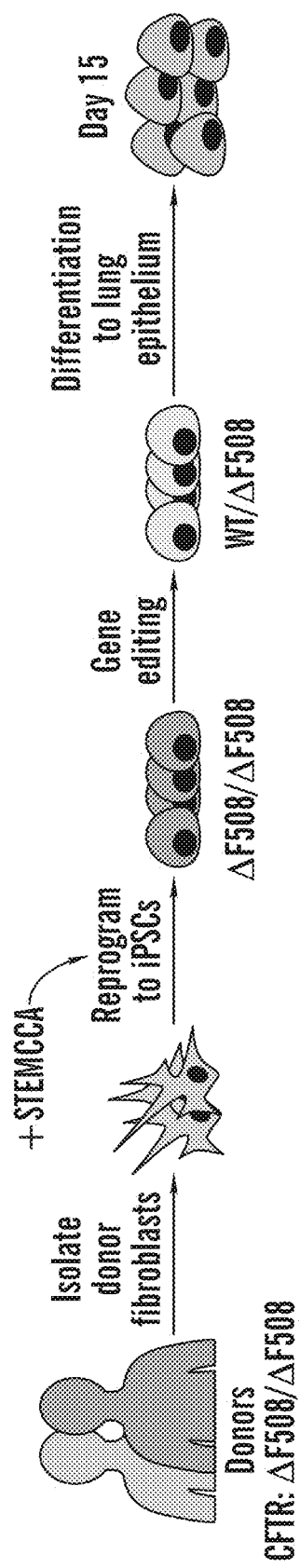
FIGS. 6A-6F shows the functional assessment of gene edited, cystic fibrosis patient-specific iPSC-derived airway organoids indicates a CFTR-dependent forskolin swelling response.
Figure 6B:
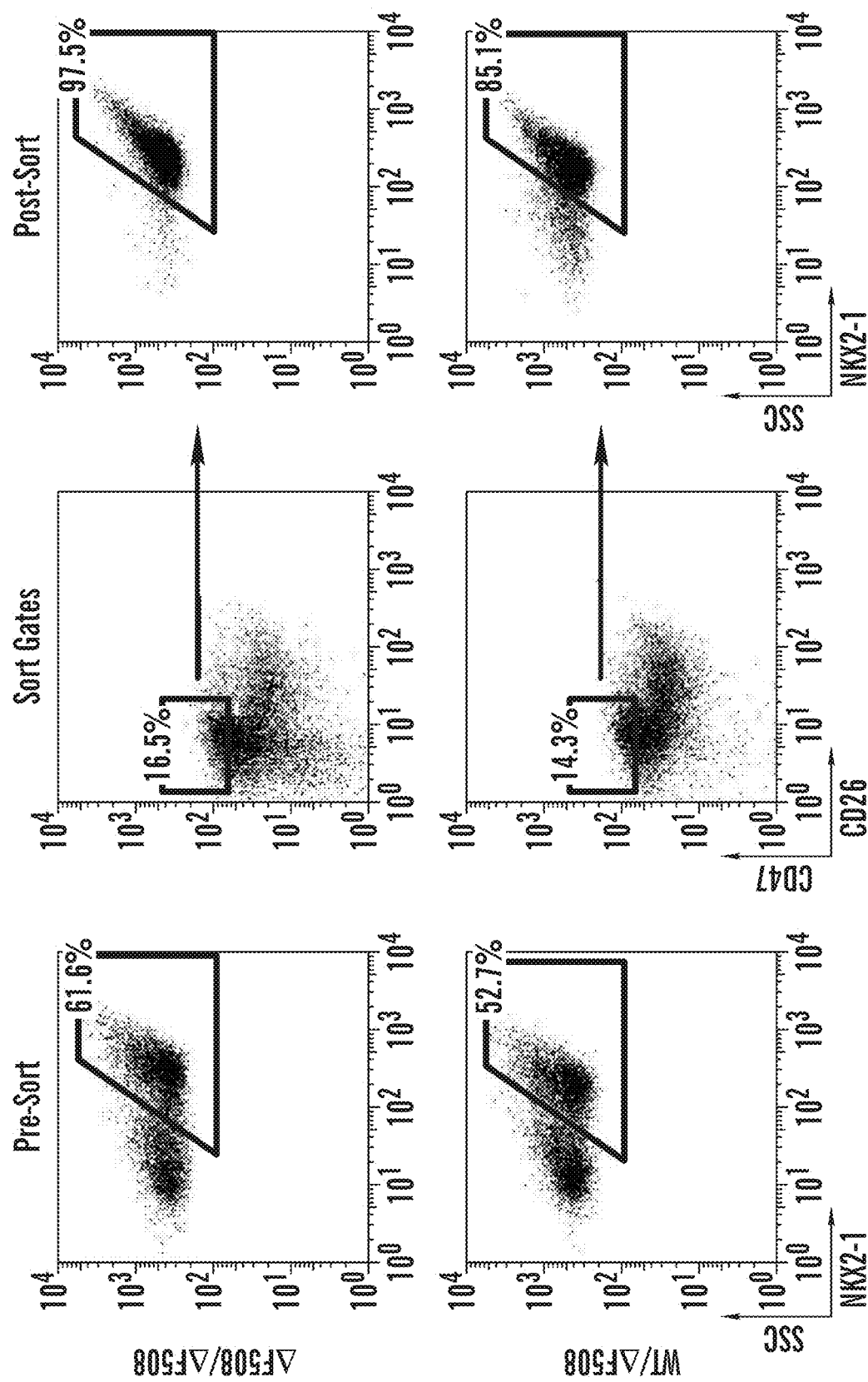
Figure 6C:
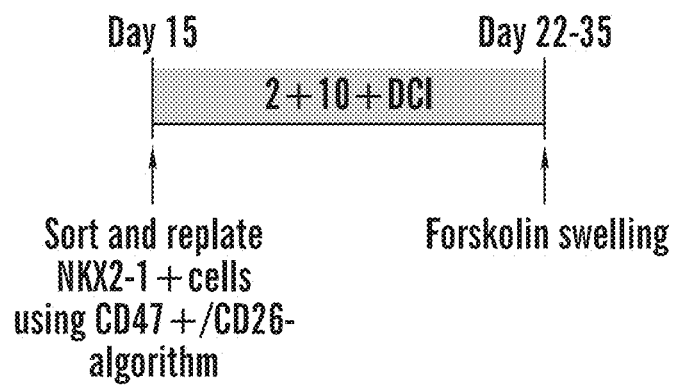
Figure 6D:
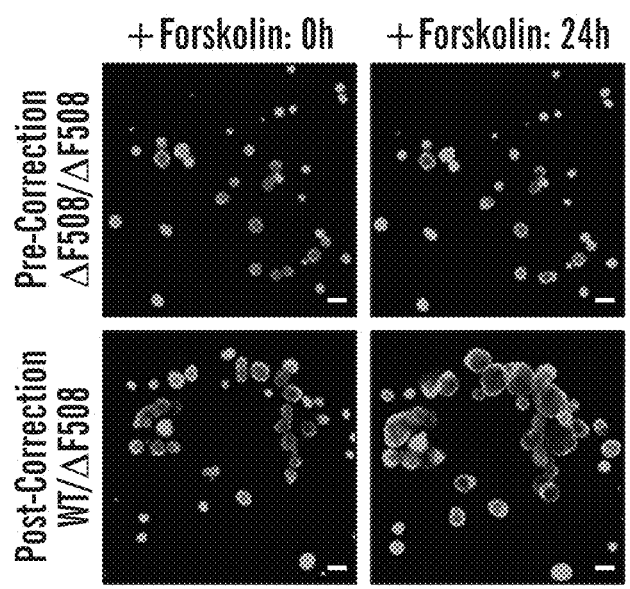
Figure 6E:
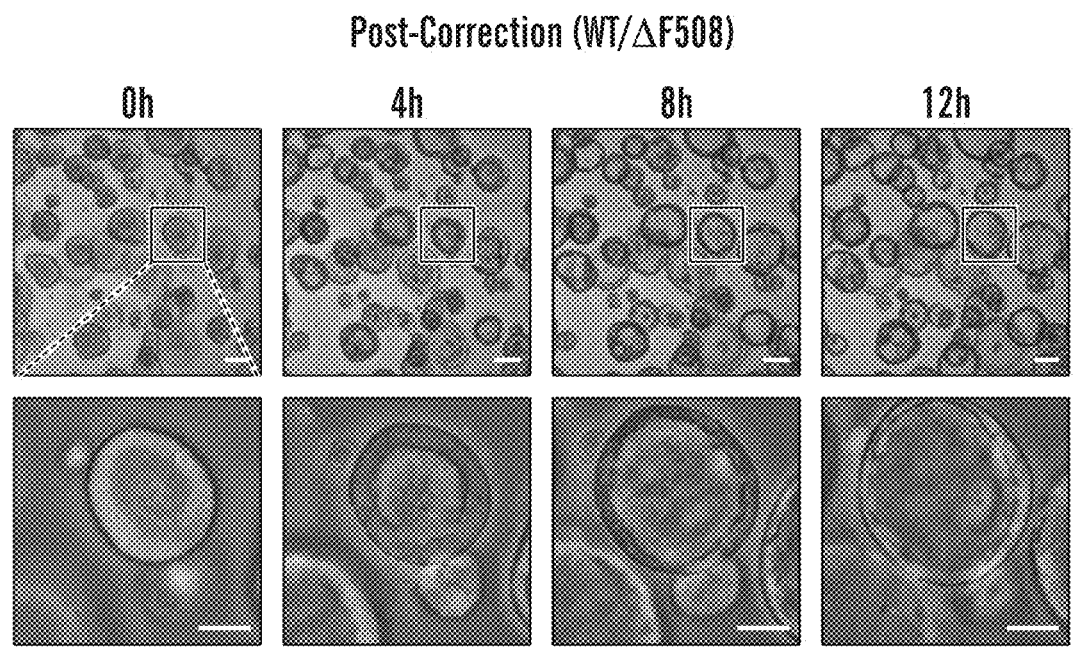
Figure 6F:
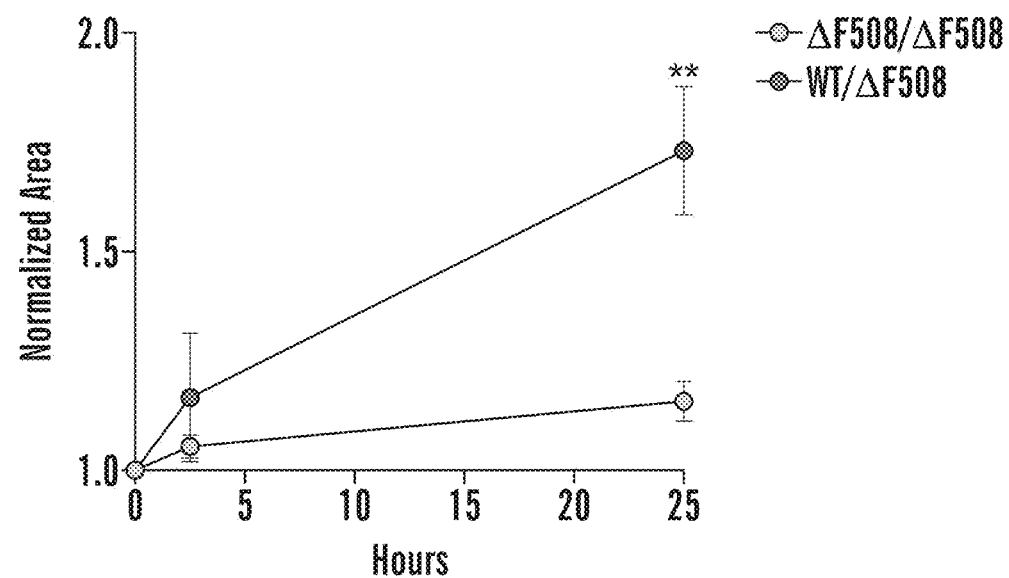

Having observed forskolin-responsive swelling in normal and not cystic fibrosis patient-derived proximalized organoids, the inventors next assessed whether this response was CFTR-dependent. To test this, gene edited clones generated from the two cystic fibrosis lines (Crane et al., 2015) where one ΔF508 mutant allele has been corrected to wildtype sequence were used (Crane et al., 2015). To compare the two diseased (ΔF508/ΔF508) iPSC lines to their syngeneic heterozygous corrected progeny (ΔF508/WT), all 4 clones were differentiated to the lung progenitor stage (FIG. 6A) and purified using FACS sorting for CD47$^{11}$1CD26− cells or CD47$^{hi}$/CD26$^{lo}$ cells (FIG. 6B) and then the organoids were further differentiated in "low-Wnt" media (FIG. 6C). After proximalization, the gene corrected ΔF508/WT RC2 202 and 204 organoids significantly swelled in response to forskolin treatment (1.73+/−0.15 fold and 1.32+/−0.09 fold, respectively). In contrast, the ΔF508/ΔF508 homozygous parental lines again showed no significant swelling in the same conditions (FIG. 6D-6F, FIG. 18E and data not shown). Taken together, the inventors have demonstrated that proximalized iPSC-derived lung organoids contain functional epithelial cells with the potential for in vitro lung-specific disease modeling and gene correction of cystic fibrosis.

Example 6

Figure 25A:
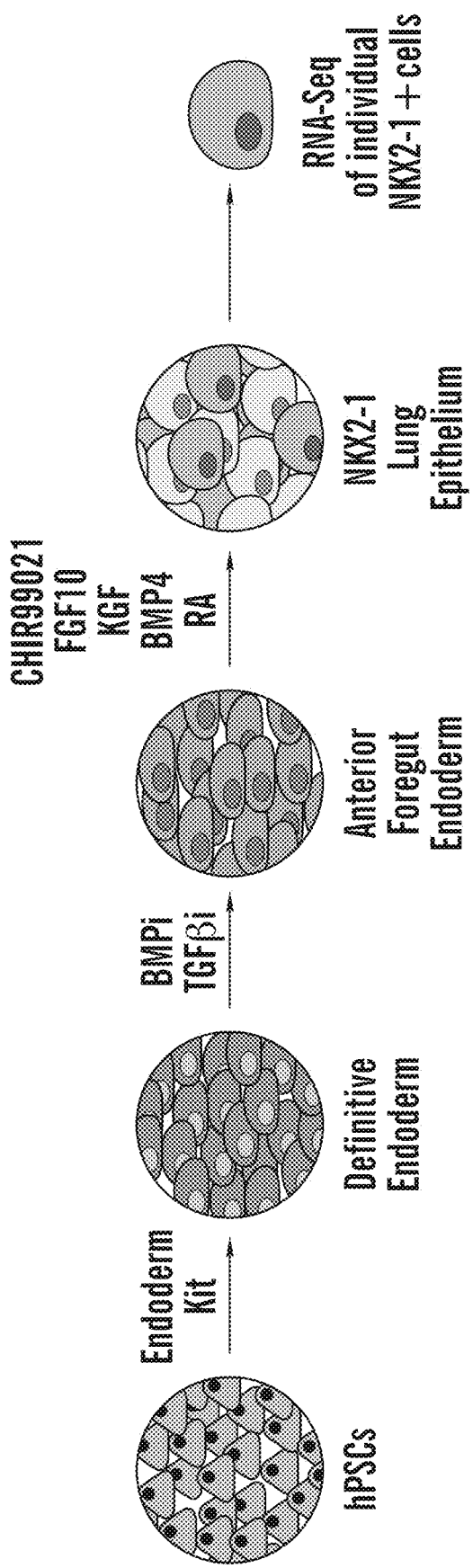
FIG. 25A-25D show lung development of NKX2-1 cells.

The inventors previously reported an induced pluripotent stem cell (iPSC) line targeted with a green fluorescent protein (GFP) reporter to the genetic locus for the essential lung transcription factor NKX2-1 (hereafter NKX2-1$^{GFP}$). Herein, the inventors derived NKX2-1$^{GFP}$+ lung epithelial progenitors via definitive endoderm and anterior foregut endoderm using defined medias in a stepwise, stage-specific approach (FIG. 25A), as has been previously described[1,2]. These NKX2-1$^{GFP+}$ progenitors further mature to cells expressing markers consistent with multiple distinct lung lineages, leading us to hypothesize that there exists important early biological heterogeneity within this system.

Figure 25B:
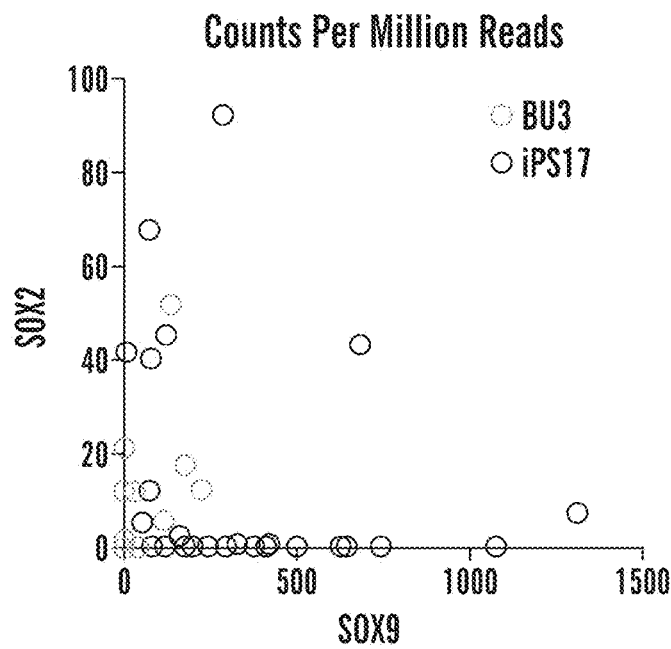
Figure 25C:
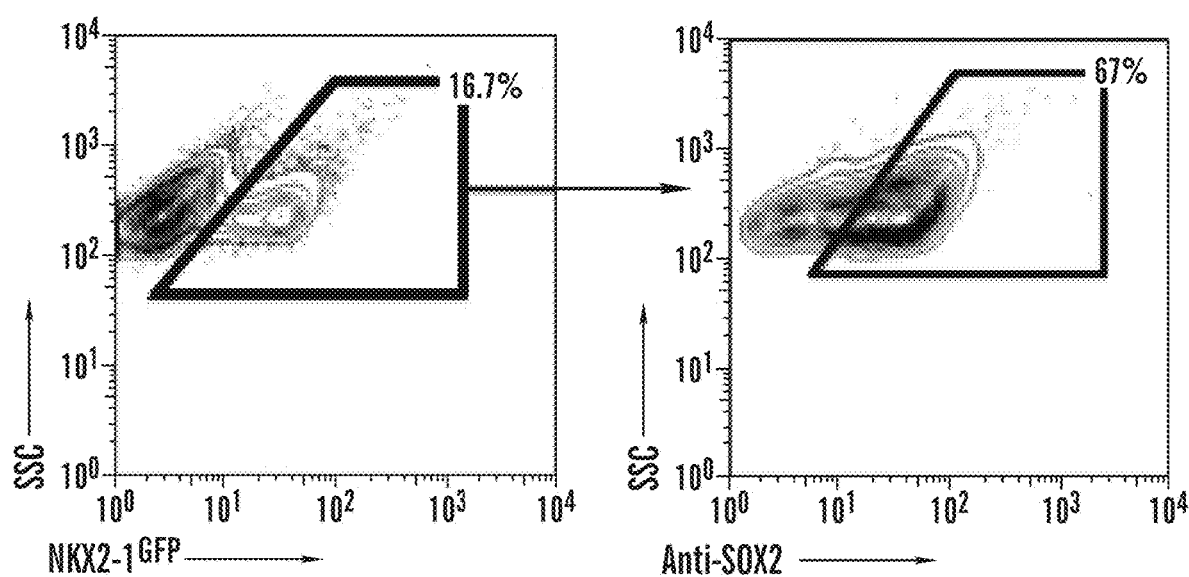
Figure 25D:
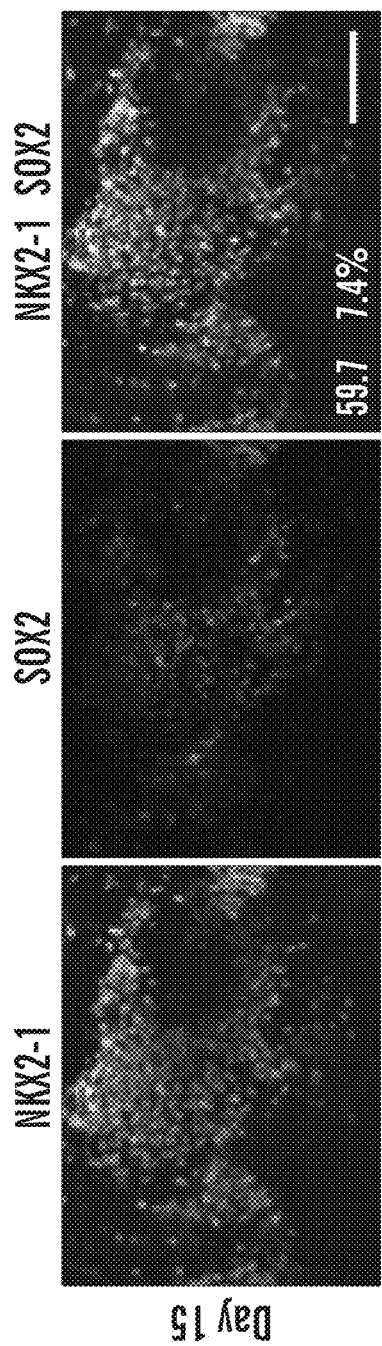
Figure 26A:
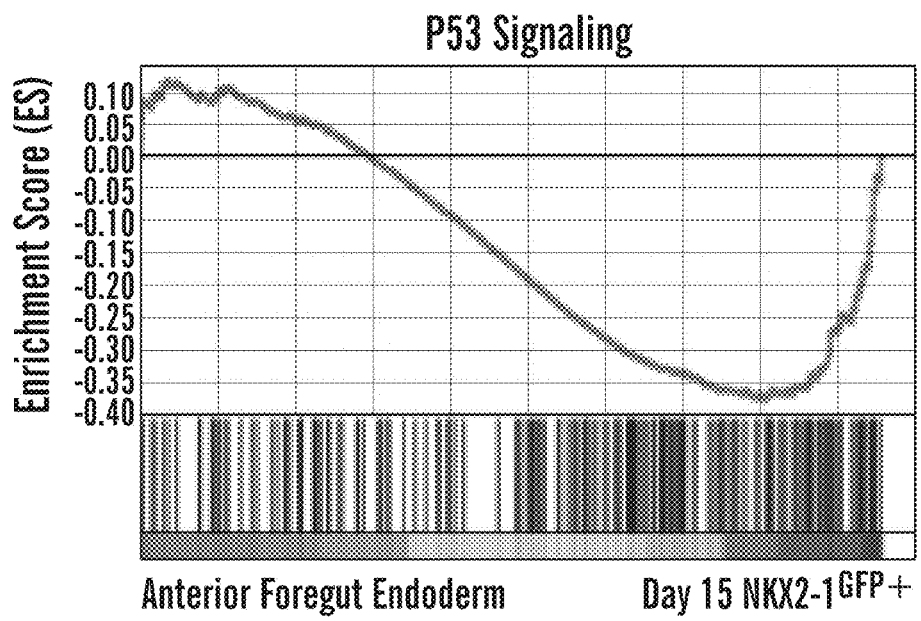
FIGS. 26A-26D shows results of microarray analysis of iPSC-derived NKX2-1+ lung progenitor cells vs. iPSC-derived anterior foregut endoderm cells showing gene expression of P53 signaling, Notch signaling, Hedgehog signaling, and Wnt/β-catenin signaling is active in Day 15 NKX2-1+ lung progenitor cells.
Figure 26B:
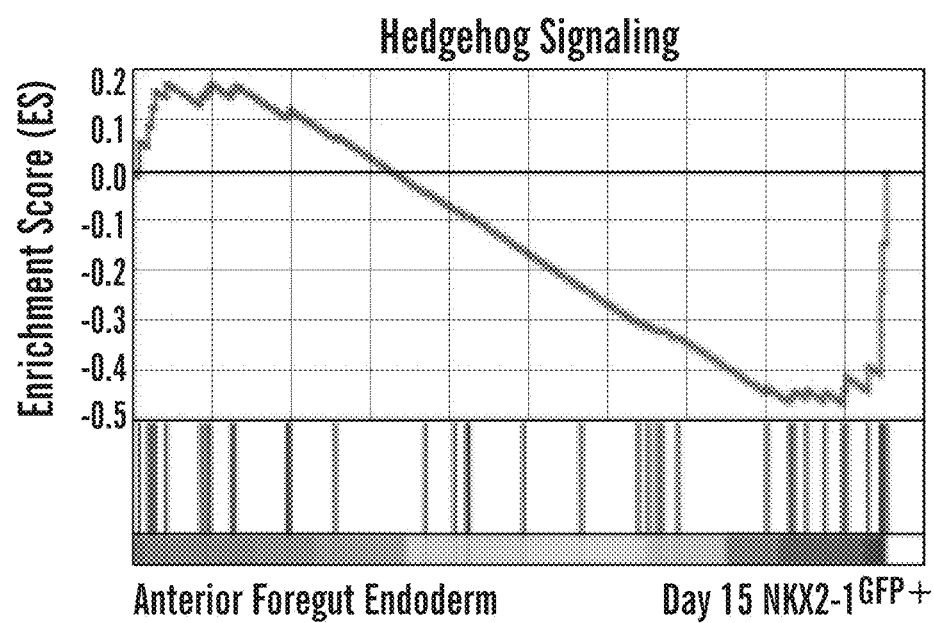
Figure 26C:
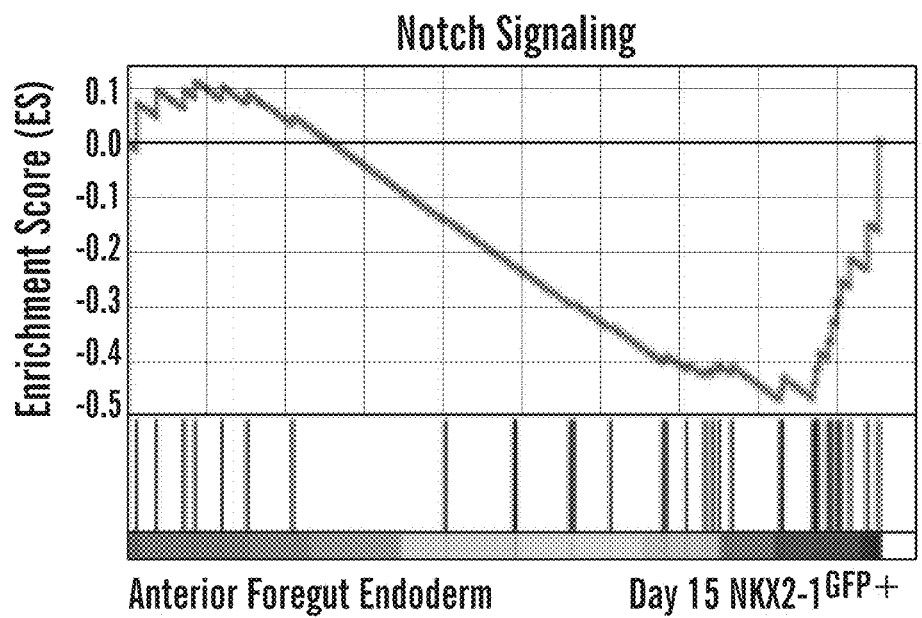
Figure 26D:
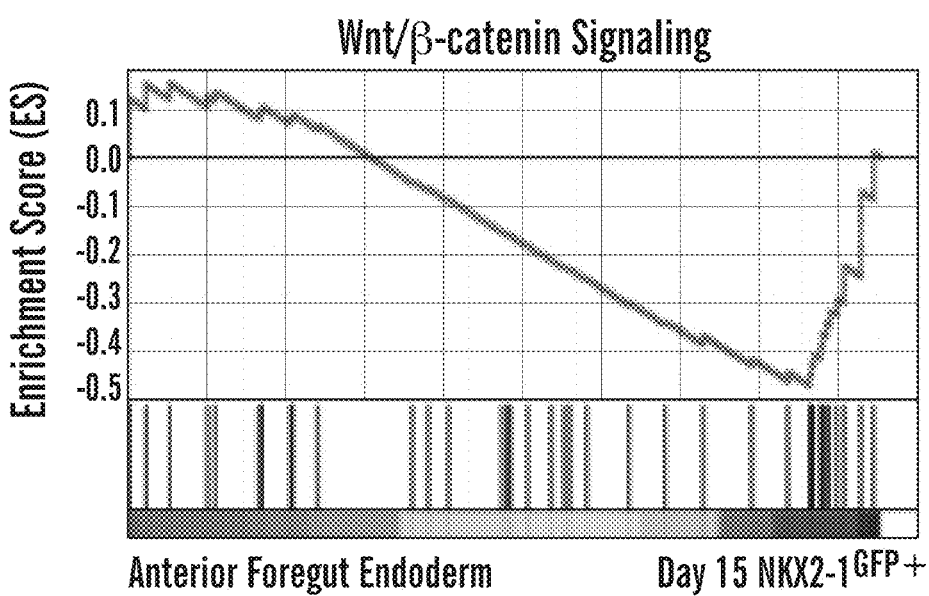

Human Pluripotent Stem Cell-Derived Lung Progenitors Heterogeneously Express Markers of Distinct Proximodistal Lung Lineages Early Post-Specification The inventors sought to further explore whether they could identify some differences between early iPSC-derived NKX2-1+ cells consistent with the development of distinct lung lineages. In particular, the lung is patterned rapidly post-specification along the proximodistal axis, which is canonically defined by the expression of key transcription factors SOX2 in the proximal developing airways and trachea and SOX9 in the budding distal tips[3,4]. Analysis of our database of single-cell RNA sequencing of Day 15 NKX2-1+ cells derived from two distinct iPSC lines revealed that many profiled cells expressed SOX9 and fewer expressed SOX2, demonstrating a distal lung bias at this stage (FIG. 25B). The inventors clarified this heterogeneity in SOX2 expression by intracellular flow cytometry, which showed some level of SOX2 expression within 55.5±3.1% of the NKX2-1+ population (FIG. 25C). Immunofluorescence staining further revealed colocalization of the nuclear NKX2-1 and SOX2 proteins in 59.7±7.4% of NKX2-1+ cells at Day 15 (FIG. 25D).

Wnt Signaling is Active in the Epithelium During the Differentiation of NKX2-1+ Lung Progenitors To understand what critical signals might be active and potentially contributing to this early heterogeneity of iPSC-derived NKX2-1+ cells during the specification stage of differentiation, an unbiased interrogation of the microarray database was performed, comparing iPSC-derived anterior foregut endoderm to purified NKX2-1$^{GFP}$+ progenitors at Day 15 of differentiation by gene set enrichment analysis (GSEA) using the MSigDB v5.1 hallmark gene sets to identify candidate pathways involved in differentiation to Day 15 NKX2-1+ progenitors. This analysis resulted in the identification of 19/50 gene sets statistically upregulated in Day 15 NKX2-1+ cells (FDR<10%), of which 4 were identifiable developmental pathways: P53 signaling, Notch signaling, Hedgehog signaling, and Wnt/β-catenin signaling (FIG. 26A-26D, and data not shown). It is noted that the potent Wnt activator CHIR99021 (CHIR), a small molecule that inhibits GSK3β from binding to and inhibiting beta-catenin, is a component of the specification media from Day 6-Day 15 of differentiation.

Further analysis of this Wnt signature revealed a constellation of changes in genes associated with this pathway in the Day 15 GFP+ population. Specifically, this result predicts several key canonical target Wnt genes, including AXIN2,NKD1, and LEF1, that are highly upregulated between these two timepoints and therefore may be particularly predictive of Wnt activity as cells progress developmentally from anterior foregut to lung epithelium (FIG. 2C, FIG. 8A). In contrast, the Wnt inhibitor DKK1 is downregulated as differentiation progresses to the NKX2-1+ lung stage. A kinetic analysis of the normalized Log 2 expression values of these genes reveals that the differential expression of these genes is maintained until Day 28 in NKX2-1+ cells cultured in media containing CHIR. (FIG. 8A). Taken together, these results demonstrate that Wnt signaling is active in iPSC-derived lung progenitors at Day 15 of differentiation and that AXIN2,NKD1, and LEF1 predict the activity of Wnt in this model. The specificity of this response is further supported by evidence that AXIN2 is upregulated by lentiviral overexpression of phosphorylation-incompetent murine beta-catenin (Fuerer & Nusse 2010) in NKX2-1+ progenitors, even in the absence of CHIR (FIG. 8C).

Wnt Signaling is Required in a Stage-Dependent Manner for Normal Lung Epithelial Specification To further understand the role of Wnt signaling in human lung development, the withdrawal of Wnt signaling pre- and post-lung specification was compared in the directed differentiation model, using both CHIR and recombinant Wnt3a. It is not known if Wnt activation in human epithelial cells is critical for the specification of the NKX2-1+ lung lineage, although in murine models, Wnt signaling is highly active during specification of the lung from the foregut endoderm, and disruption of the canonical Wnt signaling effector β-catenin results in lung agenesis[5,6].

Cells differentiated from anterior foregut endoderm in the presence of CHIR expressed significantly higher levels of NKX2-1$^{GFP}$ as early as 48 h after the initiation of specification in comparison to cells cultured without this compound, this difference was maintained until at least Day 15, and NKX2-1$^{GFP}$ expression could not be rescued in cells differentiated without CHIR to Day 15 by later addition of this molecule (FIG. 9B). To verify whether withdrawal of CHIR from the specification media resulted in decreased Wnt signaling activity, a lentivirus containing seven tandem TCF binding sites driving the expression of an mCherry construct from a minimal promoter in response to β-catenin binding during active Wnt signaling (henceforth 7TC)[7] was used. The expression of this reporter was normalized to expression of a constitutive mCherry (Ef1aL-mCherry) (FIG. 8B). The inventors discovered that cells treated with CHIR showed rapid upregulation of 7TC expression in response to addition of specification media and in comparison to vehicle alone (FIG. 9C-9G), demonstrating that CHIR activates Wnt signaling in this context and that Wnt activity in the absence of CHIR is minimal to non-existent.

Together, the inventors have discovered that that canonical Wnt activity during specification in response to treatment with CHIR is required for in vitro specification of human lung epithelial progenitors from anterior foregut endoderm and surprisingly and importantly, that this effect is limited to a window of developmental competence.

Having established that Wnt signaling is active in the epithelium during specification, the inventors tested the role of this pathway in the post-specification stage. To accomplish this, differentiating cells were cultured with either CHIR, recombinant mouse Wnt3a, or neither, from Day 15 to Day 19, and used fluorescence activated cell sorting (FACS) to purify NKX2-1$^{GFP}$+ cells for analysis at Day 19 (FIG. 2B). The inventors demonstrated that CHIR withdrawal (i.e., the absence of CHIR or Wnt signaling) reduced 7XTCF-mCherry expression within infected NKX2-1+ cells (FIG. 9F) as well as expression of the Wnt signaling responsive genes LEF1, NKD1, and AXIN2 (FIG. 2C). A comparison between NKX2-1$^{GFP}$+ cells at Day 15 and at Day 19 after culture without CHIR using an unbiased Wnt pathway specific qRT-PCR array identified these same Wnt markers within the top 15 most downregulated genes between these timepoints (FIG. 9G). Correspondingly, AXIN2 expression at Day 19 appeared to be partly rescued by treatment with soluble Wnt3a for this four day window (FIG. 2C). The incompleteness of this rescue is unsurprising given the known instability of soluble Wnt in serum free culture conditions[8]. Taken together, these results demonstrate that Wnt inhibition or low Wnt conditions (e.g., CHIR withdrawal) is an effective method to test the effects of changing Wnt signaling on differentiating lung progenitors.

CHIR Withdrawal Post-Specification Results in Changes in iPSC-Derived NKX2-1+ Lung Epithelial Cells Consistent with the Generation of Diverse Proximal Lung Lineages, including NKX2-1+P63+ Basal-Like Cells Using this validated approach of withdrawing CHIR from Day 15 to 19, the inventors assessed if Wnt signaling is important in the early post-specification patterning of human lung epithelial progenitors. While Wnt signaling has been previously reported in murine models (Shu et al. 2005; Mucenski 2003), and it has been reported that Wnt signaling may be dispensable post-specification in the maintenance of the proximal lung (Zemke et al. 2009), aberrantly active Wnt signaling can inhibit normal proximal lung development (Hashimoto et al. 2012), it is not clear if this pathway applies in human lung epithelial progenitors, or human lung epithelial progenitors derived from iPSC.

Withdrawal of CHIR from Day 15 to 19 resulted in a significantly decreased percentage of NKX2-1$^{GFP}$+ cells by Day 19 (FIG. 10A, 10B), demonstrating that some level of Wnt activation may be required to maintain or continually specify a subset of these cells. In spite of the reduction in NKX2-1 expression, cells cultured without CHIR from Day 15 to 19 typically showed increased expression of proximal lung transcription factor SOX2 as well as significantly increased expression of genes indicative of specific cellular subtypes, including SCGB3A2+ secretory cells, P63+ basal cells, and MUC5AC+ goblet cells. These cells also displayed decreased expression of SOX9 and decreased expression of the ETS domain transcription factor ETV5[9] within sorted NKX2-1$^{GFP}$+ cells, in comparison to CHIR-treated conditions. Similarly, cells treated with rhWnt3a during this same window showed intermediate expression of both SOX2 and SOX9 relative to the two other conditions, concordant with the previously reported intermediate expression of AXIN2 in this condition (FIG. 3F).

As there was only a modest change in gene expression of the proximal progenitor transcription factor SOX2 in response to changes in Wnt activation, the inventors tested whether the proportion of SOX2+ putative proximal progenitors within the NKX2-1+ population changed in response to CHIR withdrawal. Immunofluorescence staining revealed colocalization of nuclear NKX2-1 and SOX2 in both conditions cultured with and without CHIR (data not shown). However, quantification of the proportion of NKX2-1+/SOX2+ dual positive cells within the specified NKX2-1+ lung population by intracellular flow cytometry revealed that cells cultured from Day 15 to 19 without CHIR showed a small but significant increase in the percentage of NKX2-1+/SOX2+ proximal lung progenitors, with approximately 68.0±4.1% of the NKX2-1+ population expressing SOX2, in comparison to just 54.9±5.5% in CHIR-treated cells (data not shown).

As NKX2-1+/P63+ basal cells, an endogenous progenitor population capable of differentiating to multiple proximal lung lineages, are an attractive target for proximal lung epithelial directed differentiation protocols, the inventors next evaluated the changes in this population in response to CHIR withdrawal. In contrast to cells cultured with CHIR, cells cultured in FGF10 alone showed significantly increased coexpression of NKX2-1 and P63 by immunofluorescence (data not shown). A minority of the NKX2-1+/P63+ cells in the FGF10 alone cultures expressed the mature basal cell marker KRT5, demonstrating that these putatively more mature cells are rare at this stage (data not shown). Notably, the proportion of NKX2-1+/P63+ cells in conditions without CHIR was increased over those with CHIR above and beyond the changes observed in proportions of NKX2-1+/SOX2+ cells, demonstrating that Wnt signaling plays a role not only in early development of proximal progenitors, but also in the ability of these patterned cells to differentiate further into airway and tracheal lineages.

Taken together, the inventors have discovered that post-specification Wnt signaling favors the maintenance of the NKX2-1 expression and promotes a distal lung phenotype, and inhibits the development and differentiation of proximal lung cell types from NKX2-1+ progenitors. In particular, these results demonstrate the rapid emergence of developing tracheal and airway lineages in the absence of Wnt activation (i.e., by CHIR withdrawal, or an inhibitor of Wnt).

CHIR Acts Intrinsically on the Epithelium to Pattern Early Lung Progenitors

Developmental signaling cues rely on cross-talk between different lineages, with a signal acting on one tissue triggering a signaling cascade leading to cell fate changes in a neighboring tissue. The inventors assessed whether the effect of CHIR manipulation on proximodistal lung patterning was intrinsic to lung epithelial cells or reliant on altered signaling from a non-lung lineage within the culture system. To test this, FACS was used to purify NKX2-1+ epithelial lung progenitors at Day 14 and these were replated in a three-dimensional culture in media containing FGF10 and CHIR or DMSO (FIG. 3A). To support single cell outgrowth after sorting, a media comprising dexamethasone, cyclic AMP, IBMX, and ITS supplement (DCI) was used, as these factors promote proliferation, cell survival, and maintenance of NKX2-1 expression after single cell sorting (data not shown). To ensure identical populations of progenitors were analyzed after the single-cell outgrowth, the inventors re-sorted the NKX2-1+ population for analysis after 6 days of culture. The inventors discovered that cells maintained NKX2-1$^{GFP}$ expression at high levels in both culture conditions (FIG. 3C-3E) and formed small three-dimensional organoids by Day 20 (FIG. 3B, 3F). Analysis of the NKX2-1$^{GFP}$+ population at this stage demonstrated upregulation of proximal lung genes SOX2, SCGB3A2, and P63, and downregulation of distal lung genes SOX9 and ETV5. From these results, the inventors discovered that the effect of CHIR on proximodistal patterning of iPSC-derived lung epithelial cells is intrinsic to the epithelium and does not rely on exogenous signaling from contaminating non-lung cell types.

Figure 27A:
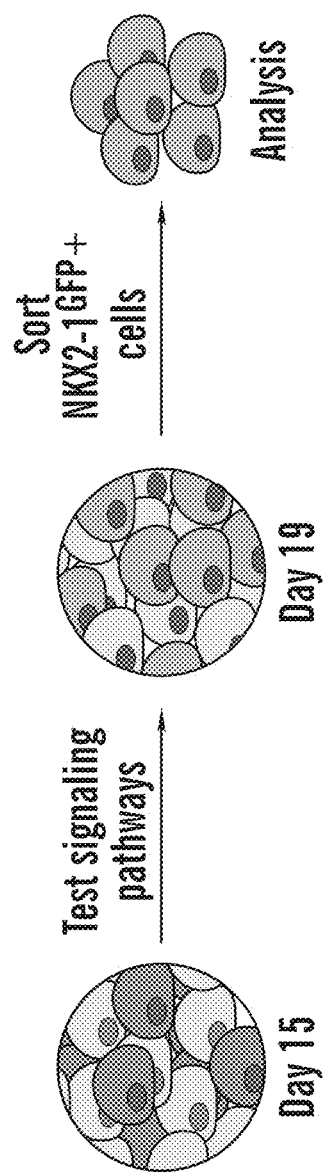
FIGS. 27A-27C shows results of gene expression in the NXK2-1+ lung progenitors after culturing from Day 15 to Day 19 in the presence of BMP4 and TGFβ.

Screening Alternate Developmental Signaling Pathways Reveals Contribution to Proximodistal Patterning from BMP Signaling In addition to Wnt, multiple developmental pathways have previously been implicated in lung proximodistal patterning. In particular, previous studies in murine and human lung systems have provided evidence for the importance of BMP4[10-12] and TGFb[13,14] signaling in early lung patterning. To test the contribution of these pathways to respiratory patterning, the inventors stimulated or inhibited BMP4 and TGFb signaling from Day 15 to Day 19 in the presence and absence of CHIR (FIG. 27A).

Furthermore, signaling via FGFR2 has also been implicated in proximodistal patterning, with previous reports of KGF and FGF10, both FGFR2 agonists, promoting distal proliferation and differentiation[15-19]. As the inventors test conditions/media contained 10 ng/mL FGF10, the inventors tested a role for FGF signaling by stimulating this pathway with using a higher concentration (100 ng/mL) FGF10 or by replacing this signaling factor with its family member FGF2.

Figure 27B:
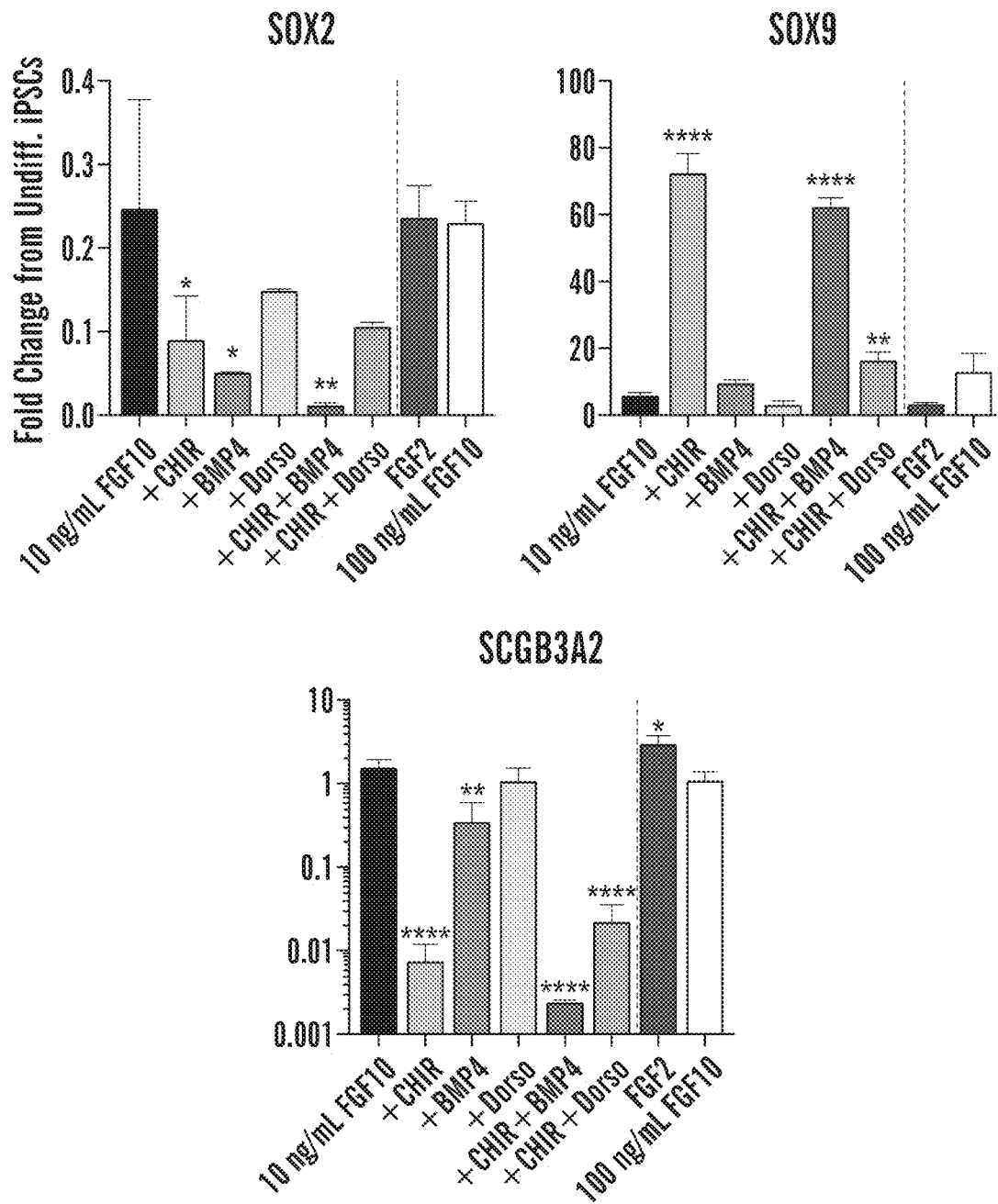
Figure 27C:
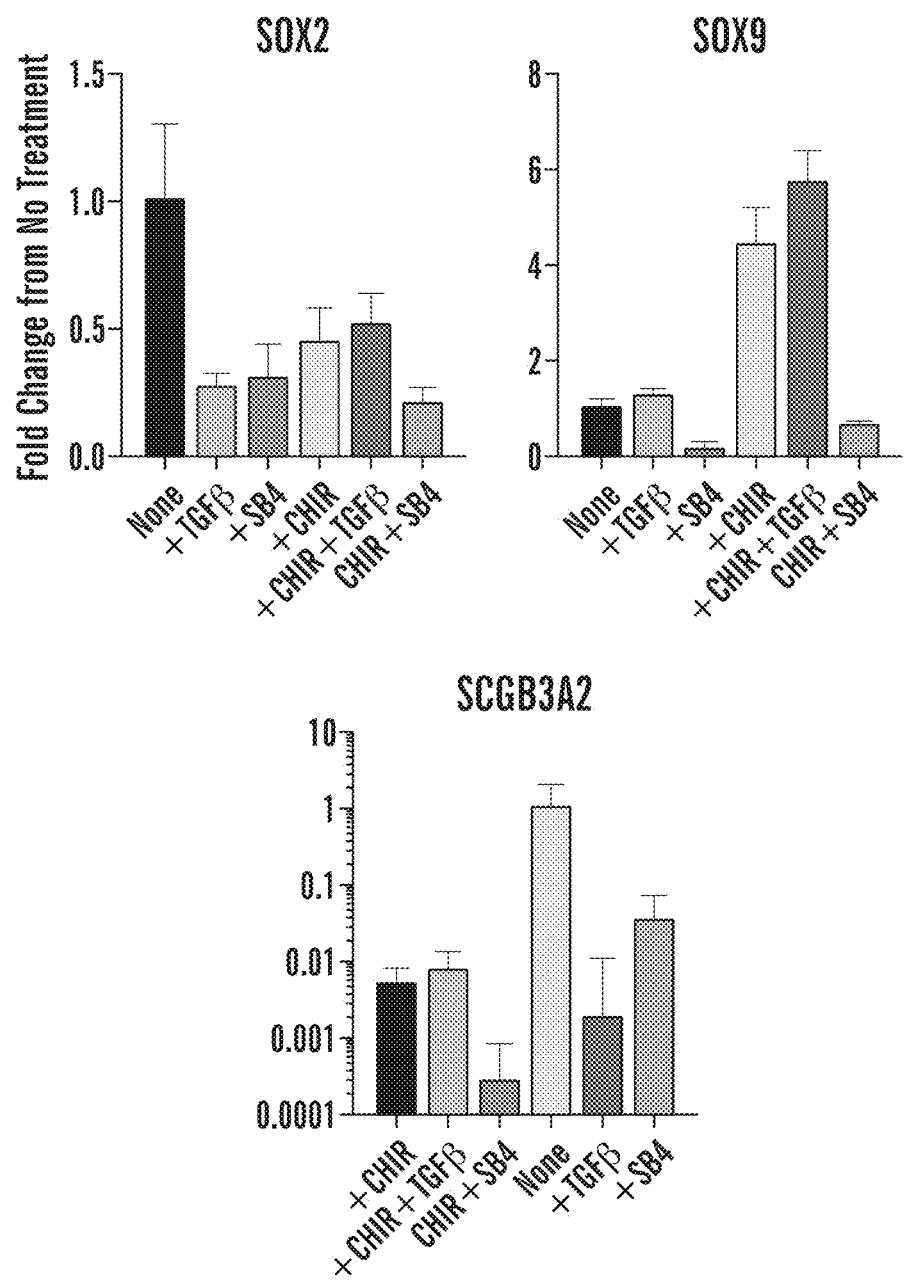
Figure 28A:
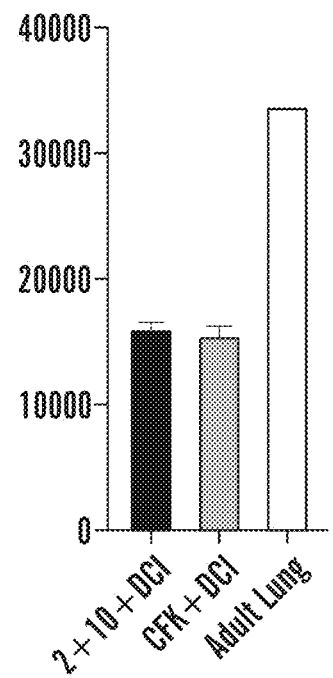
FIGS. 28A-28G shows the expression levels of NKX2-1 (FIG. 28A), P63 (FIG. 28B), SCGB1A1 (FIG. 28C), SCGB3A2(FIG. 28D), SPB (FIG. 28E), CFTR (FIG. 28F), FOXJ1 (FIG. 28G) and CDX2 (FIG. 28H) of cells treated in the presence of DCI media (cyclic AMP, IBMX and ITS supplement media), with either FGF10 and FGF2 (2+10), or CFK (+CHIR/FGF10/KGF) media (i.e., "high-wnt" media), as compared to adult lung epithelial cells.
Figure 28B:
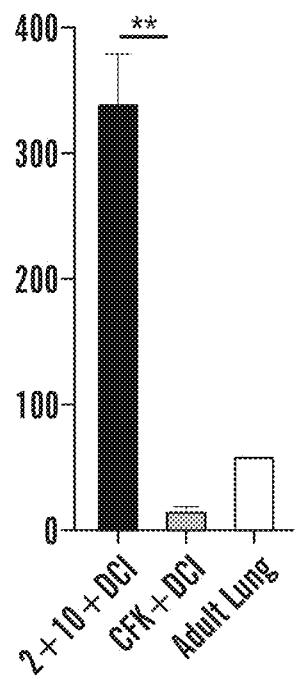
Figure 28C:
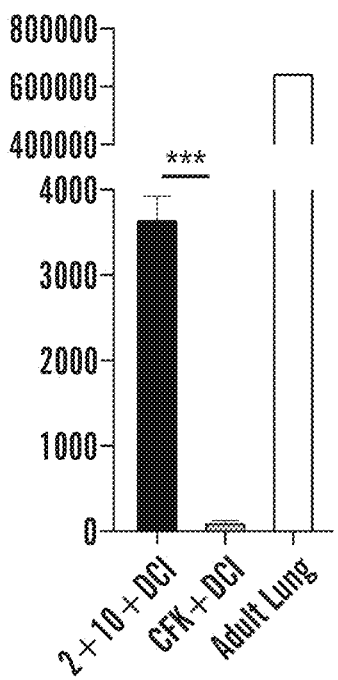
Figure 28D:
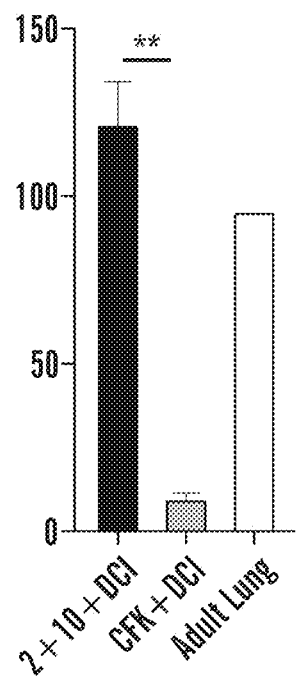
Figure 28E:
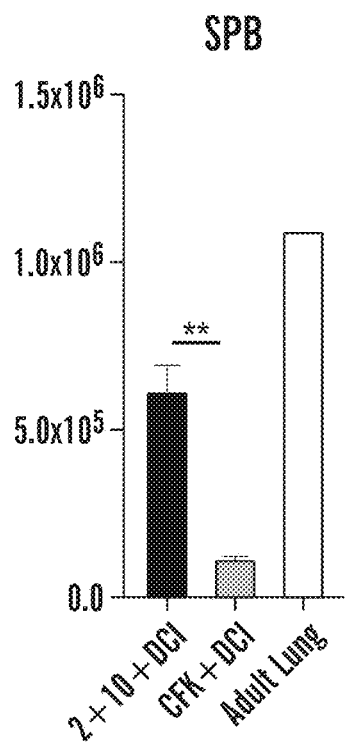
Figure 28F:
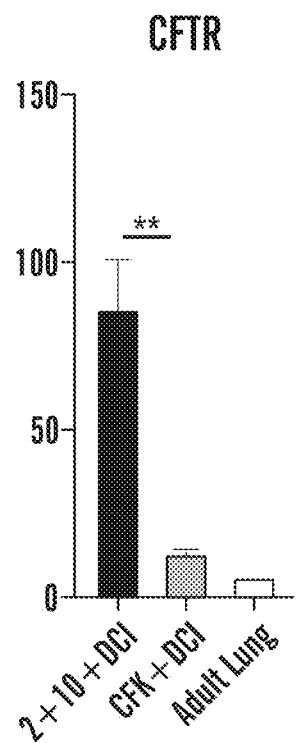
Figure 28G:
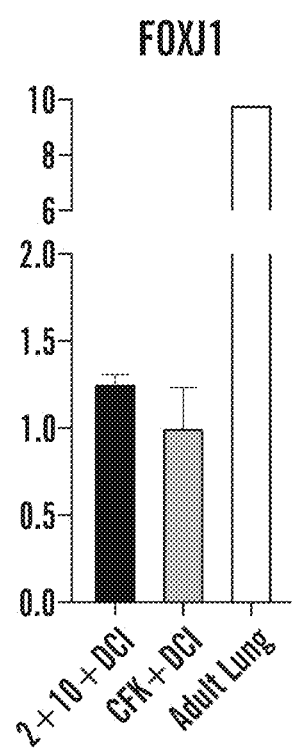
Figure 28H:
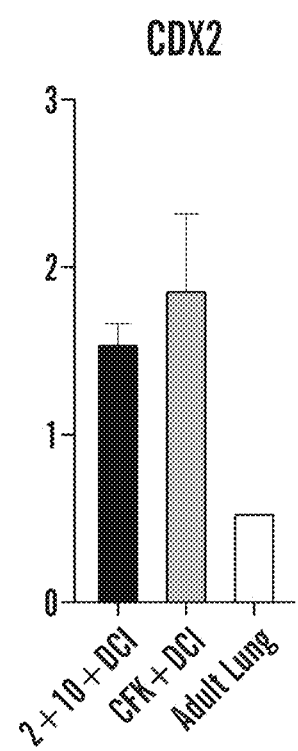

The inventors discovered that activation of BMP4 signaling contributed to distal patterning by downregulation of SOX2 and upregulation of SOX9. Concomitantly, inhibition of BMP4 by Dorsomorphin increased levels of SOX2 and SCGB3A2, even in the presence of CHIR, and decreased expression of SOX9 (FIG. 27B). FGF signaling, in contrast, showed no strong effect on proximodistal patterning, although FGF10 treatment resulted in a small upregulation in SOX9, in agreement with prior studies, and FGF2 increased expression of SCGB3A2 (FIG. 27B). TGFb signaling manipulations had no interpretable effect on marker expression (FIG. 27C).

Figure 16A:
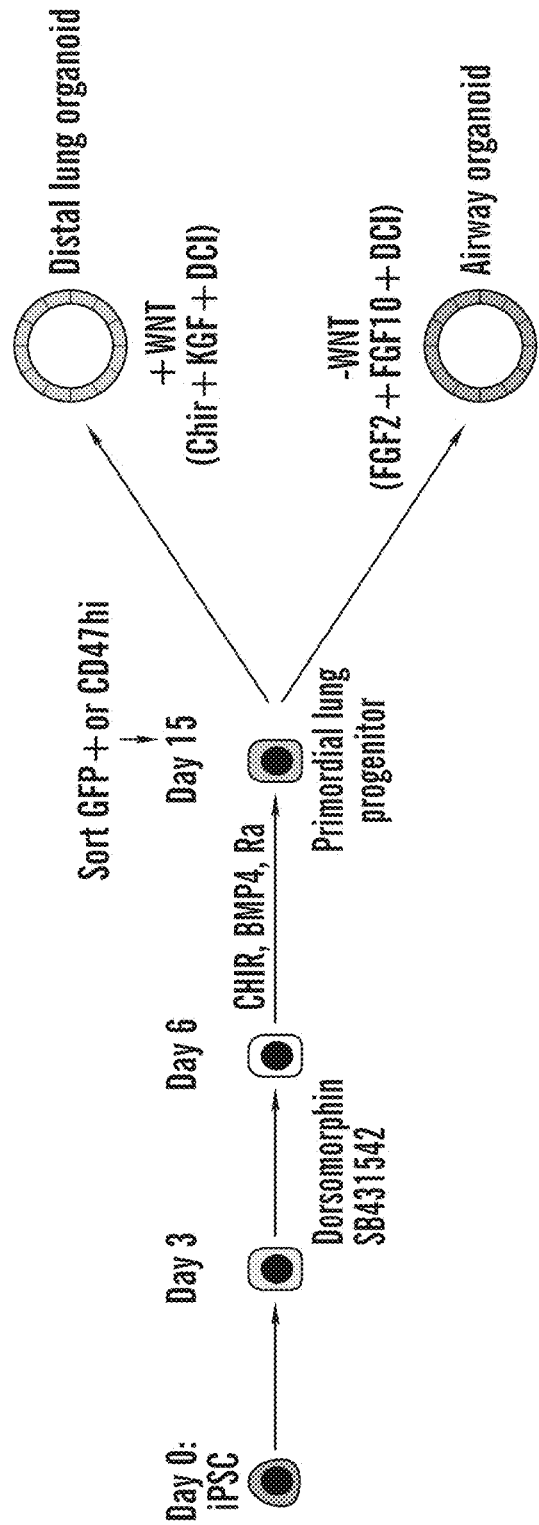
FIGS. 16A-16B.

Taken together, the inventors have demonstrated that some populations of iPSC-derived NKX2-1+ epithelial cells are competent to respond to stage-specific Wnt and BMP4 signaling to make ongoing proximodistal cell fate decisions, leading to the generation of proximal and distal lung progenitors that are capable of differentiating further to defined proximal and distal lineages (FIG. 5J and FIG. 16A). This latter result is further supported by previous reports from our group demonstrating the generation of SFTPC+ distal epithelial cells from NKX2-1+ progenitors cultured with CHIR, FGF10, and KGF, highlighting the distal developmental potential of these progenitors.

Derivation of Proximal Airway Organoids from Purified Lung Epithelial Cells

There remains a critical lack of protocols for differentiating defined airway and tracheal lineages from human pluripotent stem cells. Therefore, the inventors sought to leverage our insight into proximal airway development to generate a novel protocol for the differentiation of purified NKX2-1+ progenitors to airway lineages. Again using FACS, the inventors isolated these progenitors and resuspended them as single cells in three-dimensional Matrigel culture in various culture media.

Based on earlier results, the inventors harness the mitogenic effect of FGF agonsim to drive proliferation, but not necessarily patterning, of these lung organoids. Therefore, the inventors tested whether media containing FGF2 and FGF10 together ("2+10 media") would result in proliferation and differentiation of more proximalized lung organoids in comparison to previously published media containing CHIR, FGF10, and KGF ("CFK media") (e.g., a media with "high-wnt" due to the presence of CHIR). The inventors have previously observed the increased expression of mature lung epithelial genes, including surfactant protein C (SFTPC), in the presence of DCI, and therefore added these additional factors to our purified lung outgrowth.

NKX2-1$^{GFP}$+ cells proliferated and formed three-dimensional organoid-like structures in both medias in the presence of DCI (FIG. 5B). By Day 27, replated cells in both conditions retained 30-60% of NKX2-1$^{GFP}$ expression (FIG. 5C). In contrast, analysis of RNA expression in whole organoids demonstrated reduced expression of NKX2-1 in organoids grown in 2+10+DCI media. In spite of this reduced NKX2-1 expression, cells cultured in 2+10+DCI media expressed significantly higher levels of many airway genes than cells in CFK media, including P63, SCGB3A2, SPB, SCGB1A1, MUC5B, CFTR and FOXJ1 (FIG. 5D). In contrast, cells cultured in CFK media expressed lower levels of proximal lung markers and upregulated expression of ETV5 as well as the distal lung marker SFTPC (FIG. 5D). This result clearly demonstrates the potential of 2+10 media for differentiation and outgrowth of proximal airway cell types and provides further support for our earlier conclusion that the effect of Wnt signaling on lung differentiation is intrinsic to the epithelium.

Figure 13A:
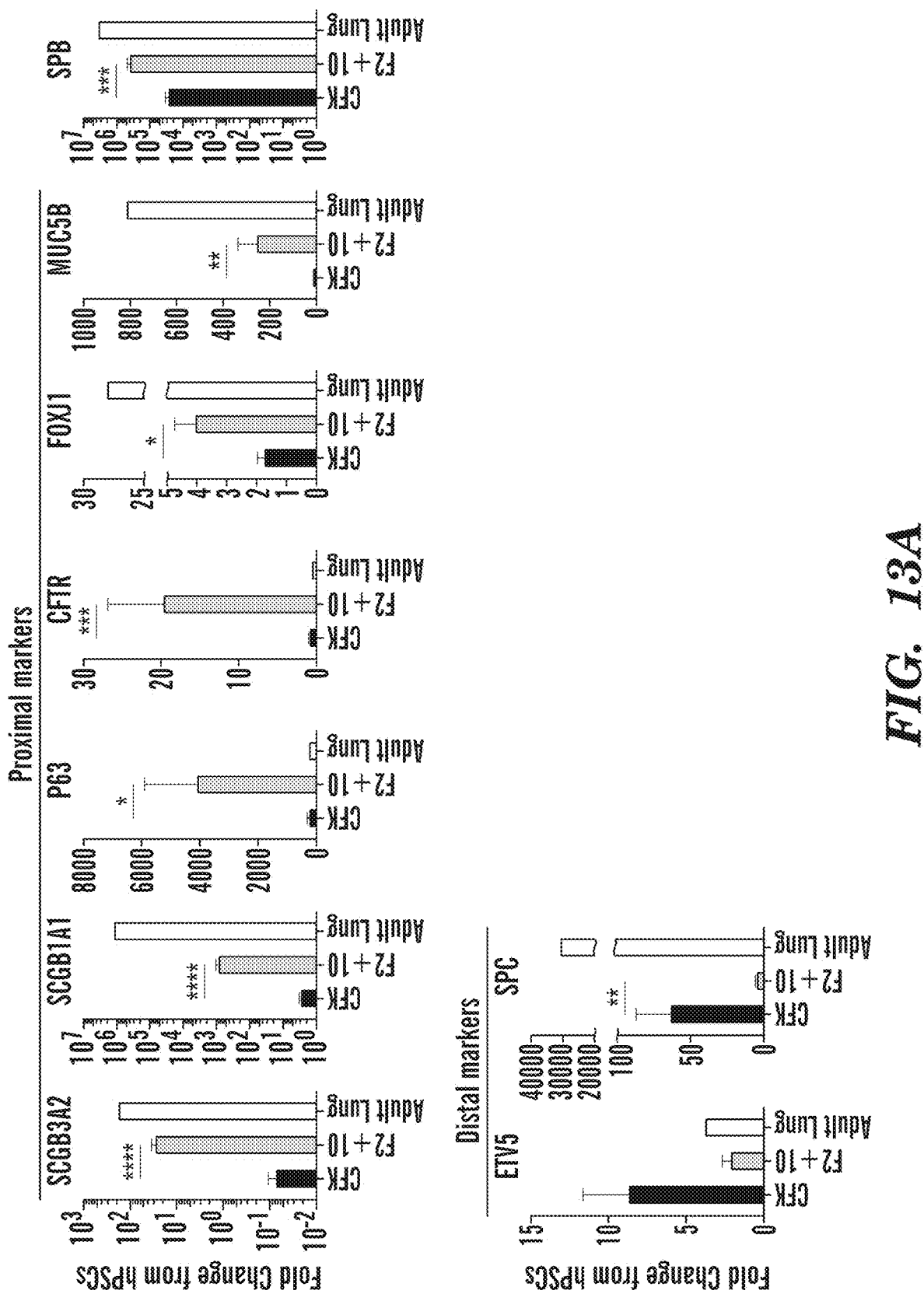
FIGS. 13A-13B show that Wnt signaling withdrawal is key to patterning primordial lung progenitors.
Figure 13B:
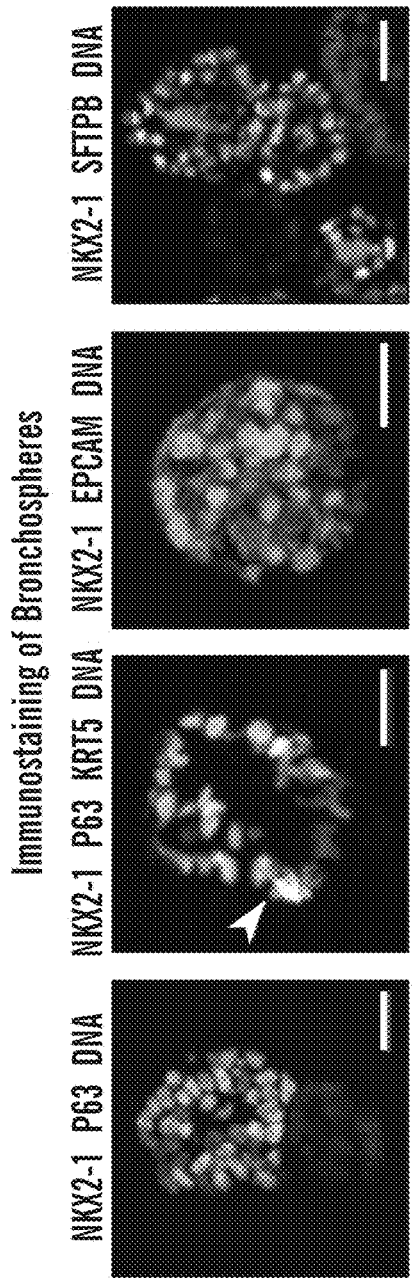
Figure 16B:
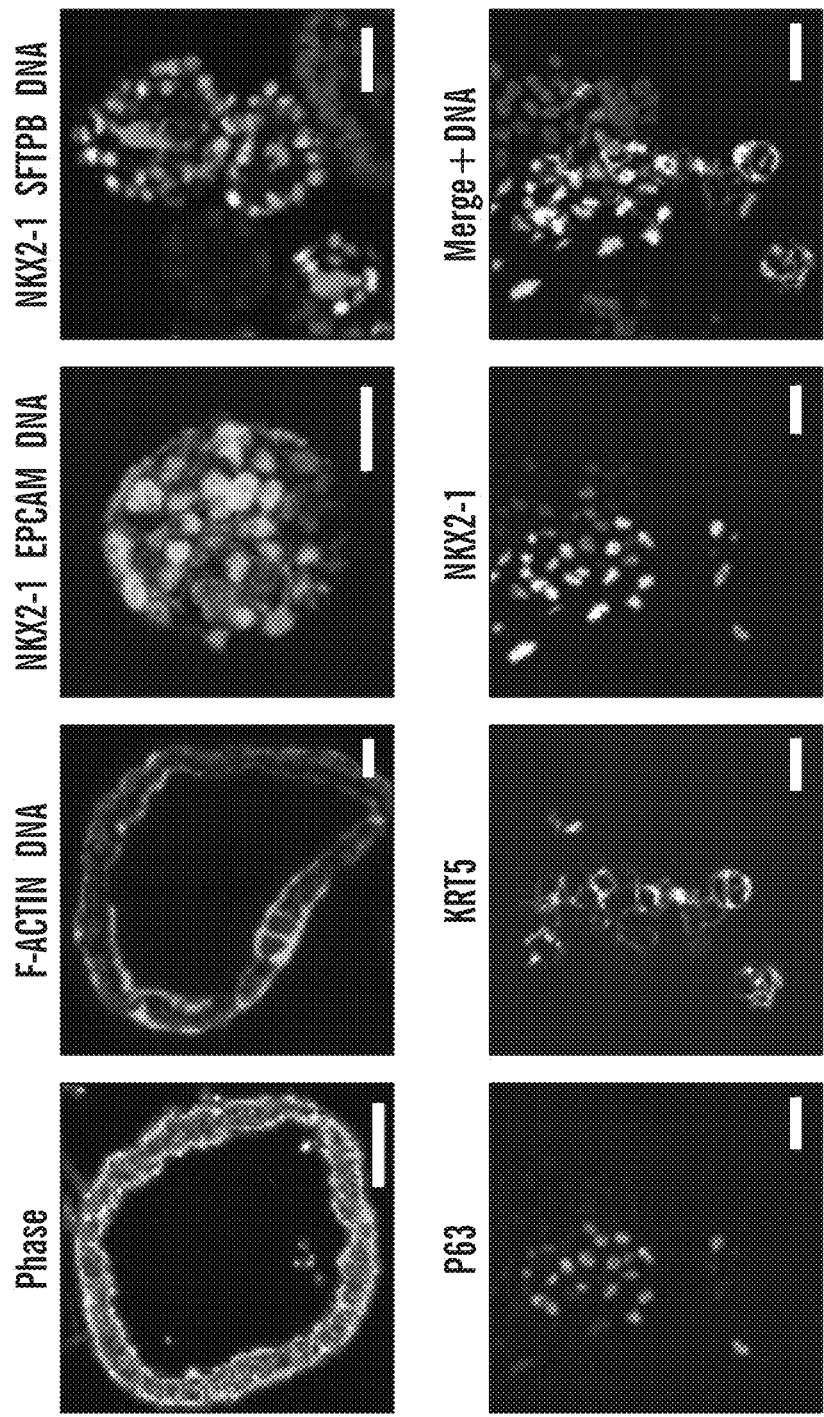

Further analysis by immunofluorescence staining reveals that these organoids represent EpCAM+ epithelial structures comprised of numerous proximal lung cell types (FIG. 13B, 16B). In particular, the inventors demonstrated populations of NKX2-1+P63+ basal-like cells within these structures (FIG. 5F, 17C).

Taken together, the inventors have demonstrated that purified lung epithelial progenitors derived from iPSCs can be reproducibly pushed to differentiate specifically towards proximal airway or distal lung lineages using precisely defined growth factor cocktails. This finding not only highlights the plasticity of early NKX2-1+ progenitors and their competence to respond to developmental cues, but further exhibits the potential for the use of these cells in complex in vitro models of pulmonary disease. In particular, the significant upregulation of the cystic fibrosis transmembrane receptor (CFTR) by 2+10+DCI-treated organoids demonstrates that this method is useful in studies of lung-specific defects in cells derived from patients with cystic fibrosis, a complex hereditary pulmonary disease caused by mutations in this gene.

Example 7 iPSC-Based Assay for the Personalized Assessment of CFTR Function: Forskolin-Induced Swelling (FIS) of iPSC-Derived Bronchospheres The inventors have previously used fluorescent lineage-reporters to purify lung and thyroid progenitors from mouse embryonic stem cells[14]. This approach proved to highly informative and identified novel signaling pathways of thyroid specification conserved across species and led to the generation of iPSC-derived thyroid progenitors that rescued hypothyroidism when transplanted in hypothyroid mice[20]. Adopting a similar approach, as discussed above in Examples 1-7, the inventors derived functional lung epithelium from human iPSCs. This led to identification of a novel surface marker to purify lung epithelium from iPSCs and growth factor combinations to derive airway epithelium from primordial lung progenitors.

Figure 12E:
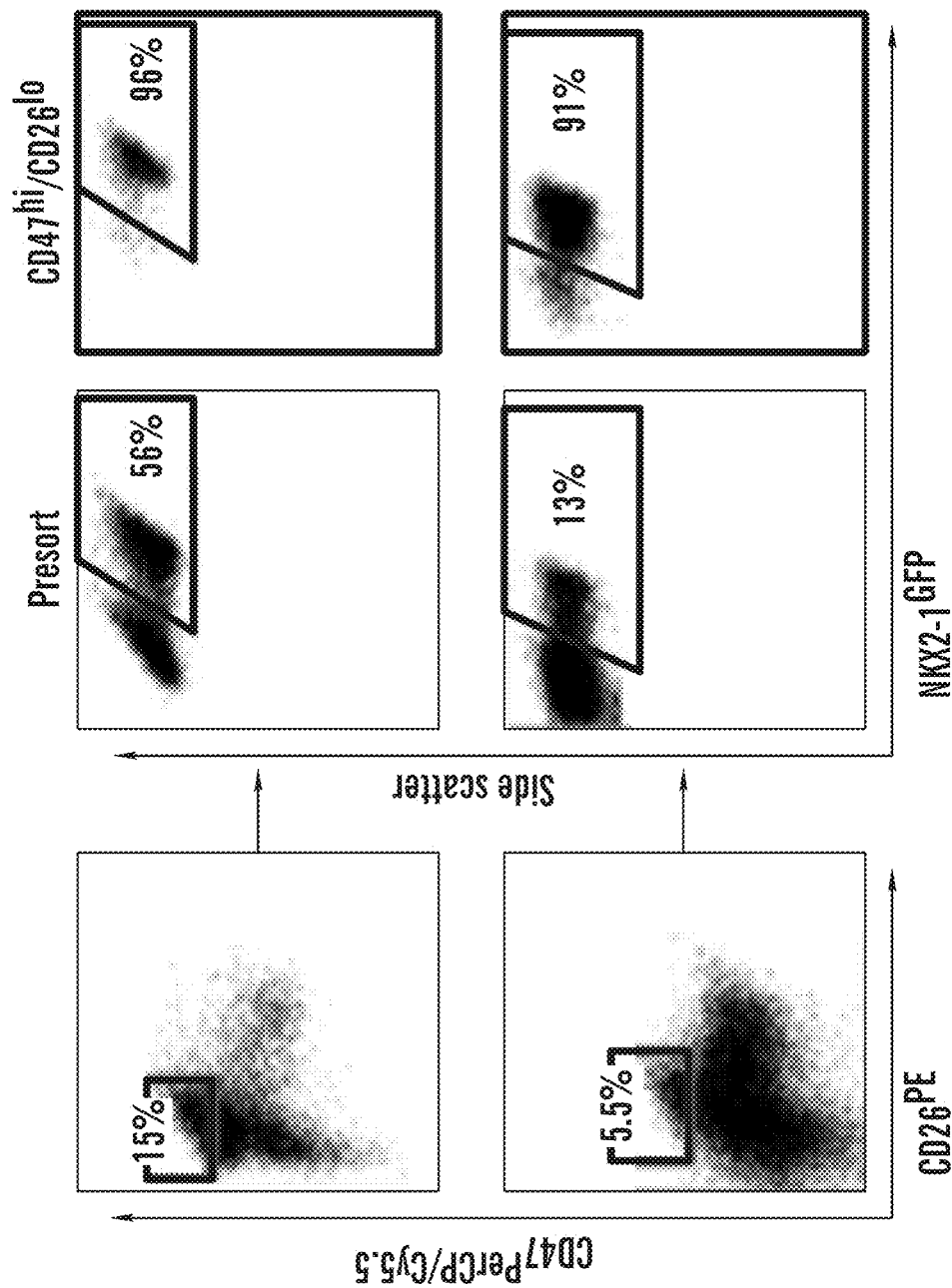

Current research suggests that all cells of the post-natal lung epithelium derive from an embryonic NKX2-1+ progenitor[21]. In order to identify and purify the earliest identifiable lung-lineage committed cells from human PSCs in vitro, we targeted a GFP reporter gene to the endogenous human NKX2-1 locus in cystic fibrosis patient-specific iPSCs. Based on protocols previously developed by us and others for the in vitro directed differentiation of human PSCs into lung we optimized the efficient and reproducible induction of NKX2-1GFP (FIG. 1A and data not shown)[14,16]. The inventors performed a detailed characterization of these early lung progenitors using global transcriptomic profiling at the population and single cell level. This analysis identified; (1) lung directed differentiations are variable in terms of NKX2-1 induction, (2) non-lung lineages including hepatic, esophageal and intestinal lineages are present within the subset of NKX2-1 negative cells, (4) novel surface markers, i.e., expression of CD47$^{hi}$/CD26$^{lo}$, can be used to prospectively isolate and expand iPSC-derived lung progenitors to overcome the heterogeneity within these differentiation protocols without the need for complex gene-editing strategies, and (5) iPSC-derived lung progenitors at this early stage (Day 15) do not express more differentiated markers of the developing lung ("primordial") (FIG. 12B-12E). In particular, FIG. 12 demonstrates the CD47$^{hi}$ population is enriched for NKX2-1-GFP+ cells (FIG. 12C) and that the CD47$^{hi}$/CD26$^{lo}$ purifies NKX2-1+ cells from lung differentiations with both poor (13%) vs reasonable (56%) efficiencies of NKX2-1 induction (FIG. 12E).

Herein, in Examples 1-7, the inventors have identified key signaling pathways to generate bronchospheres from iPSCs. This is a significant improvement over existing lung directed differentiation protocols, which typically generate non-lung lineages and also a heterogeneous mix of cells expressing airway and alveolar markers, many of which are not lung specific. The main defect in CF lungs is the airways, therefore establishing a protocol to develop airway progenitors as demonstrated herein, is very useful to assessing therapeutic treatment for CF, as well as studying the diseases, and generating personalized approach to CF treatment using a particular CF patients iPSCs to generate airway lineage cells.

As disclosed herein, the inventors have identified that withdrawal of Wnt signaling was key to patterning primordial lung progenitors towards airway lineages. Compared to published Wnt-based lung maturation media (Chin, FGF10, KGF termed "CFK"), the inventors media of FGF2 and FGF10 ("F2+10") led epithelial organoids enriched for proximal lung markers including SOX2, TP63 (basal cells), CFTR, FOXJ1 (ciliated cells), SCGB3A2 (secretory cells), SCGB1A1 (club cells) and a decrease in distal markers (SFTPC, ETV5) (FIG. 13A-13B). These organoids, hereafter termed "bronchospheres", overcome key hurdles limiting the applicability of iPSC-technology to drug discovery for lung disease and will serve as the cell-based model for CFTR assessment.

Accordingly, the inventors herein have demonstrated directed differentiation of iPSCs towards lung epithelium using an optimized version of a published serum-free, co-culture free directed differentiation protocol[16]. The major stages of the protocol include (1) definitive endoderm induction, (2) generating anterior foregut endoderm through TGF-β and BMP4 inhibition, and (3) NKX2-1 induction with media supplemented with Chir, FGF10, KGF, BMP4 and Retinoic Acid. Employing a novel $CD47^{hi}/CD26^{lo}$ sort strategy, iPSC-derived lung progenitors are sorted to purity on day 15. These cells are replated in 12-well plates at a concentration of 1,000 cells per microliter in 50 μL of growth factor reduced Matrigel in a "proximalizing" "F2+10" media. After 7-10 days, each Matrigel droplet typically contains thousands of small well-defined organoids (See FIG. 14A). These organoids, herein also referred to as "bronchospheres" can be enzymatically digested into single-cells and retain their capacity to self-organize in epithelial organoids. In some embodiments, these cells can be either frozen for future use or expanded even further to generate hundred of thousands of organoids. Herein, the inventors assess the optimal timing and conditions for freezing cells. The inventors also demonstrate that the protocol for the generation of bronchospheres is reproducible across all iPSC lines tested thus far, including the including CF and CF-corrected iPSCs.

iPSC-Derived Broncospheres can be Used to Measure CFTR Function Using the Forskolin-Induced Swelling (FIS) of iPSC-Derived Bronchospheres Originally obtained from CF Patients.

Figure 14D:
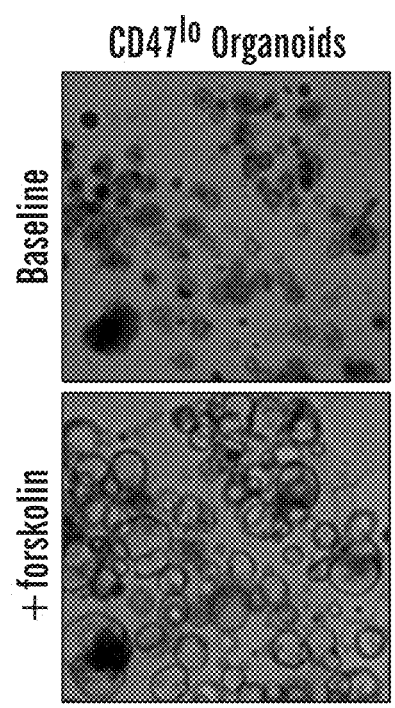
Figure 14E:
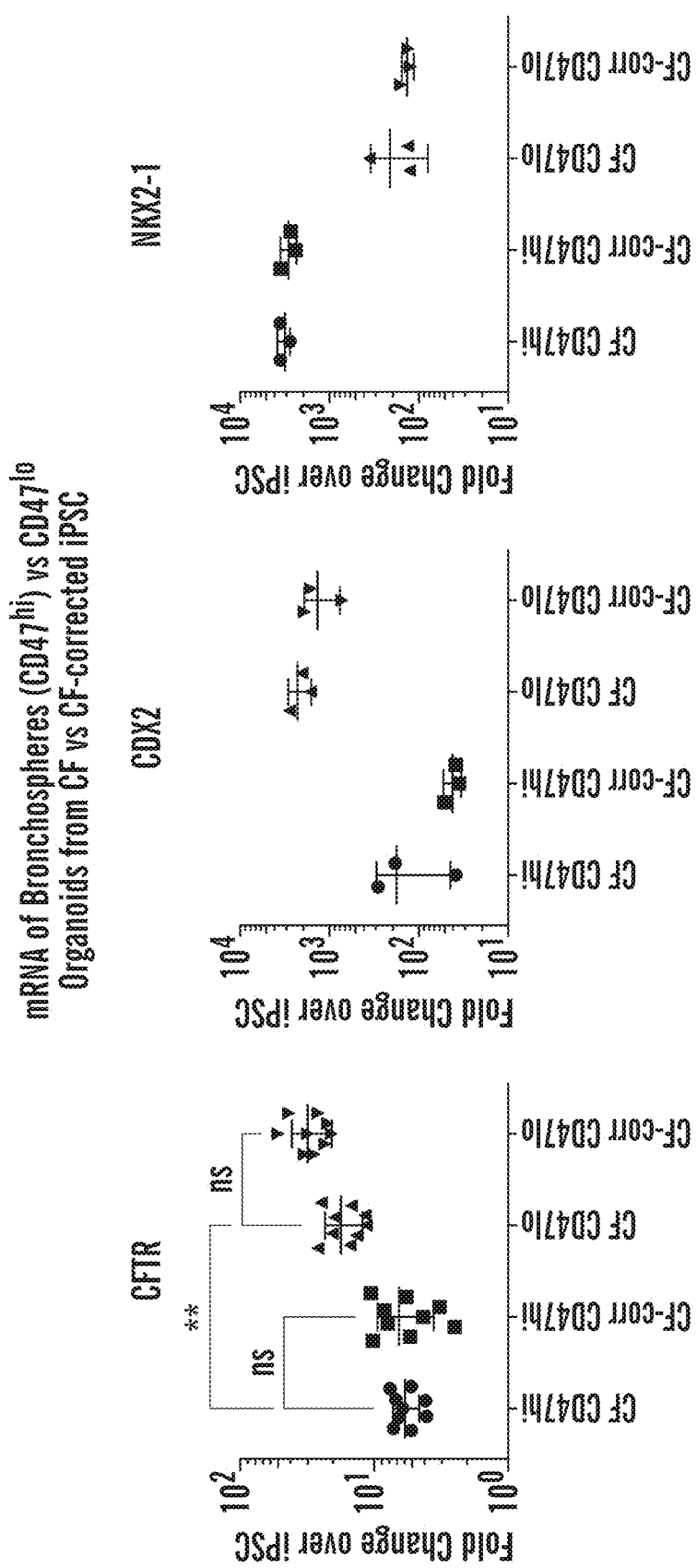
Figure 15:
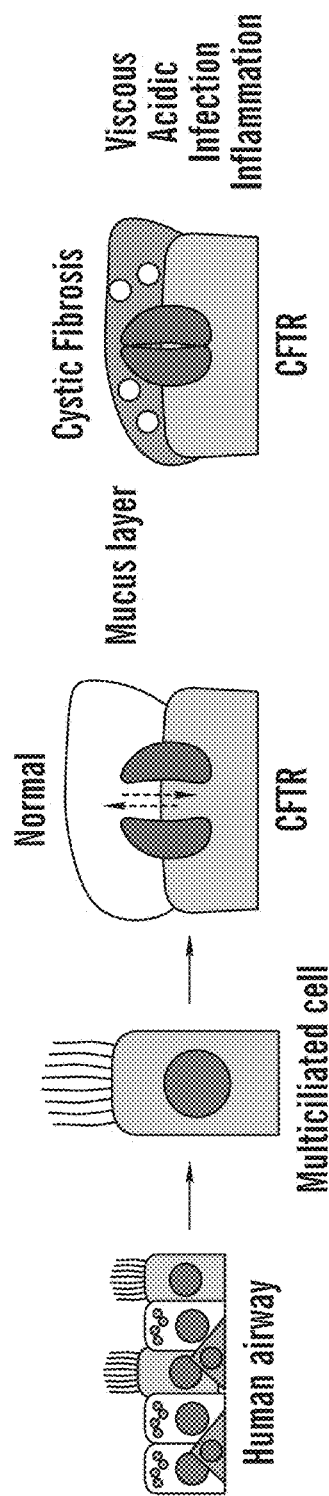
FIG. 15 shows a schematic of the effect of cystic fibrosis disease. Cystic fibrosis is a devastating genetic lung disease. For the majority of patients, effective therapy is desperately needed.

To measure CFTR function in iPSC-derived lung epithelium, the inventors developed the forskolin-induced swelling (FIS) assay, which is more suited to HTS than electrophysiological measurements. Forskolin increased intracellular cAMP and activates CFTR[22]. The swelling of intestinal organoids in response to CFTR activation using forskolin was demonstrated to be CFTR-dependent and correlated with CF disease severity[22]. This elegant assay is based on the observation that CFTR-expressing epithelial organoids will swell in response to forskolin and the degree of swelling correlates with the amount of functional CFTR protein present. When individual organoids are analyzed there is high organoid-to-organoid variability, however, when the amount of swelling is averaged over tens to hundreds of organoids the gross change in organoid surface area can be used as a quantitative measure of CFTR function. The inventors have previously demonstrated successful sequence-specific correction of two CF iPSC lines resulting in functional restoration of CFTR. Herein, the inventors provide data here confirming that the FIS assay can effectively be used to measure CFTR function in iPSC airway organoids (FIG. 14A-14E). Bronchospheres generated from CF iPSCs vs CF-corrected syngeneic iPSCs express similar amounts of CFTR mRNA yet swelling is significantly increased in the gene-corrected organoids confirming functional CFTR protein (FIG. 14B, 14E). Non-lung organoids were generated in the same experiments by re-plating the $CD47^{lo}$ cells. These organoids express higher levels of CFTR mRNA and the hindgut transcription factor CDX2 (FIG. 14E) suggesting non-lung CFTR expressing lineages. Consistent with these findings the organoids have greater FIS and this highlights the importance of using a purification step to eliminate confounding, non-lung lineages (FIG. 14D).

Establishing a HTS Workflow for FIS of iPSC-Derived Bronchospheres.

The inventors optimized the differentiation of iPSCs into bronchospheres and the FIS assay into a HTS workflow, utilizing an automated workstation for rapid, accurate pipetting and an automated imaging readout (see FIG. 23) (also referred to as a "robotic FIS assay"). Bronchospheres are dissociated from Matrigel and transferred to a HT workstation, e.g., BioMek NXp Laboratory Automation Station for efficient, precise, automated plating in 96 well plates. Bronchospheres can be plated in 3 μl droplets Matrigel/well in 60 wells/plate, with the outermost wells empty due to inaccurate imaging of these wells. Plates are left at 37° C. for 20 minutes to allow the Matrigel to gel. The BioMek is programmed to pipette 200 μl of "FGF2+10" media into each experimental well. For FIS experiments, an automated high-definition microscope (Keyence BZX 700) can be used to capture baseline and interval phase and fluorescence images of each experimental well. This microscope has tissue culture capabilities with temperature and atmosphere controls. Using Keyence software, the acquired images can be analyzed to measure the combined surface area of all organoids per well at baseline (T0) and after FIS (FIG. 14A). Appropriate thresholds to accurately detect organoid size have been determined. For quality control, random wells can be selected for manual measurement. The total organoid surface are of each well will be reported as "normalized area" (T0 normalized area=100%). The percentage average increase in total organoid surface area after FIS (hereafter "Δ forskolin") is then calculated. For example, if the surface area at baseline (T0)=1,000,000 μm2 and 1 hour after forskolin (T1 hr)=1,400,000 μm2 the "Δforskolin" normalized area is 140%.

Determining the Dynamic Range of Variability of FIS with 3 Normal iPSC Lines

Bronchospheres from iPSC lines from three healthy individuals can be assessed to determine the dynamic range of FIS in this assay. These iPSC lines (BU1, BU3 and BU7) were generated at the Center for Regenerative Medicine, Boston University (see: "www.bu.edu/dbin/stemcells/iPSC_bank"). BU1, BU3 and BU7 iPSCs were differentiated, sorted and replated as outlined above. Three replicate 96-well plates will each contain 20 wells of bronchospheres from each iPSC line. At T0 10 wells of each iPSC line will receive 5 μM forskolin (positive control) and the remaining 10 wells will receive vehicle control (negative controls). All wells will also receive calcein green. Each plate is imaged every 30 minutes for 24 hours (as shown in FIG. 14). Normalized area will be calculated for each well at all time points and graphically plotted. Statistical analyses will include calculating the mean "Δforskolin", standard deviation and coefficient of variation for positive vs negative controls at each time point. To statistically determine the duration of forskolin incubation that results in the largest effect size and assess the quality of this assay for "hit"

identification, the inventors calculate the strictly-standardized mean difference (SSMD) and Z-factor[25,26].

Figure 22A:
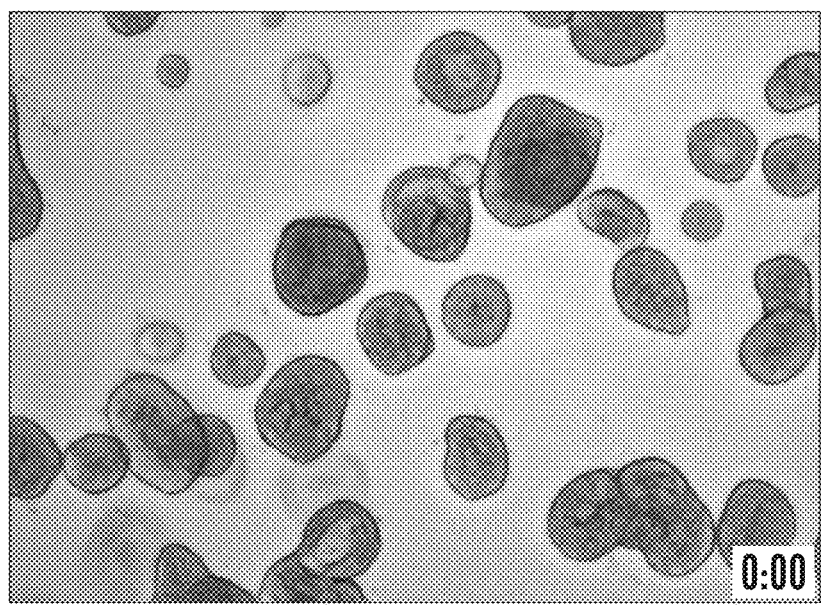
FIG. 22A-22D show the effect of gene correction on the Forskolin-induced swelling (CFTR activation) of CF bronchospheres.
Figure 22B:
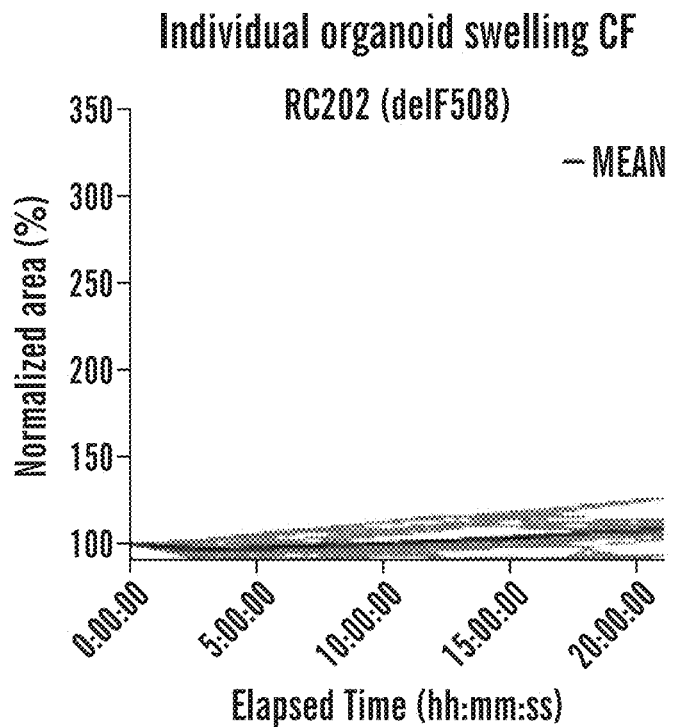
Figure 22C:
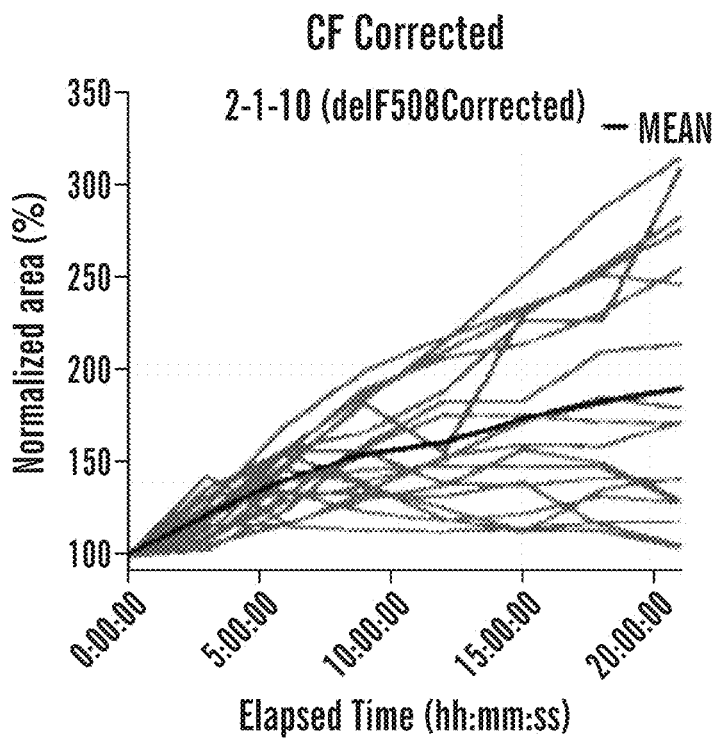
Figure 22D:
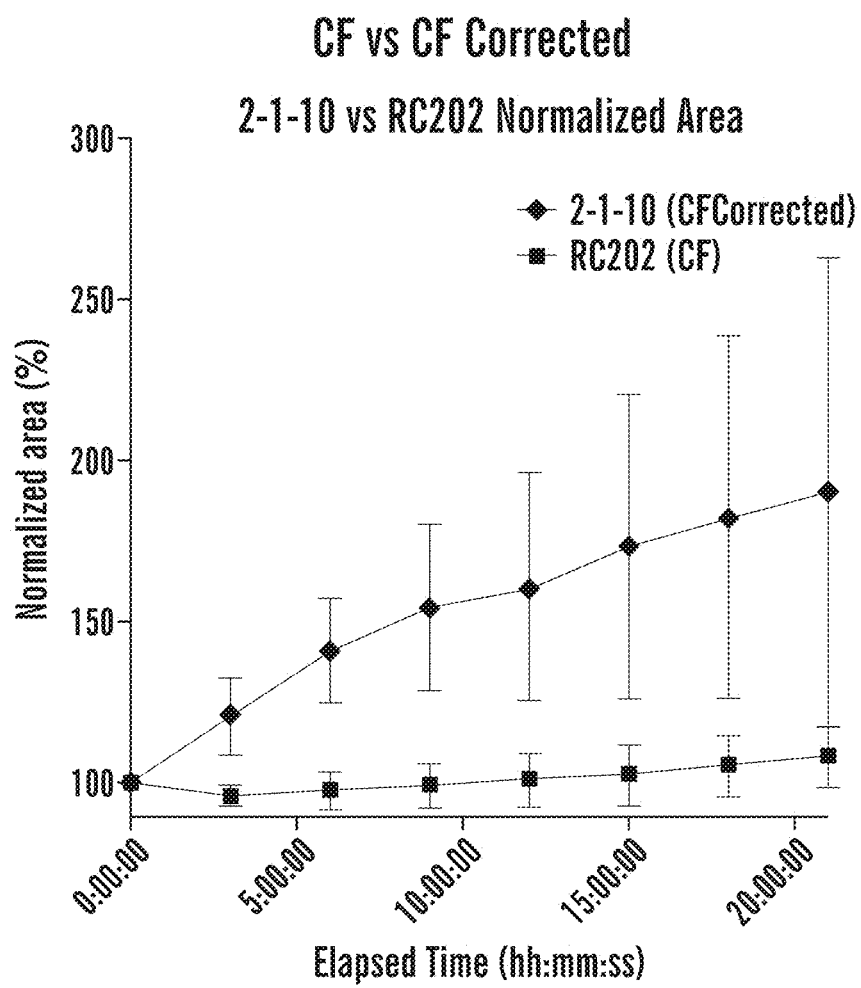

Assessment of CFTR Function in CF iPSC-Derived Bronchospheres vs Gene-Corrected Controls Using the HTS platform established above, the inventors assessed the FIS of bronchospheres derived from iPSCs from two homozygous F508del patients (RC202 and RC204) and matched gene-corrected, syngeneic iPSC controls (corrected by gene editing; total=4 iPSC lines)[10] (See FIG. 21A, 21B, 22A-22C). Student's t-test was used to assess if there is a statistically significant difference in "Δforskolin" between CF and CF corrected bronchospheres (see FIG. 22D). The inventors also tested the reproducibility of these results using cells from each patient line that have been frozen after differentiation to airway epithelium, therefore demonstrating a method for personalized CFTR quantification using iPSC-derived airway epithelium in a HTS format.

Accordingly, the inventors have demonstrated that the combination of gene-editing and iPSC technology and lung directed differentiation, together with the tools outlined above, to develop a novel, personalized, cell-based model of CFTR function: forskolin-induced swelling of iPSC-derived bronchospheres. Accordingly, the inventors have developed and successfully demonstrated a high-throughput screening (HTS) assay that can be tailored to specific CF patients by using iPSC-derived from the patients, to assess drugs that cause a functional restoration of CFTR in bronchospheres derived from the iPSCs. Additionally, such forskolin-induced swelling of iPSC-derived bronchospheres can be developed commercially, as well as used for research purposes in studying human disease.

The personalized CFTR functional assessment using iPSC-derived bronchospheres as disclosed herein is a scalable platform that can be used by academic and industry researchers. Ultimately, this technology might form part of the precision care of CF patients from infancy to adulthood. This platform also has the capacity to screen hundreds to thousands of drugs, on a personalized basis, for the treatment of CF. Accordingly, the forskolin-induced swelling of iPSC-derived bronchospheres from CF patients bridges the gap between high-throughput drug discovery approaches that can screen hundreds of thousands of compounds and the need for a pre-clinical platform to accelerate drug predictions for patients, especially children. For instance, the assay can be commercialized as a product in a number of formats; (1) preprepared frozen vials of individual or a panel (e.g. from CF, normal and gene-corrected iPSCs) iPSC derived lung progenitors provided with culture and media instructions to generate bronchospheres, (2) pre-prepared bronchosphere cultures, or (3) pre-prepared 96 well plates containing individual or a panel of iPSC-derived bronchospheres.

Example 8

Test the Capacity of iPSC-Derived Bronchospheres from Patients with Different Classes of CFTR Mutations to Recapitulate Disease and Predict Drug Responsiveness.

The inventors next determined if the assay (i.e., the forskolin-induced swelling of iPSC-derived bronchospheres from CF patients) can accurately predict drug responsiveness of different CFTR mutations.

Figure 23:
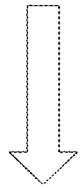
FIG. 23 is a schematic of the assay to identify drug-responsiveness of CF iPSC bronchopsheres
Figure 23:
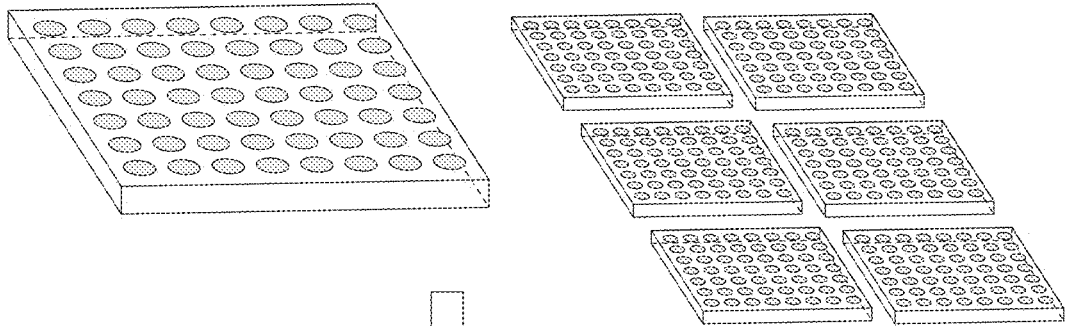
Figure 23:
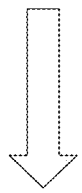
Figure 23:
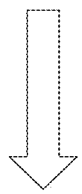
Figure 23:
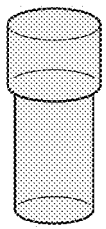
Figure 24:
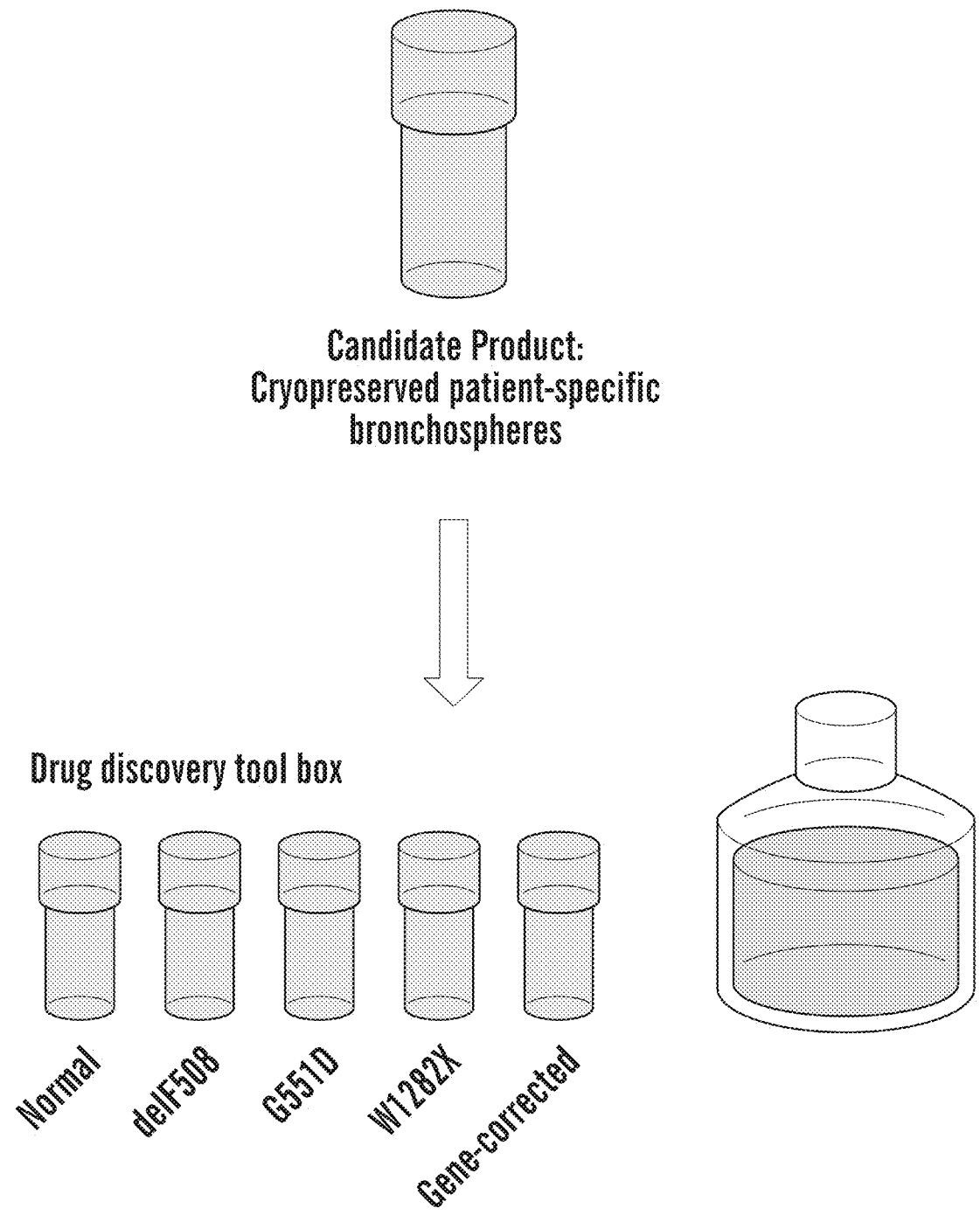
FIG. 24 is a schematic of the candidate product, which is a cryopreserved patient-specific bronchiospheres which are gene corrected.

The inventors next assessed use of the iPSC-bronchospheres to reproduce the biology, including drug rescue, of different CFTR mutations (see FIG. 23). As there are diverse consequences of distinct CFTR mutations on CFTR synthesis, trafficking and function[5], the assessment of iPSC-derived broncospheres from different CF patients will be useful to a personalized approach to CF treatment, which is highly valuable and particularity important when one considers that effective treatments for CF depend on the specific mechanism(s) of CFTR dysfunction, a cell-based model of CF that reproduces mutation-specific CFTR biology.

Accordingly, the inventors analyzed iPSCs from patients with three different CFTR mutations; F508del, G542X and G551D. The F508del mutation results in aberrant CFTR folding. The G542X mutation (class I) introduces a premature termination codon that leads to very reduced mRNA levels and absent protein. The G551D mutation (class III), the most common gating mutation, results in normal levels and trafficking yet significantly reduced activity of CFTR. Ivacaftor (VX770) increases this activity[8]. The inventors used the iPSC-derived bronchospheres platform to characterize these three mutations vs gene-corrected F508del and normal iPSC controls in terms of (1) CFTR expression levels, maturity and cellular localization, (2) severity of CFTR dysfunction at baseline, and (3) response to a panel of CFTR correctors, potentiators and premature termination codon suppressors (requested from the CFF Chemical Compound program). The inventors demonstrate that the iPSC platform disclosed herein reproduces key aspects of CF biology and thus is a highly valuable tool for characterizing CFTR mutations, as well as for personalized drug screening and drug discovery. The iPSC platform disclosed herein also is useful for assessment of other CF affected tissues.

Characterization of CFTR in iPSC-Bronchospheres from F508del, G542X and G551D Patients.

F508del, G542X and G551D iPSC were differentiated into bronchospheres as described above. Normal iPSC and CF-corrected iPSC served as controls. The amount of CFTR mRNA expressed was quantified using RT-qPCR (data not shown), and Western blot of lysates of iPSC-derived bronchospheres performed to determine the amount and form of CFTR (mature, fully glycosylated="C-band", immature protein="B-band") present in each sample (as previously published[10]) (data not shown). The inventors discovered that only the G551D bronchospheres contain mature CFTR protein (C-band). After fixation and paraffin embedding, CFTR immunostaining and confocal microscopy was performed to determine the presence and cellular localization of CFTR protein. The inventors demonstrate that F508del and G542X bronchospheres have little to no detectable CFTR protein, whereas CFTR localized to the apical membrane of G551D bronchospheres (data not shown).

Determine the Level of CFTR Function and Response to a Panel of CFTR Correctors Using FIS of F508del, G542X and G551D iPSC-Derived Bronchospheres Using the HTS approach described herein, (robotic FIS assays), the inventors next assessed the level of CFTR function in bronchospheres from F508del, G52X and G551D iPSCs. The HTS FIS assay was utilized to test whether the different mechanisms of CFTR dysfunction caused by each mutation respond to a library of CFTR correctors (including VX-809, VX-661, VX-893), potentiators (including VX-770) and read-through agents (including G418, ataluren) (see FIG. 14C). Patients with G551D mutations respond significantly to the CFTR potentiator VX-770, and the inventors demonstrate that G551D iPSC-bronchospheres also respond to VX-770 (see FIG. 14C) as predicted. Accordingly, the inventors have demonstrated that the patterns of response of the iPSC-derived bronchiospheres respond as expected in the iPSC-platform, and therefore validate this HTS FIS assay as a method to identify novel compounds for the treatment of CF.

Example 9

The inventors have demonstrated herein a method for directed differentiation of pluripotent stem cells into functional airway epithelial cells via an NKX2-1+ progenitor intermediate in response to cyclical modulation of developmental signaling pathways. Using genetic mouse models to inform pathway screening during a narrow 4-day window post-lung specification, the inventors demonstrate that tight control of Wnt signaling is important, and that Wnt signaling is a potent and key regulator of proximodistal patterning in both human and mouse PSC-derived lung epithelium. The inventors in vitro discoverys significantly extend prior obvervatojs made in mice in vivo (Bellusci et al., 1997; Cardoso et al., 1997; Chen et al., 2010; 2007; Hashimoto et al., 2012; Hyatt et al., 2004; Mucenski et al., 2003; Sekine et al., 1999; Shu et al., 2005; Y. Wang et al., 2013; Weaver et al., 2000; 1999; Zemke et al., 2009; Zhou et al., 1996), where it was not known if such pathways applied to proximal differentiation of human cells, or iPSC-derived cells. Prior reports focused on mouse studies and reported on a requirement for Wnt signaling during the narrow developmental window of lung specification (Goss et al., 2009; Harris-Johnson et al., 2009) followed by alterations in Wnt signaling levels to regulate proximodistal patterning. It was also reported that Wnt inhibition in mice promotes increases in proximalization at the expense of distal lineages (Mucenski et al., 2003; Shu et al., 2005; Volckaert et al., 2013). In contrast, forced activation of Wnt signaling in mice was reported to maintain distal lung progenitor programs while suppressing proximalization(Hashimoto et al., 2012; Li et al., 2009). Furthermore, forced hyperactivation of canonical Wnt signaling during mouse lung development blocks club cell differentiation (Hashimoto et al., 2012) or activates aberrant gastrointestinal gene expression programs in the lung epithelium (Okubo and Hogan, 2004). Interestingly, Wnt activation or inactivation in post-natal proximalized mouse lung epithelia does not result in loss of patterning (Reynolds et al., 2008; Zemke et al., 2009) in the absence of injury, but has been correlated with airway epithelial dysregulation in adult human smokers (R. Wang et al., 2011), indicating that this pathway may have important alternative roles after development of airway lineage.

Similarly, it has been reported that developing human airway epithelia are patterned by oscillations in levels of canonical Wnt signaling (Zhang et al., 2012). Herein, the inventors demonstrate that although Wnt signaling is essential for specification of respiratory progenitors from hPSCs, withdrawal of Wnt post-specification promotes rapid emergence of the proximal airway program and abrogation of distal lung fate via a mechanism intrinsic to the NKX2-1+ epithelium. This latter discovery is critical, as previous genetic mouse models have emphasized that patterning and epithelial branching morphogenesis defects in the context of abnormal Wnt signaling. In contrast, the inventors model described herein enables interrogation of epithelial-specific effects of Wnt signaling distinct from defects in lung structure or branching.

Importantly, and in contrast to previously-described iPSC protocols using extended culture conditions to generate cell types of interest (Gotoh et al., 2014; Konishi et al., 2016), the rapidity and stage-specificity of Wnt-driven proximodistal airway patterning demonstrates that temporal oscillations in signaling pathway activation are a critical component of effective directed airway differentiation. Building on these findings, the inventors developed a "low-Mint" protocol presented herein for the derivation of airway organoids from purified NKX2-1+ lung epithelial progenitors. There are at least three key features of this approach that are unique. First the use of an NKX2-1$^{GFP}$ knock-in reporter has allowed the inventors to dissect lineage relationships, establishing that the proximal airway epithelia derive directly from an NKX2-1+ lung progenitor intermediate. Second, the ability to modulate Wnt signaling in these purified NKX2-1+ "epithelial only" derivatives allows testing of intrinsic pathway effects separated from the potentially confounding responses of mesenchymal or other NKX2-1- lineages that are frequently present in unsorted heterogeneous PSC experiments. Third, the rapid, patterned response of sorted human lung progenitors to withdrawal of Mint (augmented proximalization concordant with loss of distalization within 4 days) demonstrates that directed developmental patterning is occurring rather than the stochastic overgrowth of competing proximal lineages that can occur with prolonged culture periods.

Accordingly, the inventors have demonstrated a reproducible, rapid and consistent method for the production of an inexhaustible source of human proximal airway organoids. These luminal structures contain multiple airway epithelial lineages and express airway markers at levels comparable to the adult lung. As predicted by murine models, inhibition of Notch signaling in these organoids or subsequent 2D airliquid interface culture results in ciliogenesis in a subset of cells(You et al., 2002) (Firth et al., 2014; Konishi et al., 2016) and demonstrates that organoids grown from purified NKX2-1+ lung epithelial cells in the absence of Mint signaling (e.g., absence of CHIR, a "low-wnt" media or the presence of a Mint inhibitor) provides true proximalized airway progenitors that respond as predicted to developmental signaling cues.

Additionally, the inventors also demonstrate the engineering of clinically applicable patient-specific in vitro models of airway epithelial disease and epithelial function. Herein, the inventors demonstrate a cell sorting algorithm (e.g., FACS sorting cells that are CD47$^{hi}$/CD26−) for the isolation of iPSC-derived NKX2-1+ lung progenitors possessing airway organoid competence without the need to generate NKX2-1$^{GFP}$ knock-in reporters for each patient specific line to be studied. The inventors employ this sorting algorithm and the proximalization approach (e.g., a "low-wnt" media) to produce patient-specific airway epithelial organoids both before and after gene editing to correct the CFTR genetic lesion responsible for cystic fibrosis. These airway organoids allow for the first time in vitro forskolin stimulation assays to analyze CFTR function in lung epithelial cells, opening future avenues towards high-throughput drug screening in patient-specific airway cells.

Example 10

Cystic fibrosis (CF) is the most common genetic lung disease and second only to sickle cell anemia as a life-shortening, genetic disease. It is caused by mutations in the CFTR gene. CFTR is an anion channel, important in regulating electrolyte and water flow across mucus-producing epithelia most notably the lung, pancreas and intestine. There are almost 2,000 CFTR mutations described to date. Patients with Cystic fibrosis have variable disease severity. Determinants of this heterogeneity include the type of CFTR mutation and both genetic and environmental modifiers. The discovery of Ivacaftor for treating the subset of CF patients with a G551D mutation was a significant advance in the field. For most CF patients, including those with F508del, effective treatments are not yet available. Large scale, high-throughput screens of chemical compounds using Fischer rat thyroid (FRT) cells overexpressing CFTR mutants led to the identification of a number of CFTR modulators however this platform is a poor predictor of clinical efficacy in part because thyroid cells are phenotypically different from airway epithelium and this "off the shelf" cell line does not carry the genetic background of patients. Follow-up small scale preclinical studies validated the top candidate drugs using air-liquid interface (ALI) cultures of human bronchial epithelial (HBE) cells. However, HBEs are not ideal for moderate to high-throughput screening approaches for a number of reasons, including by not limited to; an invasive procedure is required to obtain these cells, the cell numbers are limiting, they represent only one tissue-type and they are not well suited to genetic engineering. Intestinal organoids can also be used as a cell-based platform for CF, however these cells are also not ideal for use as they (1) require invasive procedures to harvest them and (2) do not represent the key organ affected by the disease. Recent reports suggests a promising role for iPSC in the study of CF. iPSCs can be routinely and non-invasively generated from any patient. They contain an individual's unique genetic background given their proliferative capacity can be expanded in culture to provide an inexhaustible supply of cells and are suitable for gene-editing approaches.

As demonstrated herein, the inventors have developed protocols to generate airway epithelial organoids from iPSCs using a cell surface marker strategy(CD47hi/CD26lo) to sort lung progenitors and using media containing FGF2 and FGF10 induce a proximal, airway phenotype. The inventors have confirmed that these airway organoids express CFTR. The inventors have demonstrated that in response to forskolin, these organoids swell over the course of hours, and have demonstrated that the amount of swelling is dependent on functional CFTR expression. Using airway organoids from normal patients, patients with delF508 CF mutation and gene-corrected controls, the inventors demonstrated that normal or gene-corrected airway organoids swell significantly in response to forskolin but delF508 airway organoids swell minimally. The inventors have also demonstrated that this platform is amenable to a medium to high throughput approach to facilitate testing hundreds of compounds for the treatment of cystic fibrosis. In addition, the inventors have demonstrated that in response to CFTR modulators, there is a measurable difference in foskolin induced swelling. The inventors have tested forskolin induced swelling in non-lung organoids that express CFTR and confirm that the assay also works in non-lung organoids, in particular, in airway epithelial organoids or bronchospheres.

Patients with Cystic fibrosis (CF) have variable disease severity, complications and survival. CF is caused by mutations in the gene CFTR. Despite recent progress major hurdles for the community include identifying more potent corrector compounds and better pre-clinical models of an individual's response to CFTR modulators. A particularly pressing issue is how to identify the patients with rare and poorly characterized mutations who might respond to currently approved therapies. A scalable, patient-specific platform for personalized functional CFTR assessment in different CF-affected tissues would be a valuable tool to accelerate drug discovery and precision therapy. Accordingly, the technology disclosed herein uses human induced pluripotent stem cells (iPSCs) differentiated into airway organoids ("bronchospheres") as a model to measure an individuals CFTR function and measure response to drug treatment. iPSCs provide an inexhaustible source of cells to generate airway organoids in our directed differentiation protocol. The bronchospheres produced by the technology disclosed herein are composed of cell types of the airway epithelium and contain cells expressing CFTR. In response to CFTR activation using forskolin, bronchospheres with normal CFTR swell. This swelling is quantifiable and provides a read-out of CFTR function thus can be used to measure an individuals CFTR function at baseline, screen libraries of drug compounds to identify therapies that improve CFTR function and test combinations of drugs to identify the optimal combinations of CFTR modulators to restore CFTR function.

The technology disclosed herein can be used for personalized drug prediction for individuals with cystic fibrosis (CF), as well as for use in medium and/or high throughput drug screening to identify novel compounds and combinations for the treatment of CF. In particular, the technology disclosed herein can be used for screening iPSCs from multiple patients to identify patients with the same pattern of response to medications, as well as provide confirmation of successful restoration of CFTR function following gene-editing approaches. The technology disclosed herein can be used to screen the effect of drugs on CFTR function in multiple tissues produced from iPSCs, including, but not limited to, lung, pancreatic, intestine, biliary. The technology disclosed herein can also be used to screen and/or develop non pharmacological methods of CFTR restoration including siRNAs.

Advantages of the technology disclosed herein is that the iPSCs can be generated from any patient with only a blood draw and result in an inexhaustible supply of autologous cells. The protocol to differentiate iPSCs into airway organoids (also referred to herein as bronchospheres), and can be easily used to generate millions of airway organoids. Presently, the currently available gold-standard cell-based model of the CF airway are human bronchial epithelial cells (HBEs). In contrast to the present invention, the HBEs require an invasive procedure and are not amenable to high throughput approaches to measure CFTR function, and require researchers use a laborious, low-throughput technique (Ussing chamber) to measure the electrophysiological properties of HBE-derived epithelium. In contrast, the technology disclosed herein can produce a large number of organoids, and these organoids, coupled with the assay of forskolin-induced swelling of bronchospheres as described herein, to measure CFTR function will facilitate the screening of hundreds to thousands of drugs. The airway epithelial cells or bronchospheres described herein can by cryopreserved as single cells either in the iPSC state or as airway epithelial cells, and can be used in the assays or alternatively, gene modified to correct a CF genetic lesion and transplanted into a subject with a pulmonary disease, e.g., CF for the treatment of CF. Additionally, the $CD47^{hi}/CD26^{lo}$ sort strategy as described herein allows a standardization that overcomes the variability of current lung directed differentiation protocols and allows the comparison of cells from multiple individuals. In some embodiments, these airway organoids (bronchospheres) could be provided as cryopreserved cells with a protocol to thaw, expand and perform forskolin-induced swelling or pre-prepared tissue culture plates containing airway organoids.

The technology described herein is unique in that it provides a platform technology for using induced pluripotent stem cells (iPSCs) and differentiates them into cells of the main organ affected by CF, the lungs. Accordingly, the technology described herein provides lung organoids from iPSCs that (1) represent an individual's unique genetic background, (2) the iPSCs can proliferate to provide an inexhaustible supply of cells, and (3) iPSCs can be differentiated in almost any cell type. The technology described herein overcomes the heterogeneity of directed differentiation protocols to improve reproducibility of the forskolin induced swelling assay and allow comparison between iPSCs from multiple individuals. The technology described herein is also suitable for high throughput screening approaches more so than any current existing cell-based model of human lung.

In some embodiments, the forskolin-induced swelling assay described herein can be used to measure CFTR function in iPSC-derived lung epithelial organoids and non-lung endodermal organoids. Thus, the technology described herein for assaying and determining CFTR function has many applications including baseline assessment of CFTR function, screening of drugs libraries to identify compounds that rescue CFTR function, predicting an individual's drug responsiveness, confirming functional restoration of CFTR function after gene-correction of CFTR mutations, comparing tissue-specific effects of CFTR mutations.

In summary, the inventors have demonstrated herein a method for the rapid generation of airway organoids by stage-dependent modulation of Wnt signaling and proof-of-principle for the utility of these organoids in lung disease modeling. Thus, the inventors have demonstrated a human in vitro PSC-based model system able to reveal basic mechanisms regulating lung developmental cell fate decisions and model airway epithelial diseases with potential clinical benefit for precision drug screening and regenerative medicine.

REFERENCES

The references cited herein and throughout the specification are incorporated herein in their entirety by reference.

Bellusci, S., Grindley, J., Emoto, H., Itoh, N., Hogan, B., 1997. Fibroblast Growth Factor 10(FGF10) and branching morphogenesis in the embryonic mouse lung 124, 4867-4878.

Berge, ten, D., Koole, W., Fuerer, C., Fish, M., Eroglu, E., Nusse, R., 2008. Wnt signaling mediates self-organization and axis formation in embryoid bodies. Cell Stem Cell 3, 508-518. doi:10.1016/j.stem.2008.09.013

Bilodeau, M., Shojaie, S., Ackerley, C., Post, M., Rossant, J., 2014. Identification of a Proximal Progenitor Population from Murine Fetal Lungs with Clonogenic and Multilineage Differentiation Potential. Stem Cell Reports 1-16. doi:10.1016/j.stemcr.2014.07.010

Cardoso, W. V., Itoh, A., Nogawa, H., Mason, I., Brody, J. S., 1997. FGF-1 and FGF-7 induce distinct patterns of growth and differentiation in embryonic lung epithelium. Dev. Dyn. 208, 398-405.

Chen, F., Cao, Y., Qian, J., Shao, F., Niederreither, K., Cardoso, W. V., 2010. A retinoic acid-dependent network in the foregut controls formation of the mouse lung primordium. J. Clin. Invest. 120, 2040-2048. doi:10.1172/JCI40253

Chen, F., Desai, T. J., Qian, J., Niederreither, K., Lü, J., Cardoso, W. V., 2007. Inhibition of Tgf beta signaling by endogenous retinoic acid is essential for primary lung bud induction. 134, 2969-2979. doi:10.1242/dev.006221

Crane, A. M., Kramer, P., Bui, J. H., Chung, W. J., Li, X. S., Gonzalez-Garay, M. L., Hawkins, F., Liao, W., Mora, D., Choi, S., Wang, J., Sun, H. C., Paschon, D. E., Guschin, D. Y., Gregory, P. D., Kotton, D. N., Holmes, M. C., Sorscher, E. J., Davis, B. R., 2015. Targeted correction and restored function of the CFTR gene in cystic fibrosis induced pluripotent stem cells. Stem Cell Reports 4, 569-577. doi:10.1016/j.stemcr.2015.02.005

De Langhe, S. P., Sala, F. G., Del Moral, P.-M., Fairbanks, T. J., Yamada, K. M., Warburton, D., Burns, R. C., Bellusci, S., 2005. Dickkopf-1 (DKK1) reveals that fibronectin is a major target of Wnt signaling in branching morphogenesis of the mouse embryonic lung. Dev. Biol. 277, 316-331. doi:10.1016/j.ydbio.2004.09.023

Dekkers, J. F., Wiegerinck, C. L., de Jonge, H. R., Bronsveld, I., Janssens, H. M., de Winter-de Groot, K. M., Brandsma, A. M., de Jong, N. W. M., Bijvelds, M. J. C., Scholte, B. J., Nieuwenhuis, E. E. S., van den Brink, S., van der Ent, C. K., Middendorp, S., Clevers, H., Beekman, J. M., 2013. A functional CFTR assay using primary cystic fibrosis intestinal organoids. Nat Med 19, 939-945. doi:10.1038/nm.3201

Dye, B. R., Hill, D. R., Ferguson, M., Tsai, Y. H., Nagy, M. S., 2015. In vitro generation of human pluripotent stem cell derived lung organoids. Elife. doi:10.7554/eLife.05098.001

Firth, A. L., Dargitz, C. T., Qualls, S. J., Menon, T., Wright, R., Singer, O., Gage, F. H., Khanna, A., Verma, I. M., 2014. Generation of multiciliated cells in functional airway epithelia from human induced pluripotent stem cells. Proceedings of the National Academy of Sciences 201403470. doi:10.1073/pnas.1403470111

Fuerer, C., Nusse, R., 2010. Lentiviral Vectors to Probe and Manipulate the Wnt Signaling Pathway. PLoS ONE 5, 1-7. doi:10.1371/journal.pone.0009370.g001

Goss, A. M., Tian, Y., Tsukiyama, T., Cohen, E. D., Zhou, D., Lu, M. M., Yamaguchi, T. P., Morrisey, E. E., 2009. Wnt2/2b and beta-catenin signaling are necessary and sufficient to specify lung progenitors in the foregut. Dev. Cell 17, 290-298. doi:10.1016/j.devcel.2009.06.005

Gotoh, S., Ito, I., Nagasaki, T., Yamamoto, Y., Konishi, S., Korogi, Y., Matsumoto, H., Muro, S., Hirai, T., Funato, M., Mae, S.-I., Toyoda, T., Sato-Otsubo, A., Ogawa, S., Osafune, K., Mishima, M., 2014. Generation of Alveolar Epithelial Spheroids via Isolated Progenitor Cells from Human Pluripotent Stem Cells. Stem Cell Reports 3, 394-403. doi:10.1016/j.stemcr.2014.07.005

Green, M. D., Chen, A., Nostro, M.-C., d'Souza, S. L., Schaniel, C., Lemischka, I. R., Gouon-Evans, V., Keller, G., Snoeck, H.-W., 2011. Nat Biotechnol 2011 Green-Generation of anterior foregut endoderm. Nature Biotechnology 29, 267-272. doi:10.1038/nbt.1788

Harris-Johnson, K. S., Domyan, E. T., Vezina, C. M., Sun, X., 2009. beta-Catenin promotes respiratory progenitor identity in mouse foregut. Proceedings of the National Academy of Sciences 106, 16287-16292. doi:10.1073/pnas.0902274106

Hashimoto, S., Chen, H., Que, J., Brockway, B. L., Drake, J. A., Snyder, J. C., Randell, S. H., Stripp, B. R., 2012. β-Catenin-SOX2 signaling regulates the fate of developing airway epithelium. J. Cell. Sci. 125, 932-942. doi: 10.1242/jcs.092734

Hawkins, F., Kramer, P., Jacob, A., Driver, I., Thomas, D. C., McCauley, K. B., Skvir, N., Crane, A. M., Kurmann, A. A., Hollenberg, A. N., Nguyen, S., Wong, B. G., Khalil, A. S., Huang, S. X. L., Guttentag, S., Rock, J. R., Shannon, J. M., Davis, B. R., Kotton, D. N., 2017. Prospective isolation of NKX2-1+/CD47+ human lung progenitors derived from pluripotent stem cells. J. Clin. Invest. in press.

Huang, S. X. L., Green, M. D., de Carvalho, A. T., Mumau, M., Chen, Y.-W., d'Souza, S. L., Snoeck, H.-W., 2015. The in vitro generation of lung and airway progenitor cells from human pluripotent stem cells. Nature Protocols 10, 413-425. doi:10.1038/nprot.2015.023

Huang, S. X. L., Islam, M. N., O'Neill, J., Hu, Z., Yang, Y.-G., Chen, Y.-W., Mumau, M., Green, M. D., Vunjak-Novakovic, G., Bhattacharya, J., Snoeck, H.-W., 2013. efficient generation of lung and airway epithelial cells from human pluripotent stem cells. Nature Biotechnology 32, 84-91. doi:10.1038/nbt.2754

Hyatt, B. A., Shangguan, X., Shannon, J. M., 2004. FGF-10 induces SP-C and Bmp4 and regulates proximal-distal patterning in embryonic tracheal epithelium. Am. J. Physiol. Lung Cell Mol. Physiol. 287, L1116-26. doi: 10.1152/ajplung.00033.2004

Ikeda, K., Clark, J. C., Shaw-White, J. R., Stahlman, M. T., Boutell, C. J., Whitsett, J. A., 1995. Gene structure and expression of human thyroid transcription factor-1 in respiratory epithelial cells. J. Biol. Chem. 270, 8108-8114.

Kim, B. R., Van de Laar, E., Cabanero, M., Tarumi, S., Hasenoeder, S., Wang, D., Virtanen, C., Suzuki, T., Bandarchi, B., Sakashita, S., Pham, N. A., Lee, S., Keshavjee, S., Waddell, T. K., Tsao, M.-S., Moghal, N., 2016. SOX2 and PI3K Cooperate to Induce and Stabilize a Squamous-Committed Stem Cell Injury State during Lung Squamous Cell Carcinoma Pathogenesis. PLoS Biol. 14, e1002581. doi: 10.1371/journal.pbio.1002581

Konishi, S., Gotoh, S., Tateishi, K., Yamamoto, Y., Korogi, Y., Nagasaki, T., Matsumoto, H., Muro, S., Hirai, T., Ito, I., Tsukita, S., Mishima, M., 2016. Directed Induction of Functional Multi-ciliated Cells in Proximal Airway Epithelial Spheroids from Human Pluripotent Stem Cells. Stem Cell Reports 6, 18-25. doi:10.1016/j.stemcr.2015.11.010

Kurmann, A. A., Serra, M., Hawkins, F., Rankin, S. A., Mori, M., Astapova, I., Ullas, S., Lin, S., Bilodeau, M., Rossant, J., Jean, J. C., Ikonomou, L., Deterding, R. R., Shannon, J. M., Zorn, A. M., Hollenberg, A. N., Kotton, D. N., 2015. Regeneration of Thyroid Function by Transplantation of Differentiated Pluripotent Stem Cells. Stem Cell 17, 527-542. doi:10.1016/j.stem.2015.09.004

Li, C., Li, A., Li, M., Xing, Y., Chen, H., Hu, L., Tiozzo, C., Anderson, S., Taketo, M. M., Minoo, P., 2009. Stabilized beta-catenin in lung epithelial cells changes cell fate and leads to tracheal and bronchial polyposis. Dev. Biol. 334, 97-108. doi:10.1016/j.ydbio.2009.07.021

Liu, Y., Hogan, B. L. M., 2002. Differential gene expression in the distal tip endoderm of the embryonic mouse lung. Gene Expression Patterns 2, 229-233. doi:10.1016/S1567-133X(02)00057-1

Liu, Y., Jiang, H., Crawford, H. C., Hogan, B. L. M., 2003. Role for ETS domain transcription factors Pea3/Erm M., Rowe, S., Engelhardt, J. F., Hsu, Y.-C., Rajagopal, J., 2016. Dual SMAD Signaling Inhibition Enables Long-Term Expansion of Diverse Epithelial Basal Cells. Cell Stem Cell 19, 217-231. doi:10.1016/j.stem.2016.05.012

Mou, H., Zhao, R., Sherwood, R., Ahfeldt, T., Lapey, A., Wain, J., Sicilian, L., Izvolsky, K., Musunuru, K., Cowan, C., Rajagopal, J., 2012. Generation of multipotent lung and airway progenitors from mouse ESCs and patient-specific cystic fibrosis iPSCs. Cell Stem Cell 10, 385-397. doi:10.1016/j.stem.2012.01.018

Mucenski, M. L., Wert, S. E., Nation, J. M., Loudy, D. E., Huelsken, J., Birchmeier, W., Morrisey, E. E., Whitsett, J. A., 2003. beta-Catenin is required for specification of proximal/distal cell fate during lung morphogenesis. J. Biol. Chem. 278, 40231-40238. doi:10.1074/jbc.M305892200

Okubo, T., Hogan, B. L. M., 2004. Hyperactive Wnt signaling changes the developmental potential of embryonic lung endoderm. J. Biol. 3, 11. doi:10.1186/jbiol3

Phelps, D. S., Floros, J., 1988. Localization of surfactant protein synthesis in human lung by in situ hybridization. Am. Rev. Respir. Dis. 137, 939-942. doi:10.1164/ajrccm/137.4.939

Ramasamy, S. K., Mailleux, A. A., Gupte, V. V., Mata, F., Sala, F. G., Veltmaat, J. M., Del Moral, P. M., De Langhe, S., Parsa, S., Kelly, L. K., Kelly, R., Shia, W., Keshet, E., Minoo, P., Warburton, D., Bellusci, S., 2007. Fgf10 dosage is critical for the amplification of epithelial cell progenitors and for the formation of multiple mesenchymal lineages during lung development. Dev. Biol. 307, 237-247. doi: 10.1016/j.ydbio.2007.04.033

Rawlins, E. L., Clark, C. P., Xue, Y., Hogan, B. L. M., 2009. The Id2+ distal tip lung epithelium contains individual multipotent embryonic progenitor cells. Development 136, 3741-3745. doi:10.1242/dev.037317

Reynolds, S. D., Zemke, A. C., Giangreco, A., 2008. Conditional Stabilization of β-Catenin Expands the Pool of Lung Stem Cells. Stem Cells. doi:10.1634/stemcells.2008-0053

Rock, J. R., Onaitis, M. W., Rawlins, E. L., Lu, Y., Clark, C. P., Xue, Y., Randell, S. H., Hogan, B. L. M., 2009. Basal cells as stem cells of the mouse trachea and human airway epithelium. Proceedings of the National Academy of Sciences 106, 12771-12775. doi:10.1073/pnas.0906850106

Sekine, K., Ohuchi, H., Fujiwara, M., Yamasaki, M., Yoshizawa, T., Sato, T., Yagishita, N., Matsui, D., Koga, Y., Itoh, N., Kato, S., 1999. Fgf10 is essential for limb and lung formation. Nat. Genet. 21, 138-141. doi: 10.1038/5096

Shu, W., Guttentag, S., Wang, Z., Andl, T., Ballard, P., Lu, M. M., Piccolo, S., Birchmeier, W., Whitsett, J. A., Millar, S. E., Morrisey, E. E., 2005. Wnt/beta-catenin signaling acts upstream of N-myc, BMP4, and FGF signaling to regulate proximal-distal patterning in the lung. Dev. Biol. 283, 226-239. doi: 10.1016/j.ydbio.2005.04.014

Somers, A., Jean, J.-C., Sommer, C. A., Omari, A., Ford, C. C., Mills, J. A., Ying, L., Sommer, A. G., Jean, J. M., Smith, B. W., Lafyatis, R., Demierre, M.-F., Weiss, D. J., French, D. L., Gadue, P., Murphy, G. J., Mostoslaysky, G., Kotton, D. N., 2010. Generation of Transgene-Free Lung Disease-Specific Human Induced Pluripotent Stem Cells Using a Single Excisable Lentiviral Stem Cell Cassette. STEM CELLS 28, 1728-1740. doi:10.1002/stem.495

Tsao, P. N., Vasconcelos, M., Izvolsky, K. I., Qian, J., Lu, J., Cardoso, W. V., 2009. Notch signaling controls the balance of ciliated and secretory cell fates in developing airways. 136, 2297-2307. doi:10.1242/dev.034884

Volckaert, T., Campbell, A., Dill, E., Li, C., Minoo, P., De Langhe, S., 2013. Localized Fgf10 expression is not required for lung branching morphogenesis but prevents differentiation of epithelial progenitors. Development 140, 3731-3742. doi:10.1242/dev.096560

Wang, R., Ahmed, J., Wang, G., Hassan, I., Strulovici-Barel, Y., Hackett, N. R., Crystal, R. G., 2011. Downregulation of the canonical Wnt β-catenin pathway in the airway epithelium of healthy smokers and smokers with COPD. PLoS ONE 6, e14793. doi:10.1371/journal.pone.0014793

Weaver, M., Dunn, N. R., Hogan, B. L., 2000. Bmp4 and Fgf10 play opposing roles during lung bud morphogenesis. 127, 2695-2704.

Weaver, M., Yingling, J. M., Dunn, N. R., Bellusci, S., Hogan, B. L., 1999. Bmp signaling regulates proximal-distal differentiation of endoderm in mouse lung development. Development 126, 4005-4015.

Wilson, A. A., Murphy, G. J., Hamakawa, H., Kwok, L. W., Srinivasan, S., Hovav, A.-H., Mulligan, R. C., Amar, S., Suki, B., Kotton, D. N., 2010. Amelioration of emphysema in mice through lentiviral transduction of long-lived pulmonary alveolar macrophages. J. Clin. Invest. 120, 379-389. doi:10.1172/JCI36666

Wong, A. P., Bear, C. E., Chin, S., Pasceri, P., Thompson, T. O., Huan, L.-J., Ratjen, F., Ellis, J., Rossant, J., 2012. Directed differentiation of human pluripotent stem cells into mature airway epithelia expressing functional CFTR protein. Nature Biotechnology 30, 876-882. doi:10.1038/nbt.2328

Xu, Y., Mizuno, T., Sridharan, A., Du, Y., Guo, M., Tang, J., Wikenheiser-Brokamp, K. A., Perl, A.-K. T., Funari, V. A., Gokey, J. J., Stripp, B. R., Whitsett, J. A., 2016. Single-cell RNA sequencing identifies diverse roles of epithelial cells in idiopathic pulmonary fibrosis. JCI Insight 1, e90558. doi:10.1172/jci.insight.90558

You, Y., Richer, E. J., Huang, T., Brody, S. L., 2002. Growth and differentiation of mouse tracheal epithelial cells: selection of a proliferative population. Am. J. Physiol. Lung Cell Mol. Physiol. 283, L1315-21. doi:10.1152/ajplung.00169.2002

Zemke, A. C., Teisanu, R. M., Giangreco, A., Drake, J. A., Brockway, B. L., Reynolds, S. D., Stripp, B. R., 2009. beta-Catenin is not necessary for maintenance or repair of the bronchiolar epithelium. Am J Respir Cell Mol Biol 41, 535-543. doi:10.1165/rcmb.2008-04070C

REFERENCES NUMBERED IN EXAMPLE 6

1. Huang, S. X. L. et al. efficient generation of lung and airway epithelial cells from human pluripotent stem cells. *Nature Biotechnology* 32, 84-91 (2013).
2. Huang, S. X. L. et al. The in vitro generation of lung and airway progenitor cells from human pluripotent stem cells. *Nature Protocols* 10, 413-425 (2015).
3. Liu, Y. & Hogan, B. L. M. Differential gene expression in the distal tip endoderm of the embryonic mouse lung. *Gene Expression Patterns* 2, 229-233 (2002).
4. Que, J., Luo, X., Schwartz, R. J. & Hogan, B. L. M. Multiple roles for Sox2 in the developing and adult mouse trachea. *Development* 136, 1899-1907 (2009).
5. Harris-Johnson, K. S., Domyan, E. T., Vezina, C. M. & Sun, X. beta-Catenin promotes respiratory progenitor identity in mouse foregut. *Proceedings of the National Academy of Sciences* 106, 16287-16292 (2009).
6. Goss, A. M. et al. Wnt2/2b and beta-catenin signaling are necessary and sufficient to specify lung progenitors in the foregut. *Dev. Cell* 17, 290-298 (2009).
7. Berge, ten, D. et al. Wnt signaling mediates self-organization and axis formation in embryoid bodies. *Cell Stem Cell* 3, 508-518 (2008).
8. Fuerer, C. & Nusse, R. Lentiviral Vectors to Probe and Manipulate the Wnt Signaling Pathway. *PLoS ONE* 5, 1-7 (2010).
9. Liu, Y., Jiang, H., Crawford, H. C. & Hogan, B. L. M. Role for ETS domain transcription factors Pea3/Erm in mouse lung development. *Dev. Biol.* 261, 10-24 (2003).
10. Weaver, M., Yingling, J. M., Dunn, N. R., Bellusci, S. & Hogan, B. L. Bmp signaling regulates proximal-distal differentiation of endoderm in mouse lung development. *Development* 126, 4005-4015 (1999).
11. Shu, W. et al. Wnt/beta-catenin signaling acts upstream of N-myc, BMP4, and FGF signaling to regulate proximal-distal patterning in the lung. *Dev. Biol.* 283, 226-239 (2005).
12. Wang, Y. et al. Development and regeneration of Sox2+ endoderm progenitors are regulated by a Hdac1/2-Bmp4/Rb1 regulatory pathway. *Dev. Cell* 24, 345-358 (2013).
13. Chen, F. et al. Inhibition of Tgf beta signaling by endogenous retinoic acid is essential for primary lung bud induction. *Development* 134, 2969-2979 (2007).
14. Zhou, L., Dey, C. R., Wert, S. E. & Whitsett, J. A. Arrested lung morphogenesis in transgenic mice bearing an SP-C-TGF-beta 1 chimeric gene. *Dev. Biol.* 175, 227-238 (1996).
15. Hyatt, B. A., Shangguan, X. & Shannon, J. M. FGF-10 induces SP-C and Bmp4 and regulates proximal-distal patterning in embryonic tracheal epithelium. *Am. J. Physiol. Lung Cell Mol. Physiol.* 287, L1116-26 (2004).
16. Weaver, M., Dunn, N. R. & Hogan, B. L. Bmp4 and Fgf10 play opposing roles during lung bud morphogenesis. *Development* 127, 2695-2704 (2000).
17. Sekine, K. et al. Fgf10 is essential for limb and lung formation. *Nat. Genet.* 21, 138-141 (1999).
18. Bellusci, S., Grindley, J., Emoto, H., Itoh, N. & Hogan, B. Fibroblast Growth Factor 10(FGF10) and branching morphogenesis in the embryonic mouse lung. *Development* 124, 4867-4878 (1997).
19. Cardoso, W. V., Itoh, A., Nogawa, H., Mason, I. & Brody, J. S. FGF-1 and FGF-7 induce distinct patterns of growth and differentiation in embryonic lung epithelium. *Dev. Dyn.* 208, 398-405 (1997).

REFERENCES NUMBERED IN EXAMPLE 10

1. CD47 identifies precusor cells of the lung epithelium derived human pluripotent stem cells
2. Efficient derivation of functional human airway epithelium from pluripotent stem cells via temporal regulation of Wnt signaling, Cell Stem Cell 2017, in press
3. GENERATION OF AIRWAY EPITHELIAL ORGANOIDS FROM HUMAN PLURIPOTENT STEM CELLS U.S. Provisional Application No. 62/443,901
4. Firth, A. L. et al. Generation of multiciliated cells in functional airway epithelia from human induced pluripotent stem cells. Proceedings of the National Academy of Sciences 201403470 (2014). doi:10.1073/pnas.1403470111
5. Dekkers, J. F. et al. A functional CFTR assay using primary cystic fibrosis intestinal organoids. Nat. Med. 19, 939-945 (2013)
6. Wong, A. P. et al. Directed differentiation of human pluripotent stem cells into mature airway epithelia expressing functional CFTR protein. Nat. Biotechnol. 30, 876-882 (2012).
7. Crane, Ana M., et al. "Targeted correction and restored function of the CFTR gene in cystic fibrosis induced pluripotent stem cells." Stem cell reports 4.4 (2015): 569-577.
8. Longmire, Tyler A., et al. "Efficient derivation of purified lung and thyroid progenitors from embryonic stem cells." Cell stem cell 10.4 (2012): 398-411.

The invention claimed is:

1. A method for producing airway epithelial organoids comprising at least 70% airway epithelial NKX2-1$^+$/SOX2$^+$ cells, NKX2-1$^+$/P63$^+$ cells or NKX2-1$^+$/P63$^+$/K5 cells, the method consisting essentially of:
  (i) obtaining a population of NKX2-1 lung epithelial progenitors, wherein the population of NKX2-1 lung epithelial progenitors express makers NKX2-1, CD47 and CD26, wherein the expression of CD47 is at higher level as compared to the level of expression of CD26 (NKX2-1$^+$, CD47$^{hi}$ and CD26$^{low}$), wherein the NKX2-1+ lung epithelial progenitors are produced using a high wnt media, or in the presence of a Wnt activator that results high levels of Wnt signaling activity, and
  (ii) culturing the population of NKX2-1 lung epithelial progenitors in a low-Wnt media that results in decreased Wnt signaling activity in NKX2-1 lung epithelial progenitors, wherein the NKX2-1 lung epithelial progenitors are cultured for a sufficient amount of time to direct their differentiation along a proximal epithelial differentiation pathway rather than along a distal pathway, to generate airway epithelial organoids comprising airway epithelial cells having proximal airway markers selected from any of NKX2-1$^+$/SOX2$^+$, NKX2-1$^+$/P63$^+$ or NKX2-1$^+$/P63+/K5.

2. The method of claim 1, wherein the airway epithelial organoids further comprise one or both of:
  a. cells that also express at least one of the proximal markers selected from the group consisting of: Secretoglobin Family 3A Member 2 (SCGB3A2)+, Tumor Protein 63 (TP63)+, Mucin 5AC (MUC5AC)+ and Secretoglobin Family 1A Member 1 (Scgb1a1)+;
  b. cells that do not express the distal markers selected from the group consisting of: Surfactant Protein C (SFTPC), Sex Determining Region Y-Box 9 (SOX9).

3. The method of claim 1, wherein low-Wnt media that results in decreased Wnt signaling activity comprises:
  a. Fibroblast Growth Factor 2 (FGF2) and FGF10, and/or
  b. does not comprise a Wnt activator or comprises a wnt inhibitory agent.

4. The method of claim 1, wherein the population of NKX2-1 lung epithelial progenitors are differentiated from a population of human induced pluripotent stem cell (iPSC) or human embryonic stem cells (ESCs).

5. The method of claim 4, wherein the human iPSC are derived from a subject with a pulmonary disease or has cystic fibrosis.

6. The method of claim 3, wherein the wnt inhibitory agent is withdrawal of a Wnt activator or is an inhibitory agent which inhibits Wnt or Wnt3 selected from any of
  a. Wnt ligand secretion mediator (Wls/Evi), Frizzled, dishevelled, Low-Density Lipoprotein Receptor-Related Protein (LRP)-5, LRP-6, "division abnormally delayed" (Dally), Dally-like, Prader-Willi/Angelman region-1 (PAR1), β-catenin, transcription factor (TCF), Lymphoid Enhancer Binding Factor 1 (lef-1) or dishevelled binding antagonist of beta catenin 1 (DACT1/Frodo);
  b. a RNAi agent which inhibits the RNA transcript of Wls/Evi;
  c. SEQ ID NO:1 or SEQ ID NO:2;
  d. Dickkopf-1 (DKK1), WNT Inhibitory Factor 1 (WIF-1), cerberus, secreted frizzled-related proteins (sFRP), sFRP-1, sFRP-2, collagen 18 (collagen XVIII), endostatin, carboxypeptidase Z, receptor tyrosine kinase, corin, dish large tumor suppressor protein (Dlg), Dapper, pertussis toxin, naked, Frizzled (Frz)-related proteins or Low Density Lipoprotein Receptor-Related Protein (LRP) lacking the intracellular domain;
  e. an inhibitor of β-catenin is selected from the group consisting of; protein phosphatase 2A (PP2A), chibby, promtin 52, Nemo/LNK kinase, MHG homobox factors, XSox17, High Mobility Group Box Transcription Factor 1 (HBP1), Adenomatous Polyposis Coli (APC), Axin, disabled-2 (dab-2) and gruncho (grg);

f. increases the activity and/or expression of Glycogen Synthase Kinase 3 (GSK-3) and/or GSK3β or is a peptide of GSK3β;

g. an agent which activates the Protein Kinase B (PKB) pathway or wortannin; or h. a peptide of DKK1.

7. The method of claim 1, wherein the population of NKX2-1 lung epithelial progenitors are differentiated from a population of iPSCs obtained from a subject with cystic fibrosis, and where the population of NKX2-1 lung epithelial progenitors are genetically modified to correct a Cystic Fibrosis Transmembrane Conductance Regulator (CTFR) genetic lesion responsible for the cystic fibrosis in the subject.

8. The method of claim 3, wherein the Wnt activator is CHIR99021 or 6-bromoindirubin-3'-oxime (BIO), or both.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cacaaatcct ttctacagta t                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggttaccgt gatgatatg                                                 19

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Glu Ala Pro Pro Ala Pro Pro Gln Ser Pro
1               5                   10

<210> SEQ ID NO 4
<211> LENGTH: 2791
<212> TYPE: DNA
<213> ORGANISM: Mus musculus

<400> SEQUENCE: 4
agagggccca gcgccactgc agccgcgcca cctcccaggg ccgggccagc ccaggcgtcc     60
gcgctctcgg ggtggactcc ccccgctgcg cgctcaagcc ggcgatggct cctctcggat    120
acctcttagt gctctgcagc ctgaagcagg ctctgggcag ctacccgatc tggtggtcct    180
tggctgtggg acccccagtac tcctctctga gcactcagcc cattctctgt gccagcatcc    240
caggcctggt accgaagcag ctgcgcttct gcaggaacta cgtggagatc atgcccagcg    300
tggctgaggg tgtcaaagcg ggcatccagg agtgccagca ccagttccga ggccggcgtt    360
ggaactgcac caccgtcagc aacagcctgg ccatctttgg ccctgttctg gacaaagcca    420
cccgggagtc agcctttgtc catgccatcg cctccgctgg agtagctttc gcagtgacac    480
gctcctgtgc agagggatca gctgctatct gtgggtgcag cagccgcctc cagggctccc    540
caggcgaggg ctggaagtgg ggcggctgta gtgaggacat tgaatttgga ggaatggtct    600
ctcgggagtt tgccgatgcc agggagaacc ggccggatgc ccgctctgcc atgaaccgtc    660
acaacaatga ggctgggcgc caggccatcg ccagtcacat gcacctcaag tgcaaatgcc    720
acgggctatc tggcagctgt gaagtgaaga cctgctggtg gtcgcagccg gacttccgca    780
ccatcgggga tttcctcaag gacaagtatg acagtgcctc ggagatggtg gtagagaaac    840
accgagagtc tcgtggctgg gtggagaccc tgaggccacg ttacacgtac ttcaaggtgc    900

-continued

```
cgacagaacg cgacctggtc tactacgagg cctcacccaa cttctgcgaa cctaaccccg    960
aaaccggctc cttcgggacg cgtgaccgca cctgcaatgt gagctcgcat ggcatagatg   1020
ggtgcgacct gttgtgctgc gggcgcgggc ataacgcgcg cactgagcga cggagggaga   1080
aatgccactg tgttttccat tggtgctgct acgtcagctg ccaggagtgc acacgtgtct   1140
atgacgtgca cacctgcaag taggagagct cctaacacgg gagcagggtt cattccgagg   1200
ggcaaggttc ctacctgggg gcggggttcc tacttggagg ggtctcttac ttggggactc   1260
ggttcttact tgagggcgga gatcctacct gtgagggtct catacctaag gacccggttt   1320
ctgccttcag cctgggctcc tatttgggat ctgggttcct ttttagggga gaagctcctg   1380
tctgggatac gggtttctgc ccgagggtgg ggctccactt ggggatggaa ttccaatttg   1440
ggccggaagt cctacctcaa tggcttggac tcctctcttg acccgacagg gctcaaatgg   1500
agacaggtaa gctactccct caactaggtg gggttcgtgc ggatgggtgg gaggggagag   1560
attagggtcc ctcctcccag aggcactgct ctatctagat acatgagagg gtgcttcagg   1620
gtgggcccta tttgggcttg aggatcccgt ggggcgggg cttcaccccg actgggtgga   1680
acttttggag acccccttcc actggggcaa ggcttcactg aagactcatg ggatggagct   1740
ccacggaagg aggagttcct gagcgagcct gggctctgag caggccatcc agctcccatc   1800
tggccccttt ccagtcctgg tgtaaggttc aacctgcaag cctcatctgc gcagagcagg   1860
atctcctggc agaatgaggc atggagaaga actcaggggt gataccaaga cctaacaaac   1920
cccgtgcctg ggtacctctt ttaaagctct gcaccccttc ttcaagggct ttcctagtct   1980
ccttggcaga gctttcctga ggaagatttg cagtccccca gagttcaagt gaacacccat   2040
agaacagaac agactctatc ctgagtagag agggttctct aggaatctct atggggactg   2100
ctaggaagga tcctgggcat gacagcctcg tatgatagcc tgcatccgct ctgacactta   2160
atactcagat ctcccgggaa acccagctca tccggtccgt gatgtccatg ccccaaaatgc   2220 ctcagagatg ttgcctcact ttgagttgta tgaacttcgg agacatgggg acacagtcaa   2280
gccgcagagc cagggttgtt tcaggaccca tctgattccc cagagcctgc tgttgaggca   2340
atggtcacca gatccgttgg ccaccaccct gtcccgagct tctctagtgt ctgtctggcc   2400
tggaagtgag gtgctacata cagcccatct gccacaagag cttcctgatt ggtaccactg   2460
tgaaccgtcc ctccccctc cagacagggg agggatgtg gccatacagg agtgtgcctg   2520
gagagcgcgg aaagaggaag agaggctgca cacgcgtggt gactgactgt cttctgcctg   2580
gaactttgcg ttcgcgcttg taactttatt ttcaatgctg ctatatccac ccaccactgg   2640
atttagacaa aagtgatttt ctttttttt ttttcttttc tttctatgaa agaaattatt   2700
ttagtttata gtatgtttgt ttcaaataat ggggaaagta aaagagaga aaaaaaaaa   2760 aaaaaaaaa aaaaaaaaa aaaaaaaaa a                                    2791
```

<210> SEQ ID NO 5
<211> LENGTH: 3385
<212> TYPE: DNA
<213> ORGANISM: Homo sapiens

<400> SEQUENCE: 5

```
tgctccgcgc tgggctcggg aggggggcgg ctgcgggtgg aggtgcgctt ctgacaagcc     60
cgaaagtcat ttccaatctc aagtggactt tgttccaact attggggggcg tcgttccccc   120 tcttcatggt cgcgggcaaa cttcctcctc ggcgcctctt ctaatggagc cccacctgct   180
```

```
cgggctgctc ctcggcctcc tgctcggtgg caccagggtc ctcgctggct acccaatttg    240
gtggtccctg gccctgggcc agcagtacac atctctgggc tcacagcccc tgctctgcgg    300
ctccatccca ggcctggtcc ccaagcaact gcgcttctgc cgcaattaca tcgagatcat    360
gcccagcgtg gccgagggcg tgaagctggg catccaggag tgccagcacc agttccgggg    420
ccgccgctgg aactgcacca ccatagatga cagcctggcc atctttgggc ccgtcctcga    480
caaagccacc cgcgagtcgg ccttcgttca cgccatcgcc tcggccggcg tggccttcgc    540
cgtcacccgc tcctgcgccg agggcacctc caccatttgc ggctgtgact cgcatcataa    600
ggggccgcct ggcgaaggct ggaagtgggg cggctgcagc gaggacgctg acttcggcgt    660
gttagtgtcc agggagttcg cggatgcgcg cgagaacagg ccggacgcgc gctcggccat    720
gaacaagcac aacaacgagg cgggccgcac gactatcctg gaccacatgc acctcaaatg    780
caagtgccac gggctgtcgg gcagctgtga ggtgaagacc tgctggtggg cgcagcctga    840
cttccgtgcc atcggtgact cctcaagga caagtatgac agcgcctcgg agatggtagt    900
agagaagcac cgtgagtccc gaggctgggt ggagaccctc cgggcaagt actcgctctt    960 caagccaccc acggagaggg acctggtcta ctacgagaac tcccccaact tttgtgagcc   1020
caacccagag acgggttcct ttggcacaag ggaccggact tgcaatgtca cctcccacgg   1080
catcgatggc tgcgatctgc tctgctgtgg ccggggccac aacacgagga cggagaagcg   1140
gaaggaaaaa tgccactgca tcttccactg gtgctgctac gtcagctgcc aggagtgtat   1200
tcgcatctac gacgtgcaca cctgcaagta gggcaccagg cgctgggaa ggggtgaagt   1260 gtgtggctgg gcggattcag cgaagtctca tgggaagcag acctagagc cgggcacagc   1320 cctcagcgtc agacagcaag gaactgtcac cagccgcacg cgtggtaaat gacccagacc   1380
caactcgcct gtggacgggg aggctctccc tctctctcat cttacatttc tcaccctact   1440
ctggatggtg tgtggttttt aagaagggg ctttcttttt tagttctcta gggtctgata   1500
ggaacagacc tgaggcttat ctttgcacat gttaaagaaa ataaaaatga aaaaaaattt   1560
gactccaaca gaacaggctg ggctaatgtg agctctcagc ctggcagtca agacatcagc   1620
atgggcaagg ttctgtttcc aaactgctgc ttctggtgac attccaagac gcctggaggg   1680
tgggagtcag gaagtaggac acacccctgc agtctccttt tcttggtcca ctcccattca   1740
aatttgagct aatttctcat tctgataaaa gccataggtt tagctaggat gaagtggtag   1800
gaaggtccgt ggcagttgtt agagtaggat ttggagtttg gaagaactgg cagctcaggg   1860
tggcctggtc agccgtttga agagcagcca tgtgttcttc tcagtctcat tttctctata   1920
accctgttct gcacgagggg cagtcagatc tcaaaatctt tttctaccat tctgcagttt   1980
ccaccgtcaa tgcagttttt tttttgtttt tttgtttttt tttttttttg gtggtagtgg   2040
accttgtaaa taggctatgt aagggggcaa gtcttctcta gctcaaatgg cttcctaaat   2100
aaataagcgg tatcttcaga aggggccatt cagtccttcc cagccctgct cacctgcaga   2160
ttctctgtac aaataactcc aggtagagca gttggactcc aggtcaccctt agtataagtt   2220 agacaaaggg tccgtgaggg agtagccatc aattcctgaa attccaactt tgtgactagc   2280
agatggggag gatgaaaacc atcccttttgc ttcctctcca atacggaccc atcttactgt   2340
gtcctttcct ctctggggcc aatgtgagta acacagaca cagagttctt tccccagct   2400 cttcctccct cacctgcatg ctgagatagc ttccatccat gcagttccca aggatctgga   2460
ttagaagttc aaaggggaac cagcagtcac ctactccctt aggtgaagca tctcacggct   2520
gagttctccc tgaggcatac tggtccagct gagcgtccta gagaaagcta gcaaaaggga   2580
```

| | | |
|---|---|---|
| ggcacatgga tttcacagta tgaattggtt caacaactgt cttagggaga atcagaaaga | 2640 |
| agagatgcag caggggaatg agcagaacaa agatttttct ttctccccct tctctctggg | 2700 |
| gtctacctaa ccctgaccta aaataccagg gcagcgatct cccagctggt gcaggtgggc | 2760 |
| ttgccaagat ggtcgtccag gagcccgcct tcacttctaa atctgctggc cacaagccct | 2820 |
| gctaaagata cacatctcac cccctccgcc aagtctgaaa tgcccctccc catctcacct | 2880 |
| tagactgaaa agttttaaat catgtcaact ggataatact tgctttatgt gagaatactt | 2940 |
| cagcagaatg gatacgaatt ttcaaaacaa tcttttcata tctatgtatt ctatattaaa | 3000 |
| agtgataaag tcatgtttct ggggcgtatt caagtagctg acaagtaatt atttaataat | 3060 |
| agtacatgag tgcattgtaa tgattctcgc cgtagtcagg taatagtatc caaccgaaat | 3120 |
| ttcctaccaa cctgctgtat ccaaagtttt gtaaaaagtt gtagaagttg ttgatctttt | 3180 |
| tgattttata ttcaaaaagt ctcttttttat aaatattatt tattatacaa tgtatatacc | 3240 |
| tttgagttaa ctaagattat atattatata aatatatata tatttggaga aaatatattt | 3300 |
| catcatgcag ttttttttctg ttaagtcatt aaagagaagg taaacaaacc taaaaaaaaa | 3360 |
| aaaaaaaaaa aaaaaaaaaa aaaaa | 3385 |

<210> SEQ ID NO 6
<211> LENGTH: 2988
<212> TYPE: DNA
<213> ORGANISM: Homo sapiens

<400> SEQUENCE: 6

| | | |
|---|---|---|
| gcaggagggc ccagcgacgc cgccgcgcca gctcccaggg cccggccccc cccggcgctc | 60 |
| acgctctcgg ggcggactcc cggccctccg cgccctctcg cgcggcgatg gccccactcg | 120 |
| gatacttctt actcctctgc agcctgaagc aggctctggg cagctacccg atctggtggt | 180 |
| cgctggctgt tgggccacag tattcctccc tgggctcgca gcccatcctg tgtgccagca | 240 |
| tcccgggcct ggtccccaag cagctccgct tctgcaggaa ctacgtggag atcatgccca | 300 |
| gcgtggccga gggcatcaag attggcatca aggagtgcca gcaccagttc cgcgccgcc | 360 |
| ggtggaactg caccaccgtc cacgacagcc tggccatctt cgggcccgtg ctggacaaag | 420 |
| ctaccaggga gtcggccttt gtccacgcca ttgcctcagc cggtgtggcc tttgcagtga | 480 |
| cacgctcatg tgcagaaggc acggccgcca tctgtggctg cagcagccgc caccagggct | 540 |
| caccaggcaa gggctggaag tggggtggct gtagcgagga catcgagttt ggtgggatgg | 600 |
| tgtctcggga gttcgccgac gcccgggaga accggccaga tgcccgctca gccatgaacc | 660 |
| gccacaacaa cgaggctggg cgccaggcca tcgccagcca catgcacctc aagtgcaagt | 720 |
| gccacgggct gtcgggcagc tgcgaggtga agacatgctg gtggtcgcaa cccgacttcc | 780 |
| gcgccatcgg tgacttcctc aaggacaagt acgacagcgc ctcggagatg gtggtggaga | 840 |
| agcaccggga gtcccgcggc tgggtggaga ccctgcggcc gcgctacacc tacttcaagg | 900 |
| tgcccacgga gcgcgacctg gtctactacg aggcctcgcc caacttctgc gagcccaacc | 960 |
| ctgagacggg ctccttcggc acgcgcgacc gcacctgcaa cgtcagctcg cacggcatcg | 1020 |
| acggctgcga cctgctgtgc tgcggccgcg gccacaacgc gcgagcggag cggcgccggg | 1080 |
| agaagtgccg ctgcgtgttc cactggtgct gctacgtcag ctgccaggag tgcacgcgcg | 1140 |
| tctacgacgt gcacacctgc aagtaggcac cggccgcggc tcccctggac cggggcgggc | 1200 |
| cctgcctgag ggtgggcttt tccctgggtg gagcaggact cccacctaaa cggggcagta | 1260 |

| | |
|---|---|
| ctcctccctg ggggcgggac tcctccctgg gggtggggct cctacctggg ggcagaactc | 1320 |
| ctacctgaag gcagggctcc tccctggagc tagtgtctcc tctctggtgg ctgggctgct | 1380 |
| cctgaatgag gcggagctcc aggatgggga ggggctctgc gttggcttct ccctggggac | 1440 |
| ggggctcccc tggacagagg cggggctaca gattgggcgg ggcttctctt gggtgggaca | 1500 |
| gggcttctcc tgcggggggcg aggcccctcc cagtaagggc gtggctctgg gtgggcgggg | 1560 |
| cactaggtag gcttctacct gcaggcgggg ctcctcctga aggaggcggg gctctaggat | 1620 |
| ggggcacggc tctgggtag gctgctccct gagggcggag cgcctcctta ggagtggggt | 1680 |
| tttatggtgg atgaggcttc ttcctggatg gggcagagct tctcctgacc agggcaaggc | 1740 |
| cccttccacg ggggctgtgg ctctgggtgg gcgtggcctg cataggctcc ttcctgtggg | 1800 |
| tggggcttct ctgggaccag gctccaatgg ggcggggctt ctctccgcgg gtgggactct | 1860 |
| tccctgggaa ccgccctcct gattaaggcg tggcttctgc aggaatcccg gctccagagc | 1920 |
| aggaaattca gcccaccagc cacctcatcc ccaaccccct gtaaggttcc atccacccct | 1980 |
| gcgtcgagct gggaaggttc catgaagcga gtcgggtccc caacccgtgc ccctgggatc | 2040 |
| cgagggcccc tctccaagcg cctggctttg gaatgctcca ggcgcgccga cgcctgtgcc | 2100 |
| accccttcct cagcctgggg tttgaccacc cacctgacca ggggccctac ctggggaaag | 2160 |
| cctgaagggc ctcccagccc ccaaccccaa gaccaagctt agtcctggga aggacaggg | 2220 |
| acttcgcaga ggcaagcgac cgaggccctc ccaaagaggc ccgccctgcc cgggctccca | 2280 |
| caccgtcagg tactcctgcc agggaactgg cctgctgcgc cccaggcccc gcccgtctct | 2340 |
| gctctgctca gctgcgcccc cttctttgca gctgcccagc ccctcctccc tgccctcggg | 2400 |
| tctccccacc tgcactccat ccagctacag gagagataga agcctctcgt cccgtccctc | 2460 |
| cctttcctcc gcctgtccac agcccttaa gggaaaggta ggaagagagg tccagccccc | 2520 |
| caggctgccc agagctgctg gtctcatttg ggggcgttcg ggaggtttgg ggggcatcaa | 2580 |
| ccccccgact gtgctgctcg cgaaggtccc acagccctga gatgggccgg ccccttcct | 2640 |
| ggcccctcat ggcgggactg gagaaatggt ccgctttcct ggagccaatg gcccggcccc | 2700 |
| tcctgactca tccgcctggc ccgggaatga atggggaggc cgctgaaccc acccggccca | 2760 |
| tatccctggt tgcctcatgg ccagcgcccc tcagcctctg ccactgtgaa ccggctccca | 2820 |
| ccctcaaggt gcggggagaa gaagcggcca ggcggggcgc cccaagagcc caaaagaggg | 2880 |
| cacaccgcca tcctctgcct caaattctgc gttttttggtt ttaatgttat atctgatgct | 2940 |
| gctatatcca ctgtccaacg gagttagacg aaaaaaaaaa aaaaaaaa | 2988 |

<210> SEQ ID NO 7
<211> LENGTH: 7134
<212> TYPE: DNA
<213> ORGANISM: Homo sapiens

<400> SEQUENCE: 7

| | |
|---|---|
| cgggcttgtg ccgccgccgc cgccgccgcc gcccgggcca agtgacaaag gaaggaagga | 60 |
| agcgaggagg agccggcccc gcagccgctg acagggctct gggctggggc aaagcgcgga | 120 |
| cacttcctga gcgggcaccg agcagagccg aggggcggga gggcggccga gctgttgccg | 180 |
| cggacggggg agggggcccc gagggacgga agcggttgcc gggttcccat gtcccggcg | 240 |
| aatggggaac agtcgaggag ccgctgcctg gggtctgaag ggagctgcct ccgccaccgc | 300 |
| catgccgct ggatccagcc gccgcctgca gctgctcctg gcgcaatgag gagaggagcc | 360 |
| gccgccaccg ccaccgcccg cctctgactg actcgcgact ccgccgccct ctagttcgcc | 420 |

```
gggcccctgc cgtcagcccg ccggatcccg cggcttgccg gagctgcagc gtttcccgtc    480
gcatctccga gccacccct ccctccctct ccctccctcc tacccatccc cctttctctt    540
caagcgtgag actcgtgatc cttccgccgc ttcccttctt cattgactcg gaaaaaaaat    600
ccccgaggaa aatataatat tcgaagtact cattttcaat caagtatttg cccccgtttc    660
acgtgataca tattttttta ggatttgccc tctcttttct ctcctcccag gaaagggagg    720
ggaaagaatt gtatttttc ccaagtccta aatcatctat atgttaaata tccgtgccga    780
tctgtcttga aggagaaata tatcgcttgt tttgtttttt atagtataca aaggagtga    840
aaagccaaga ggacgaagtc tttttctttt tcttctgtgg gagaacttaa tgctgcattt    900
atcgttaacc taacacccca acataaagac aaaaggaaga aaaggaggaa ggaaggaaaa    960
ggtgattcgc gaagagagtg atcatgtcag ggcggcccag aaccacctcc tttgcggaga   1020
gctgcaagcc ggtgcagcag ccttcagctt ttggcagcat gaaagttagc agagacaagg   1080
acggcagcaa ggtgacaaca gtggtggcaa ctcctgggca gggtccagac aggccacaag   1140
aagtcagcta tacagacact aaagtgattg gaaatggatc atttggtgtg gtatatcaag   1200
ccaaactttg tgattcagga gaactggtcg ccatcaagaa agtattgcag acaagagat    1260
ttaagaatcg agagctccag atcatgagaa agctagatca ctgtaacata gtccgattgc   1320
gttatttctt ctactccagt ggtgagaaga aagatgaggc tatcttaat ctggtgctgg   1380
actatgttcc ggaaacagta tacagagttg ccagacacta tagtcgagcc aaacagacgc   1440
tccctgtgat ttatgtcaag ttgtatatgt atcagctgtt ccgaagtta gcctatatcc   1500
attcctttgg aatctgccat cgggatatta accgcagaa cctcttgttg atcctgata    1560
ctgctgtatt aaaactctgt gactttggaa gtgcaaagca gctggtccga ggagaaccca   1620
atgtttcgta tatctgttct cggtactata gggcaccaga gttgatcttt ggagccactg   1680
attatacctc tagtatagat gtatggtctg ctggctgtgt gttggctgag ctgttactag   1740
gacaaccaat atttccaggg gatagtggtg tggatcagtt ggtagaaata atcaaggtcc   1800
tgggaactcc aacaagggag caaatcagag aaatgaaccc aaactacaca gaatttaaat   1860
tccctcaaat taaggcacat ccttggacta aggattcgtc aggaacagga catttcacct   1920
caggagtgcg ggtcttccga ccccgaactc caccggaggc aattgcactg tgtagccgtc   1980
tgctggagta tacccaact gcccgactaa caccactgga agcttgtgca cattcatttt   2040
ttgatgaatt acgggaccca aatgtcaaac taccaaatgg gcgagacaca cctgcactct   2100
tcaacttcac cactcaagaa ctgtcaagta atccacctct ggctaccatc cttattcctc   2160
ctcatgctcg gattcaagca gctgcttcaa cccccacaaa tgccacagca gcgtcagatg   2220
ctaatactgt agaccgtgga cagaccaata atgctgcttc tgcatcagct tccaactcca   2280
cctgaacagt cccgagcagc cagctgcaca ggaaaaacca ccagttactt gagtgtcact   2340
cagcaacact ggtcacgttt ggaagaata ttaaaaagag aaaaaaatcc tgttcatttt   2400
agtgttcaat ttttttatta ttattgttgt tcttatttaa ccttgtaaaa tatctataaa   2460
tacaaaccaa tttcattgta ttctcacttt gagggagatc cagggggtgg gaggggttgt   2520
ggggagggg aaagcggagc actagaacat acaatctctc tcccacgaca atctttttt    2580
attaaaagtc tgctgttgta tactttaaaa acaggactcc tgcctcatgc cccttccaca   2640
aaagaagaaa accttttct gtgctgatgg gttttttga actttgtttt cttttaaagt   2700
ctagtgtgag actttggtat agtgcacagc ttgaaattgg ttgggagctt agcaggtata   2760
```

```
actcaacggg gacttaaatg tcacttgtaa aattaatcca tatcttcggg tatttataga    2820
cttgcctttg gcatgttggt ggcaggtgtg gcagacaaag aaatgtgtat cattcgtaac    2880
ccagggaggt caataaagtt tggaactcta cagggaagat tcttagtaga tttgttaagg    2940
ttttgttttg ctctcagtta gtgctagtga tgtagaggct tgtacaggag gctgccagag    3000
gggaagcagc aagcaagact caggcacaca tgctctacag gtggctcttt gtttgcctga    3060
ccaaagttct ttgcaaatct tagcacagtt tcaaactagt gacctgggag gagatggaag    3120
gggtgttgag caggctgagc tagctgctga ggtcaaaggc tgatgagccc agaggaaggg    3180
gacaggtcag ggatacatct caccactgtg aataagtttg tccagatttt tttctaaagt    3240
tacttcccct tggaaagatac acttgagagg acattgtagt taaataatgt gaactgtaac    3300
agtcatctac tggtttattt ttcatatttt ttaattgaaa attgagcttg cagaaatagc    3360
cacattctac acatagttct aattttaaat ccaaatctag aatctgtatt taatttgttt    3420
tttaacctca tgcttttttac atttatttat tgatgcatgt cagatggtag aaatattaaa    3480
aactacacat cagaatgata cagtcactta tacctgctga ctttatagga aagctgatga    3540
tataaatgtg tgtatatatg ttatatatac atatattcaa tactgccttt tttttttgtct    3600 acagtatcaa aattgactgg ttgaagcatg agaagaatgt tcccccaca cccagttaag    3660 agttttgtg tctgttttct ttgtgtatca gtgaacgatg ttaagaatca gtctctcttt    3720
ttgaagaaaa agcaatattc cttggaaagc aaggagaatt gaaggactat gtttgccgtg    3780
aggaaataga ttttcatgac tagtttgttt tatacttttta aggttggcat ctatgtgggc    3840
cttatatact ctaaaatgaa ctttagtcac cttggtgctt atgggccatt acttgaccta    3900
tgaatcttta aggcacaatc agttgtactt tacatttaaa gatcacttga gtgatggccg    3960
cctttccctc ctacccgctc cttccccaca tgccttccaa ggttagctgg taactgtagg    4020
gctgcagagc tgagcccatg gttgtgtgta acttgccctc accctcctca ttgccacctt    4080
aggtcacttt atgggtctcg tcctccagag ggttcggaag tggagtctgt tggcagccct    4140
cctgcaggcc ctagcaccct gtcctgctcc ttaactgtgt gtgtgactct ccaagagagt    4200
tgtcctgcct gctgaagtga accagtaccc agaaagacaa ctgtgagcca tcttggtttt    4260
cactcgctgt ttagctgagg tcttgggcca caaaggggt tcacaaacc tctggatata    4320 tcagagttta tgagaaagga acatgctca gtcaaaccaa atcaaacaaa ttgaatttta    4380
tgttttataa agtgcttctg aaagctaaga tttgaaagaa gtctgaaatc aaagtatttg    4440
gcagcataac tccttaaagg tagtggcgtt gatagaccat tttcagacag aatttataaa    4500
gaatctgaaa aggcaggtct gtgatagaga aatggacctg cattcagatc caactgccca    4560
gcaagcgttt ggatgcagac actgctctgg acgtggtata ctccccagag tccataaaaa    4620
tcagtgctta ttttaggaaa caggttgccc cccacaactg gggtaaaaga agagagaaaa    4680
gtcacgcttt tctctcattt cattgtgtgt gcatgtgtgc gtgtgtgtgt gtgtgtgtgt    4740
gtgctgagat gtgtgatttt tctttctcaa ggatcatggt gggatcacag aactctttta    4800
tacaagtgag atccaggtct ctgaatatct ttttgtatat aataataata aaaagctcct    4860
caccaaattc aagcttgtac attatatttt cttctgtgt ttttaaattt aagttttatt    4920
gttttgtatg taaatatgtg gacccaggaa ctgttattaa tgagcaaaaa gttactgttc    4980
agggcagtga ttctgtttaa taatcagaca aaatgtagac gagcttttta aagccatata    5040
gttttaactc tgtacagtag gtaccggcct gtattattgt aacaataact ctagcaatgt    5100
atagtgtatc tatatagttt ggagtgcctt cgcttccatg tgttttttttt tttaatttgt    5160
```

-continued

```
tcttttttaa attttaattg gtttccttta tccatgtctc cctgtccacc ccctttccct      5220
ttgaaataat aactcactca taacagtatc tttgcccctt ccacagttaa gtttcagtga      5280
taccatactc aggagtggga agaggaaatc atattcgtaa tttcatttcg ttgaagccct      5340
gcctttgttt tggttctgaa tgtctttcct cctcggtagc agtgagaccg gtttcatttc      5400
atacttagtc cattcaggga cttagtgtag caccagggag ccctagagct ggaggatatc      5460
gaatagatta aattttgctc gtctcttcca caagccctaa ccatgggtct taaaaacagc      5520
agattctggg agccttccat gctctctctc tctcctcttt tatctacttc cctcccaaat      5580
gagagagtga cagagaattg tttttttata atcgaagtt tcttaatagt atcaggtttt       5640
gatacgtcag tggtctaaaa tgctatagtg caattactag cagttactgc acggagtgcc      5700
accgtgccaa tagaggactg ttgttttaac aagggaactc ttagcccatt tcctccctcc      5760
cgccatctct acccttgctc aatgaaatat catttaatt tcttttaaaa aaaatcagtt       5820
taattcttac tgtgtgccca acacgaaggc cttttttgaa agaaaaatag aatgttttgc      5880
ctcaaagtag tccatataaa atgtcttgaa tagaagaaaa aactaccaaa ccaaaggtta      5940
ctatttttga aacatcgtgt gttcattcca gcaaggcaga agactgcacc ttcttttccag     6000 tgacatgctg tgtcattttt tttaagtcct cttaattttt agacacattt ttggtttatg      6060
ttttaacaat gtatgcctaa ccagtcatct tgtctgcacc aatgcaaagg tttctgagag      6120
gagtattctc tatccctgtg gatatgaaga cactggcatt tcatctattt ttcccttttcc     6180 tttttaaagg atttaactttt ggaatcttcc aaaggaagtt tggccaatgc cagatcccca     6240
ggaatttggg gggttttctt tcttttcaac tgaaattgta tctgattcct actgttcatg      6300
ttagtgatca tctaatcaca gagccaaaca cttttctccc ctgtgtggaa aagtaggtat      6360
gctttacaat aaaatctgtc ttttctggta gaaacctgag ccactgaaaa taaaagagac      6420
aactagaagc acagtagagt cccagactga gatctacctt tgagaggctt tgaaagtaat      6480
ccctggggtt tggattattt tcacaagggt tatgccgttt tattcaagtt tgttgctccg      6540
ttttgcacct ctgcaataaa agcaaaatga caaccagtac ataagggtt agcttgacaa       6600 agtagacttc cttgtgttaa ttttttaagtt tttttttcct taactatatc tgtctacagg     6660
cagatacaga tagttgtatg aaaatctgct tgcctgtaaa atttgcattt ataaatgtgt      6720
tgccgatgga tcacttgggc ctgtacacat accaattagc gtgaccactt ccatcttaaa      6780
aacaaaccta aaaacaaaa tttattatat atatatatat atatatataa aggactgtgg       6840
gttgtataca aactattgca aacacttgtg caaatctgtc ttgatataaa ggaaaagcaa      6900
aatctgtata acattattac tacttgaatg cctctgtgac tgattttttt tcatttaa       6960 atataaactt ttttgtgaaa agtatgctca atgttttttt tccctttccc cattcccttg      7020
taaatacatt ttgttctatg tgacttggtt tggaaatagt taactggtac tgtaatttgc      7080
attaaataaa aagtaggtta gcctggaaat gaaattaaaa aaaaaaaaa aaaa            7134
```

<210> SEQ ID NO 8
<211> LENGTH: 3362
<212> TYPE: DNA
<213> ORGANISM: Homo sapiens

<400> SEQUENCE: 8

```
aagcctctcg gtctgtggca gcagcgttgg cccggccccg ggagcggaga gcgaggggag       60
gcggagacgg aggaaggtct gaggagcagc ttcagtcccc gccgagccgc caccgcaggt      120
```

```
cgaggacggt cggactcccg cggcgggagg agcctgttcc cctgagggta tttgaagtat    180
accatacaac tgttttgaaa atccagcgtg acaatggct actcaagctg atttgatgga    240
gttggacatg gccatggaac cagacagaaa agcggctgtt agtcactggc agcaacagtc    300
ttacctggac tctggaatcc attctggtgc cactaccaca gctccttctc tgagtggtaa    360
aggcaatcct gaggaagagg atgtggatac ctcccaagtc ctgtatgagt gggaacaggg    420
attttctcag tccttcactc aagaacaagt agctgatatt gatggacagt atgcaatgac    480
tcgagctcag agggtacgag ctgctatgtt ccctgagaca ttagatgagg gcatgcagat    540
cccatctaca cagtttgatg ctgctcatcc cactaatgtc cagcgtttgg ctgaaccatc    600
acagatgctg aaacatgcag ttgtaaactt gattaactat caagatgatg cagaacttgc    660
cacacgtgca atccctgaac tgacaaaact gctaaatgac gaggaccagg tggtggttaa    720
taaggctgca gttatggtcc atcagctttc taaaaaggaa gcttccagac acgctatcat    780
gcgttctcct cagatggtgt ctgctattgt acgtaccatg cagaatacaa atgatgtaga    840
aacagctcgt tgtaccgctg ggaccttgca taacctttcc catcatcgtg agggcttact    900
ggccatcttt aagtctggag gcattcctgc cctggtgaaa atgcttggtt caccagtgga    960
ttctgtgttg ttttatgcca ttacaactct ccacaacctt ttattacatc aagaaggagc   1020
taaaatggca gtgcgtttag ctggtgggct gcagaaaatg gttgccttgc tcaacaaaac   1080
aaatgttaaa ttcttggcta ttacgacaga ctgccttcaa attttagctt atggcaacca   1140
agaaagcaag ctcatcatac tggctagtgg tggaccccaa gctttagtaa atataatgag   1200
gacctatact tacgaaaaac tactgtggac cacaagcaga gtgctgaagg tgctatctgt   1260
ctgctctagt aataagccgg ctattgtaga agctggtgga atgcaagctt taggacttca   1320
cctgacagat ccaagtcaac gtcttgttca gaactgtctt tggactctca ggaatctttc   1380
agatgctgca actaaacagg aagggatgga aggtctcctt gggactcttg ttcagcttct   1440
gggttcagat gatataaatg tggtcacctg tgcagctgga attctttcta acctcacttg   1500
caataattat aagaacaaga tgatggtctg ccaagtgggt ggtatagagg ctcttgtgcg   1560
tactgtcctt cgggctggtg acagggaaga catcactgag cctgccatct gtgctcttcg   1620
tcatctgacc agccgacacc aagaagcaga gatggcccag aatgcagttc gccttcacta   1680
tggactacca gttgtggtta agctcttaca cccaccatcc cactggcctc tgataaaggc   1740
tactgttgga ttgattcgaa atcttgccct ttgtcccgca aatcatgcac ctttgcgtga   1800
gcagggtgcc attccacgac tagttcagtt gcttgttcgt gcacatcagg atacccagcg   1860
ccgtacgtcc atgggtggga cacagcagca atttgtggag ggggtccgca tggaagaaat   1920
agttgaaggt tgtaccggag cccttcacat cctagctcgg gatgttcaca accgaattgt   1980
tatcagagga ctaaatacca ttccattgtt tgtgcagctg ctttattctc ccattgaaaa   2040
catccaaaga gtagctgcag gggtcctctg tgaacttgct caggacaagg aagctgcaga   2100
agctattgaa gctgagggag ccacagctcc tctgacagag ttacttcact ctaggaatga   2160
aggtgtggcg acatatgcag ctgctgtttt gttccgaatg tctgaggaca agccacaaga   2220
ttacaagaaa cggctttcag ttgagctgac cagctctctc ttcagaacag agccaatggc   2280
ttggaatgag actgctgatc ttggacttga tattggtgcc cagggagaac cccttggata   2340
tcgccaggat gatcctagct atcgttcttt tcactctggt ggatatgcc aggatgcctt    2400
gggtatggac cccatgatgg aacatgagat gggtggccac cacccctggtg ctgactatcc   2460
agttgatggg ctgccagatc tggggcatgc ccaggacctc atggatgggc tgcctccagg   2520
```

```
tgacagcaat cagctggcct ggtttgatac tgacctgtaa atcatccttt agctgtattg    2580
tctgaacttg cattgtgatt ggcctgtaga gttgctgaga gggctcgagg ggtgggctgg    2640
tatctcagaa agtgcctgac acactaacca agctgagttt cctatgggaa caattgaagt    2700
aaactttttg ttctggtcct ttttggtcga ggagtaacaa tacaaatgga tttttgggagt   2760 gactcaagaa gtgaagaatg cacaagaatg gatcacaaga tggaatttag caaaccctag    2820
ccttgcttgt taaaattttt tttttttttt tttaagaat atctgtaatg gtactgactt     2880
tgcttgcttt gaagtagctc tttttttttt tttttttttt tttttttgca gtaactgttt    2940
tttaagtctc tcgtagtgtt aagttatagt gaatactgct acagcaattt ctaatttta     3000 agaattgagt aatggtgtag aacactaatt aattcataat cactctaatt aattgtaatc    3060
tgaataaagt gtaacaattg tgtagccttt ttgtataaaa tagacaaata gaaaatggtc    3120
caattagttt cctttttaat atgcttaaaa taagcaggtg gatctatttc atgtttttga    3180
tcaaaaacta tttgggatat gtatgggtag ggtaaatcag taagaggtgt tatttggaac    3240
cttgttttgg acagtttacc agttgccttt tatcccaaag ttgttgtaac ctgctgtgat    3300
acgatgcttc aagagaaaat gcggttataa aaaatggttc agaattaaac ttttaattca    3360
tt                                                                   3362
```